US010053415B2

(12) United States Patent
Harwig et al.

(10) Patent No.: US 10,053,415 B2
(45) Date of Patent: Aug. 21, 2018

(54) SYNTHESIS OF A SUBSTITUTED INDENE DERIVATIVE

(71) Applicant: AQUINOX PHARMACEUTICALS (CANADA) INC., Vancouver (CA)

(72) Inventors: Curtis Harwig, Vancouver (CA); Jeyaprakashnarayanan Seenisamy, Bangalore (IN); Mahesh Narayan Keregadde, Sirsi (IN); Lakshindra Chetia, Bangalore (IN)

(73) Assignee: Aquinox Pharmaceuticals (Canada) Inc., Vancouver (CA)

( * ) Notice: Subject to any disclaimer, the term of this patent is extended or adjusted under 35 U.S.C. 154(b) by 0 days.

(21) Appl. No.: 15/411,863

(22) Filed: Jan. 20, 2017

(65) Prior Publication Data

US 2017/0204048 A1 Jul. 20, 2017
US 2018/0086691 A9 Mar. 29, 2018

Related U.S. Application Data

(60) Provisional application No. 62/281,082, filed on Jan. 20, 2016, provisional application No. 62/342,765, filed on May 27, 2016, provisional application No. 62/344,851, filed on Jun. 2, 2016.

(51) Int. Cl.
*C07C 209/30* (2006.01)

(52) U.S. Cl.
CPC ........ *C07C 209/30* (2013.01); *C07C 2601/14* (2017.05); *C07C 2602/02* (2017.05)

(58) Field of Classification Search
CPC ... C07C 13/465; C07C 209/30; C07C 213/00; C07C 249/12; C07C 2101/14; C07C 2102/02; C07C 2601/14; C07C 2602/24; C07D 307/77; C07D 317/70; C07D 317/72; C07J 1/0011; C07J 1/0022; C07J 13/007; C07J 21/008; C07J 31/006; C07J 51/00; C07J 71/0026; C07J 73/003; C07J 73/005; C07B 2200/07
See application file for complete search history.

(56) References Cited

U.S. PATENT DOCUMENTS

| | | | |
|---|---|---|---|
| 3,682,983 A | 8/1972 | Prezewowsky et al. | |
| 3,869,467 A | 3/1975 | Guthrie et al. | |
| 3,962,275 A | 6/1976 | Guthrie et al. | |
| 5,686,621 A | 11/1997 | Clark et al. | |
| 6,046,185 A | 4/2000 | Burgoyne et al. | |
| 6,635,629 B2 | 10/2003 | Raymond et al. | |
| 6,696,580 B2 | 2/2004 | Burgoyne et al. | |
| 6,982,329 B2 | 1/2006 | Burgoyne et al. | |
| 7,601,874 B2 | 10/2009 | Raymond et al. | |
| 7,999,010 B2 | 8/2011 | Raymond et al. | |
| 8,084,503 B2 | 12/2011 | Raymond et al. | |
| 8,673,975 B2 | 3/2014 | Raymond et al. | |
| 9,000,050 B2 | 4/2015 | Wang et al. | |
| 2001/0010293 A1 | 8/2001 | Ishida et al. | |
| 2005/0004086 A1* | 1/2005 | Raymond | C07C 35/21 514/169 |
| 2010/0323990 A1 | 12/2010 | Andersen et al. | |
| 2011/0263539 A1 | 10/2011 | Andersen et al. | |
| 2014/0371252 A1 | 12/2014 | Raymond et al. | |
| 2016/0031899 A1 | 2/2016 | MacKenzie et al. | |
| 2016/0083387 A1 | 3/2016 | MacKenzie et al. | |
| 2016/0376222 A1 | 12/2016 | MacKenzie et al. | |

FOREIGN PATENT DOCUMENTS

| | | |
|---|---|---|
| DE | 1 084 718 | 7/1960 |
| GB | 1291644 | 10/1972 |
| JP | 1-290624 A | 11/1989 |
| JP | 5-221901 A | 8/1993 |
| JP | 5-221924 A | 8/1993 |
| WO | WO 93/13124 A1 | 7/1993 |
| WO | WO 94/14833 A2 | 7/1994 |
| WO | WO 95/01960 A1 | 1/1995 |
| WO | WO 96/11939 A1 | 4/1996 |
| WO | WO 03/033517 A1 | 4/2003 |
| WO | WO 2004/035601 A1 | 4/2004 |
| WO | WO 2004/092100 A1 | 10/2004 |
| WO | WO 2007/147251 A1 | 12/2007 |
| WO | WO 2007/147252 A1 | 12/2007 |
| WO | WO 2011/069118 A1 | 6/2011 |
| WO | WO 2014/143561 A1 | 9/2014 |
| WO | WO 2014/158654 A1 | 10/2014 |
| WO | WO 2016/210146 A1 | 12/2016 |
| WO | WO 2017/127753 A1 | 7/2017 |

OTHER PUBLICATIONS

Ahmad and Khan, "The Baeyer-Villiger Oxidation of 5α-Cholestane-3,6-Dione," *Acta Chim. Acad. Sci. Hung.* 106(2): 111-113, 1981.

Altomare et al., "*SIR97*: a new tool for crystal structure determination and refinement," *J. Appl. Cryst.* 32: 115-119, 1999.

Barber et al., "PI3Kγ inhibition blocks glomerulonephritis and extends lifespan in a mouse model of systemic lupus," *Nature Medicine* 11(9): 933-935, Sep. 2005.

(Continued)

*Primary Examiner* — Pancham Bakshi
*Assistant Examiner* — Mark R Luderer
(74) *Attorney, Agent, or Firm* — Seed IP Law Group LLP

(57) ABSTRACT

This invention is directed to methods of preparing AQX-1125 having the formula:

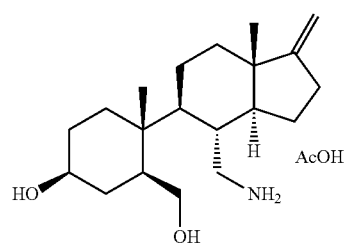

This invention is also directed to intermediates utilized in the methods of preparing AQX-1125.

42 Claims, No Drawings

(56) References Cited

OTHER PUBLICATIONS

Buckingham et al., "6-Phenylazocholestane derivatives: Reassignment of the Structures of Products from Phenylhydrazine and Ozonised Cholesterol Derivatives," *J. Chem. Soc.*(C) 18: 1703-1706, 1967.
Camps et al., "Blockade of PI3Kγ suppresses joint inflammation and damage in mouse models of rheumatoid arthritis," *Nature Medicine 11*(9): 936-943, Sep. 2005.
Clinton et al., "Steroidal[3,2-c]pyrazoles. II. Androstanes, 19-Norandrostanes and their Unsaturated Analogs," *Journal of the American Chemical Society 83*: 1478-1491, Mar. 20, 1961.
Cookson et al., "Photochemical Rearrangement of α-Hydroxyketones to Lactones," *J. Chem. Soc.* (C): 2494-2500, 1968.
Dauben and Brookhart, "Stereocontrolled Synthesis of Steroidal Side Chains," *J. Am. Chem. Soc. 103*: 237-238, 1981.
Fan et al., "A dual PI3 kinase/mTOR inhibitor reveals emergent efficacy in glioma," *Cancer Cell 9*: 341-349, May 2006.
Feuer et al., "The Reduction of Oximes, Oxime Ethers, and Oxime Esters with Diborane. A Novel Synthesis of Amines," *The Journal of Organic Chemistry 34*(6): 1817-1821, Jun. 1969.
Goclik et al., "Pelorol from the Tropical Marine Sponge *Dactylospongia elegans*," *J. Nat. Prod. 63*: 1150-1152, 2000.
Gumulka et al, "Oxidative Cleavage of the Double Bond of 7-Dehydrocholesterol Acetate Peroxide," *Polish Journal of Chemistry 57*(4/5/6): 403-411, 1983.
Hara "Azasteroid. IV. Synthesis of B-Azacholane Derivative," Chemical Abstracts Online, Accession No. 1959:17427, 1959. See also *Yakugaku Zasshi 78*(9): 1030-1033, Sep. 1958.
Hazen et al., "SHIP is required for a functional hematopoietic stem cell niche," *Blood* 113(13): 2924-2933, Mar. 26, 2009.
Hennessy et al., "Exploiting the PI3K/AKT Pathway for Cancer Drug Discovery," *Nature Reviews|Drug Discovery 4*: 988-1004, Dec. 2005.
Ibers et al., "Dispersion corrections and crystal structure refinements," *Acta Cryst. 17*: 781-782, 1964.
Kaspar and Witzel, "Steroid Binding to the Cytosolic Estrogen Receptor From Rat Uterus. Influence of the Orientation of Substituents in the 17-Position of the 8β- and 8α-Series," *J. steroid Biochem. 23*(3): 259-265, 1985.
Knight et al., "A Pharmacological Map of the PI3-K Family Defines a Role for p110α in Insulin Signaling," *Cell 125*: 733-747, May 19, 2006.
Kwak et al., "Sesquiterpene Quinols/Quinones from the Micronesian Sponge *Petrosaspongia metachromia*," *J. Nat. Prod. 63*: 1153-1156, 2000.
Lettré and Werner, "Polyols from steroids and steroid derivatives. IV. 7,8-Seco-derivatives of cholestanols," Chemical Abstracts Online, Accession No. 1967:46521, 1967. See Also *Justus Liebigs Annalen Der Chemie 697*: 217-221, 1966.
Lettré and Werner, "Mehrwertige Alkohole aus Sterinen und Sterinderivaten. IV. 7.8-seco-Derivate des Cholestanols," *Justus Liebigs Annalen Der Chemie 697*: 217-221, 1966.
Ley et al., "Microencapsulation of Osmium Tetroxide in Polyurea," *Organic Letters 5*(2): 185-187, 2003.
MacRae et al., "*Mercury CSD 2.0*—new features for the visualization and investigation of crystal structures," *J. Appl. Cryst. 41*: 466-470, 2008.
Madaio et al., "Minor 5,6-Secosterols From the Marine Sponge *Hippospongia Communis*. Isolation and Synthesis of (7Z,22E,24R)-24-Methyl-5,6-Secocholesta-7,22-Diene-3β,5β,6-Triol," *Journal of Natural Products 53*(3): 565-572, May-Jun. 1990.
Manson et al., "Steroidal Heterocycles. VII. Androstano[2,3-d]isoxazoles and Related Compounds," *J. Med. Chem. 6*(1): 1-9, Jan. 18, 1963.
Mincione and Bovicelli, Synthesis via Organoiron Complexes of 9-(4-Keto-1-Methylcyclohex-2-enyl)-8-Keto-des-AB-Ergost-22,23-ene; A Useful Chiral Intermediate in Steroid Synthesis, *Heterocycles 23*(7): 1607-1610, 1985.

Mirjafary et al., "Oxime ethers as versatile precursors in organic synthesis: a review," *RSC Adv. 5*: 79361-79384, 2015.
Nicolaou et al., "An Expedient Procedure for the Oxidative Cleavage of Olefinic Bonds with PhI(OAc)$_2$, NMO, and Catalytic OsO$_4$," *Org. Lett. 12*(7): 1552-1555, Apr. 2, 2010.
Ong et al., "Small-molecule agonists of SHIP1 inhibit the phosphoinositide 3-kinase pathway in hematopoietic cells," *Blood 110*(6): 1942-1949, Sep. 15, 2007.
Reichstein and Meystre, "Über Bestandteile der Nebennierenrinde und verwandte Stoffe—Allo-pregnan-diol-(3, 17)-Derivate der 17(β)-Reihe. Weiterer Beweis für die Zugehörigkeit der Substanzen P und K zur 17(β)-Reihe," *Helv. Chim. Acta 22*(III): 728-741, 1939.
Rodewald and Piotrowski, "Secosteroids. I. Synthesis of vic-Diols in B-Secocholestane Group," *Journal Prakt. Chem. 330*(5): 775-881, 1988.
Rodewald and Wielogórski, "Selective Esterification of Hydroxyl Groups in Methyl Ester of 3β,8α-Dihydroxy-7,8-Secocholestan-7-oic Acid," *Roczniki Chemii Ann. Soc. Chim. Polonorum 51*(4): 809-814, 1977.
Rohrschneider et al., "Structure, function, and biology of SHIP proteins," *Genes & Development 14*: 505-520, 2000.
Savitzky et al., "Smoothing and Differentiation of Data by Simplified Least Squares Procedures," *Analytical Chemistry 36*(8): 1627-1639, Jul. 1964.
Simon, "Using Isoform-Specific Inhibitors to Target Lipid Kinases," *Cell 125*: 647-649, May 19, 2006.
Seto et al., "Epimerization at C-5 of brassinolide with sodium methoxide and the biological activity of 5-epi-brassinolide in the rice lamina inclination test," *J. Chem. Soc., Perkin Trans. 1*: 3355-3358, 1998.
Speckamp et al., "6-Thiasteroids a Novel Stereoselective Preparation of 6-Heterosteroids," *Tetrahedron Letters 38*: 3405-3408, 1974.
Stenton et al., "Characterization of AQX-1125, a small-molecule SHIP1 activator Part 1. Effects on inflammatory cell activation and chemotaxis in vitro and pharmacokinetic characterization in vivo," *British Journal of Pharmacology 168*: 1506-1518, 2013.
Suginome and Yamada, "Photoinduced Transformations. 77. A Four-Step Substitution of a Carbonyl Group of Steroidal Ketones by an Oxygen Atom. A New Method for the Synthesis of Cyclic Ethers," *Journal of Organic Chemistry 50*(14): 2489-2494, 1985.
Westmijze et al., "Ag(I)-Assisted Hydrolysis of Mestranol Methanesulfonate Into Epimestranol," *Tetrahedron Letters 21*: 2665-2666, Apr. 15, 1980.
Workman et al., "Drugging the PI3 kinome," *Nature Biotechnology 24*(7): 794-796, Jul. 2006.
Xing et al., "Gold(I)-Catalyzed Oxidative Cleavage of a C-C Double Bond in Water," *Organic Letters 8*(4): 693-696, 2006.
Yang et al., "Ruthenium-Catalyzed Oxidative Cleavage of Olefins to Aldehydes," *J. Org. Chem. 66*: 4814-4818, 2001.
Yong et al., "Synthesis of CD-ring modified 1α,25-dihydroxy vitamin D analogues: Five-membered D-ring analogues," *Bioorganic & Medicinal Chemistry Letters 7*(7): 923-928, 1997.
Chemical Abstracts Database, Accession No. 120:77523, Aug. 1993.
Chemical Abstracts Database, Accession No. 112:211000, Nov. 1989.
Chemical Abstracts Database, Accession No. 101:192278, 1983.
Chemical Abstracts Database, Accession No. 82:73301, 1974.
Beilstein Database, Beilstein Registry No. 3061562, 1968.
Beilstein Database, Beilstein Registry No. 3102039, 1967.
International Search Report, dated Sep. 6, 2016, for PCTAN PCT/US2016/039040, 6 pages.
Written Opinion of the International Searching Authority, dated Sep. 6, 2016, for PCTAN PCT/US2016/039040, 9 pages.
International Search Report, dated Mar. 13, 2017, for PCTAN PCT/US2017/014446, 5 pages.
Written Opinion of the International Searching Authority, dated Mar. 13, 2017, for PCTAN PCT/US2017/014446, 7 pages.
Coggeshall et al., "How do inhibitory phosphatases work?,"*Molecular Immunology 39*: 521-529, 2002.

(56) References Cited

OTHER PUBLICATIONS

Damen et al., "The 145-kDa protein induced to associate with Shc by multiple cytokines is an inositol tetraphosphate and phosphatidylinositol 3,4,5-trisphosphate 5-phosphatase," *Proc. Natl. Acad. Sci. USA 93*: 1689-1693, Feb. 1996.
Deane et al., "Phosphoinositide 3-Kinase: Diverse Roles in Immune Cell Activation," *Annu. Rev. Immunol.* 22: 563-598, 2004.
Fukuda et al., "Alteration of phosphatidylinositol 3-kinase cascade in the multilobulated nuclear formation of adult T cell leukemia/lymphoma (ATLL)," *PNAS 102*(42): 15213-15218, Oct. 18, 2005.
Gallou et al., "Practical Synthesis of Unsymmetrical Ureas from Isopropenyl Carbamates," *J. Org. Chem 70*: 6960-6963, 2005.
Halpern et al., "On the Nature of the Chemical Mediators Involved in Anaphylactic Reactions in Mice," *Brit. J. Pharmacol.* 20: 389-398, 1963.
Helgason et al., "A Dual Role for Src Homology 2 Domain-containing Inositol-5-Phosphatase (SHIP) in Immunity: Aberrant Development and Enhanced Function of B Lymphocytes in SHIP$^{-/-}$ Mice," *J. Exp. Med. 191*(5): 781-794, Mar. 6, 2000.
Helgason et al., "Targeted disruption of SHIP leads to hemopoietic perturbations, lung pathology, and a shortened life span," *Genes & Development 12*: 1610-1620, 1998.
Kalesnikoff et al., "The role of SHIP in cytokine-induced signaling," *Rev. Physiol. Biochem. Pharmacol. 149*: 87-103, 2003.
Kubinyi, (3D QSAR in Drug Design: Ligand-Protein Interactions and Molecular Similarity, vol. 2-3, Springer, 1998, 800 pages), pp. 243-244 provided.
Liang et al., "Quantification of change in phosphorylation of BCR-ABL kinase and its substrates in response to Imatinib treatment in human chronic myelogenous leukemia cells," *Proteomics 6*: 4554-4564, 2006.
Luo et al., "Mutation Analysis of SHIP Gene in Acute Leukemia," *Journal of Experimental Hematology 12*(4): 420-426, 2004.
Ovary et al., "Passive Cutaneous Anaphylaxis in the Mouse," *J. Immunol. 81*: 355-357, 1958.
Sly et al., "SHIP, SHIP2, and PTEN activities are regulated in vivo by modulation of their protein levels: SHIP is up-regulated in macrophages and mast cells by lipopolysaccharide," *Experimental Hematology 31*: 1170-1181, 2003.
Sly et al., "LPS-Induced Upregulation of SHIP Is Essential for Endotoxin Tolerance," *Immunity 21*: 227-239, Aug. 2004.
Vanderwinden et al., "Differences in signaling pathways and expression level of the phosphoinositide phosphatase SHIP1 between two oncogenic mutants of the receptor tyrosine kinase KIT," *Cellular Signalling 18*: 661-669, 2006.
Vivanco et al., "The Phosphatidylinositol 3-Kinase-AKT Pathway in Human Cancer," *Nature Reviews: Cancer 2*: 489-501, Jul. 2002.
Vonakis et al., "Src homology 2 domain-containing inositol 5' phosphatase is negatively associated with histamine release to human recombinant histamine-releasing factor in human basophils," *J. Allergy Clin. Immunol. 108*: 822-831, 2001.
Wermuth, The Practice of Medicinal Chemistry, 2nd ed. (2003), 768 pages, Chapters 9-10 provided.
Winter et al., "Carrageenin-Induced Edema in Hind Paw of the Rat as an Assay for Antiinflammatory Drugs," *Proc. Soc. Exp. Biol. Med. 111*: 544-547, 1962.
Yang et al., "Synthesis of Pelorol and Analogues: Activators of the Inositol 5-Phosphatase SHIP," *Organic Letters 7*(6): 1073-1076, 2005.
Chemical Abstracts Online, Accession No. 1959:17427, 1959, 2 pages.
Chemical Abstracts Online, Accession No. 1967:46521, 1966, 2 pages.
Chemical Abstracts Online, Accession No. 2013:381943, 2013, 2 pages.
International Preliminary Report on Patentability, dated Oct. 21, 2005, for International Application No. PCT/CA2004/000566, 8 pages.
International Preliminary Report on Patentability, dated Sep. 15, 2015, for International Application No. PCT/US2014/019125, 8 pages.
International Preliminary Report on Patentability, dated Sep. 15, 2015, for International Application No. PCT/US2014/019126, 11 pages.

\* cited by examiner

SYNTHESIS OF A SUBSTITUTED INDENE DERIVATIVE

FIELD OF THE INVENTION

The present invention is directed to methods of preparing a substituted indene derivative which is useful as a SHIP1 modulator. In particular, the present invention is directed to the methods of preparing a substituted indene derivative known as AQX-1125.

BACKGROUND OF THE INVENTION

Dysregulated activation of the PI3K pathway contributes to inflammatory/immune disorders and cancer. Efforts have been made to develop modulators of PI3K as well as downstream kinases (Workman et al., *Nat. Biotechnol.* 24, 794-796, 2006; Simon, *Cell* 125, 647-649, 2006; Hennessy et al., *Nat. Rev. Drug. Discov.* 4, 988-1004, 2005; Knight et al., *Cell* 125, 733-747, 2006; Ong et al., *Blood* (2007), Vol. 110, No. 6, pp 1942-1949). A number of promising new PI3K isoform specific inhibitors with minimal toxicities have recently been developed and used mouse models of inflammatory disease (Camps et al., *Nat. Med.* 11, 936-943, 2005; Barber et al., *Nat. Med.* 11, 933-935, 2005) and glioma (Fan et al., *Cancer Cell* 9, 341-349, 2006). However, because of the dynamic interplay between phosphatases and kinases in regulating biological processes, inositol phosphatase activators represent a complementary, alternative approach to reduce $PIP_3$ levels. Of the phosphoinositol phosphatases that degrade $PIP_3$, SHIP1 is a particularly ideal target for development of therapeutics for treating immune and hemopoietic disorders because of its hematopietic-restricted expression (Hazen et al., *Blood* 113, 2924-2933, 2009; Rohrschneider et al., *Genes Dev.* 14, 505-520, 2000).

Small molecule SHIP1 modulators have been disclosed, including sesquiterpene compounds such as pelorol. Pelorol is a natural product isolated from the tropical marine sponge *Dactylospongia elegans* (Kwak et al., *J. Nat. Prod.* 63, 1153-1156, 2000; Goclik et al., *J. Nat. Prod.* 63, 1150-1152, 2000). Other reported SHIP1 modulators include the compounds set forth in PCT Published Patent Applications Nos. WO 2003/033517, WO 2004/035601, WO 2004/092100, WO 2007/147251, WO 2007/147252, WO 2011/069118, WO 2014/143561 and WO 2014/158654 and in U.S. Pat. Nos. 7,601,874 and 7,999,010.

One such molecule is AQX-1125, which is the acetate salt of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (AQX-1125). AQX-1125 is a compound with anti-inflammatory activity and is described in U.S. Pat. Nos. 7,601,874 and 7,999,010, the relevant disclosures of which are incorporated in full by reference in their entirety, particularly with respect to the preparation of AQX-1125, pharmaceutical compositions comprising AQX-1125 and methods of using AQX-1125.

AQX-1125 has the molecular formula, $C_{20}H_{36}NO_2^+ \cdot C_2H_3O_2^-$, a molecular weight of 381.5 g/mole and has the following structural formula:

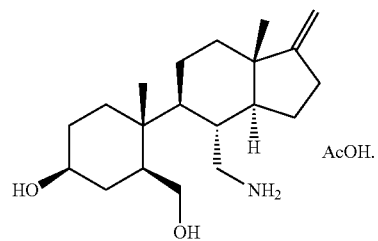 [SMILES: C=C1CC[C@H]2[C@H](CN)[C@@H]([C@@]3(C)CC[C@H](O)C[C@@H]3CO)CC[C@]12C]

AQX-1125 is useful in treating disorders and conditions that benefit from SHIP1 modulation, such as cancers, inflammatory disorders and conditions and immune disorders and conditions. AQX-1125 is also useful in the preparation of a medicament for the treatment of such disorders and conditions.

Synthetic methods for preparing AQX-1125 are disclosed in U.S. Pat. Nos. 7,601,874 and 7,999,010. There exists, therefore, a need for improved methods of preparing AQX-1125.

SUMMARY OF THE INVENTION

The invention is directed to methods for preparing AQX-1125. These methods provide an increased overall yield of AQX-1125 with a cost-effective reduction of steps and reagents from the previously disclosed methods.

Accordingly, in a first aspect, this invention is directed to a method of preparing AQX-1125, which has the following formula:

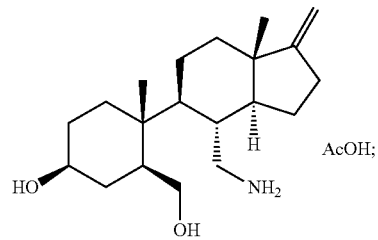

wherein the method comprises:
(a) treating compound 53A having the formula:

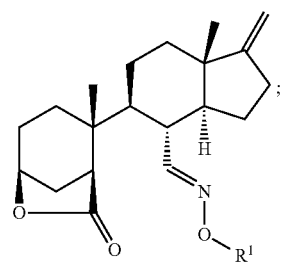

where $R^1$ is hydrogen, methyl or ethyl, under suitable lactone and oxime O-ether reduction conditions to provide compound 16 having the formula:

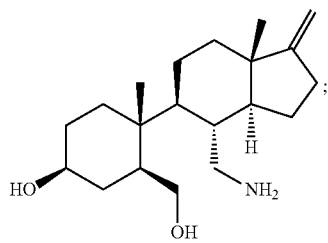

16

(b) treating compound 16 under suitable acetate salt formation conditions to provide AQX-1125.

In a second aspect, this invention is directed to another method of preparing AQX-1125, as defined above, wherein the method comprises:

(a) treating Compound 1 having the formula:

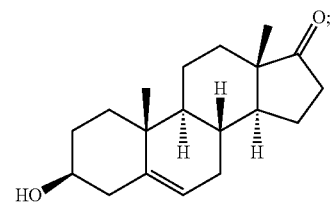

1 under suitable carbonyl protection conditions to provide Compound 69A having the formula:

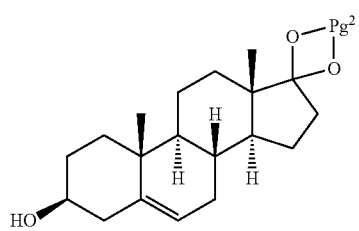

69A wherein Pg$^2$ is a carbonyl protecting group;

(b) treating Compound 69A under suitable hydroxyl protection conditions to provide Compound 70A having the formula:

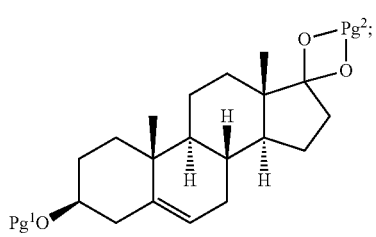

70A wherein Pg$^1$ is an oxygen-protecting group and Pg$^2$ is a carbonyl protecting group;

(c) treating Compound 70A under suitable allylic oxidation conditions to provide Compound 71A having the formula:

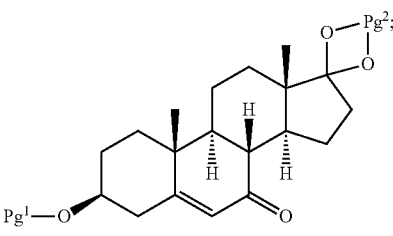

71A wherein Pg$^1$ is an oxygen-protecting group and Pg$^2$ is a carbonyl protecting group;

(d) treating Compound 71A under suitable carbonyl reduction and hydroboration-oxidation conditions to provide Compound 72A having the formula:

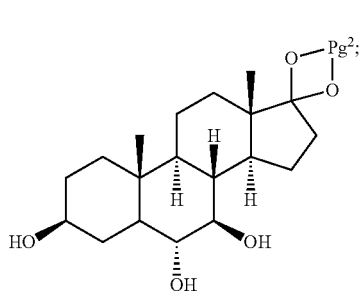

72A wherein Pg$^2$ is a carbonyl protecting group;

(e) treating Compound 72A under suitable carbonyl deprotection conditions to provide Compound 6 having the formula:

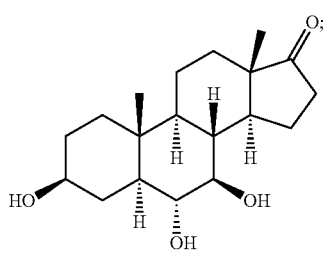

6

(f) treating Compound 6 under suitable olefination or Wittig reaction conditions to provide Compound 54 having the formula:

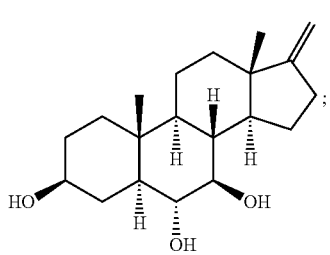

54

(g) treating Compound 54 under suitable 1,2-diol oxidative carbon-carbon bond cleavage conditions to provide Compound 51 having the formula:

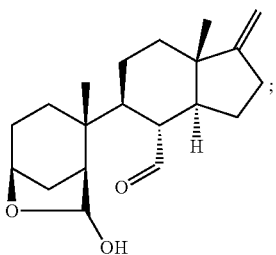

(h) treating Compound 51 under suitable oxidation conditions to provide Compound 52 having the formula:

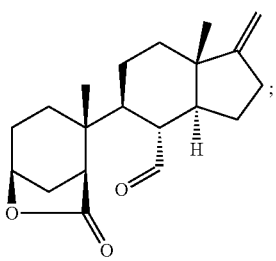

(i) treating Compound 52 under suitable oxime or oxime O-ether formation conditions to provide Compound 53A having the formula:

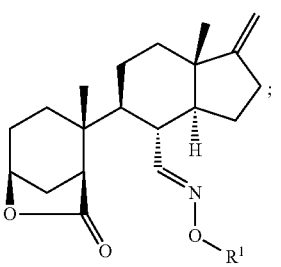

where $R^1$ is hydrogen, methyl or ethyl;

(j) treating Compound 53A under suitable lactone and oxime O-ether reduction conditions to provide compound 16 having the formula:

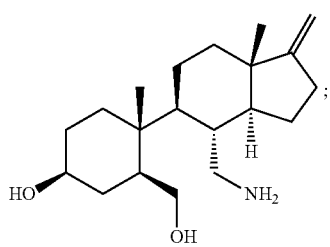

and (k) treating Compound 16 under suitable acetate salt formation conditions to provide AQX-1125.

In a third aspect, this invention is directed to another method of preparing AQX-1125, as defined above, wherein the method comprises:

(a) treating compound 53A having the formula:

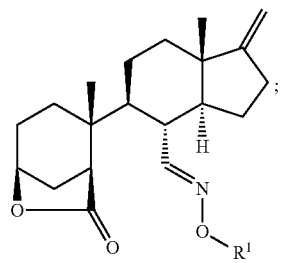

where $R^1$ is hydrogen, methyl or ethyl, under suitable lactone and oxime O-ether reduction conditions to provide compound 16 having the formula:

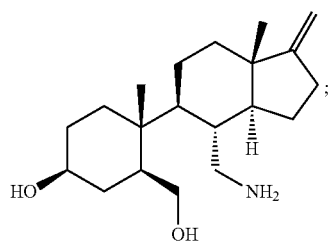

(b) treating compound 16 under suitable acetate salt formation conditions to provide AQX-1125.

In a fourth aspect, this invention is directed to another method of preparing AQX-1125, as defined above, wherein the method comprises:

(a) treating Compound 1 having the formula:

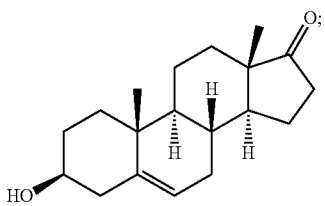

under suitable carbonyl protection conditions to provide Compound 2A having the formula:

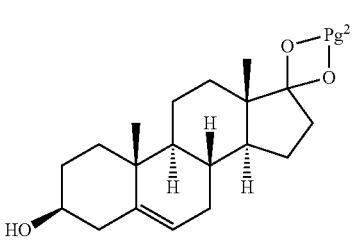

wherein $Pg^2$ is a carbonyl protecting group;

(b) treating Compound 2A under suitable hydroxyl protection conditions to provide Compound 3A having the formula:

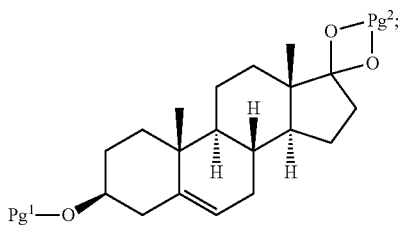

3A wherein Pg¹ is an oxygen-protecting group and Pg² is a carbonyl protecting group;

(c) treating Compound 3A under suitable hydroboration-oxidation conditions to provide Compound 23A having the formula:

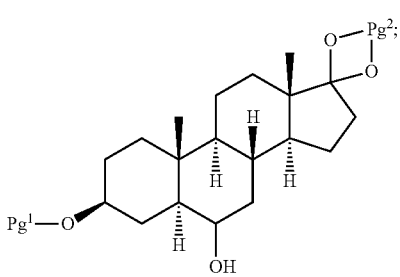

23A wherein Pg¹ is an oxygen-protecting group and Pg² is a carbonyl protecting group;

(d) treating Compound 23A under suitable oxidation conditions to provide Compound 17A having the formula:

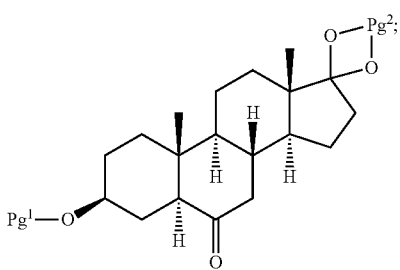

17A wherein Pg¹ is an oxygen-protecting group and Pg² is a carbonyl protecting group;

(e) treating Compound 17A under suitable enol ether formation conditions to provide Compound 19A having the formula:

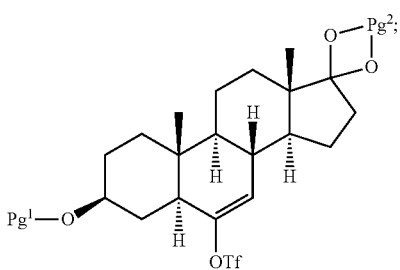

19A wherein Pg¹ is an oxygen-protecting group and Pg² is a carbonyl protecting group;

(f) treating Compound 19A under suitable oxidative carbon-carbon bond cleavage conditions to provide Compound 18A having the formula:

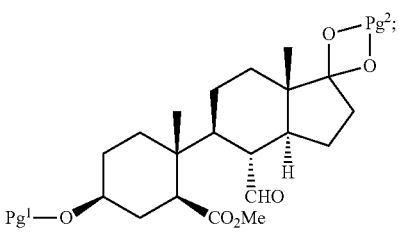

18A wherein Pg¹ is an oxygen-protecting group and Pg² is a carbonyl protecting group;

(g) treating Compound 18A under suitable oxime or oxime O-ether formation conditions to provide Compound 66A having the formula:

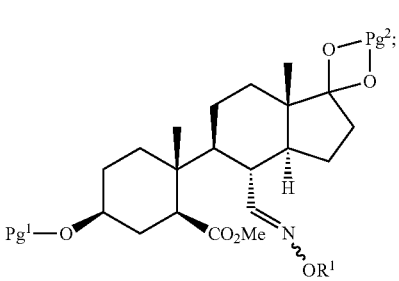

66A wherein R¹ is hydrogen, methyl or ethyl, Pg¹ is an oxygen-protecting group and Pg² is a carbonyl protecting group;

(h) treating Compound 66A under suitable carbonyl deprotection conditions to provide Compound 67A having the formula:

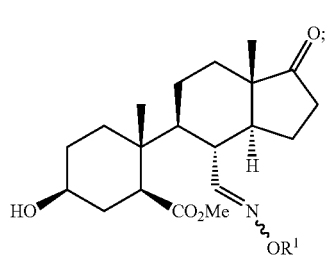

67A wherein R¹ is hydrogen, methyl or ethyl;

(i) treating Compound 67A under suitable Wittig reaction or olefination conditions to provide Compound 53A having the formula:

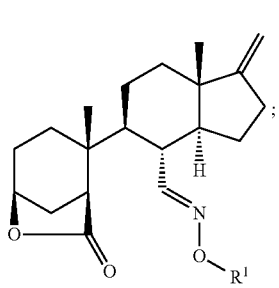

53A where R¹ is hydrogen, methyl or ethyl;

(j) treating Compound 53A under suitable lactone and oxime O-ether reduction conditions to provide compound 16 having the formula:

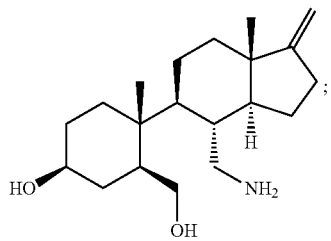 [SMILES: C=C1CC[C@H]2[C@H](CN)[C@@H]([C@@]3(C)CC[C@H](O)C[C@@H]3CO)CC[C@]12C]

and (k) treating Compound 16 under suitable acetate salt formation conditions to provide AQX-1125.

In a fifth aspect, this invention is directed to novel intermediates prepared and/or utilized in the methods disclosed herein.

These aspects of the invention and other aspects are described in more detail below.

DETAILED DESCRIPTION OF THE INVENTION

Methods are disclosed herein for the preparation of AQX-1125. Such methods provide a cost effective synthetic route to AQX-1125 by increasing the overall yield from the previously-disclosed methods, reducing the number of steps in the methods and utilizing relatively less expensive starting materials and reagents.

ABBREVIATIONS

As used herein, the following abbreviations have the following meaning:
ACN: acetonitrile
Ac: acetyl
AcOH: Acetic Acid
$Ac_2O$: acetic anhydride
Aq: aqueous
bpy: 2,2'-bipyridine
CuOTf: copper(I) triflate
DCM: dichloromethane
DHEA: dehydroepiandrosterone
DMAP: dimethylaminopyridine
DMF: dimethylformamide
DMSO: dimethylsulfoxide
ELSD: Evaporative Light Scattering Detection
EtOH: ethanol
HPLC: high performance liquid chromatography
IPA: isopropyl alcohol
KOtBu: potassium tert-butoxide
LC: liquid chromatography
LCMS: liquid chromatography-mass spectrometry
LDA: lithium diisopropylamide
LAH: lithium aluminum hydride
Me: methyl
MeOH: methanol
Ms: methanesulfonyl
MsCl: methanesulfonyl chloride
MTBE: methyl tert-butyl ether
NCS: N-chlorosuccinimide
NLT: not less than
NMI: N-methylimidazole
NMR: nuclear magnetic resonance
NMT: not more than
n-BuLi: n-butyllithium
OTf: triflate
PG: protecting group
Ph: phenyl
$PhNTf_2$: N-phenyl triflimide
$Py-SO_3$: pyridine-sulfur trioxide
PTFE/PP: polytetrafluoroethylene/polypropylene
PTSA: para-toluenesulfonic acid
RB: round bottom
$R_f$: retention factor
RT: room temperature
t-Bu: tert-butyl
TBAC: tetrabutylammonium chloride
TBHP: tert-butyl hydroperoxide
TBSCl: tert-butyldimethylsilyl chloride
TBS: tert-butyldimethylsilyl
t-BuOOH: tert-butyl hydroperoxide
T3P: propylphosphonic anhydride
TEA: triethylamine
TEMPO: (2,2,6,6-Tetramethylpiperidin-1-yl)oxyl
TFA: trifluoroacetic acid
THF: tetrahydrofuran
TLC: thin layer chromatography
TsOH: para-toluenesulfonic acid
UV: ultraviolet Abbreviations not defined above are given their common English meanings known to one skilled in the organic chemistry field.

Methods of the Invention

It is understood that one skilled in the art would be able to make AQX-1125 in a similar manner as described below by modifying the parameters of the synthesis as needed. In general, starting components and reagents may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *Advanced Organic Chemistry: Reactions*, Mechanisms, and Structure, 5th edition (Wiley, December 2000)), or synthesized by methods similar to those described in U.S. Pat. Nos. 6,635,629; 6,696,580; 6,982,329; 7,601,874; and 7,999,010, the relevant disclosure of each incorporated in full herein by reference.

For convenience, AQX-1125 is depicted in the following Reaction Schemes as follows:

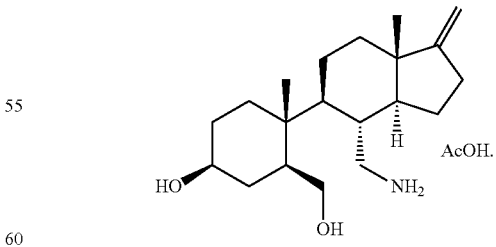

When a reaction mixture or solution is characterized herein as being at or allowed to come to "room temperature" (often abbreviated as "RT") or "ambient temperature", it is intended to mean that the temperature of the mixture or solution is close to, or the same as, that of the space, e.g., the room or fume hood, in which the mixture or solution is located. Typically, room temperature is from about 20° C. to about 30° C., or about 22° C. to about 27° C., or about 25° C.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

It will be appreciated by those skilled in the art that in the process described below the functional groups of intermediate compounds may need to be protected by suitable protecting groups. Such functional groups include hydroxy, amino, mercapto, carbonyl and carboxylic acid. Suitable protecting groups for an oxygen atom ("oxygen protecting groups" or "hydroxyl protecting groups") include, but are not limited to, acetyl, trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for a nitrogen atom ("nitrogen protecting groups") include, but are not limited to, benzhydryl (diphenylmethyl), t-butoxycarbonyl, benzyloxycarbonyl, and the like. Suitable protecting groups for a sulfur atom ("sulfur protecting groups") include —C(O)—R (where R is alkyl, aryl or aralkyl), p-methoxybenzyl, trityl and the like. Suitable protecting groups for carbonyls include but are not limited to, dimethyl acetal, 1,3-dioxane, 5,5-dimethyl-1,3-dioxane, 1,3-dioxolane, 1,3-dithiane, 1,3-dithiolanes and the like. Suitable protecting groups for carboxylic acid include alkyl, aryl or arylalkyl esters. For purposes of this invention, the term "hydroxyl protecting group reagent" refers to a compound, such as acetic anhydride or t-butyldimethylsilyl chloride, which provides a hydroxyl protecting group upon reaction with the molecule to be protected.

Protecting groups may be added or removed in accordance with standard techniques, which are known to one skilled in the art and as described herein.

"Oxygen protecting groups", "nitrogen protecting groups", carbonyl protecting groups, "suitable protection conditions" and "suitable deprotection conditions" as used herein are further described herein in the description of Reaction Scheme 1 and Reaction Scheme 2 and are described in further detail in Greene, T. W. and P. G. M. Wuts, *Greene's Protective Groups in Organic Synthesis* (2006), 4*th* Ed., Wiley.

"Leaving group" refers to a substituent which is easily removed from the rest of the molecule upon attack by the appropriate nucleophile. The hydroxyl substituent is not a good leaving group and must therefore be converted to a group that does leave. One way is to protonate the hydroxyl radical (to form a more acidic leaving group). Another is to convert the hydroxyl to a reactive ester, most commonly, to a sulfonic ester. The sulfonic ester groups tosylate, brosylate, nosylate and mesylate are frequently used. Other leaving groups include oxonium ions, alkyl perchorates, ammonioalkanesulfonate esters, alkyl fluorosulfonates and the fluorinated compounds triflates and nonaflates.

In the chemical structures depicted herein all bonds are identified, except for some carbon atoms, which are assumed to be bonded to sufficient hydrogen atoms to complete the valency. Stereochemistry is designated herein through the use of the conventional solid wedge bonds and dashed wedge bonds, i.e., a solid wedge bond indicates that the bond is above the plane of the paper and a dashed wedge bond indicates that the bond is below the plane of the paper. Non-wedge bonds are intended to include all possible stereochemical configurations.

EMBODIMENTS OF THE INVENTION

Of the various aspects of the invention disclosed above in the Summary of the Invention, certain embodiments are preferred. Formulae of the compounds disclosed in this section are provided below in the Methods of the Invention Section One aspect of the invention described herein is a method of preparing AQX-1125 by treating compound 53A, where $R^1$ is hydrogen, methyl or ethyl, under suitable lactone and oxime O-ether reduction conditions to provide compound 16 and then treating compound 16 under suitable acetate salt formation conditions to provide AQX-1125.

One embodiment of this method is where $R^1$ is hydrogen.

Another embodiment of this method is where $R^1$ is methyl.

Another embodiment of this method is where the suitable lactone and oxime O-ether reduction conditions comprise treating Compound 53A in a polar aprotic solvent comprising tetrahydrofuran, 2-methyl tetrahydrofuran or dioxane, with a reducing agent comprising lithium aluminum hydride.

Another embodiment of this method further comprises an oxime or oxime O-ether formation step prior to treating Compound 53A under suitable lactone and oxime O-ether reduction conditions, wherein the oxime or oxime O-ether formation step comprises treating Compound 52 under suitable oxime or oxime O-ether formation conditions to provide Compound 53A.

An embodiment of this embodiment is wherein the suitable oxime or oxime O-ether formation conditions comprise treating Compound 52 in a suitable basic organic solvent comprising pyridine with a suitable reagent comprising O-methyl hydroxylamine hydrochloride.

Another embodiment of this method further comprises an oxidation step prior to treating Compound 52 under suitable oxime or oxime O-ether formation conditions, wherein the oxidation step comprises treating Compound 51 under suitable oxidation conditions to provide Compound 52.

An embodiment of this embodiment is wherein the suitable oxidation conditions comprise treating Compound 51, in a suitable solvent system comprising dichloromethane and water, with an oxidizing agent comprising N-chlorosuccinimide and a suitable catalyst such as (2,2,6,6-tetramethylpiperidin-1-yl)oxyl, a base comprising potassium carbonate and sodium bicarbonate, and a phase transfer reagent comprising tetrabutylammonium chloride.

Another embodiment of this method further comprises an 1,2-diol oxidative carbon-carbon bond cleaving step prior to treating Compound 51 under suitable oxidation conditions, wherein the 1,2-diol oxidative carbon-carbon bond cleaving step comprises treating Compound 54 under suitable 1,2-diol oxidative carbon-carbon bond cleavage conditions to provide Compound 51.

An embodiment of this embodiment is wherein the suitable 1,2-diol oxidative carbon-carbon bond cleavage conditions comprise treating Compound 54 in a polar solvent comprising tetrahydrofuran and water with a suitable oxidizing agent comprising sodium metaperiodate.

Another embodiment of this method further comprises a Wittig or olefination step prior to treating Compound 54 under suitable 1,2-diol oxidative carbon-carbon bond cleavage conditions, wherein the Wittig or olefination step comprises treating Compound 6 under suitable olefination or Wittig reaction conditions to provide Compound 54.

An embodiment of this embodiment is wherein suitable olefination or Wittig reaction conditions comprise treating Compound 6 in a suitable organic solvent comprising dimethyl sulfoxide and tetrahydrofuran with a ylide generated using a phosphonium salt comprising methyltriphenylphosphonium bromide and a base comprising potassium tert-butoxide.

Another embodiment of this method further comprises a carbonyl deprotection step prior to treating Compound 6 under suitable olefination or Wittig reaction conditions, wherein the carbonyl deprotection step comprises treating Compound 72A where $Pg^2$ is a carbonyl protecting group, under suitable carbonyl protection conditions to provide Compound 6.

An embodiment of this embodiment is wherein the suitable carbonyl deprotection conditions comprise treating Compound 72A in a polar protic solvent comprising methanol and water with a suitable acid comprising p-toluenesulfonic acid.

Another embodiment of this method further comprises a carbonyl reduction and hydroboration-oxidation step prior to treating Compound 72A under suitable carbonyl protection conditions, wherein the carbonyl reduction and hydroboration-oxidation step comprises treating Compound 71A where $Pg^1$ is an oxygen-protecting group and $Pg^2$ is a carbonyl protecting group, under suitable carbonyl reduction and hydroboration-oxidation conditions to provide Compound 72A.

An embodiment of this embodiment is wherein the suitable carbonyl reduction and hydroboration-oxidation conditions comprise treating Compound 71A in a polar aprotic solvent comprising tetrahydrofuran with a reducing agent comprising borane and a hydroboration reagent comprising borane in tetrahydrofuran, followed by oxidation using an oxidant comprising sodium perborate.

Another embodiment of this method further comprises an allylic oxidation step prior to treating Compound 71A under suitable carbonyl reduction and hydroboration-oxidation conditions, wherein the allylic oxidation step comprises treating Compound 70A wherein $Pg^1$ is an oxygen-protecting group and $Pg^2$ is a carbonyl protecting group, under suitable allylic oxidation conditions to provide Compound 71A.

An embodiment of this embodiment is wherein the suitable allylic oxidation conditions comprise treating Compound 70A in an organic solvent comprising dichloromethane, acetonitrile and/or pyridine with a peroxide comprising tert-butyl hydroperoxide in the presence of a metal catalyst comprising copper iodide.

Another embodiment of this method further comprises a hydroxyl protection step prior to treating Compound 70A under suitable allylic oxidation conditions, wherein the hydroxyl protection step comprises treating Compound 69A where $Pg^2$ is a carbonyl protecting group, under suitable hydroxyl protection conditions to provide Compound 70A.

An embodiment of this embodiment is wherein the suitable hydroxyl protection conditions comprise treating Compound 69A in a suitable organic solvent comprising as dichloromethane with a hydroxyl-protecting group reagent comprising acetic anhydride in the presence of a base comprising pyridine or imidazole, and, optionally, a suitable nucleophilic catalyst comprising 4-dimethylaminopyridine.

Another embodiment of this method further comprises a carbonyl protection step prior to treating Compound 69A under suitable hydroxyl protection conditions, wherein the carbonyl protection step comprises treating Compound 1 under suitable carbonyl protection conditions to provide Compound 69A.

An embodiment of this embodiment is wherein the suitable carbonyl protection conditions comprise treating Compound 1 in an organic solvent comprising cyclohexane with a carbonyl protecting group reagent comprising neopentyl glycol or ethylene glycol in the presence of an acid catalyst comprising camphor sulfonic acid.

Another aspect of the invention described herein is a method of preparing AQX-1125 by treating compound 53A where $R^1$ is hydrogen, methyl or ethyl, under suitable lactone and oxime O-ether reduction conditions to provide compound 16 and then treating compound 16 under suitable acetate salt formation conditions to provide AQX-1125.

One embodiment of this method is where $R^1$ is hydrogen.

Another embodiment of this method is where $R^1$ is methyl.

Another embodiment of this method is wherein the suitable lactone and oxime O-ether reduction conditions comprise treating Compound 53A in a polar aprotic solvent comprising tetrahydrofuran, 2-methyl tetrahydrofuran or dioxane, with a reducing agent comprising lithium aluminum hydride.

Another embodiment of this method further comprises a Wittig reaction or olefination step prior to treating Compound 53A under suitable lactone and oxime O-ether reduction conditions, wherein the Wittig or olefination step comprises treating Compound 67A where $R^1$ is hydrogen, methyl or ethyl, under suitable Wittig reaction or olefination conditions to provide Compound 53A.

An embodiment of this embodiment is wherein the suitable Wittig reaction or olefination conditions comprise treating Compound 67A in a suitable organic solvent comprising toluene or tetrahydrofuran with a ylide generated using a phosphonium salt comprising methyltriphenylphosphonium bromide, and a base comprising potassium tert-butoxide.

Another embodiment of this method further comprises a carbonyl deprotection step prior to treating Compound 67A under suitable Wittig reaction or olefination conditions, wherein the carbonyl deprotection step comprises treating Compound 66A where $R^1$ is hydrogen, methyl or ethyl, $Pg^1$ is an oxygen-protecting group and $Pg^2$ is a carbonyl protecting group, under suitable carbonyl deprotection conditions to provide Compound 67A.

An embodiment of this embodiment is wherein the suitable carbonyl deprotection conditions comprise treating Compound 66A in a polar protic solvent comprising water with a suitable acid comprising as acetic acid.

Another embodiment of this method further comprises an oxime or oxime O-ether formation step prior to treating Compound 66A under suitable carbonyl deprotection conditions, wherein the oxime or oxime O-ether formation step comprises treating Compound 18A where $Pg^1$ is an oxygen-protecting group and Pg² is a carbonyl protecting group, under suitable oxime or oxime O-ether formation conditions to provide Compound 66A.

An embodiment of this embodiment is wherein the suitable oxime or oxime O-ether formation conditions comprise treating Compound 18A in a suitable polar protic solvent comprising methanol with a suitable reagent comprising hydroxylamine hydrochloride, in the presence of a base comprising trimethylamine.

Another embodiment of this method further comprises an oxidative carbon-carbon bond cleavage step prior to treating Compound 18A under suitable oxime or oxime O-ether formation conditions, wherein the oxidative carbon-carbon bond cleavage step comprises treating Compound 19A where Pg¹ is an oxygen-protecting group and Pg² is a carbonyl protecting group, under suitable oxidative carbon-carbon bond cleavage conditions to provide Compound 18A.

An embodiment of this embodiment is wherein the suitable oxidative carbon-carbon bond cleavage conditions comprise treating Compound 19A in a polar protic solvent comprising methanol with a suitable oxidizing agent comprising ozone, followed by reduction with a suitable reducing agent comprising sodium borohydride.

Another embodiment of this method further comprises an enol ether formation step prior to treating Compound 19A under suitable oxidative carbon-carbon bond cleavage conditions, wherein the enol ether formation step comprises treating Compound 17A where Pg¹ is an oxygen-protecting group and Pg² is a carbonyl protecting group, under suitable enol ether formation conditions to provide Compound 19A.

An embodiment of this embodiment is wherein the suitable enol ether formation conditions comprise treating Compound 17A in a suitable polar aprotic solvent comprising tetrahydrofuran with a strong base comprising lithium diisopropylamide and a suitable electrophilic reagent comprising N-phenyl triflimide.

Another embodiment of this method further comprises an oxidation step prior to treating Compound 17A under suitable enol ether formation conditions, wherein the oxidation step comprises treating Compound 23A where Pg¹ is an oxygen-protecting group and Pg² is a carbonyl protecting group, under suitable oxidation conditions to provide Compound 17A.

An embodiment of this embodiment is wherein the suitable oxidation conditions comprise treating Compound 23A in a suitable organic solvent comprising dichloromethane with an oxidizing agent comprising dimethyl sulfoxide and a suitable activating reagent comprising pyridine-sulfur trioxide complex in the presence of a base comprising triethylamine.

Another embodiment of this method further comprises a hydroboration-oxidation step prior to treating Compound 23A under suitable oxidation conditions, wherein the hydroboration-oxidation step comprises treating Compound 3A wherein Pg¹ is an oxygen-protecting group and Pg² is a carbonyl protecting group, under suitable hydroboration-oxidation conditions to provide Compound 23A.

An embodiment of this embodiment is wherein the suitable hydroboration-oxidation conditions comprise treating Compound 3A in a polar aprotic solvent comprising tetrahydrofuran with a hydroboration reagent comprising borane in tetrahydrofuran, followed by oxidation using an oxidant comprising hydrogen peroxide.

Another embodiment of this method further comprises a hydroxyl protection step prior to treating Compound 3A under suitable hydroboration-oxidation conditions, wherein the hydroxyl protection step comprises treating Compound 2A where Pg² is a carbonyl protecting group, under suitable hydroxyl protection conditions to provide Compound 3A.

An embodiment of this embodiment is wherein the suitable hydroxyl protection conditions comprise treating Compound 2A in an organic solvent comprising dichloromethane with a hydroxyl protecting group reagent comprising tert-butyldimethylsilyl chloride in the presence of a base comprising imidazole.

Another embodiment of this method further comprises a carbonyl protection step prior to treating Compound 2A under suitable hydroxyl protection conditions, wherein the carbonyl protection step comprises treating Compound 1 under suitable carbonyl protection conditions to provide Compound 2A.

An embodiment of this embodiment is wherein the suitable carbonyl protection conditions comprise treating Compound 1 in an organic solvent comprising cyclohexane with a carbonyl protecting group reagent comprising ethylene glycol in the presence of an acid catalyst comprising camphor sulfonic acid or p-toluene sulfonic acid.

In addition to the foregoing embodiments, certain embodiments of preparing AQX-1125 are disclosed herein Reaction Schemes 1-22.

Specific embodiments of the methods of the invention, including the suitable conditions for each of the above described steps, are described in more detail below in the Methods of the Invention and the Synthetic Examples. It is understood that the descriptions of the suitable conditions for each of the above described steps utilize standard reaction condition descriptions and reagents known to one skilled in the organic chemistry field.

Analytical Methods

Representative analytical methods utilized to characterize products and intermediates of the methods of the invention are described below.

Method A: LCMS/HPLC Method Using Atlantis Column

LCMS and/or ELSD (HPLC) analysis was performed using an Atlantis dC18 column (50×4.6 mm, 5μ), using positive mode with the following LC parameters:
A: 0.1% TFA in $H_2O$; B: 0.1% TFA in ACN; Flow Rate: 1.5 mL/min.

|  | Time (min) | | | | |
| --- | --- | --- | --- | --- | --- |
|  | 0.0 | 2.5 | 4.5 | 4.6 | 6.0 |
| % B | 10 | 95 | 95 | 10 | 10 |

Method B: LCMS/HPLC Method 1 Using an Xbridge Column

LCMS and/or ELSD (HPLC) analysis was performed using an XBridge C8 column (50×4.6 mm, 3.5μ), using positive mode with the following LC parameters:
A: 0.1% TFA in $H_2O$; B: 0.1% TFA in ACN; Flow Rate: 2.0 mL/min.

|  | Time (min) | | | | |
| --- | --- | --- | --- | --- | --- |
|  | 0.0 | 8.0 | 8.1 | 8.5 | 10.0 |
| % B | 5 | 100 | 100 | 5 | 5 |

Method C: LCMS Method 1 Using Formic Acid and Atlantis Column

LCMS and/or ELSD (HPLC) analysis was performed using an Atlantis dC18 column (50×4.6 mm, 5µ), using positive mode with the following LC parameters:
A: 0.1% Formic acid in $H_2O$; B: ACN; Flow Rate: 0.7 mL/min.

| Time (min) | | | | |
|---|---|---|---|---|
| 0.0 | 3.0 | 7.5 | 8.5 | 11.5 |
| % B 65 | 98 | 98 | 65 | 65 |

Method D: HPLC Method Using Chromolith Column

HPLC analysis was performed using an Chromolith RP-18 e 100-4.6 mm, column temperature 40° C., detection wavelength 210 nm dC18 column (50×4.6 mm, 5µ), using positive mode with the following LC parameters:
A: 0.1% Formic acid in $H_2O$; B: ACN; Flow Rate: 0.7 mL/min.

| Time (min) | | | | |
|---|---|---|---|---|
| 0.0 | 3.0 | 7.5 | 8.5 | 11.5 |
| % B 65 | 98 | 98 | 65 | 65 |

Method E: LCMS Method 2 Using Formic Acid and Atlantis Column

LCMS and/or ELSD (HPLC) analysis was performed using an Atlantis dC18 column (50×4.6 mm, 5µ), using positive mode with the following LC parameters.
A: 0.1% Formic acid in $H_2O$; B: ACN; Flow Rate: 1.0 mL/min.

| Time (min) | | | | |
|---|---|---|---|---|
| 0.0 | 3.0 | 6.0 | 6.1 | 9.0 |
| % B 30 | 100 | 100 | 30 | 30 |

Method F: LCMS/HPLC Method 2 Using an Xbridge Column

LCMS and/or ELSD (HPLC) analysis was performed using an XBridge C8 column (50×4.6 mm, 3.5µ), column temperature 40° C. using positive mode with the following LC parameters:
A: $H_2O$; B: ACN; Flow Rate: 2.0 mL/min.

| Time (min) | | | | | |
|---|---|---|---|---|---|
| 0.0 | 5.0 | 15.0 | 25.0 | 25.1 | 30.0 |
| % B 20 | 20 | 95 | 95 | 20 | 20 |

Method G: LCMS/HPLC Method 3 Using an Xbridge Column

LCMS and/or ELSD (HPLC) Analysis was performed using an XBridge C8 column (50×4.6 mm, 3.5µ), column temperature 40° C. using positive mode with the following LC parameters:
A: $H_2O$; B: ACN; Flow Rate: 2.0 mL/min.

| Time (min) | | | | | |
|---|---|---|---|---|---|
| 0.0 | 5.0 | 15.0 | 25.0 | 25.1 | 30.0 |
| % B 20 | 70 | 95 | 95 | 20 | 20 |

Method H: HPLC Method Using Ascentis Column

HPLC Analysis was performed using an Ascentis Express C18 column (150×4.6 mm, 2.7 µm, column temperature 25° C., detection wavelength 200 nm C18 column (150×4.6 mm, 2.7µ) with the following LC parameters. A: 10 mm $KH_2PO_4$ in water, pH 2.5 using o-phosphoric acid, B: ACN; Flow Rate: 1.0 mL/min.

| Time (min) | | | | | | | |
|---|---|---|---|---|---|---|---|
| 0.0 | 1.0 | 20.0 | 30.0 | 35.0 | 40.0 | 45.0 | 46.0 |
| % B 05 | 05 | 25 | 50 | 50 | 80 | 80 | 05 |

Synthetic Methods

AQX-1125 can be prepared by the methods disclosed in the following Reaction Schemes and Synthetic Examples.

A. Synthetic Method 1

In one aspect of the invention, AQX-1125 was prepared by the method described below in Reaction Scheme 1 where $Pg^1$ is an oxygen-protecting group, $Pg^2$ is a carbonyl protecting group, $Lg^1$ is a leaving group and X is bromo or chloro:

REACTION SCHEME 1

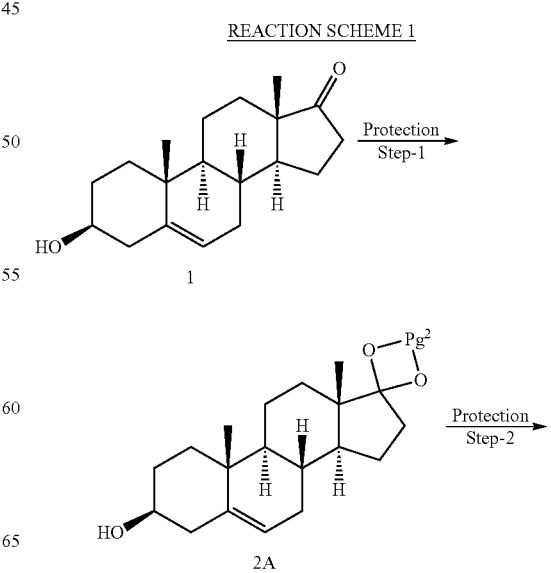

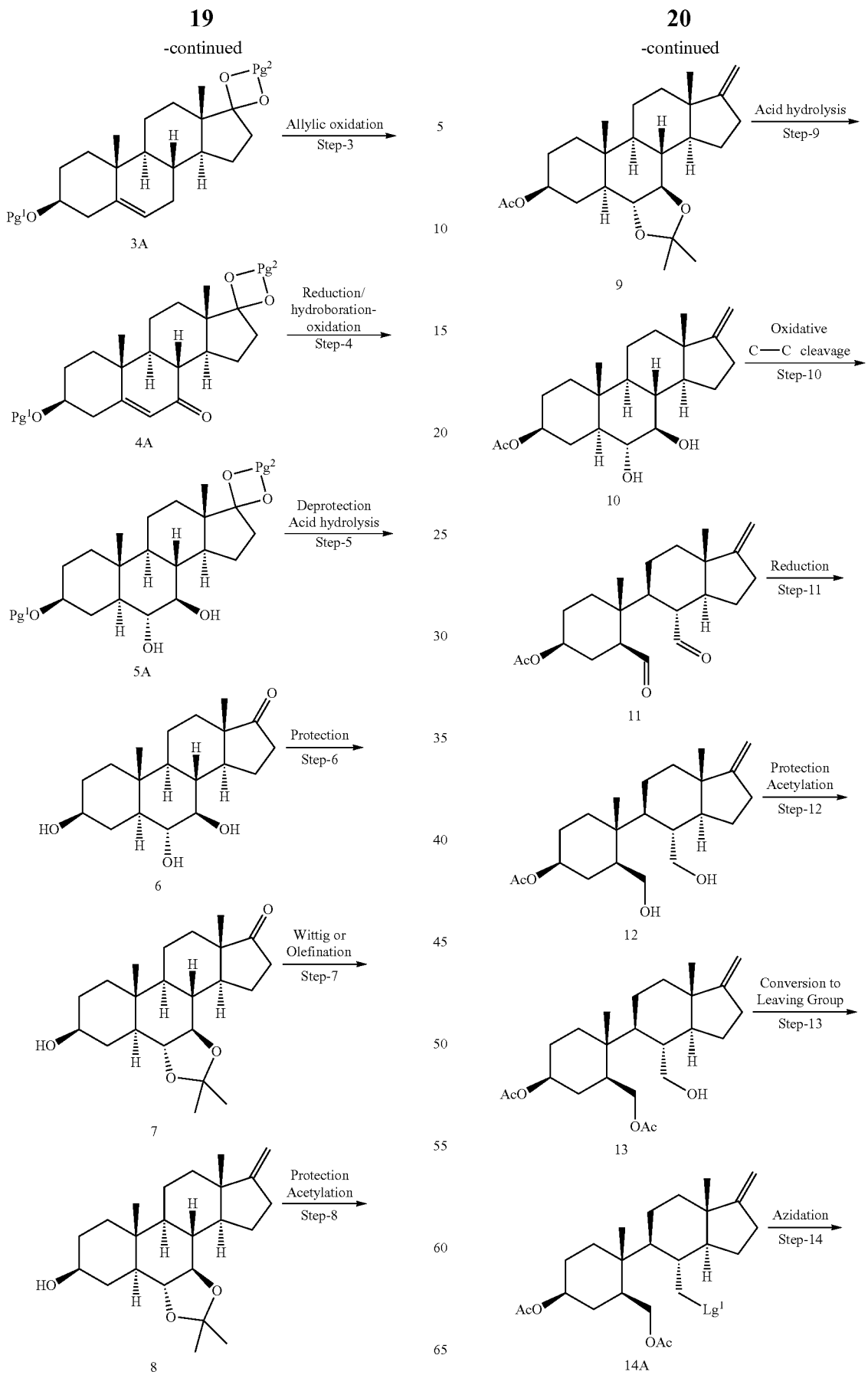

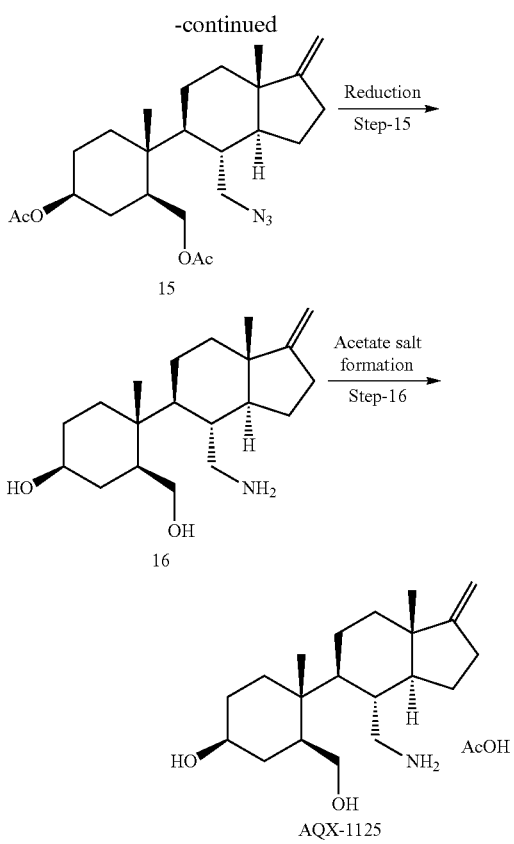

Compound 1, which is dehydroepiandrosterone, is commercially available or can be made by methods known to one skilled in the art.

In general, AQX-1125 is prepared as described above in Reaction Scheme 1 by first treating Compound 1 under suitable carbonyl protection conditions to provide Compound 2A, such as treating Compound 1 in an organic solvent, such as cyclohexane, with a carbonyl protecting group reagent, such as ethylene glycol in the presence of an acid catalyst, such as camphor sulfonic acid or p-toluene sulfonic acid.

Compound 2A is then treated under suitable hydroxyl protection conditions to provide Compound 3A, such as treating Compound 2A in an organic solvent, such as dichloromethane, with a hydroxyl protecting group reagent, such as tert-butyldimethylsilyl chloride, in the presence of a base, such as imidazole.

Compound 3A is then treated under allylic oxidation conditions to provide Compound 4A, such as treating Compound 3A in an organic solvent, such as dichloromethane, acetonitrile and pyridine, with a peroxide, such as tert-butyl hydroperoxide, in the presence of a metal catalyst, such as copper iodide.

Compound 4A is then treated under suitable carbonyl reduction and hydroboration-oxidation conditions to provide Compound 5A, such as treating Compound 4A in a polar aprotic solvent, such as tetrahydrofuran, with a reducing agent, such as borane, and a hydroboration reagent, such as borane in tetrahydrofuran, followed by oxidative work-up using an oxidant, such as sodium perborate.

Compound 5A is then treated under suitable carbonyl deprotection conditions to provide Compound 6, such as treating Compound 5A in a polar protic solvent, such as water, with a suitable acid, such as acetic acid.

Compound 6 is then treated under suitable 1,2-diol protection conditions to provide Compound 7, such as treating Compound 6 in a suitable organic solvent, such as 2,2-dimethoxypropane, in the presence of an acid catalyst, such as camphor sulfonic acid or p-toluene sulfonic acid.

Compound 7 is then treated under suitable olefination or Wittig reaction conditions to provide Compound 8, such as treating Compound 7 in a suitable organic solvent, such as toluene, with a ylide generated using a phosphonium salt, such as methyltriphenylphosphonium bromide, and a base, such as potassium tert-butoxide.

Compound 8 is then treated under suitable hydroxyl protection conditions to provide Compound 9, such as treating Compound 8 in a suitable basic organic solvent, such as pyridine, with a hydroxyl protecting group reagent, such as acetic anhydride for acetylation, in the presence of a suitable nucleophilic catalyst, such as 4-dimethylaminopyridine.

Compound 9 is then treated under suitable 1,2-diol deprotection conditions to provide Compound 10, such as treating Compound 9 in a polar protic solvent, such as water, with a suitable acid, such as acetic acid.

Compound 10 is then treated under suitable 1,2-diol oxidative carbon-carbon bond cleavage conditions to provide Compound 11, such as treating Compound 10 in a polar solvent, such as tetrahydrofuran and water, with a suitable oxidizing agent, such as sodium metaperiodate.

Compound 11 is then treated under suitable carbonyl or aldehyde reduction conditions to provide Compound 12, such as treating Compound 11 in a polar protic solvent, such as methanol, with a reducing agent, such as sodium borohydride.

Compound 12 is then treated under suitable hydroxyl protection conditions to provide Compound 13, such as treating Compound 12 in a suitable basic organic solvent, such as pyridine, with a hydroxyl protecting group reagent, such as acetic anhydride for acetylation, in the presence of a suitable nucleophilic catalyst, such as 4-dimethylaminopyridine.

Compound 13 is then converted into a suitable leaving group, such as a mesylate, to provide Compound 14A, such as treating Compound 13 in a suitable polar aprotic solvent, such as tetrahydrofuran, with an appropriate electrophilic leaving group reagent, such as methanesulphonyl chloride for mesylation, in the presence of a base, such as triethylamine.

Compound 14A is then treated under suitable nucleophilic substitution conditions, such as azidation or azide displacement, to provide Compound 15, such as treating Compound 14A in a suitable polar aprotic solvent, such as dimethylformamide, with an appropriate nucleophile, such as sodium azide.

Compound 15 is then treated under suitable carbonyl and azide reduction conditions to provide Compound 16, such as treating Compound 15 in a polar aprotic solvent, such as tetrahydrofuran, with a reducing agent, such as lithium aluminum hydride.

Compound 16 is then treated under suitable acetic acid salt formation conditions to provide AQX-1125, such as treating Compound 16 in a polar protic solvent, such as methanol, with glacial acetic acid, followed by treatment with a less polar organic solvent, such as methyl tert-butyl ether.

A specific method of preparing AQX-1125, as set forth above in Reaction Scheme 1, is illustrated below in Reaction Scheme 1A:

REACTION SCHEME 1A
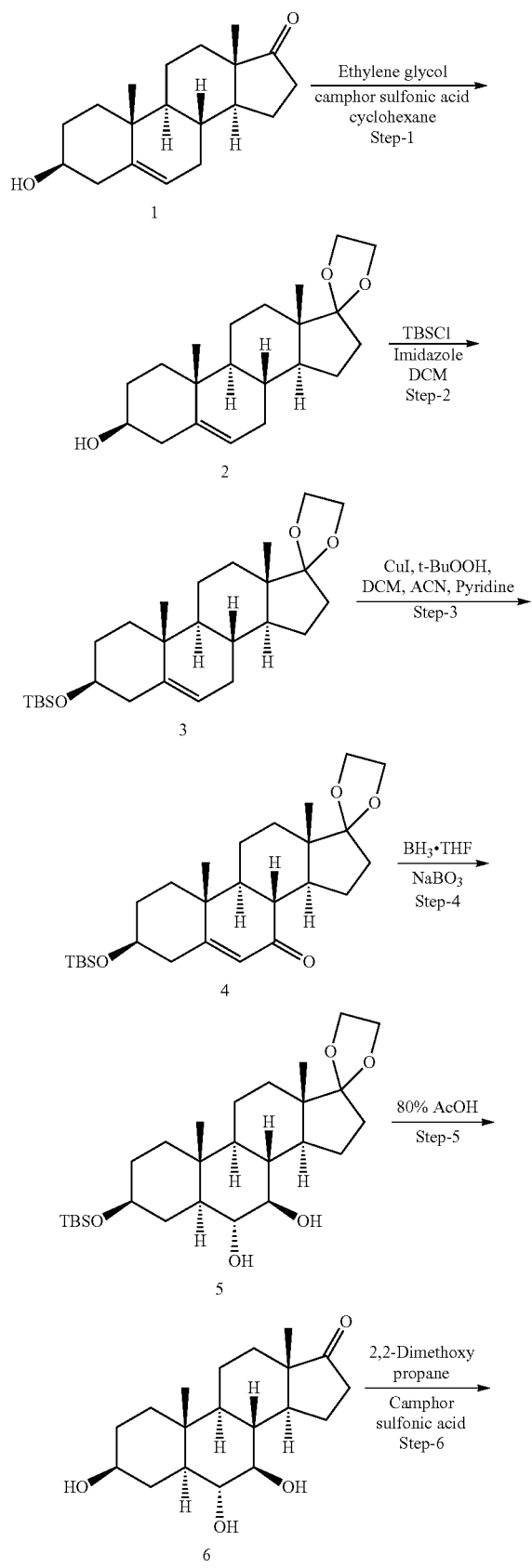
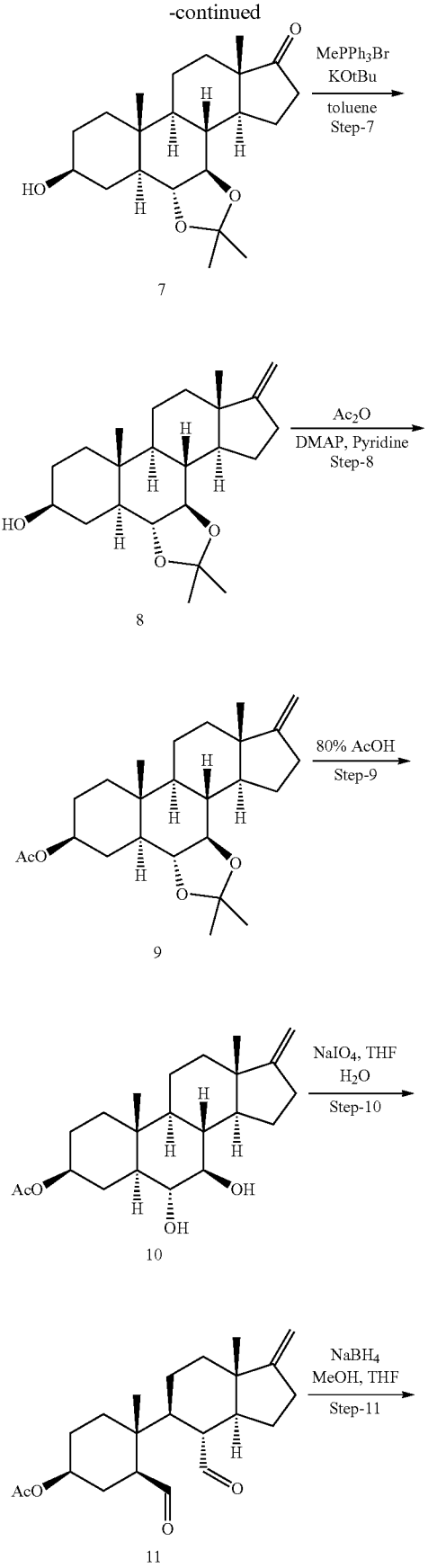

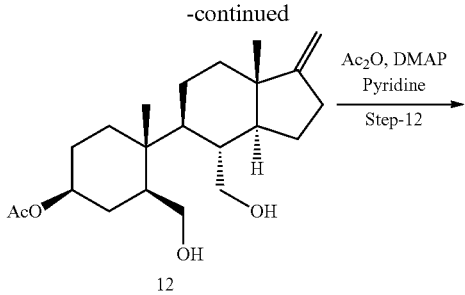

12

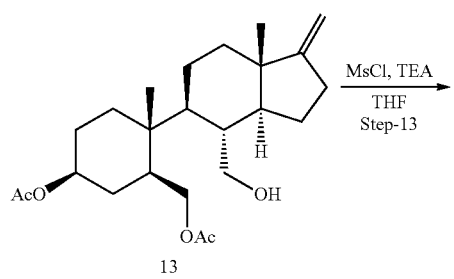

13

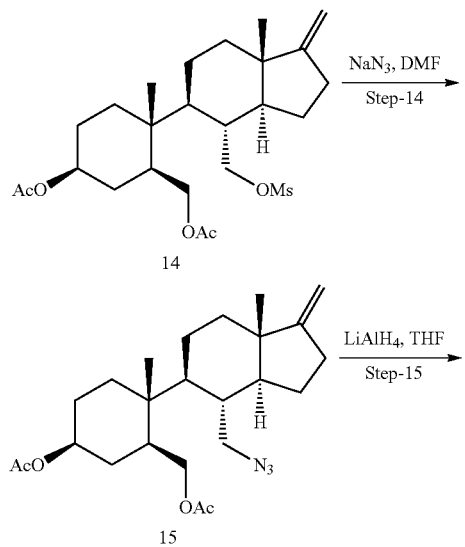

14

15

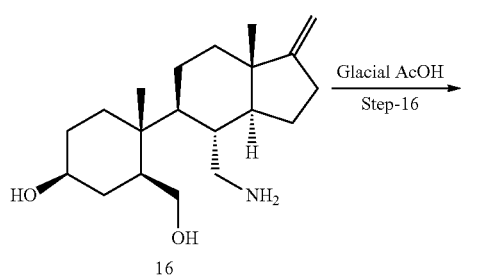

16

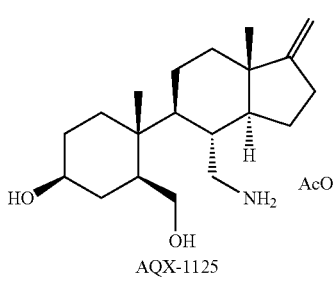

AQX-1125

The following Synthetic Examples, which are directed to the steps and products as set forth above in Reaction Scheme 1A, are provided as a guide to assist in the practice of the invention, and are not intended as a limitation on the scope of the invention.

Synthetic Example 1

Step 1: Conversion of Compound 1 to Compound 2

A. Cyclohexane (468.0 kg) was added to the reactor at 25±5° C. Compound 1 (60.0 kg) was added to the reactor at 25±5° C. under nitrogen atmosphere. The reaction mass was stirred for 5-10 minutes at 25±5° C. (+/−)-10-Camphor sulphonic acid (0.96 kg) was added to the reaction mass and the mass stirred for 5-10 minutes at 25±5° C. Ethylene glycol (64.80 kg) was added to the reaction mass at 25±5° C. and the mass was stirred for 5-10 minutes at 25±5° C. The temperature was raised to 80±5° C. and the mass stirred under azeotropic reflux by removing water, for 16 hours. The reaction mass was cooled to 35±5° C. and then concentrated (below 40° C.) under vacuum (NLT 550 mmHg), until no distillate was observed.

B. The resulting mass was cooled to 8±2° C. Sodium bicarbonate solution (~8.0% w/v, ~240 L) was added with stirring for 5-10 minutes followed by dichloromethane (1320 kg) with stirring for 5-10 minutes followed by settling for 10-15 minutes. The bottom organic layer was separated and collected and washed again with sodium bicarbonate solution (~8.0% w/v, ~240 L) with stirring for 5-10 minutes followed by settling for 10-15 minutes. The bottom organic layer was separated, collected and washed with sodium chloride solution (~10% w/v, 240.0 L, 4.0 Vol), twice, with stirring for 5-10 minutes and settling for 10-15 minutes. The organic layer, which was 97.6% pure Compound 2 by HPLC, was then dried with sodium sulphate (12.0 kg) with stirring, for 5-10 minutes and the resulting mixture filtered using CELITE™ (5.0 kg) in a Nutsche filter and washing with dichloromethane (15.0 kg). The mass was concentrated under vacuum (NLT 550 mmHg) below 40° C. until 9.0-9.5 Volume mass remained inside the reactor. The resulting mass containing Compound 2 was used in without further purification.

Synthetic Example 2

Step 2: Conversion of Compound 2 to Compound 3

A. The resulting mass containing Compound 2 from Synthetic Example 1 was cooled to 25±5° C. and imidazole (36.0 kg) was added at 25±5° C. tert-Butyldimethylsilyl chloride (42.60 kg) was added to the concentrated mass in 3 equal lots by maintaining the temperature at 25±5° C. The mass was stirred at 25±5° C. for 3 hours.

B. The reaction mass was washed with purified water (300.0 L, 5.0 Vol) with stirring for 5-10 minutes, followed by settling for 10-15 minutes. The organic layer was then concentrated under vacuum (NLT 550 mmHg) below 35° C., until no distillate was observed. Methanol (142.2 Kg) was added to the concentrated mass below 35° C. and stirred for 10-15 minutes at a temperature below 35° C. The mass was cooled to 3±2° C. and stirred for 1 hour. The mass was then filtered using a Nutsche filter and the filtrate was collected. Purified water (300.0 L, 5.0 Vol) was added to the reactor and the collected filtrate was added to the reactor followed by stirring at 25±5° C. for 30-45 minutes. The mass was filtered by centrifuge. The reactor was rinsed with purified water (60.0 L) and the rinse water was used to wash the wet material in the centrifuge and the material spin-dried for 45-60 minutes. Compound 3 (88.45 kg (on dry basis), 97.7 to 99.9% pure, yield 90.4 to 95.2% (steps 1 and 2 combined)) was obtained.

Synthetic Example 3

Step 3: Conversion of Compound 3 to Compound 4

A. Dichloromethane (159.80 kg, 2.0 Vol) was added to the reactor, followed by Compound 3 (from Synthetic Example 2, 80.30 kg on dry basis), pyridine (78.70 kg, 1.0 Vol) and acetonitrile (94.75 kg) at 25±5° C. Copper iodide solution was prepared by dissolving copper iodide (0.68 kg) into acetonitrile (6.34 kg) and pyridine (4.01 kg), in a container with stirring for 20 to 30 minutes. One fifth of this solution was added to the reactor. tert-Butyl hydroperoxide solution (70%, 46.57 kg) was slowly added to the reactor at 25±5° C. The reaction mass was then heated to 40±5° C. The reaction was exothermic. The reaction mass was then cooled to 25±5° C. The addition of copper iodide solution and tert-butyl hydroperoxide solution was repeated, as above, four more times, until all of the copper iodide solution had been utilized. The final mixture was then stirred at 40±5° C. for 4 hours (until starting material was no longer present) and then the mixture was cooled to 25±5° C.

B. Sodium thiosulphate (~33% w/v, 674.5 L) was then slowly added to the reaction mass at 25±5° C. and stirred at 25±5° C. for 1-2 hours. Dichloromethane (1064.78 kg, 13.3 Vol) was added into the reactor and stirred for 10-20 minutes followed by settling for 10-20 minutes. The bottom organic layer was collected and dichloromethane (532.39 kg, 6.6 Vol) was added to the aqueous layer in the reactor and stirred for 10 to 15 minutes followed by settling for 20-30 minutes. The organic layer was collected and combined with the previously collected organic layer and added back to the empty reactor. The combined organic layers were washed with sodium thiosulphate (~33% w/v, 224.84 L) (with stirring for 10-15 minutes and settling for 20-30 minutes) and then with sodium chloride solution (~5% w/v, 20.08 kg sodium chloride in 401.5 kg purified water) with 10-15 minutes stirring and 10-15 minutes settling time. The organic layer was tested for peroxide content before continuing.

C. The organic layer was concentrated under vacuum (NLT 550 mm Hg) below 55° C. until 1:5.0 w/w [with respect to Compound 3 input] concentrated mass remained inside the reactor. Purified water (160.0 kg, 2.0 Vol) was added and the mass concentrated under vacuum (NLT 550 mm Hg) below 55° C. until 1:1.0 w/w [with respect to Compound 3 input] concentrated mass remained inside the reactor. Purified water (160.0 kg, 2.0 Vol) was added and the mass concentrated under vacuum (NLT 550 mm Hg) below 55° C. until 1:2.0 w/w [with respect to Compound 3 input] concentrated mass remained inside the reactor. The concentrated mass was cooled to 25±5° C. and the water was separated. Methanol (253.74 kg) was added and the mass temperature was raised to 50±5° C. and the mass was stirred for 10-15 minutes. The mass was cooled to 10±5° C. and stirred a further 10-15 minutes. The mass was filtered through centrifuge, spin-dried for 20-30 minutes and the wet material collected into a double-lined polyethylene bag placed in HDPE container. The material was dried under vacuum (NLT 550 mmHg) at 38±2° C. until methanol content was not more than 0.5% w/w. The drier was then cooled to 25±5° C. and Compound 4 (36.50 kg, 77.1-90.7% pure, 39.0-45.4% yield) was obtained and used further.

Synthetic Example 4

Step 4: Conversion of Compound 4 to Compound 5

Tetrahydrofuran (226.20 kg) was added to a dry reactor. Additional tetrahydrofuran (102.66 kg) was added to Compound 4 (58.0 kg, from Synthetic Example 3) in a container, stirred for 5-10 minutes and the resulting slurry added to the reactor under nitrogen atmosphere. The mixture was cooled to −3±2° C. and chilled borane in tetrahydrofuran (1 M, 260.42 L) was slowly added over a period of 1-3 hours at −3±2° C. and the mixture stirred for 6 hours, until complete. Purified water (371.20 kg, 6.4 Vol) was pre-chilled to 7±2° C. in a separate reactor and transferred slowly into the reaction mass at −3±2° C. over a period of 1-2 hours. Tetrahydrofuran (102.66 kg) was added to the reactor under vacuum. The reaction mass became a clear solution. Sodium perborate monohydrate (24.94 kg) was added to the reaction mass at −3±2° C. and the mass temperature raised to 22±3° C. and stirred for 6 hours. The reaction mass was filtered through a Nutsche filter and the filtrate was collected and the remaining material was vacuum dried for 10-15 minutes and then washed in a Nutsche filter using tetrahydrofuran (205.32 kg) and the material was further vacuum dried for 20-30 minutes. The combined filtrates were charged to the reactor and sodium chloride (92.80 kg) was added. The mass was stirred for 30-40 minutes and allowed to settle for 15-20 minutes. The bottom aqueous layer was discarded and the retained organic layer was concentrated under vacuum (NLT 500 mmHg) below 40° C. until no distillate was observed, then cooled to 25±5° C. Compound 5 was collected and used further as is.

Synthetic Example 5

Step 5: Conversion of Compound 5 to Compound of 6

A. Acetic acid (80% w/v, 48.14 kg purified water in 201.84 kg acetic acid) was added to the concentrated mass (Compound 5) from Synthetic Example 4 and stirred at 25±5° C. for 8 hours, until reaction complete.

B. Petroleum ether (114.26 kg) was added to the concentrated mass and stirred for 10-15 minutes and allowed to settle for 20-30 minutes. The acetic acid layer (bottom) was collected and the organic layer discarded. The acetic acid layer was washed with petroleum ether (114.26 kg) (with stirring for 10-15 minutes and settling for 20-30 minutes), collected and concentrated under vacuum (NLT 500 mmHg) below 55° C. until ~1:2.0-2.5 w/v of concentrated mass remained inside the reactor. The concentrated mass was cooled to 25±5° C. A reactor was charged with purified water (464.0 kg) and cooled to 12±3° C. The acetic acid concentrated layer was slowly added to the cooled reactor over a period of 40-60 minutes at 20±5° C. The reaction mass was cooled to 8±2° C. and stirred for 3.0 hours. The mass was filtered in a centrifuge and spin-dried for 10-15 minutes and the filtrate was collected. The wet cake in centrifuge was washed with purified water (116.0 kg), dried for 60-90 minutes and collected into a double lined polyethylene bag placed in HDPE container. The material was dried under vacuum (NLT 550 mmHg) at 60±5° C. Compound 6 was collected (29.75 kg, 90.9-97.1% pure, yield 53.5-65.5% (steps 4 and 5 combined)).

Synthetic Example 6

Step 6: Conversion of Compound 6 to Compound 7

A. Into a reactor, 2,2-dimethyloxypropane (665.0 kg) was added followed by Compound 6 (from Synthetic Example 5, 52.00 kg) and (+/−)-10-camphorsulphonic acid (0.75 kg). The resulting mixture was stirred at 25±5° C. for 1 hour. The mass was concentrated under vacuum (NLT 550 mmHg) below 45° C. until 1:2.0 w/w [with respect to Compound 6 input] mass remained inside the reactor.

B. Dichloromethane (691.60 kg) was added and the mixture cooled to 12±3° C. The mixture was washed with sodium bicarbonate solution (~2.0% w/v, 3.12 kg of sodium carbonate in 156.0 kg of purified water) with stirring for 2-3 minutes and settling for 20-30 minutes. The bottom organic layer was then washed with sodium chloride solution (~15% w/v, 23.40 kg of sodium chloride in 156.0 kg of purified water) with stirring for 10-15 minutes and settling for 20-30 minutes. The organic layer was collected and dried with sodium sulphate (50.0 kg), with stirring for 10-15 minutes and 20-30 minutes of settling time. The mass was filtered through a Nutsche filter, vacuum-dried for 20-30 minutes and the filtrate collected in an HDPE container. The filtrate was concentrated under vacuum (NLT 500 mmHg) below 55° C. until no distillate was observed. Toluene (89.96 kg) was added and the mass stirred for 10-15 minutes. Solvent was distilled under vacuum (NLT 500 mmHg) below 55° C. until no distillate was observed and the residue cooled to 25±5° C. Toluene (135.20 kg) was added under vacuum and the mass stirred for 10-15 minutes to yield a solution of Compound 7 (98.2% pure) that was used further as is.

Synthetic Example 7

Step 7: Conversion of Compound 7 to Compound 8

A. Toluene (641.84 kg) and methyltriphenylphosphonium bromide (134.0 kg) were added to a reactor and the temperature of the reaction mass was raised to 105±5° C. The reaction was maintained under azeotropic reflux at 105±5° C. for 2.0 to 2.5 hours. It was cooled to 10±5° C. and potassium tert-butoxide (50.0 kg) was added to the reactor. The temperature was raised to 25±3° C. for 1.0-1.5 hours where the reaction mixture turned yellow in colour. Compound 7 solution from Synthetic Example 6, was added to the reactor. The temperature was raised to 60±5° C. and the mixture stirred for 2 hours until reaction was complete, where it was cooled to 25±5° C. Purified water (520 kg) was added to the reactor, with stirring for 5-10 minutes and settling time of 10-15 minutes. The bottom aqueous layer was separated while the organic layer was retained in the reactor.

B. The organic layer was washed with sodium chloride solution (~20% w/v, 52 kg of sodium chloride in 260.0 kg of purified water) with stirring for 5-10 minutes and settling time of 15-20 minutes. The organic layer was collected and concentrated under vacuum (NLT 500 mmHg) below 55° C. until no distillate was observed. Cyclohexane (202.80 kg) was added to the reactor and the mass was concentrated under vacuum (NLT 500 mmHg) below 55° C. until no distillate was observed. Cyclohexane (810.16 kg) was again added to the reaction mixture and the mass temperature was raised to 55±5° C. and stirred for 30-40 minutes. The mass was cooled to 5±2° C. and stirred for a further 1.0-1.5 hours. The mixture was filtered through a Nutsche filter and the material vacuum dried for 10-15 minutes. The filtrate, containing product, was collected.

C. Wet material (which includes triphenylphosphine oxide), was loaded into double polyethylene bags placed into the HDPE container. Cyclohexane (202.80 kg) was added to a reactor and material was loaded into the reactor and stirred for 10-15 minutes. The temperature of the mass was raised to 55±5° C. and the mass was stirred for 30-40 minutes, then cooled to 5±2° C. and stirred for a further 30-40 minutes. The mass was filtered through a Nutsche filter and vacuum dried for 10-15 minutes, while the filtrate was collected. Cyclohexane (202.80 kg) was again added to a reactor and wet material was loaded into the reactor and stirred for 10-15 minutes. The temperature of the mass was raised to 55±5° C. and the mass was stirred for 30-40 minutes, then cooled to 5±2° C. and stirred for a further 30-40 minutes. The mass was filtered through a Nutsche filter and vacuum dried for 10-15 minutes, while the filtrate was collected. The combined filtrates were concentrated under vacuum (NLT 500 mmHg) below 55° C. until no distillate was observed and then cooled to 25±5° C. and collected.

D. Silica gel (60-120 mesh, 100 kg) was added to the crude mass and dried under vacuum (NLT 550 mmHg) at 25±5° C. for 4-6 hours. The crude mass was divided into 4 equal lots for column chromatographic purification using ethyl acetate (10%, 637.0 L) in petroleum ether (3064.0 L) while gradually increasing the % ethyl acetate from 10% to 35% as the mobile phase. Product fractions were collected after TLC analysis and the product concentrated under vacuum (NLT 500 mmHg) below 50° C. until 10-20 kg mass remained inside the reactor followed by cooling to 25±5° C. All concentrated product fractions are combined in a reactor and further concentrated under vacuum (NLT 500 mmHg) below 50° C. until 20-30 Kg mass remained inside the reactor. The combined concentrated mass was further concentrated in a rotary evaporator under (NLT 500 mmHg) below 50° C. until no distillate was observed followed by further drying under vacuum (NLT 500 mmHg) below 45-50° C. Compound 8 was obtained (34.50 kg, 73.4-94.9% pure (by HPLC-UV, 98.3-100% pure by HPLC-ELSD, 34.6 to 59.2% yield).

Synthetic Example 8

Step 8: Conversion of Compound 8 to Compound 9

A. Pyridine (233.02 kg) and Compound 8 (from Synthetic Example 7, 42.60 kg) were added to a reactor and the mixture stirred for 15-20 minutes. 4-Dimethylaminopyridine (1.44 kg) was added to the mixture and the mixture stirred for 10-15 minutes. The mixture was cooled to 3±2° C. and acetic anhydride (24.28 kg) was slowly added at 3±2° C. and stirred for 15-20 minutes. The mass was stirred at 23±2° C. until the reaction was complete (1 hour).

B. Reaction mass was collected and the reactor charged with purified water (639.0 kg) which was chilled to 3±2° C. The collected reaction mass was added to the chilled purified water at 3±2° C. The mixture was washed three times with n-heptane (204.05 kg, 87.33 kg and 58.36 kg respectively) each with stirring for 10-15 minutes and settling time for 20-30 minutes. Each time the bottom aqueous and top organic layers were collected and the aqueous layer placed back into the reactor to be re-washed. The organic layers were combined in the reactor and washed three times with purified water (213.0 kg each time) with stirring for 10-15 minutes and settling for 20-30 minutes. The organic layer was separated and then washed with brine solution (~10% solution, 21.30 kg of sodium chloride in 191.70 kg of purified water) with stirring for 15 minutes and settling time of 20-30 minutes. The organic layer was collected and dried with sodium sulphate (21.30 kg) for 5-10 minutes (with stirring). The mixture was filtered through a Nutsche filter and vacuum dried for 10-15 minutes. The filtrate was concentrated under vacuum (NLT 500 mmHg) below 50° C. until no distillate was observed. Compound 9 was obtained (98.3% pure by HPLC) and used further as is.

Synthetic Example 9

Step 9: Conversion of Compound 9 to Compound 10

A. Dilute acetic acid (~80% w/v, 166.14 kg of acetic acid in 39.61 kg of purified water) was slowly added to the concentrated mass (Compound 9) from Synthetic Example 8, cooled to 23±2° C. in a reactor maintaining a temperature of 23±2° C. The mixture was further stirred until reaction was complete (5 hours).

B. The mixture was washed twice with n-heptane (87.33 kg) with stirring for 10-15 minutes and settling for 20-30 minutes. The aqueous layer was charged into a reactor and purified water (1065.0 kg) was added slowly at 23±2° C., and stirred for 10-15 minutes. The mass was filtered through a centrifuge and spin-dried for 10-15 minutes. The wet material and filtrate were collected. Dichloromethane (283.29 kg) was added to the reactor and the wet material was added and the mixture stirred until a clear solution was obtained. The dichloromethane solution was washed with sodium bicarbonate solution (~0.22% w/v, 0.85 kg of sodium bicarbonate in 383.40 kg of purified water), in three equal portions. The organic layer was added to a reactor and washed with purified water (127.80 kg). The collected organic layer was concentrated under (NLT 500 mmHg) below 45° C. until 1:1.0 w/v [with respect to Compound of 9 input] mass remained inside the reactor. n-Heptane (28.97 kg) was added to the concentrated mass and further concentrated under (NLT 500 mmHg) below 45° C. until no distillate was observed. A further aliquot of n-heptane (87.33 kg) was added and the mass filtered through a centrifuge and spin-dried for 10-15 minutes. The reactor was rinsed with n-heptane (14.48 kg) and this solution used to wash the wet material in the centrifuge, followed by spin drying for 20-30 minutes. The material was further dried under vacuum (NLT 550 mmHg) at 55±5° C. for 10 hours. Compound 10 was obtained (30.90 kg, 95.4 to 97.7% purity by UV, 99.6 to 100% purity by ELSD, 60.7 to 71.8% yield).

Synthetic Example 10

Step 10: Conversion of Compound 10 to Compound 11

A. Tetrahydrofuran (242.8 L, 16.80 Vol) and Compound 10 (14.45 kg, from Synthetic Example 9) were added to the reactor and stirred for 5-10 minutes. Sodium metaperiodate solution (~14% w/v, 17.05 kg of sodium metaperiodate in 121.4 L, 8.4 Vol) of purified water) was slowly added into the reaction mass at 25±5° C. and the mass stirred at 25±5° C. for 15 minutes. Purified water (242.7 L, 16.80 Vol) was slowly added into the reaction mass at 25±5° C. and stirred for 10-15 minutes.

B. The aqueous mixture from Paragraph A was washed three times with ethyl acetate (115.6 L, 8.0 Vol each time) with stirring for 10-15 minutes and allowed to settle for 20-30 minutes and the organic layers collected and stored. The organic layers were combined in the reactor and ethyl acetate (231.2 L, 16.0 Vol) was added and the mixture stirred for 15 minutes. The organic layers were washed with brine solution (~11% w/v, 34.68 kg of sodium chloride in 312.1 L, 21.6 Vol) in three equal lots (~115.6 kg each). The organic layer was then dried with sodium sulphate (7.22 kg) with stirring for 5-10 minutes and the mixture filtered through a Nutsche filter and vacuum dried for 5-10 minutes. The collected filtrate was loaded into the reactor and concentrated under vacuum (NLT 500 mmHg) below 45° C. until 1:1.0 w/w mass was remained inside the reactor. n-Heptane (43.3 L, 3.0 Vol) was added to the reactor and the mixture concentrated under vacuum (NLT 500 mmHg) below 45° C. until 1:1.0 w/w [with respect to Compound 10 input], concentrated mass remained inside the reactor. A further aliquot of n-heptane (43.3 L, 3.0 Vol) was added and the mixture cooled to 12±2° C. The mixture was stirred for 10-15 minutes at 25±5° C. and filtered through a Nutsche filter and vacuum dried for 20-30 minutes. The wet material in the Nutsche filter was washed with n-heptane (14.5 L, 1.0 Vol) and vacuum dried for 20-30 minutes. When purity did not comply, additional washes using 3-5 Vol n-heptane were performed. The material was further dried under vacuum (NLT 550 mmHg) at 25±5° C. until water content was achieved (6 hours), with material being shuffled every 3-6 hours. Compound 11 was obtained (12.75 kg, 97.9 to 98.9% purity, yield 81.7 to 89.1%).

Synthetic Example 11

Step 11: Conversion of Compound 11 to Compound 12

A. Tetrahydrofuran (113.4 L, 9.0 Vol, not more than 0.10% w/w moisture) was added to the reactor, stirred for 5-10 minutes and tested for moisture content (not more than 0.10% w/w). Methanol (37.80 L, 3.0 Vol, not more than 0.10% w/w moisture) was added to the reactor, stirred for 5-10 minutes and tested for moisture content (not more than 0.10% w/w). Compound 11 (12.60 kg, from Synthetic Example 10) was added to the reactor and the mass stirred for 5-10 minutes. The reaction was cooled to −20±2° C. and sodium borohydride (1.26 kg) was added lot-wise into the reactor between −22 and −10° C. The reaction was exothermic. Following addition, the temperature was raised to 17±3° C. and stirred until reaction was complete (1 hour). The mixture was cooled to −15±2° C. and dilute acetic acid (11.08 L, 0.88 Vol of acetic acid with 2.77 L, 0.22 Vol of purified water) was slowly added at −15±2° C. The temperature was raised to −23±2° C. The mass was concentrated under vacuum (NLT 500 mmHg) below 40° C. until no distillate was observed.

B. Ethyl acetate (214.2 L, 17.0 Vol) was added to the reactor and stirred for 10-15 minutes and allowed to settle for 20-30 minutes. The aqueous layer was collected and the organic layer retained inside the reactor. The organic layer was washed with sodium bicarbonate (~25% w/v, 52.92 kg of sodium bicarbonate in 210.7 L, 16.7 Vol purified water), in three equal lots (~65.91 kg in each lot) with stirring for 10-15 minutes and settling for 20-30 minutes for each washing. The organic layer was then washed with brine (25% w/v, 26.20 kg of sodium chloride in 105.6 L, 8.4 Vol purified water) in 2 equal lots (~65.9 kg for each washing) with stirring for 10-15 minutes and settling for 20-30 minutes for each washing. The organic layer was dried with sodium sulphate (12.60 kg) with stirring for 10-15 minutes, filtered through a Nutsche filter and vacuum dried for 10-15 minutes. The filtrate was collected, added to the reactor and concentrated under vacuum (NLT 500 mmHg) below 40° C. until no distillate was observed. n-Heptane (50.4 L, 4.0 Vol) was added to the concentrated mass and the mixture cooled to 3±2° C. and further stirred for 1 hour. The mixture was filtered through a Nutsche filter and vacuum dried for 10-15 minutes. The reactor was rinsed with n-heptane (12.6 L, 1.0 Vol) and the wet material was washed with the rinsed n-heptane and vacuum dried for 20 to 30 minutes. The wet material was removed from the filter and further dried under vacuum (NLT 550 mmHg) at 25±5° C. for 6 hours, shuffling material every 4-6 hours. Compound 12 was obtained (11.25 kg, 84.7 to 95.5% purity, yield 84.3 to 88.3%.

Synthetic Example 12

Step 12: Conversion of Compound 12 to Compound 13

A. Pyridine (61.0 L, 5.5 Vol), Compound 12 (11.10 kg, from Synthetic Example 11) and 4-dimethylaminopyridine (0.36 kg) were added to the reactor. The reaction mass was cooled to −15±5° C. and stirred for 20-30 minutes. Acetic anhydride (2.88 kg) was added slowly to the reactor at −15±5° C. and it was further stirred for 45-60 minutes. Additional amounts of acetic anhydride (0.31 kg each time) were added slowly at −15±5° C. and further stirred for 45-60 minutes, until the reaction went to completion. Purified water (111.0 L, 10.0 Vol) was added to another reactor and cooled to 2.5±2.5° C. The chilled purified water was added to the reaction mass at −15±5° C. over a period of 1-2 hours. The temperature was raised to 25±5° C. and the mixture stirred for 20-30 minutes.

B. Ethyl acetate (222.0 L, 20.0 Vol) was added to the reactor and stirred for 20-30 minutes followed by settling for 20-30 minutes. The aqueous layer was removed and the organic layer was washed with sodium chloride solution (55.5 kg of sodium chloride in 222.0 L, 20.0 Vol, of purified water), in 4 lots (~69.4 kg each) with stirring for 10-15 minutes and settling time of 20-30 minutes for each lot. The top organic layer was retained in the reactor and dried with sodium sulphate (2.22 kg) with 10-15 minutes of stirring. The sodium sulphate was collected by filtration in a Nutsche filter and vacuum dried for 10-15 minutes. The filtrate was collected. The residue was washed with ethyl acetate (33.3 L, 3.0 Vol) that had been used to rinse the reactor and the residue was vacuum dried a further 10-15 minutes. The combined filtrate was added to the reactor and concentrated under vacuum (NLT 500 mmHg) below 45° C. until 1:2.0% w/w [with respect to Compound 12 input] concentrated mass remained inside the reactor. The concentrated mass was divided equally into two parts, for column chromatography. Each half was charged into a container and silica gel (60-100, 18.5 kg) was added for adsorption. Column chromatography was performed using a mobile phase of ethyl acetate (10%, 280.0 L) and n-heptane (1910.0 L) while gradually increasing the percentage of ethyl acetate to 20%. Product fractions were collected after TLC analysis and the product concentrated under vacuum (NLT 500 mmHg) below 60° C. until no distillate was observed. The concentrated mass was cooled to 15±5° C. n-Heptane (29.5 L, 2.0 Vol) was added to the reactor and stirred for 10-15 minutes. The mixture was filtered through a Nutsche filter and vacuum dried for 40-60 minutes. The material was unloaded and further dried under vacuum (NLT 550 mmHg) at 45±5° C., until dry, 10 hours, with manual shuffling of the material every 4-6 hours. Compound 13 was obtained (7.75 kg, 97.1 to 99.5% pure, yield 55.6 to 62.6%).

Synthetic Example 13

Step 13: Conversion of Compound 13 to Compound 14

A. Tetrahydrofuran (87.75 L, 15.0 Vol) and Compound 13 (5.85 kg, from Synthetic Example 12) was added into the reactor and stirred for 10-15 minutes. Triethylamine (6.02 L, 1.0 Vol) was added and stirred for 10-15 minutes. Methyl sulphonyl chloride (2.2 L, 0.38 Vol) was added slowly at 0±5° C. and further stirred for 20-30 minutes. The temperature was raised to 25±3° C. until reaction was complete (2 hours). The reaction mixture was cooled to 0±5° C. Sodium bicarbonate solution (~11% w/v, 35.10 kg of a solution of 3.51 kg of sodium bicarbonate in 31.59 L, 5.40 Vol purified water) was added slowly at 0±5° C. The reaction was exothermic. The temperature was raised to 25±3° C. and stirred for 20-30 minutes.

B. Ethyl acetate (87.8 kg, 15.0 Vol) was added to the reactor and stirred for 10-15 minutes and settled for 20-30 minutes. The aqueous layer was further washed with ethyl acetate (43.90 L, 7.5 Vol) with stirring for 10-15 minutes and settling for 20-30 minutes and the organic layers were collected and combined. Purified water (58.5 L, 10.0 Vol) was added and the mixture stirred for 10-15 minutes and settling for 20-30 minutes. The organic layer was further washed with purified water (58.5 L, 10.0 Vol) with stirring for 10-15 minutes and settling for 20-30 minutes. The retained organic layer was washed with sodium chloride solution (~56% w/v, 21.06 kg of sodium chloride in 37.40 L, 6.4 Vol purified water) with stirring for 10-15 minutes and settling for 20-30 minutes. The separated organic layer was dried with sodium sulphate (1.17 kg) and stirred for 10-15 minutes. The mixture was filtered through a Nutsche filter and vacuum dried for 10-15 minutes. The collected filtrate was charged back into the reactor and concentrated under vacuum (NLT 500 mmHg) below 45° C. until no distillate was observed. n-Heptane (29.2 L, 5.0 Vol) was added to the concentrated mass below 45° C. and concentrated under vacuum (NLT 500 mmHg) below 45° C. until no distillate was observed. This process was repeated again with n-heptane (29.2 L, 5.0 Vol). n-Heptane (40.95 L, 7.0 Vol) was added to the reactor under vacuum below 45° C. and the concentrated mass was cooled to 25±3° C. and stirred for 20-30 minutes. The mixture was filtered through a Nutsche filter with the material being vacuum dried for 10-15 minutes. The reactor was rinsed with n-heptane (17.55 L, 3.0 vol) and that solvent was used to wash the residue in the Nutsche filter, and the material allowed to vacuum dry for 10-15 minutes. The collected material was further dried under vacuum (NLT 550 mmHg) at 35±5° C., until dry, 15 hours, with manual shuffling of material every 4-6 hours. The drier was cooled to 25±5° C. and Compound 14 was obtained (6.55 kg, 91.1 to 99.4% pure, yield 88.2 to 94.1%).

Synthetic Example 14

Step 14: Conversion of Compound 14 to Compound 15

A. Dimethylformamide (43.90 L, 4.5 Vol) and Compound 14 were added to the reactor and stirred for 10-15 minutes. Sodium azide (2.61 kg) was added to the reactor, the temperature was raised to 57±3° C. and the mass stirred at 57±3° C. until reaction was complete (2 hours). The reaction mass was cooled to 0±5° C. Purified water (117.0 L, 12.0 Vol) was added to another reactor and chilled to 0±5° C. The chilled purified water was slowly added to the reaction mass at 0±5° C. The temperature was raised to 25±5° C. and the mass was stirred for 2.0-2.5 hours. The reaction mass was filtered through a Nutsche filter and the material vacuum dried for 10-15 minutes. The wet material was collected. Purified water (438.80 L, 45.0 Vol) and the wet material were added to the reactor and stirred for 10-15 minutes. The mass was again filtered through a Nutsche filter and vacuum dried for 10-15 minutes. The reactor was rinsed using purified water (48.75 L, 5.0 Vol) and that water was used to wash the wet material in the Nutsche filter, and the material was vacuum dried a further 20 to 30 minutes. Isopropyl alcohol (19.5 L, 2.0 Vol) was chilled to 0±5° C. and used to wash the material in the Nutsche filter. The material was vacuum dried for 40-60 minutes. The material was further dried under vacuum (NLT 550 mmHg) at 40±5° C. until dry (5 hours). Compound 15 was obtained (8.10 kg, 95.8 to 97.3% pure, yield 88.3 to 93.3%).

Synthetic Example 15

Step 15: Conversion of Compound 15 to Compound 16

A. Tetrahydrofuran (105.0 L, 15.0 Vol, not more than 0.1% w/v moisture) was added to a reactor and stirred for 5-10 minutes and tested for moisture content. Compound 15 (7.0 kg, from Synthetic Example 14) was added to the reactor and the mixture was cooled to −10±5° C. Lithium aluminum hydride (2M solution in THF, 26.0 L, 3.7 Vol) was slowly added to the reactor and stirred at −10±5° C. for 30-40 minutes. The temperature of the mixture was raised to 25±3° C. and stirred until reaction was complete (1 hour). Solution was cooled to −10±5° C. Sodium sulphate solution (~40% w/v, 14.0 kg of anhydrous sodium sulphate in 35.0, 5.0 Vol, purified water) was slowly added to the reaction at −10±5° C. The temperature was raised to 25±3° C. and the mixture stirred for 1.0 to 1.5 hours. A CELITE™ bed (5.0 kg) was prepared into the Nutsche filter using tetrahydrofuran (25.0 L). The reaction mixture was filtered through the CELITE™ bed. Clear filtrate was required to proceed. Reactor was rinsed with a mixture of tetrahydrofuran (5.25 L, 0.75 Vol and dichloromethane (15.25 L, 2.25 Vol) and the collected material in the Nutsche filter was washed with that solvent mixture. Clear filtrate was required to proceed. Filtrate was added back to the reactor and rinsed twice with brine solution (~36% w/v, 15.4 kg sodium chloride in 42.0 L, 6.0 Vol purified water), with stirring for 10-15 minutes and settling for 30 to 45 minutes. Each time the organic layer was retained in the reactor. The organic layer was washed with purified water (17.5 L, 2.5 Vol) with stirring for 10-15 minutes and settling of 30-45 minutes. The organic layer was concentrated under vacuum (NLT 500 mmHg) below 50° C. until no distillate was observed. The mixture was co-distilled with n-heptane (21.0 L, 3.0 vol) under vacuum (NLT 500 mmHg) below 50° C. until no distillate was observed for 4 times. n-Heptane (35.0 L, 5.0 vol) was added to the concentrated mass and the mass was cooled to 25±3° C. and stirred at 23±3° C. for 1.0-1.5 hours before being filtered through a Nutsche filter and the material vacuum dried for 10-15 minutes. The reactor was rinsed with n-heptane (21.0 L, 3.0 Vol) and that solvent was used to wash the wet material in the Nutsche filter and the material further vacuum dried 60-90 minutes. The collected material was then further dried under vacuum (NLT 550 mmHg) at 40±5° C. until water content was achieved (6 hours). The drier was cooled to 25±5° C. and Compound 16 was obtained (4.25 kg, 94.0 to 97.0% pure, yield 81.5 to 89.5%).

Synthetic Example 16

Step 16: Conversion of Compound 16 to AQX-1125

A. Methanol (19.5 L, 3.0 Vol) and Compound 16 (6.50 kg, from Synthetic Example 15) were added to a reactor and the mixture was cooled to 10±3° C. Glacial acetic acid (5.78 L, 0.9 Vol) was slowly added at 10±3° C. and the mass was stirred for 15-20 minutes at 10±3° C. The temperature of the mass was raised to 25±3° C. and the mass was stirred for 10-15 minutes. The reaction mass was filtered through cartridge filters (0.5µ PTFE/PP followed by 0.2µ PTFE/PP) and collected into stainless steel containers. The reactor was rinsed using methanol (6.5 L, 1.0 Vol), filtered through cartridge filters and collected into stainless steel containers as above. The filtrate was charged into a reactor (inside clean room) and concentrated under vacuum (NLT 550 mmHg) below 30° C. until 1:2.0% w/w concentrated mass remains inside the reactor. Methyl tert-butyl ether (39.0 L, 6.0 Vol) was slowly added from addition vessel into the concentrated mass by maintaining the mass temperature at 25±3° C. and the mass stirred for 10-15 minutes. The mass was slowly cooled to 10±5° C. over a period of 1.0-1.5 hours and stirred a further 15-30 minutes at 10±5° C. The mass was slowly fed into the centrifuge and spin dried for 10-15 minutes. Methyl tert-butyl ether (3.3 L, 0.5 Vol, cartridge filtered) was added to the reactor and cooled to 10±5° C. The wet cake in the centrifuge was washed with the cooled methyl tert-butyl ether from the reactor and the material was spin dried for 45-60 minutes and collected. Methyl tert-butyl ether (39.0 L, 6.0 Vol, cartridge filtered) was added to the reactor and the wet collected material was added, stirred at 25±3° C. for 30-45 minutes and slowly fed into the centrifuge and spin dried for 10-15 minutes. The reactor was rinsed with filtered methyl tert-butyl ether (13.0 L, 2.0 Vol) and this solvent was used to rinse the material in the centrifuge. The material was spin dried for 45 to 60 minutes and collected. The material was further dried under vacuum (NLT 550 mmHg) at 25±5° C. until desired water content was achieved. Material was sifted through a 20-mesh sieve and collected. AQX-1125 was obtained (6.05 kg, 98.6 to 99.3% pure, yield 78.4 to 79.0%)
B. Synthetic Methods 2-11

In addition to the method disclosed in Reaction Schemes 1 and 1A, the following methods, as disclosed in Reaction Schemes 2-11 below, may be utilized in preparing AQX-1125 and/or in preparing intermediates utilized in the preparation of AQX-1125.

REACTION SCHEME 2
Carbon-carbon bond cleavage by enol triflate ozonolyis

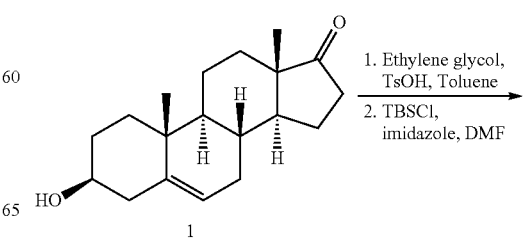

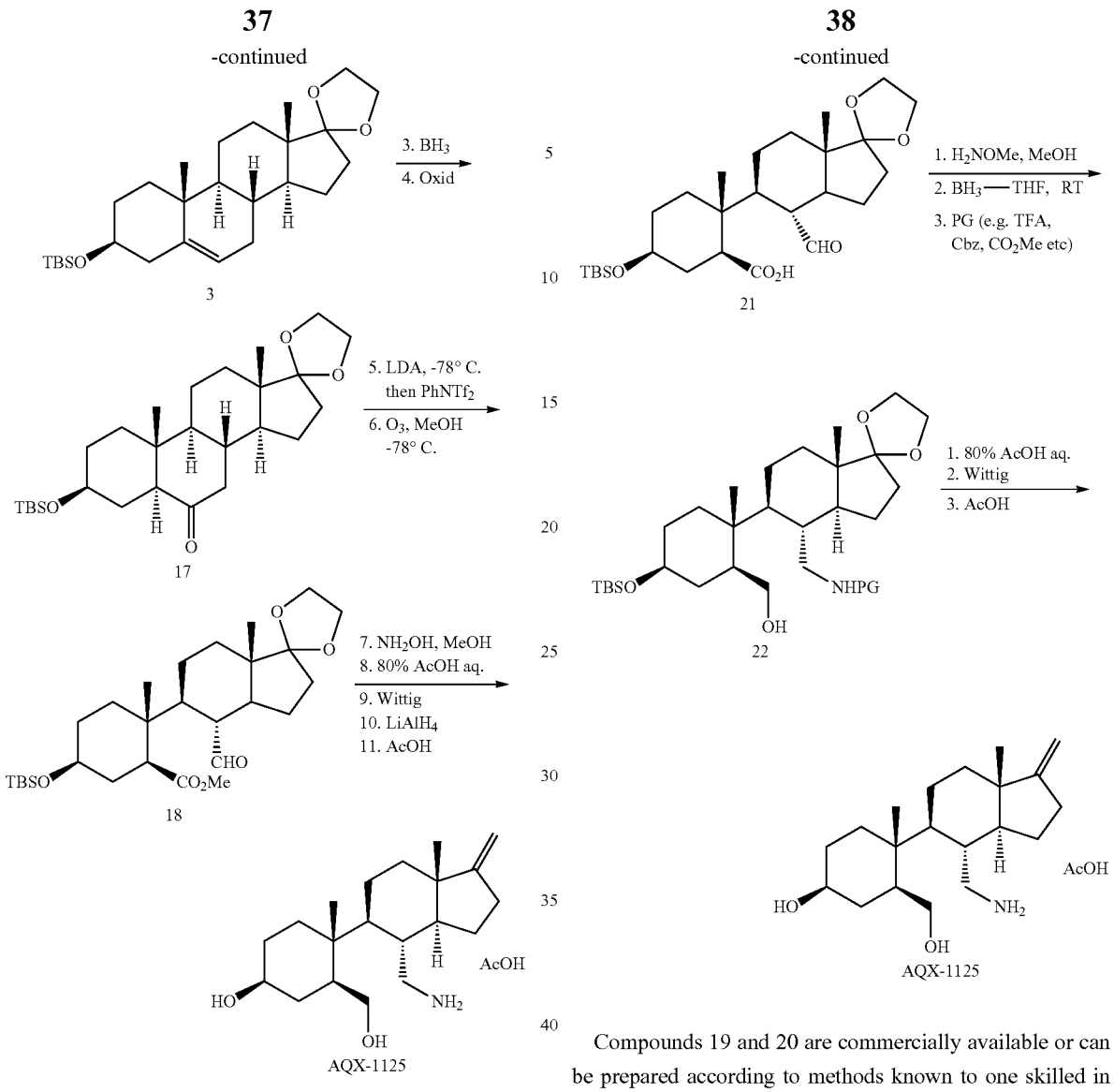

Compound 1, which is dehydroepiandrosterone, is commercially available or can be made by methods known to one skilled in the art.

In a manner similar to that described in PCT Published Patent Application WO 1995/001960 and/or Yong et al., *Bioorg. Med. Chem. Lett.* 1997, Vol 7 (7), p 923, AQX-1125 may be prepared as set forth above in Reaction Scheme 2.

Compounds 19 and 20 are commercially available or can be prepared according to methods known to one skilled in the art.

In a manner similar to that described in Yang, D.; Zhang, C., *J. Org. Chem.* 2001, 66, 4814, Mirjafary et al., *RSC Advances* 2015, 5, 79361 and Feuer, H.; Braunstein, D. *J. Org. Chem.* 1969, 34, 1817, AQX-1125 may be prepared as set forth above in Reaction Scheme 3.

REACTION SCHEME 3

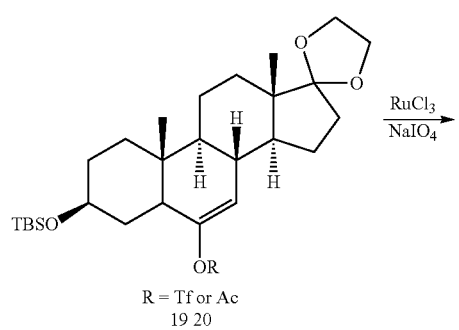

REACTION SCHEME 4

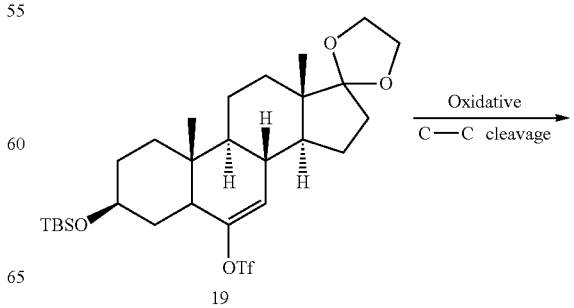

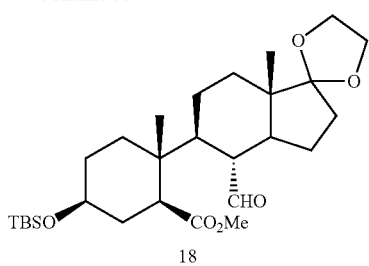
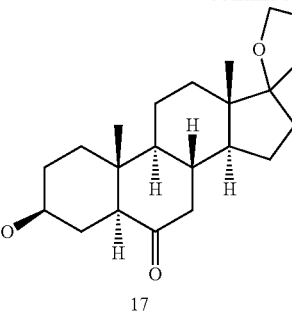
Compound 19 is commercially available or can be prepared according to methods known to one skilled in the art.
In a manner similar to that described in Ley et al. *Org. Lett.* 2003, 5, 185, Xing et al., 2006, 6, 693, Nicolaou et al., *Org. Lett.* 2010, 12, 1552, Compound 18, which is utilized in Reaction Scheme 2 above, may be prepared as set forth above in Reaction Scheme 4.
REACTION SCHEME 5
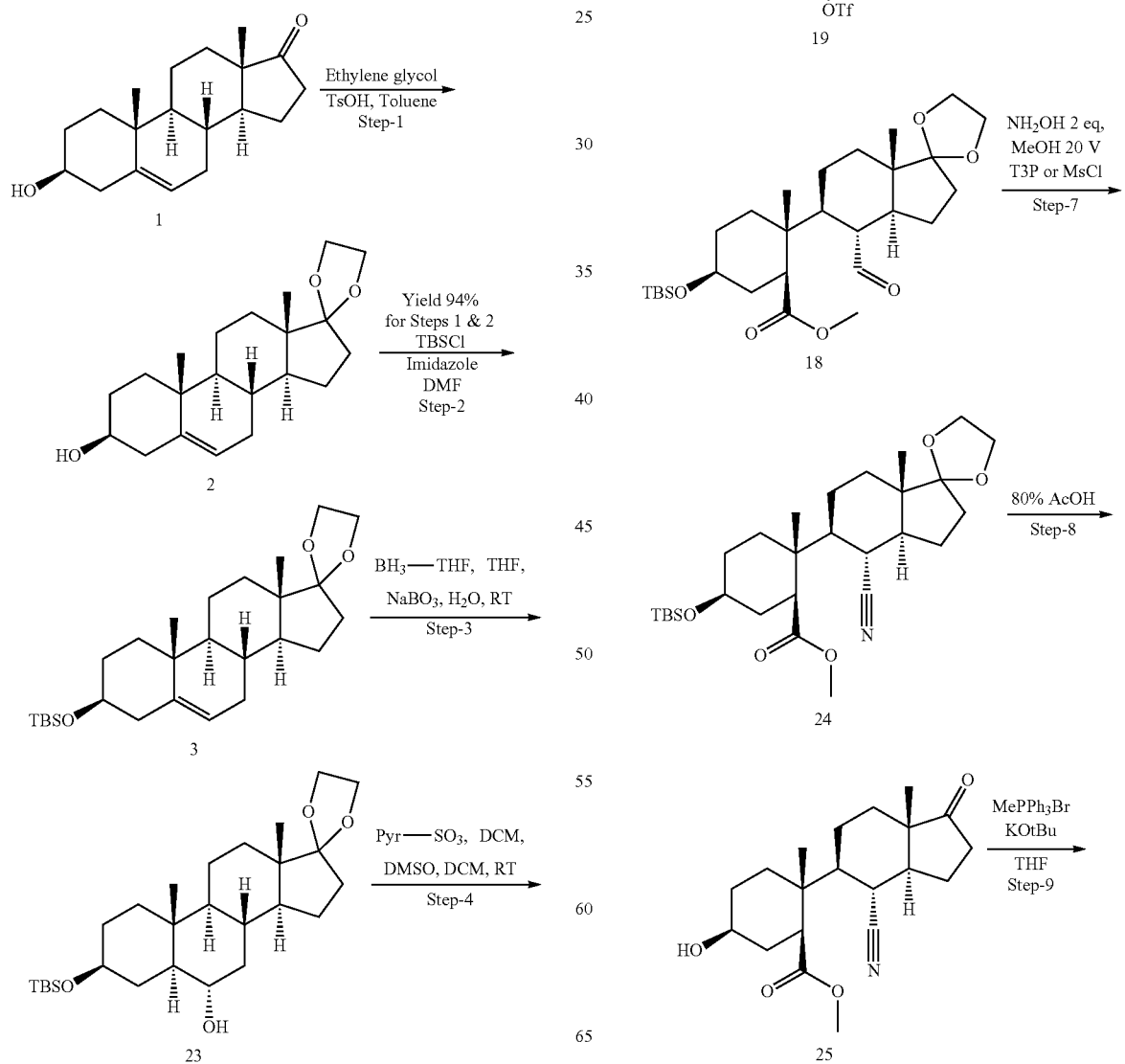

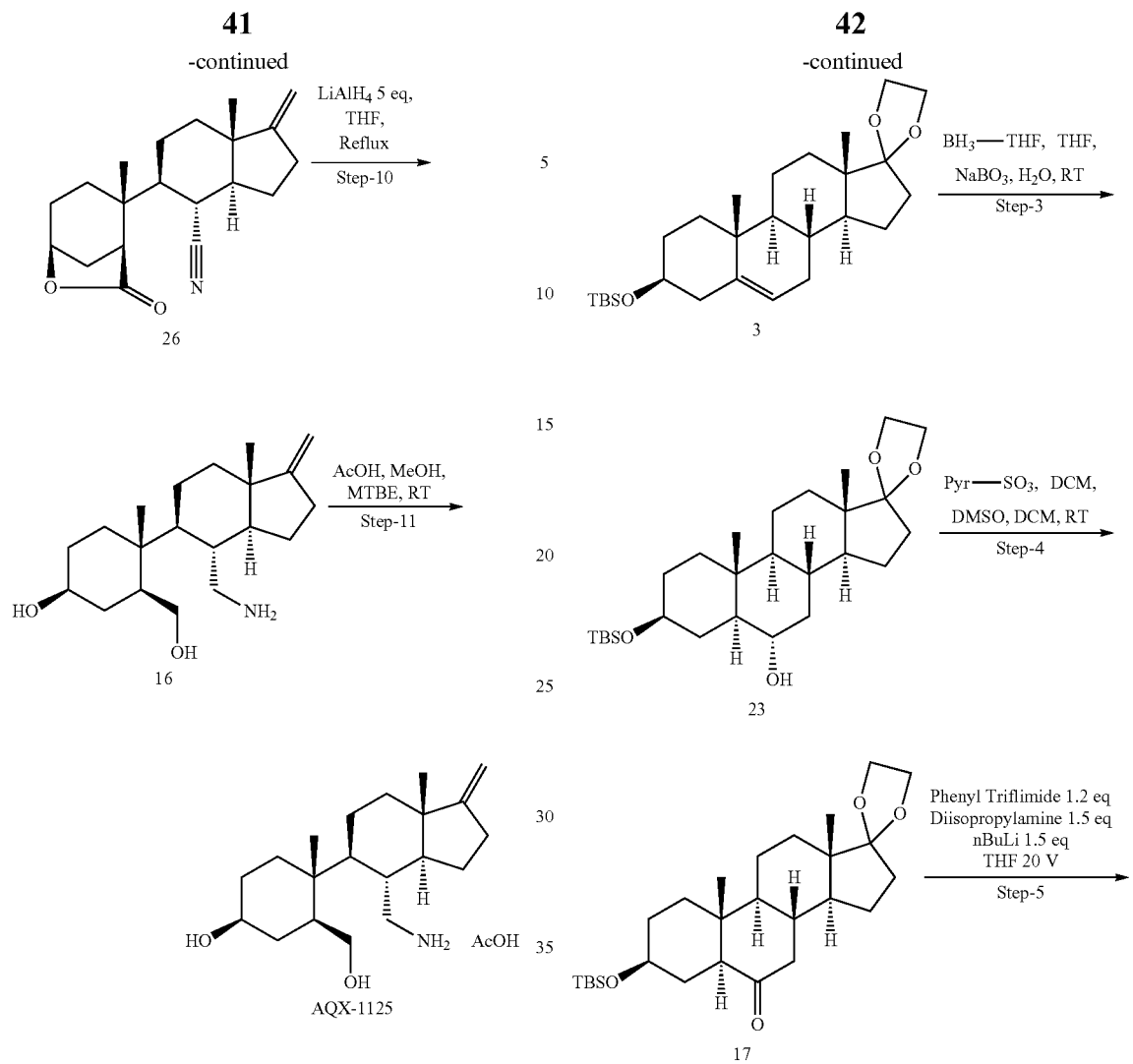
Compound 1, which is dehydroepiandrosterone, is commercially available or can be made by methods known to one skilled in the art. AQX-1125 may be prepared by the method disclosed above in Reaction Scheme 5.
REACTION SCHEME 6
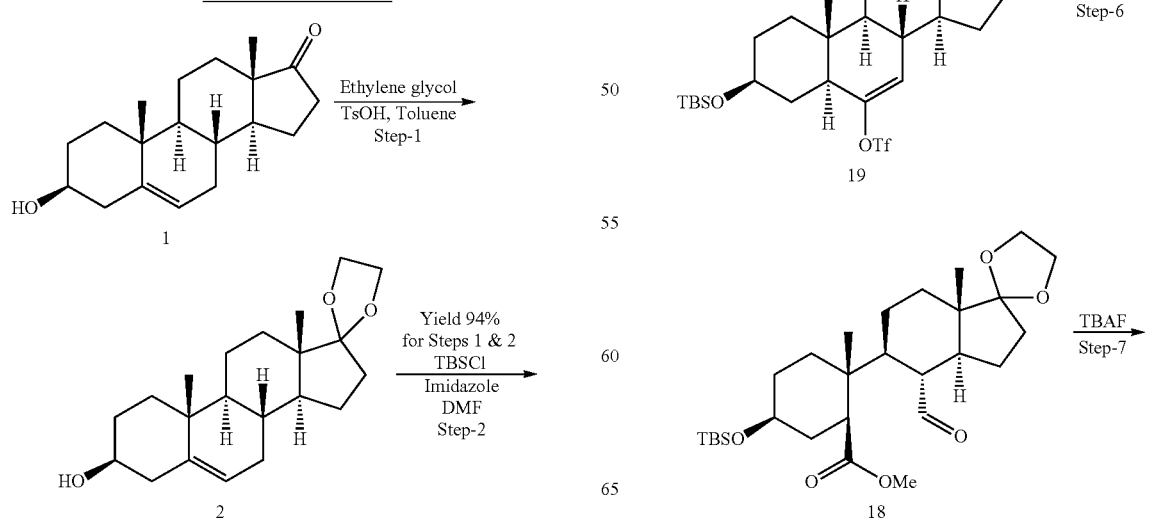

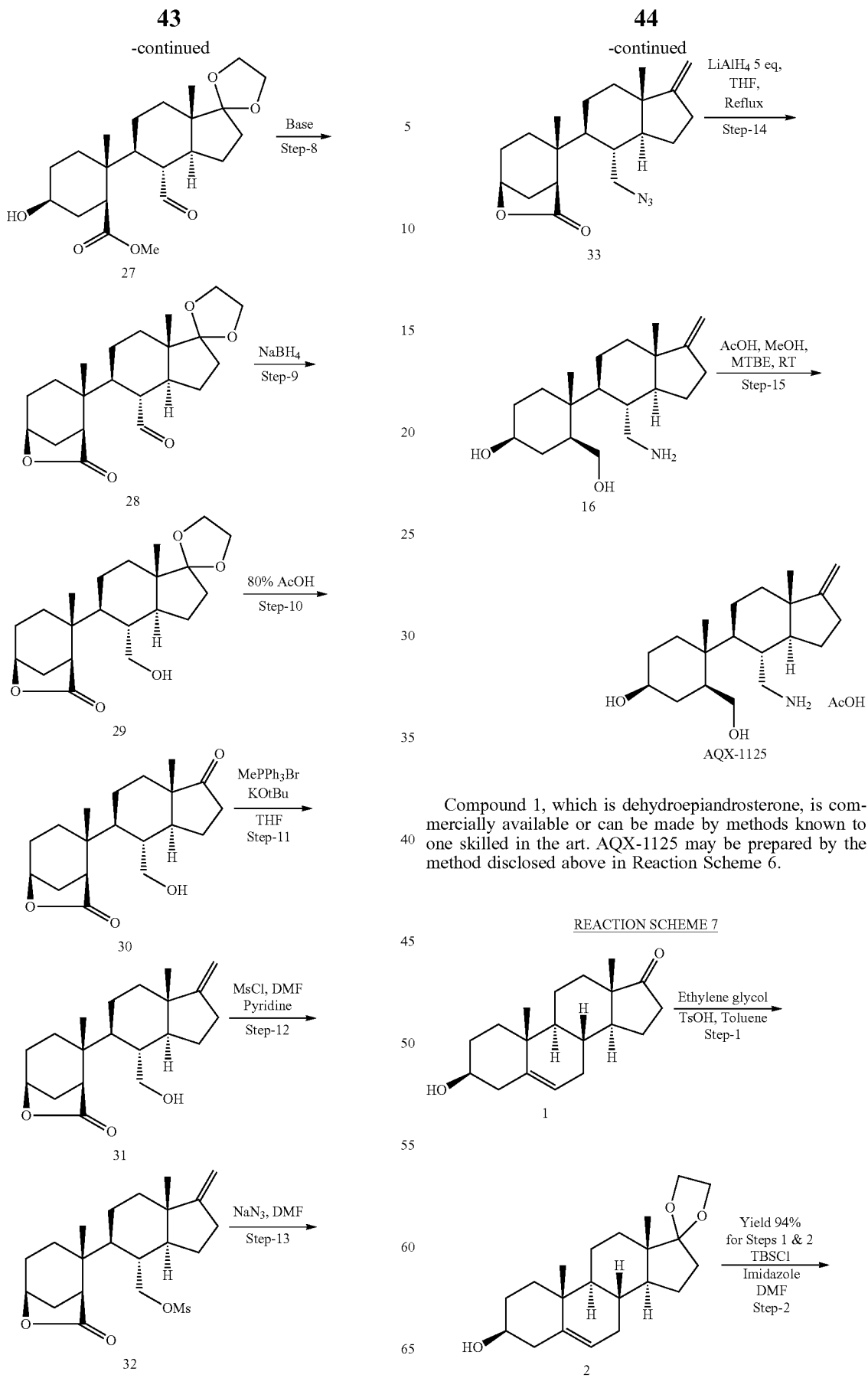
Compound 1, which is dehydroepiandrosterone, is commercially available or can be made by methods known to one skilled in the art. AQX-1125 may be prepared by the method disclosed above in Reaction Scheme 6.
REACTION SCHEME 7

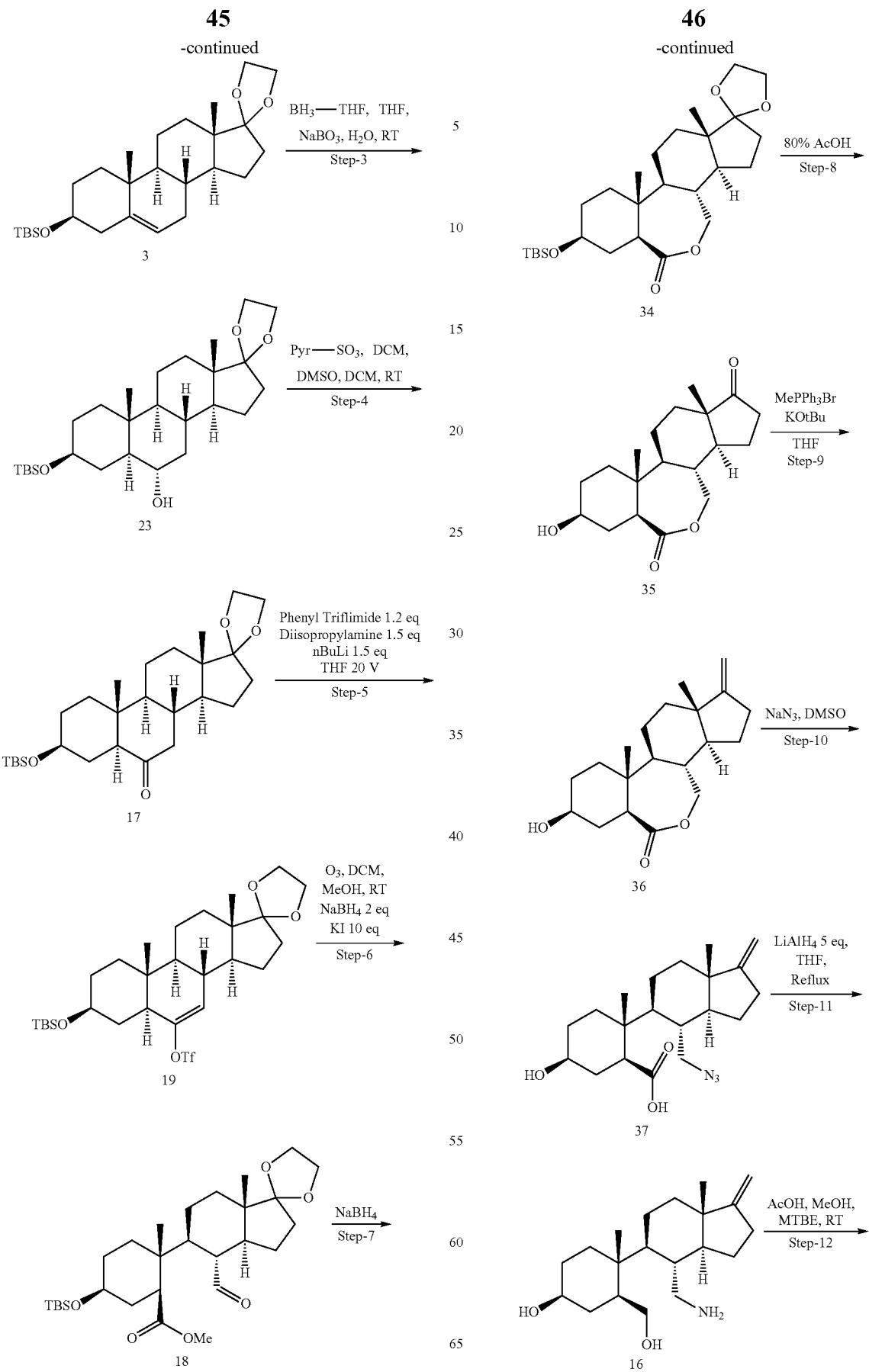

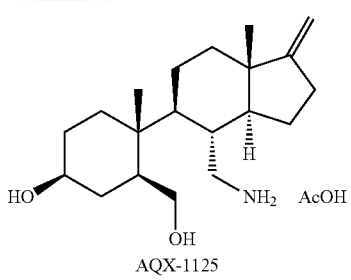

AQX-1125

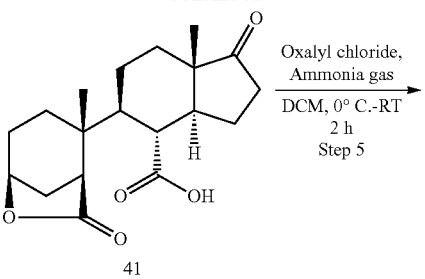

Compound 1, which is dehydroepiandrosterone, is commercially available or can be made by methods known to one skilled in the art. AQX-1125 may be prepared by the method disclosed above in Reaction Scheme 7.

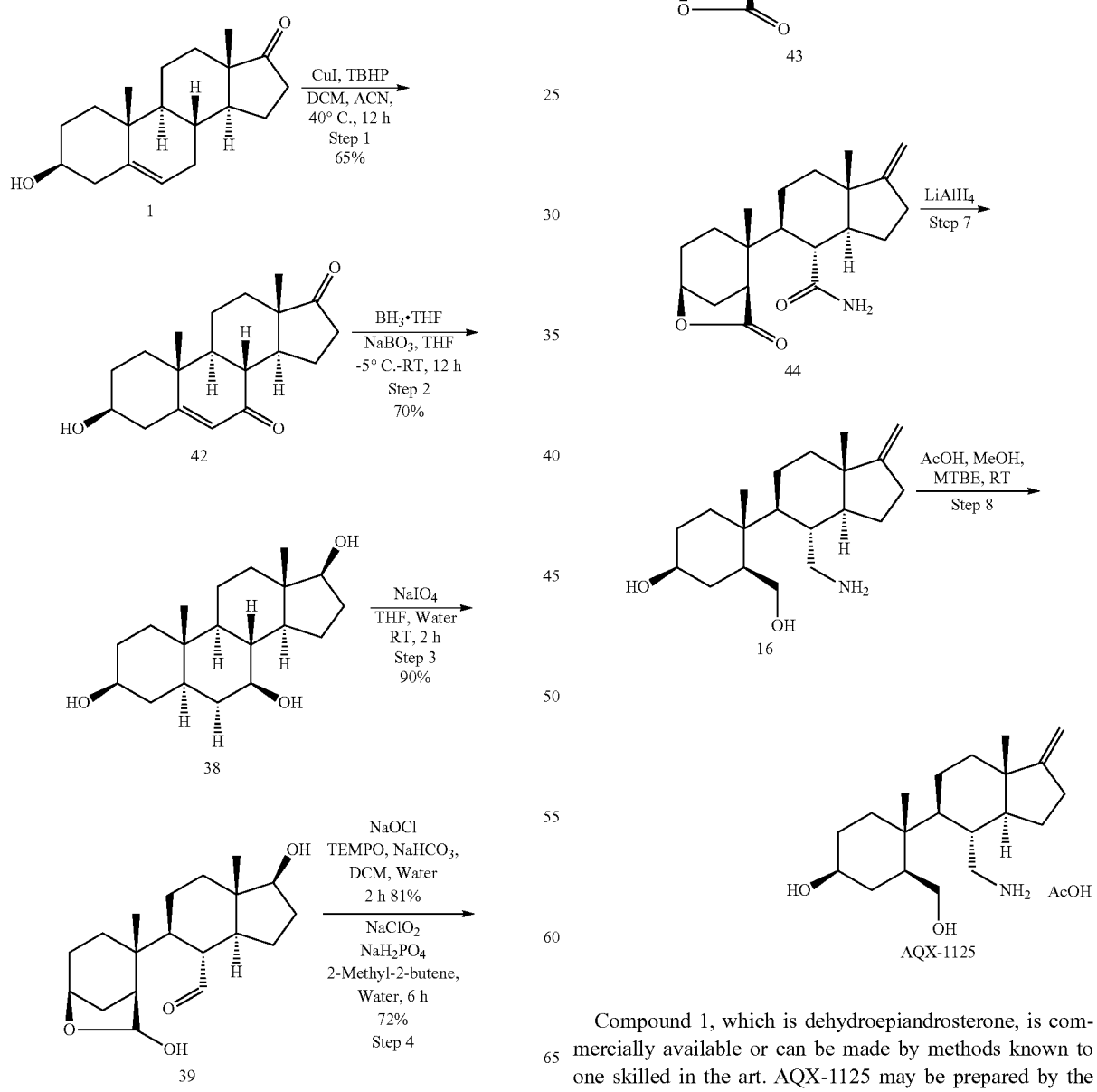

Compound 1, which is dehydroepiandrosterone, is commercially available or can be made by methods known to one skilled in the art. AQX-1125 may be prepared by the method disclosed above in Reaction Scheme 8.

REACTION SCHEME 9
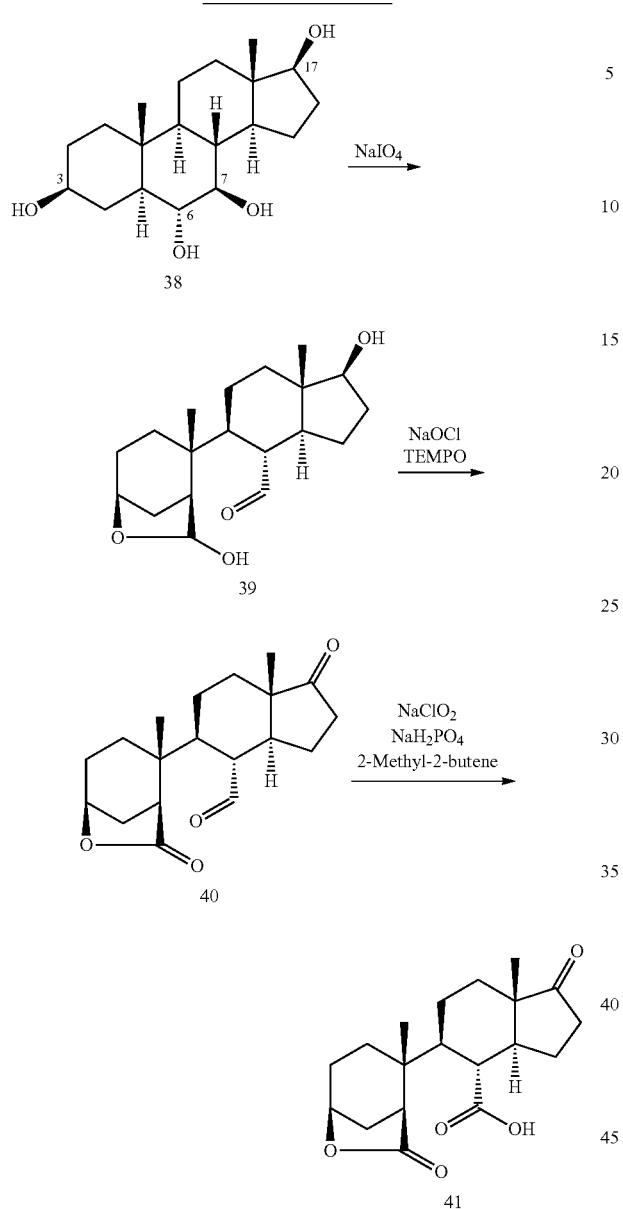
Compound 38 is commercially available or can be made by methods known to one skilled in the art. Alternatively, to Reaction Scheme 8, Compound 41 may be prepared from Compound 40 as set forth above in Reaction Scheme 9.
REACTION SCHEME 10
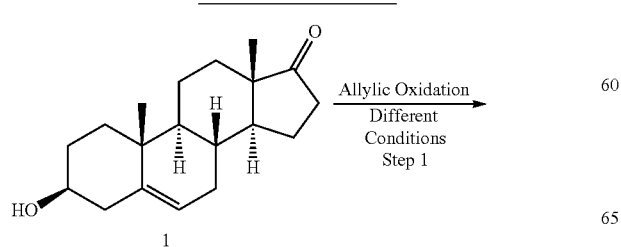
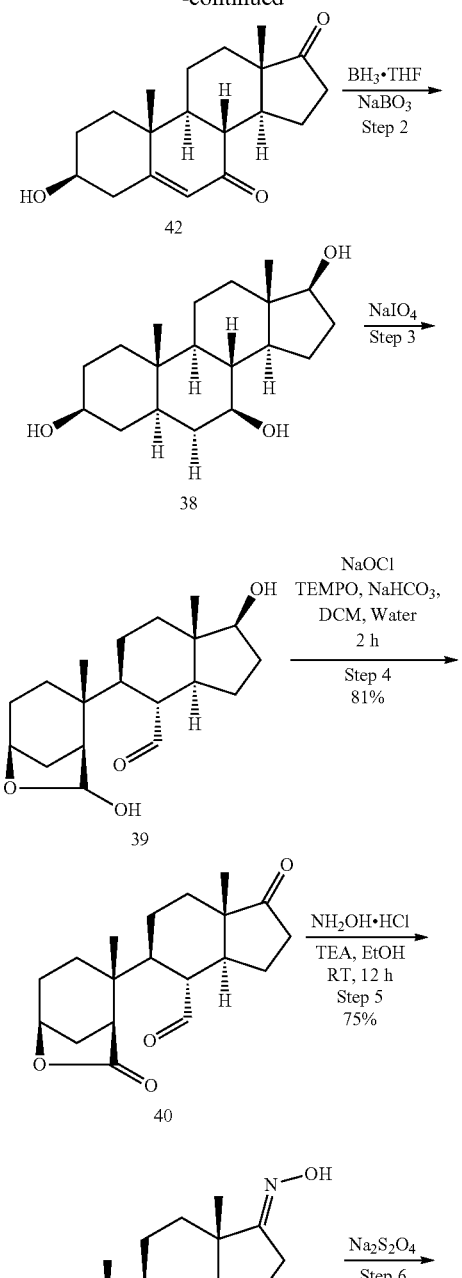

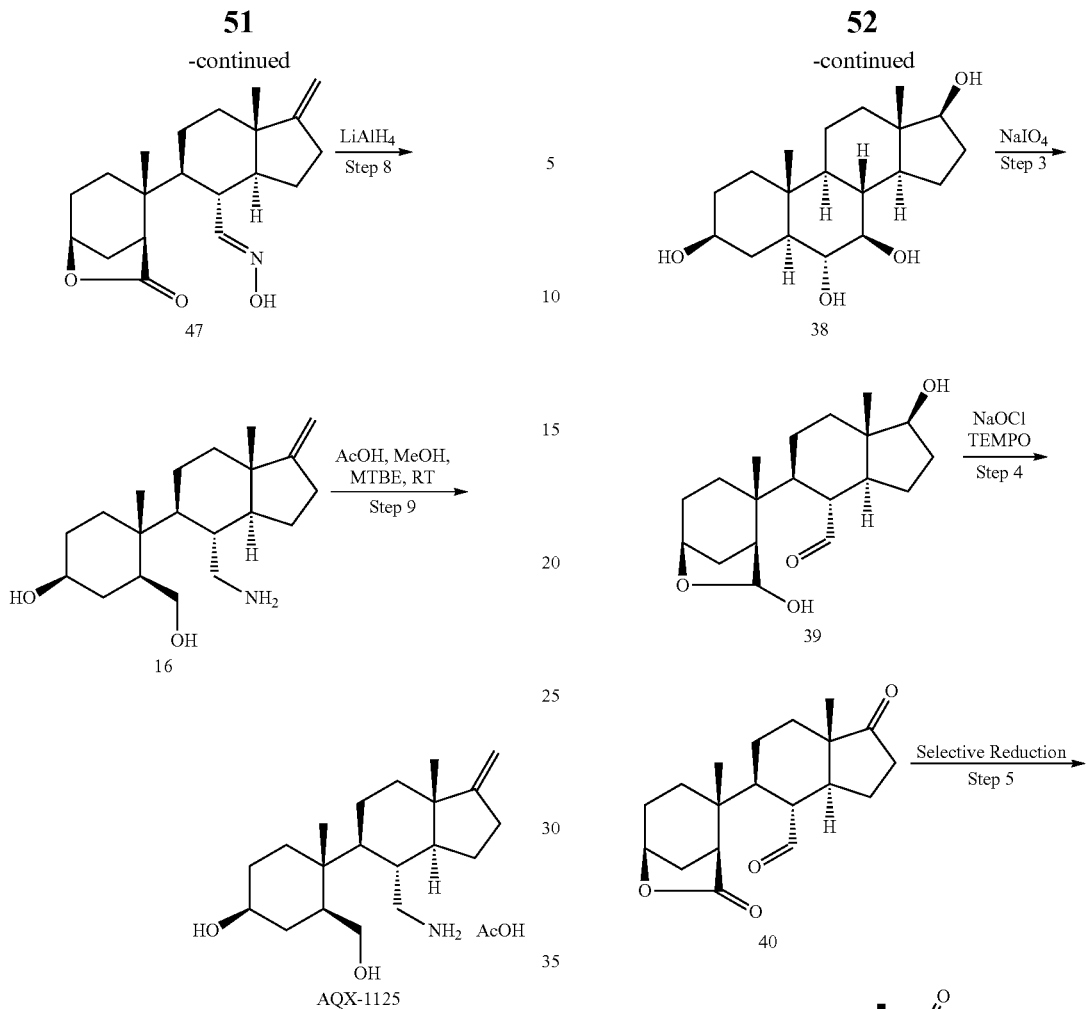
Compound 1, which is dehydroepiandrosterone, is commercially available or can be made by methods known to one skilled in the art. AQX-1125 may be prepared by the method disclosed above in Reaction Scheme 10.
REACTION SCHEME 11
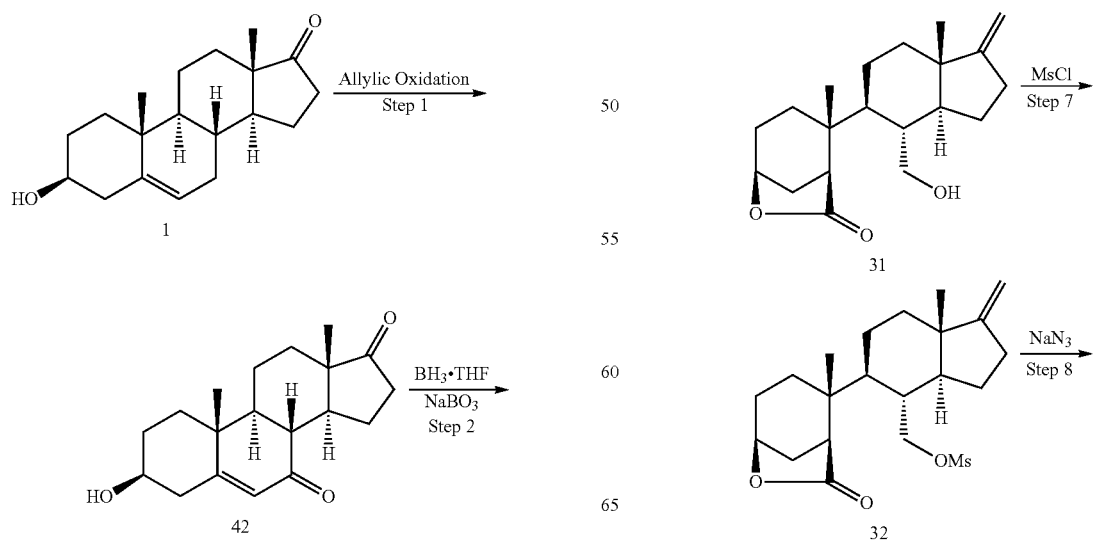

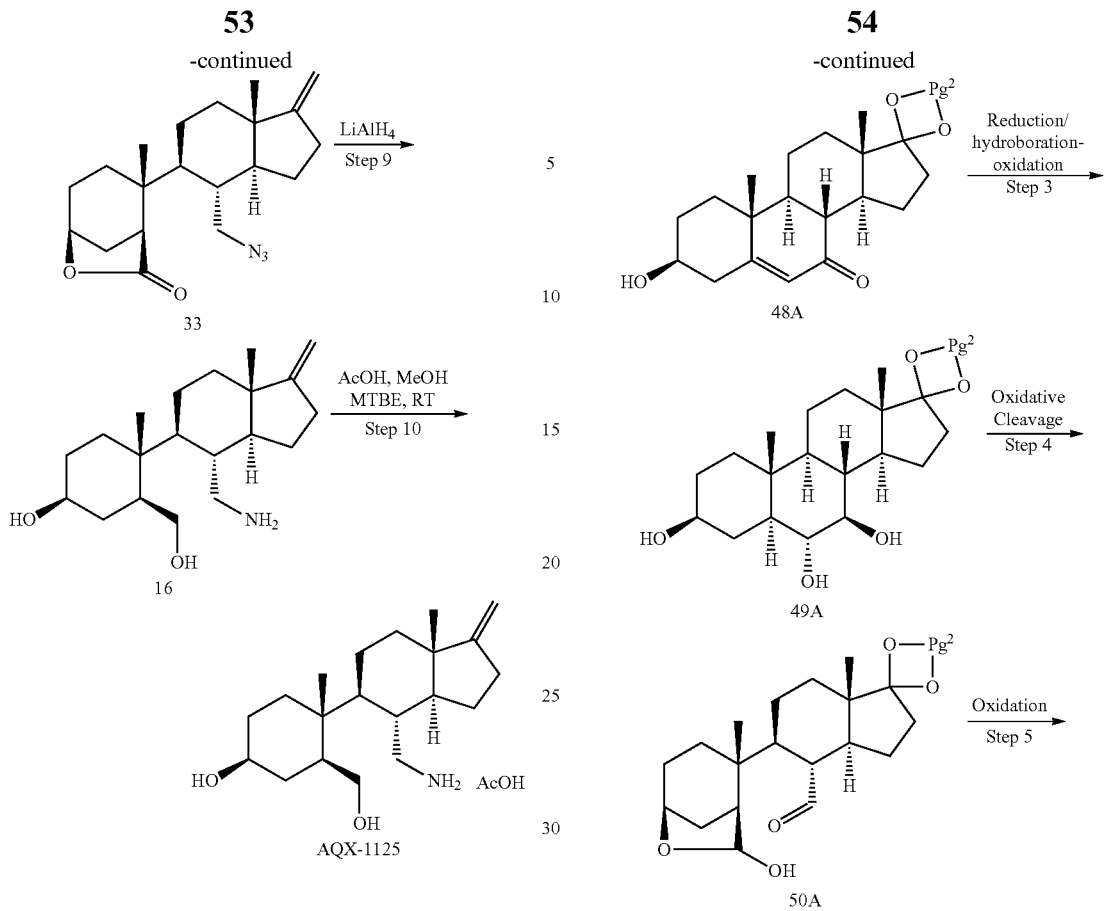

Compound 1, which is dehydroepiandrosterone, is commercially available or can be made by methods known to one skilled in the art. AQX-1125 may be prepared by the method disclosed above in Reaction Scheme 7.

C. Synthetic Methods 12 and 13

The following Reaction Schemes 12 and 13 provide increased yields of AQX-1125 and reduce the number of synthetic steps from Reaction Scheme 1 above.

AQX-1125 may be prepared by the method disclosed in Reaction Scheme 12, wherein $Pg^2$ is a carbonyl protecting group and $Lg^1$ represents an appropriate leaving group.

REACTION SCHEME 12

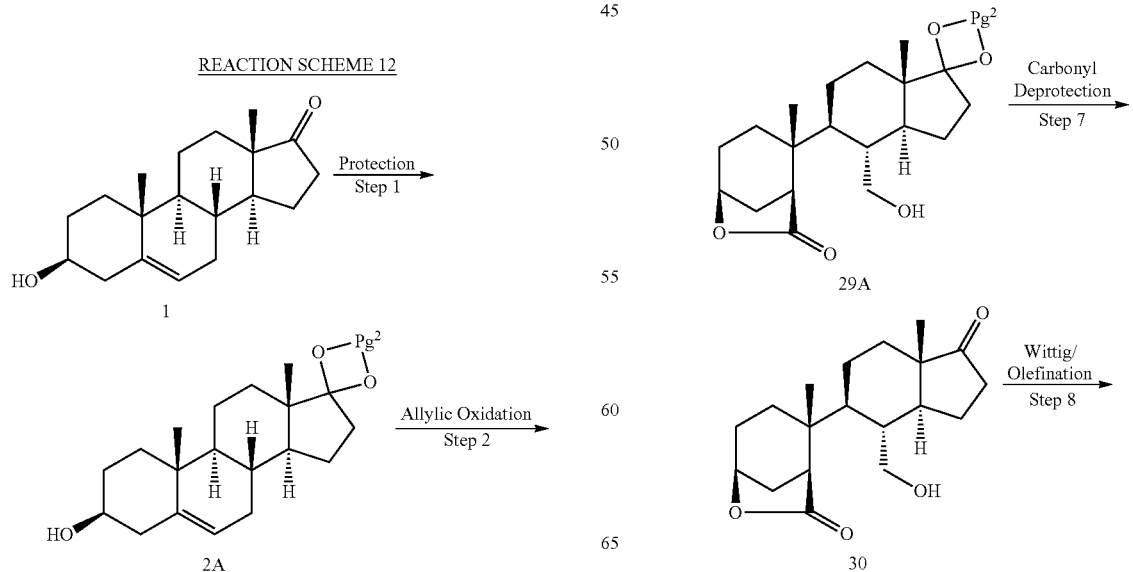

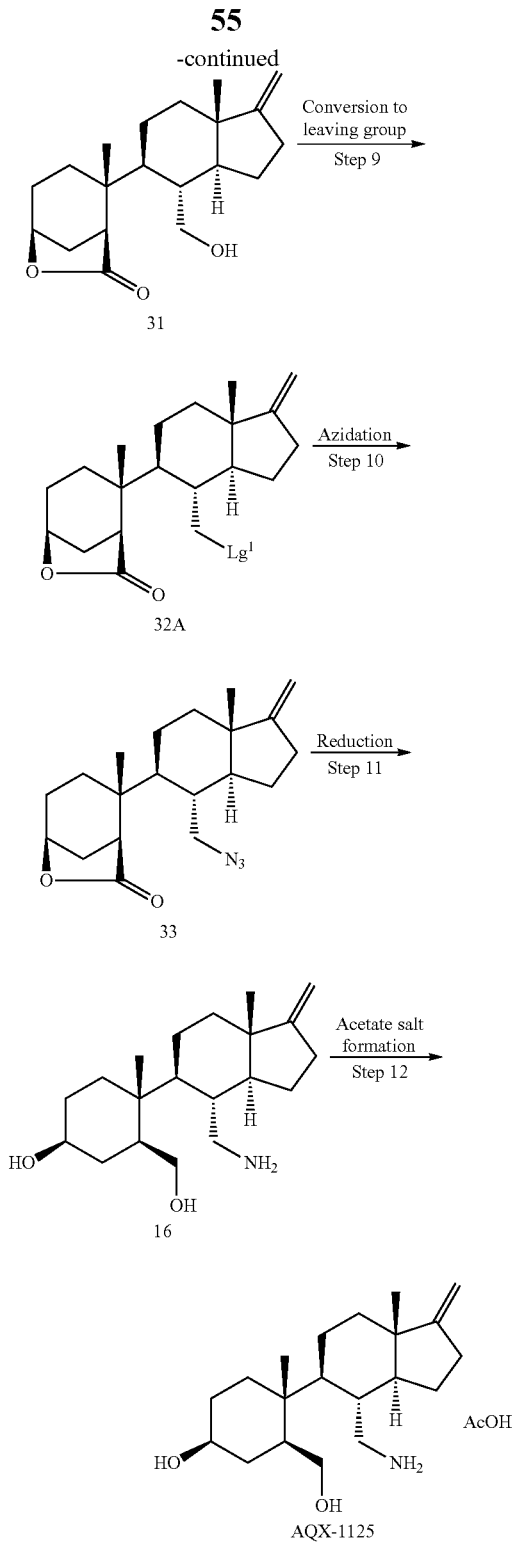

group reagent, such as ethylene glycol in the presence of an acid catalyst, such as camphor sulfonic acid or p-toluene sulfonic acid.

Compound 2A is then treated under allylic oxidation conditions to provide Compound 48A, such as treating Compound 2 in an organic solvent, such as dichloromethane, acetonitrile and pyridine, with a peroxide, such as tert-butyl hydroperoxide in the presence of a metal catalyst, such as copper iodide.

Compound 48A is then treated under suitable carbonyl reduction and hydroboration-oxidation conditions to provide Compound 49A, such as treating Compound 48A in a polar aprotic solvent, such as tetrahydrofuran, with a reducing agent, such as borane, and a hydroboration reagent, such as borane in tetrahydrofuran, followed by oxidative work-up using an oxidant, such as sodium perborate.

Compound 49A is then treated under suitable 1,2-diol oxidative carbon-carbon bond cleavage conditions to provide Compound 50A, such as treating Compound 49A in a polar solvent, such as tetrahydrofuran and water, with a suitable oxidizing agent, such as sodium metaperiodate.

Compound 50A is then treated under suitable oxidation conditions to provide Compound 28A, such as treating Compound 50A in a suitable organic solvent, such as dichloromethane, with an oxidizing agent, such as iodine in the presence of a base, such as potassium carbonate.

Compound 28A is then treated under suitable aldehyde reduction conditions to provide Compound 29A, such as treating Compound 28A in a polar protic solvent, such as methanol, with a reducing agent, such as sodium borohydride.

Compound 29A is then treated under suitable carbonyl deprotection conditions to provide Compound 30, such as treating Compound 29A in a polar protic solvent, such as water, with a suitable acid, such as acetic acid.

Compound 30 is then treated under suitable olefination or Wittig reaction conditions to provide Compound 31, such as treating Compound 30 in a suitable organic solvent, such as toluene or tetrahydrofuran, with a ylide generated using a phosphonium salt, such as methyltriphenylphosphonium bromide, and a base, such as potassium tert-butoxide.

Compound 31 is then converted into a suitable leaving group, such as a mesylate, to provide Compound 32A, such as treating Compound 31 in a suitable polar, basic organic solvent, such as pyridine, with an appropriate electrophilic leaving group reagent, such as methanesulphonyl chloride for mesylation.

Compound 32A is then treated under suitable nucleophilic substitution conditions, such as azidation, to provide Compound 33, such as treating Compound 32A in a suitable polar aprotic solvent, such as dimethylformamide, with an appropriate nucleophile, such as sodium azide.

Compound 33 is then treated under suitable lactone and azide reduction conditions to provide Compound 16, such as treating Compound 33 in a polar aprotic solvent, such as tetrahydrofuran, with a reducing agent, such as lithium aluminum hydride.

Compound 16 is then treated under suitable acetic salt formation conditions to provide AQX-1125, such as treating Compound 16 in a polar protic solvent, such as methanol, with glacial acetic, followed by a less polar organic solvent, such as methyl tert-butyl ether.

A specific method of preparing AQX-1125, as set forth above in Reaction Scheme 12, is illustrated below in Reaction Scheme 12A:

Compound 1, which is dehydroepiandrosterone, is commercially available or can be made by methods known to one skilled in the art.

In general, AQX-1125 is prepared as described above in Reaction Scheme 12 by first treating Compound 1 under suitable carbonyl protection conditions to provide Compound 2A, such as treating Compound 1 in an organic solvent, such as cyclohexane, with a carbonyl protecting REACTION SCHEME 12A
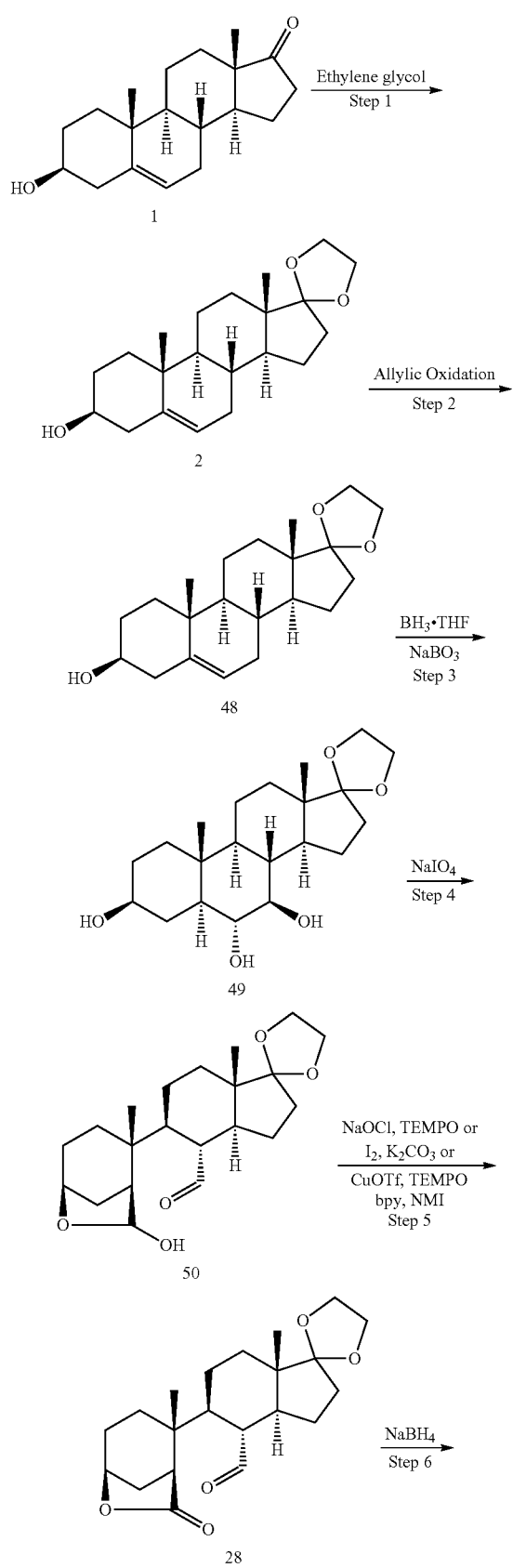
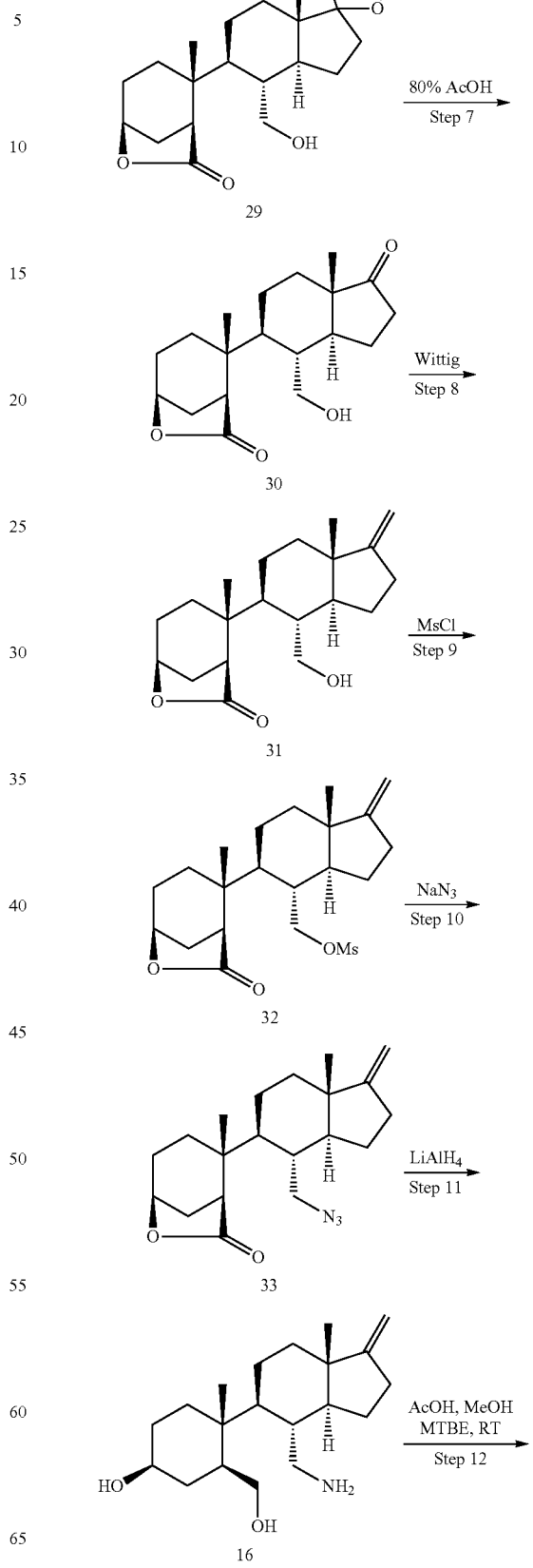

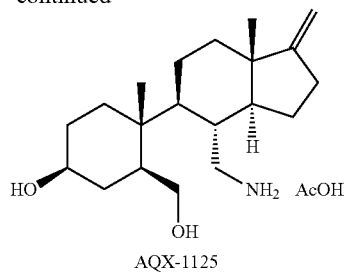

AQX-1125

The following Synthetic Examples, which are directed to the steps and products as set forth above in Reaction Scheme 12A, are provided as a guide to assist in the practice of the invention, and are not intended as a limitation on the scope of the invention.

Synthetic Example 17

Step 1: Conversion of Compound 1 to Compound 2

A. To a solution of (3S,8R,9S,10R,13S,14S)-3-hydroxy-10,13-dimethyl-1,2,3,4,7,8,9,10,11,12,13,14,15,16-tetradecahydro-17H-cyclopenta[a]phenanthren-17-one (Compound 1, 50.0 g, 173.3 mmol, 1.0 eq.) in cyclohexane (500 mL) in a dry 1000 mL RB flask fitted with a Dean-Stark apparatus was added p-toluene sulphonic acid (800 mg, 3.43 mmol) followed by ethylene glycol (54.0 g, 866.7 mmol) at room temperature (RT). The reaction mass was heated to 85° C. under reflux for 16 hours for azeotropic removal of water. The reaction mixture was monitored by HPLC analysis.

B. After completion of reaction, the reaction mixture cooled to RT. Cyclohexane was removed under vacuum below 50° C. and a sodium bicarbonate solution (10% (aq), 150 mL) was added followed by dichloromethane (500 mL) (Note: The sequence of addition was critical to avoid reversal of reaction under acidic conditions). The slurry was stirred to get a clear biphasic solution. The layers were separated and the dichloromethane layer was again washed with a sodium bicarbonate solution (10% (aq), 150 mL). The organic layer was washed with a brine solution (200 mL) and dried ($Na_2SO_4$). The organic layer was evaporated to dryness to afford (3S,8R,9S,10R,13S,14S)-10,13-dimethyl-1,2,3,4,7,8,9,10,11,12,13,14,15,16-tetradecahydrospiro[cyclopenta[a]phenanthrene-17,2'-[1,3]dioxolan]-3-ol as an off-white solid (Compound 2, 50 g, yield 87%). LCMS (Method A): MS m/z: 333.3 [M+1]+, Retention time: 3.25 min, $^1$H NMR: 400 MHz, DMSO-d6: δ 5.27 (d, J=3.2 Hz, 1H), 4.61-4.60 (m, 1H), 3.84-3.77 (m, 4H), 3.28-3.26 (m, 1H), 2.15-2.09 (m, 2H), 1.97-1.75 (m, 2H), 1.70-1.59 (m, 3H), 1.56-1.46 (m, 4H), 1.42-1.31 (m, 5H), 1.22-1.19 (m, 1H), 1.01-0.95 (m, 2H), 0.97 (s, 3H), 0.79 (s, 3H).

Synthetic Example 18

Step 2: Conversion of Compound 2 to Compound 48

A. To a solution of (3S,9S,10R,13S,14S)-10,13-dimethyl-1,2,3,4,7,8,9,10,11,12,13,14,15,16-tetradecahydrospiro[cyclopenta(a)phenanthrene-17,2'-[1,3]dioxolan]-3-ol (Compound 2, 40 g, 121 mmol, 1.0 eq., from Synthetic Example 17) in dichloromethane/acetonitrile (400 mL, 1:1) was added pyridine (40 mL) at 20° C. A copper iodide solution (145 mg, 7.8 mmol, 0.02 eq., dissolved in pyridine/acetoni- trile (1:2, 15 mL) and a TBHP solution (70% (aq), 165 mL, 1210 mmol, 10 eq.) were added to reaction mixture simultaneously at 20-25° C. for 1 h. After completion of addition, the reaction mixture heated to 45° C. for 3 h. The reaction mixture was monitored by LCMS which showed absence of starting material.

B. The reaction mixture was cooled to 20° C. and then a sodium thiosulfate solution (33% (aq), 400 mL) was added. The organic layer was separated and the aqueous layer washed with dichloromethane (200 mL). The combined organic layers were washed with a sodium thiosulfate solution (10% (aq), 200 mL) followed by a brine solution (200 mL). The organic layer was dried ($Na_2SO_4$) and evaporated to dryness. The crude product was triturated with methanol and the precipitated solids were collected by filtration to afford (3S,8R,9S,10R,13S,14S)-3-hydroxy-10,13-dimethyl-1,3,4,8,9,10,11,12,13,14,15,16-dodecahydrospiro[cyclopenta[a]phenanthrene-17,2'-[1,3]dioxolan]-7(2H)-one as white solid (Compound 48, 25 g, yield 60%). LCMS (Method A): MS m/z: 347.2 [M+1]+, Retention time: 2.66 min. HPLC (Method B): Retention time: 2.66 min, purity: 99.83 area %, $^1$H NMR: 400 MHz, DMSO-d6: δ 5.60 (s, 1H), 4.92 (d, J=6.4 Hz, 1H), 3.84-3.77 (m, 4H), 3.41-3.31 (m, 1H), 2.38-2.24 (m, 3H), 1.88-1.83 (m, 2H), 1.72-1.56 (m, 5H), 1.53-1.34 (m, 5H), 1.17-1.10 (m, 2H), 1.15 (s, 3H), 0.81 (s, 3H).

Synthetic Example 19

Step 3: Conversion of Compound 48 to Compound 49

A. To a stirred solution of (3S,8R,9S,10R,13S,14S)-3-hydroxy-10,13-dimethyl-1,3,4,8,9,10,11,12,13,14,15,16-dodecahydrospiro[cyclopenta[a]phenanthrene-17,2'-[1,3]dioxolan]-7(2H)-one (Compound 48, 25 g, 72.2 mmol, 1.0 eq., from Synthetic Example 18) in THF at −5° C. under nitrogen atmosphere and was added solution of $BH_3$ in THF (1.0 M, 144 mL, 164.4 mmol, 2 eq.). The reaction mixture was stirred for overnight by slowly raising the temperature to RT. Completion of the reaction was confirmed by LCMS. After completion, the reaction mixture was quenched with cold water (25 mL) at 0° C. and stirred for another 1 h. Sodium perborate tetrahydrate (22.35 g, 145 mmol, 2.0 eq.) was added to the reaction mixture as a suspension in water (100 mL) and stirred for 5 h at 20-25° C.

B. After completion of reaction as monitored by TLC (19:1 dichloromethane:methanol, $R_f$=0.3, $KMnO_4$ stain), the reaction mixture was filtered to remove inorganic solids. The organic layer was separated and aqueous layer washed with ethyl acetate (2×100 mL). The combined organic layer was dried ($Na_2SO_4$), evaporated to dryness to afford (3S,5S,6R,7R,8R,9S,10R,13S,14S)-10,13-dimethylhexadecahydrospiro[cyclopenta[a]phenanthrene-17,2'-[1,3]dioxolane]-3,6,7-triol as white solid (Compound 49, 25 g, yield 94.5%). LCMS (Method A): MS m/z: 367.5 [M+1]+, Retention time: 2.27 min.

Synthetic Example 20

Step 4: Conversion of Compound 49 to Compound 50

A. To a solution of (3S,5S,6R,7R,8R,9S,10R,13S,14S)-10,13-dimethylhexadecahydrospiro[cyclopenta[a]phenanthrene-17,2'-[1,3]dioxolane]-3,6,7-triol (Compound 49, 16 g, 43.65 mmol, from Synthetic Example 19) in tetrahydrofuran (112 mL) and water (48 mL) was added portion-wise sodium metaperiodate (18.6 g, 87.31 mmol) and the reaction stirred for 1 h at RT. Completion of the reaction was monitored by TLC (1:1 hexanes:ethyl acetate, $R_f$=0.4, KMnO$_4$ stain).

B. The reaction mixture was concentrated by rotary evaporation and the crude residue obtained was partitioned between ethyl acetate (50 mL) and water (50 mL). The aqueous layer was extracted with ethyl acetate (2×50 mL). The combined organic layers were washed with brine (25 mL), dried (Na$_2$SO$_4$) and concentrated by rotary evaporation. The residue was purified using chromatography on silica gel (25% ethyl acetate in hexanes) to afford (3aS,4R,5S,7aS)-5-((1S,2R,5S,7R)-7-hydroxy-2-methyl-6-oxabicyclo[3.2.1]octan-2-yl)-7a-methyloctahydrospiro[indene-1,2'-[1,3]dioxolane]-4-carbaldehyde (Compound 50, 9 g, 56%) as an off-white solid. $^1$H NMR: 400 MHz, DMSO-d6: δ 9.48 (d, J=5.60 Hz, 1H), 5.92 (d, J=5.60 Hz, 1H), 5.19 (d, J=5.60 Hz, 1H), 4.24 (t, J=4.80 Hz, 1H), 3.87-3.78 (m, 3H), 3.32 (s, 1H), 2.26-2.16 (m, 2H), 1.94-1.84 (m, 3H), 1.73-1.55 (m, 6H), 1.39-1.30 (m, 5H), 1.29-1.24 (m, 2H), 0.90 (s, 3H), 0.76 (s, 3H).

Synthetic Example 21

Step 5: Conversion of Compound 50 to Compound 28 Using Iodine

A. To a solution of (3aS,4R,5S,7aS)-5-((1S,2R,5S,7R)-7-hydroxy-2-methyl-6-oxabicyclo[3.2.1]octan-2-yl)-7a-methyloctahydrospiro[indene-1,2'-[1,3]dioxolane]-4-carbaldehyde (Compound 50, 9 g, 24.69 mmol, from Synthetic Example 20) in dry dichloromethane (90 mL) in a dry 500 mL RB flask was added potassium carbonate (17 g, 123.4 mmol) and Iodine (15.6 g, 123.4 mmol) and the reaction stirred using a magnetic stirrer for 48 h at RT. Completion of the reaction was monitored by TLC analysis (1:1 hexanes:ethyl acetate, $R_f$=0.6, KMnO$_4$ stain).

B. The reaction mixture was partitioned between dichloromethane (50 mL) and water (100 mL). The aqueous layer was extracted with dichloromethane (2×50 mL). The combined organic layers were washed with a sodium thiosulphate solution (saturated (aq.), 50 mL) and brine (25 mL), dried (Na$_2$SO$_4$) and concentrated by rotary evaporation. The crude residue was directly taken to the next step without further purification to afford (3aS,4R,5S,7aS)-7a-methyl-5-((1S,2R,5S)-2-methyl-7-oxo-6-oxabicyclo[3.2.1]octan-2-yl)octahydrospiro[indene-1,2'-[1,3]dioxolane]-4-carbaldehyde (Compound 28, 7.5 g, crude) as a pale brown solid. LCMS (Method A): MS m/z: 363.3 [M+1]$^+$, Retention time: 2.77 min, Purity: 99.49 area %.

Synthetic Example 22

Step 6: Conversion of Compound 28 to Compound 29

A. To a solution of (3aS,4R,5S,7aS)-7a-methyl-5-((1S,2R,5S)-2-methyl-7-oxo-6-oxabicyclo[3.2.1]octan-2-yl)octahydrospiro[indene-1,2'-[1,3]dioxolane]-4-carbaldehyde (Compound 28, 4 g, crude, ~11 mmol, from Synthetic Example 21) in methanol (40 mL) in a dry 100 mL RB flask was added sodium borohydride (626 mg, 16.55 mmol) and the reaction stirred using a magnetic stirrer for 1 h at RT. Completion of the reaction was monitored by TLC analysis (1:1 hexanes:ethyl acetate, $R_f$=0.35, KMnO$_4$ stain).

B. The reaction mixture was concentrated by rotary evaporation and the crude residue obtained was partitioned between ethyl acetate (25 mL) and water (25 mL). The aqueous layer was extracted with ethyl acetate (2×20 mL). The combined organic layers were washed with brine (25 mL), dried (Na$_2$SO$_4$) and concentrated by rotary evaporation. The residue was purified using chromatography on silica gel (30% ethyl acetate in hexanes) to afford (1S,2R,5S)-2-((3aS,4R,5S,7aS)-4-(hydroxymethyl)-7a-methyloctahydrospiro[indene-1,2'-[1,3]dioxolan]-5-yl)-2-methyl-6-oxabicyclo[3.2.1]octan-7-one (Compound 29, 2.8 g, Yield 82%) as a white solid. LCMS (Method A): MS m/z: 365.2 [M+1]$^+$, Retention time: 2.67 min, Purity: 85.50 area %, $^1$H NMR: 400 MHz, DMSO-d6: δ 4.71-4.63 (m, 1H), 4.32-4.16 (m, 1H), 3.86-3.75 (m, 4H), 3.56 (s, 1H), 2.65 (d, J=6.80 Hz, 1H), 2.36 (d, J=16.80 Hz, 1H), 2.20-2.06 (m, 1H), 1.90-1.83 (m, 3H), 1.69-1.56 (m, 7H), 1.42-1.11 (m, 6H), 0.96 (s, 3H), 0.75 (s, 3H).

Synthetic Example 23

Step 7: Conversion of Compound 29 to Compound 30

A. A solution of (1S,2R,5S)-2-((3aS,4R,5S,7aS)-4-(hydroxymethyl)-7a-methyloctahydrospiro[indene-1,2'-[1,3]dioxolan]-5-yl)-2-methyl-6-oxabicyclo[3.2.1]octan-7-one (Compound 29, 2.8 g, 7.68 mmol, from Synthetic Example 22) in acetic acid (22.4 mL) and water (5.6 mL) in a 100 mL RB flask fitted with a reflux condenser was stirred using a magnetic stirrer at 60° C. for 1 h. Completion of the reaction was monitored by TLC analysis (1:1 hexanes:ethyl acetate, $R_f$=0.3, KMnO$_4$ stain).

B. The reaction mixture was concentrated by rotary evaporation and the crude residue obtained was partitioned between ethyl acetate (25 mL) and water (25 mL). The aqueous layer was extracted with ethyl acetate (2×20 mL). The combined organic layers were washed with a sodium bicarbonate solution (10% (aq), 20 mL) and brine (20 mL), dried (Na$_2$SO$_4$) and concentrated by rotary evaporation. The residue was purified by using chromatography on silica gel (40% ethyl acetate in hexanes) to afford (1S,2R,5S)-2-((3aS,4R,5S,7aS)-4-(hydroxymethyl)-7a-methyl-1-oxooctahydro-1H-inden-5-yl)-2-methyl-6-oxabicyclo[3.2.1]octan-7-one (Compound 30, 2 g, Yield 81%) as a white solid. LCMS (Method A): MS m/z: 321.2 [M+1]$^+$, Retention time: 2.37 min, Purity: 99.47 area %, $^1$H NMR: 400 MHz, DMSO-d6: δ 4.72 (t, J=6.00 Hz, 1H), 4.42 (t, J=5.20 Hz, 1H), 3.72-3.64 (m, 1H), 3.47-3.53 (m, 1H), 2.66 (d, J=7.20 Hz, 1H), 2.39-2.33 (m, 2H), 2.13-1.87 (m, 5H), 1.71-1.12 (m, 10H), 0.97 (s, 3H), 0.77 (s, 3H).

Synthetic Example 24

Step 8: Conversion of Compound 30 to Compound 31

A. A mixture of methyltriphenylphosphonium bromide (8.91 g, 24.96 mmol) and potassium tert-butoxide (2.8 g, 24.96 mmol) in anhydrous tetrahydrofuran (10 mL) in a dry 100 mL RB flask was stirred using a magnetic stirrer for 1 h at 0° C. then stirred at 30° C. for 1 h. The mixture was then re-cooled to 0° C. and a solution of (1S,2R,5S)-2-((3aS,4R,5S,7aS)-4-(hydroxymethyl)-7a-methyl-1-oxooctahydro-1H-inden-5-yl)-2-methyl-6-oxabicyclo[3.2.1]octan-7-one (Compound 30, 2 g, 6.24 mmol, from Synthetic Example 23) in tetrahydrofuran (10 mL) was added drop-wise via dropping funnel into the reaction mixture at 0° C. The reaction was warmed to RT and stirred for 16 h. Completion of the reaction was monitored by TLC analysis (1:1 hexanes: ethyl acetate, $R_f$=0.35, $KMnO_4$ stain and UV).

B. The reaction mixture was concentrated by rotary evaporation and the crude residue obtained was partitioned between ethyl acetate (25 mL) and water (25 mL). The aqueous layer was extracted with ethyl acetate (2×20 mL). The combined organic layers were washed with brine (20 mL), dried ($Na_2SO_4$) and concentrated by rotary evaporation. The residue was purified by using chromatography on silica gel (35-40% ethyl acetate in hexanes) to afford (1S,2R,5S)-2-((3aS,4R,5S,7aS)-4-(hydroxymethyl)-7a-methyl-1-methyleneoctahydro-1H-inden-5-yl)-2-methyl-6-oxabicyclo[3.2.1]octan-7-one (Compound 31, 700 mg, Yield 35%) as a white solid. The reaction mixture was purified three times by silica gel flash column chromatography to remove closely eluting triphenylphosphine oxide from the required product. LCMS (Method A): MS m/z: 319.2 [M+1]$^+$, Retention time: 2.93 min, Purity: 99.98 area %, $^1$H NMR: 400 MHz, DMSO-d6: δ 4.62 (s, 2H), 4.57 (d, J=4.40 Hz, 1H), 4.24-4.18 (m, 1H), 3.96 (d, J=11.60 Hz, 1H), 3.33 (s, 1H), 3.05 (t, J=8.40 Hz, 1H), 2.45-2.37 (m, 1H), 2.23-2.14 (m, 1H), 2.13-1.98 (m, 1H), 1.93-1.76 (m, 3H), 1.66-1.57 (m, 4H), 1.40-1.31 (m, 2H), 1.21-1.15 (m, 4H), 1.12-1.01 (m, 1H), 0.77 (s, 3H), 0.76 (s, 3H).

Synthetic Example 25

Step 9: Conversion of Compound 31 to Compound 32

A. To a solution of (1S,2R,5S)-2-((3aS,4R,5S,7aS)-4-(hydroxymethyl)-7a-methyl-1-methyleneoctahydro-1H-inden-5-yl)-2-methyl-6-oxabicyclo[3.2.1]octan-7-one (Compound 31, 700 mg, 2.19 mmol, from Synthetic Example 24) in anhydrous pyridine (1 mL) in a dry 25 mL RB flask was added methanesulfonyl chloride (0.22 mL, 3.29 mmol) at 0° C. The reaction mixture was stirred using a magnetic stirrer for 1 h at RT. Completion of the reaction was monitored by TLC analysis (1:1 hexanes:ethyl acetate, $R_f$=0.6, $KMnO_4$ stain).

B. The reaction mixture was added to a solution of sodium bicarbonate (10% (aq), 5 mL) and the resulting solid was filtered. The residue was further washed with water (5 mL), diethyl ether (5 mL) and dried under line vacuum to afford ((3aS,4R,5S,7aS)-7a-methyl-5-((1S,2R,5S)-2-methyl-7-oxo-6-oxabicyclo[3.2.1]octan-2-yl)-1-methyleneoctahydro-1H-inden-4-yl)methyl methanesulfonate (Compound 32, 650 mg, Yield 74%) as an off white solid. $^1$H NMR: 400 MHz, DMSO-d6: δ 4.61 (s, 2H), 4.56-4.50 (m, 1H), 4.21-4.15 (m, 1H), 3.99 (d, J=12.80 Hz, 1H), 3.27-3.23 (m, 1H), 3.16 (s, 3H), 2.45-2.37 (m, 1H), 2.23-2.14 (m, 1H), 2.01-1.87 (m, 4H), 1.81-1.76 (m, 3H), 1.66-1.61 (m, 1H), 1.59-1.46 (m, 1H), 1.43-1.34 (m, 3H), 1.27-1.08 (m, 3H), 0.85 (s, 3H), 0.77 (s, 3H).

Synthetic Example 26

Step 10: Conversion of Compound 32 to Compound 33

A. To a solution of ((3aS,4R,5S,7aS)-7a-methyl-5-((1S,2R,5S)-2-methyl-7-oxo-6-oxabicyclo[3.2.1]octan-2-yl)-1-methyleneoctahydro-1H-inden-4-yl)methyl methanesulfonate (Compound 32, 650 mg, 1.63 mmol, from Synthetic Example 25) in dry dimethylformamide (5 mL) in a dry 25 ml RB flask fitted with a reflux condenser was added sodium azide (210 mg, 3.27 mmol). The reaction mixture was stirred using a magnetic stirrer at 70° C. for 16 h. Completion of the reaction was monitored by TLC analysis (1:1 hexanes:ethyl acetate, $R_f$=0.4, $KMnO_4$ stain and UV).

B. The reaction mixture was concentrated by rotary evaporation and the crude residue obtained was partitioned between ethyl acetate (15 mL) and water (15 mL). The aqueous layer was extracted with ethyl acetate (2×10 mL). The combined organic layers were washed with brine (20 mL), dried ($Na_2SO_4$) and concentrated by rotary evaporation. The residue was purified using chromatography on silica gel (25-30% ethyl acetate in hexanes) to afford (1S,2R,5S)-2-((3aS,4R,5S,7aS)-4-(azidomethyl)-7a-methyl-1-methyleneoctahydro-1H-inden-5-yl)-2-methyl-6-oxabicyclo[3.2.1]octan-7-one (Compound 33, 450 mg, Yield 80%) as a white solid. LCMS (Method A): MS m/z: 344.3 [M+1]$^+$, Retention time: 3.52 min, Purity: 99.24 area %, $^1$H NMR: 400 MHz, DMSO-d6: δ 4.63 (s, 2H), 4.30-4.25 (m, 1H), 4.09 (t, J=2.80 Hz, 1H), 3.97 (d, J=12.80 Hz, 1H), 3.09 (dd, J=4.00, 12.00 Hz, 1H), 2.45-2.37 (m, 1H), 2.22-2.20 (m, 1H), 2.04-2.03 (m, 1H), 1.83-1.72 (m, 4H), 1.63-1.61 (m, 4H), 1.40-1.26 (m, 4H), 1.20-1.09 (m, 2H), 0.82 (s, 3H), 0.78 (s, 3H).

Synthetic Example 27

Step 11: Conversion of Compound 33 to Compound 16 and Preparation of AQX-1125

A. To a solution of (1S,2R,5S)-2-((3aS,4R,5S,7aS)-4-(azidomethyl)-7a-methyl-1-methyleneoctahydro-1H-inden-5-yl)-2-methyl-6-oxabicyclo[3.2.1]octan-7-one (Compound 33, 450 mg, 1.31 mmol, from Synthetic Example 26) in anhydrous tetrahydrofuran (4 mL) in a dry 25 mL RB flask was added a solution of lithium aluminium hydride in THF (1 M, 5.2 ml, 5.2 mmol). The reaction mixture was stirred using a magnetic stirrer for 1 h at 0° C. to RT. Completion of the reaction was monitored by TLC analysis (4:1 dichloromethane:methanol, $R_f$=0.2, $KMnO_4$ stain and UV).

B. The reaction mixture was quenched by the drop-wise addition of an aqueous solution of sodium sulfate (1.0 g in 5 mL of $H_2O$), filtered through CELITE™ bed on a glass-fritted funnel and concentrated by rotary evaporation to get a crude residue, which was further purified by chromatography on silica gel (20-25% methanol in dichloromethane) to afford (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexan-1-ol (Compound 16, 130 mg, Yield 28%) as a white solid. LCMS (Method A): MS m/z: 322.5 [M+1]$^+$, Retention time: 2.35 min, Purity: 98.15 area %, $^1$H NMR: 400 MHz, DMSO-d6: δ 4.59 (s, 2H), 4.21 (br s, 1H), 4.07 (s, 1H), 3.52 (d, J=9.20 Hz, 1H), 3.54-3.52 (m, 1H), 3.17-3.12 (m, 3H), 2.87 (br s, 1H), 2.45-2.39 (m, 1H), 2.17-2.10 (m, 2H), 1.81-1.08 (m, 16H), 0.97 (s, 3H), 0.77 (s, 3H).

C. AQX-1125 was prepared from Compound 16 in the same manner as described above in Synthetic Example 16.

AQX-1125 may also be prepared according to the method disclosed below in Reaction Scheme 13 wherein Lg$^1$ represents an appropriate leaving group:

REACTION SCHEME 13

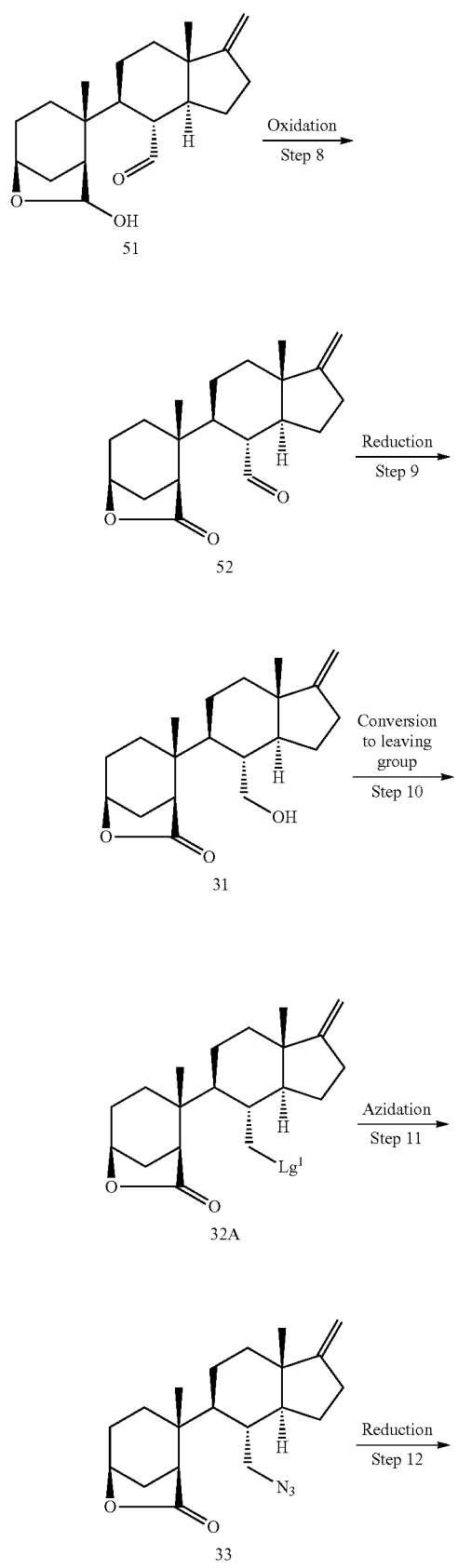

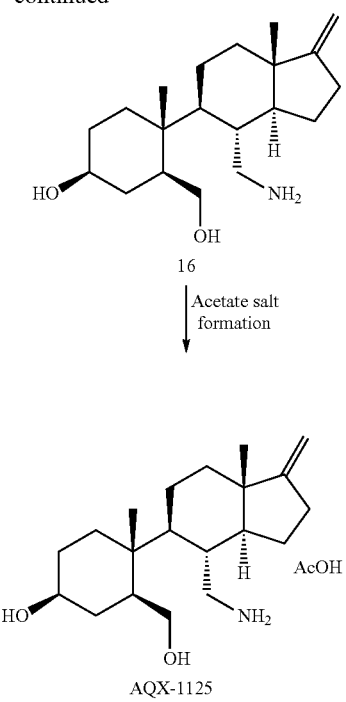

In general, AQX-1125 is prepared as described above in Reaction Scheme 13 by first treating Compound 51 under suitable oxidation conditions to provide Compound 52, such as treating Compound 51 in a suitable organic solvent, such as toluene, with an oxidizing agent, such as silver carbonate.

Compound 52 is then treated under suitable aldehyde reduction conditions to provide Compound 31, such as treating Compound 52 in a polar solvent, such as methanol and tetrahydrofuran, with a reducing agent, such as sodium borohydride.

Compound 31 is then converted into a suitable leaving group, such as a mesylate, to provide Compound 32A, such as treating Compound 31 in a suitable polar, basic organic solvent, such as pyridine, with an appropriate electrophilic leaving group reagent, such as methanesulphonyl chloride for mesylation.

Compound 32A is then treated under suitable nucleophilic substitution conditions, such as azidation, to provide Compound 33, such as treating Compound 32A in a suitable polar aprotic solvent, such as dimethylformamide, with an appropriate nucleophile, such as sodium azide.

Compound 33 is then treated under suitable lactone and azide reduction conditions to provide Compound 16, such as treating Compound 33 in a polar aprotic solvent, such as tetrahydrofuran, with a reducing agent, such as lithium aluminum hydride.

Compound 16 may then be treated under suitable acetic salt formation conditions to provide AQX-1125, such as treating Compound 16 in a polar protic solvent, such as methanol, with glacial acetic, followed by a less polar organic solvent, such as methyl tert-butyl ether.

A specific method of preparing AQX-1125, as set forth above in Reaction Scheme 13, is illustrated below in Reaction Scheme 13A:

REACTION SCHEME 13A

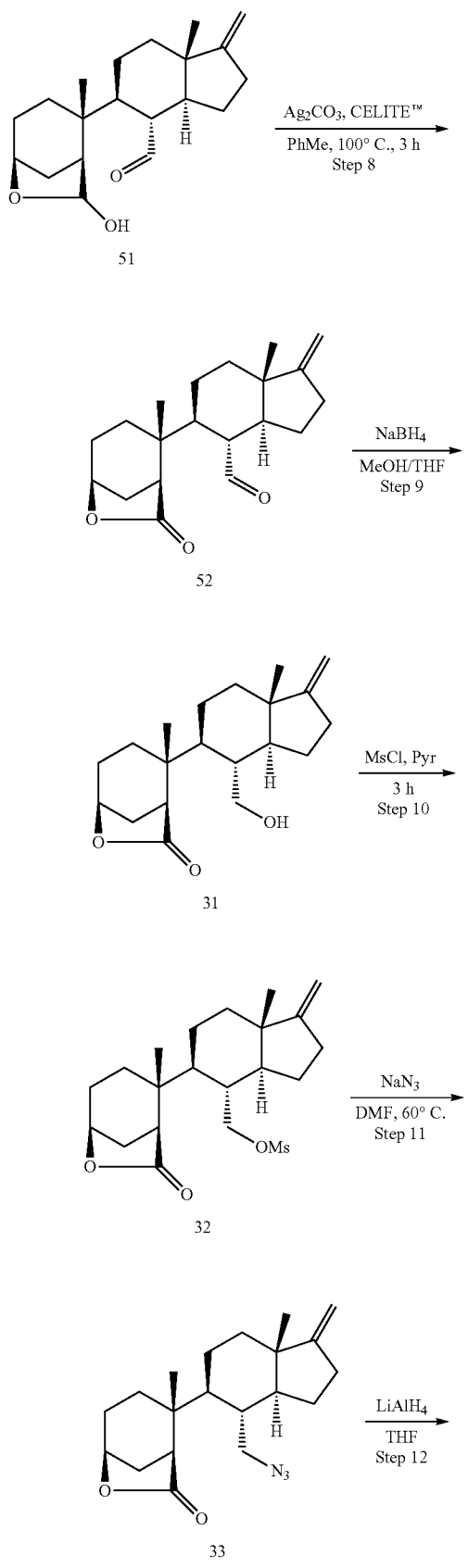

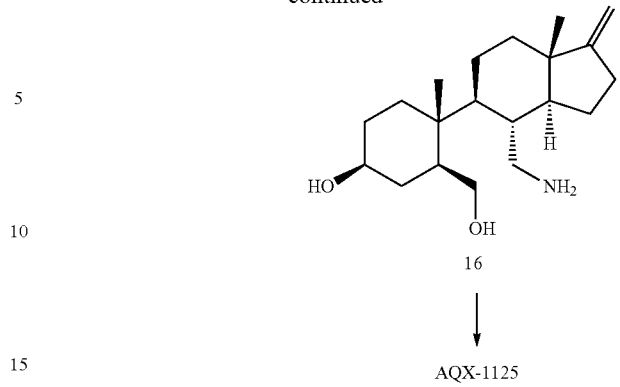

AQX-1125

The following Synthetic Examples, which are directed to the steps and products as set forth above in Reaction Scheme 13A, are provided as a guide to assist in the practice of the invention, and are not intended as a limitation on the scope of the invention.

Synthetic Example 28

Step 8: Conversion of Compound 51 to Compound 52

A. To a stirred solution of (3aS,4R,5S,7aS)-5-((1S,2R,5S,7R)-7-hydroxy-2-methyl-6-oxabicyclo[3.2.1]octan-2-yl)-7a-methyl-1-methyleneoctahydro-1H-indene-4-carbaldehyde (Compound 51, 14 g, 0.0440 mol, 1 eq., from Synthetic Example 38) in toluene (420 mL, 30 V) was added CELITE™ (14 g) and silver carbonate (12.13 g, 0.0440 mol, 1 eq). The resulting suspension was heated to 100° C. and stirred for 3 h. The progress of the reaction was monitored by TLC (7:3 hexanes:ethyl acetate, $R_f$=0.4, $KMnO_4$ stain).

B. After completion, the reaction mixture was cooled to room temperature and filtered through CELITE™. The CELITE™ was further washed with dichloromethane (500 mL). The combined filtrates were concentrated to dryness to afford (3aS,4R,5S,7aS)-7a-methyl-5-((1S,2R,5S)-2-methyl-7-oxo-6-oxabicyclo[3.2.1]octan-2-yl)-1-methyleneoctahydro-1H-indene-4-carbaldehyde (Compound 52, 13 g, yield 93.5%) as an off-white solid. LCMS (Method A): MS m/z: 317.3 [M+1], Retention time: 3.08 min, Purity 99.6 area %.

Synthetic Example 29

Step 9: Conversion of Compound 52 to Compound 31

A. To a solution of (3aS,4R,5S,7aS)-7a-methyl-5-((1S,2R,5S)-2-methyl-7-oxo-6-oxabicyclo[3.2.1]octan-2-yl)-1-methyleneoctahydro-1H-indene-4-carbaldehyde (Compound 52, 3 g, 9 mmol, from Synthetic Example 28) in tetrahydrofuran/methanol (10 V, 30 mL, 7:3) in a dry 100 mL RB flask was added sodium borohydride (717 mg, 18 mmol) at 10° C. under a nitrogen atmosphere. The reaction was stirred for 1 h at room temperature. Completion of the reaction was confirmed by TLC analysis (1:1 hexanes:ethyl acetate, $R_f$=0.35, $KMnO_4$ stain).

B. After completion, the reaction mixture was concentrated by rotary evaporation and the crude mass was partitioned between ethyl acetate (25 mL) and water (25 mL). The layers were separated. The aqueous layer was extracted with ethyl acetate (2×20 mL). The combined organic layers were washed with brine (25 mL), dried (Na$_2$SO$_4$) and concentrated to dryness to afford (1S,2R,5S)-2-((3aS,4R,5S,7aS)-4-(hydroxymethyl)-7a-methyl-1-methyleneoctahydro-1H-inden-5-yl)-2-methyl-6-oxabicyclo[3.2.1]octan-7-one (Compound 31, 3.0 g, Yield 99%) as a white gummy solid and used without further purification in the next step. LCMS (Method A): MS m/z: 319.2 [M+1], Retention time: 3.06 min, Purity 99.5 area %.

Synthetic Example 30

Step 10: Conversion of Compound 31 to Compound 32

A. To a solution of (1S,2R,5S)-2-((3aS,4R,5S,7aS)-4-(hydroxymethyl)-7a-methyl-1-methyleneoctahydro-1H-inden-5-yl)-2-methyl-6-oxabicyclo[3.2.1]octan-7-one (Compound 31, 3 g, 9.4 mmol, 1.0 eq., from Synthetic Example 29) in pyridine (30 mL, 10 V) was added methanesulfonyl chloride (1.1 ml, 14 mmol, 1.5 eq.) at 0° C. under a nitrogen atmosphere. The reaction mixture was stirred at room temperature for 3 h. Completion of reaction was confirmed by TLC analysis (9:1 dichloromethane:methanol, R$_f$=0.4, KMnO$_4$ stain).

B. After completion, the reaction mixture was concentrated by rotary evaporation and crude mass was partitioned between ethyl acetate (25 mL) and water (25 mL). The layers were separated. The aqueous layer was extracted with ethyl acetate (2×20 mL). The combined organic layers were washed with brine (25 mL), dried (Na$_2$SO$_4$) and concentrated to dryness to afford ((3aS,4R,5S,7aS)-7a-methyl-5-((1S,2R,5S)-2-methyl-7-oxo-6-oxabicyclo[3.2.1]octan-2-yl)-1-methyleneoctahydro-1H-inden-4-yl)methyl methanesulfonate (Compound 32, 3.6 g, Yield 96.5%) as a pale brown solid that was used without further purification in the next step. LCMS (Method A): MS m/z: 414.2 [M+18, H$_2$O adduct], Retention time: 3.12 min, Purity 98.7 area %.

Synthetic Example 31

Step 11: Conversion of Compound 32 to Compound 33

A. To a solution of ((3aS,4R,5S,7aS)-7a-methyl-5-((1S,2R,5S)-2-methyl-7-oxo-6-oxabicyclo[3.2.1]octan-2-yl)-1-methyleneoctahydro-1H-inden-4-yl)methyl methanesulfonate (Compound 32, 3.6 g, 9 mmol, 1.0 eq., from Synthetic Example 30) in DMF (36 mL, 10 V) was added sodium azide (1.18 g, 18 mmol, 2.0 eq.) under a nitrogen atmosphere at room temperature. The reaction mixture was heated to 60° C. and stirred for 3 h. Completion of the reaction was confirmed by TLC analysis (1:1 hexanes:ethyl acetate, R$_f$=0.45, KMnO$_4$ stain).

B. After completion, the reaction mixture was cooled to room temperature and partitioned between ethyl acetate (25 mL) and water (25 mL). The layers were separated. The aqueous layer was extracted with ethyl acetate (2×20 mL). The combined organic layers were washed with brine (25 mL), dried (Na$_2$SO$_4$) and concentrated to dryness to afford (1S,2R,5S)-2-((3aS,4R,5S,7aS)-4-(azidomethyl)-7a-methyl-1-methyleneoctahydro-1H-inden-5-yl)-2-methyl-6-oxabicyclo[3.2.1]octan-7-one (Compound 33, 3.07 g, Yield 98.7%) as an off-white solid. LCMS (Method A): MS m/z: 344.3 [M+1], Retention time: 3.38 min, Purity 98.1 area %.

Synthetic Example 32

Step 12: Conversion of Compound 33 to Compound 16 and Preparation of AQX-1125

A. To a solution of (1S,2R,5S)-2-((3aS,4R,5S,7aS)-4-(azidomethyl)-7a-methyl-1-methyleneoctahydro-1H-inden-5-yl)-2-methyl-6-oxabicyclo[3.2.1]octan-7-one (Compound 33, 3.07 g, 8.7 mmol, 1.0 eq., from Synthetic Example 31) in THF (30 mL, 10 V) was added a solution of LiAlH$_4$ (13.4 mL, 2.0 M in THF, 26.2 mmol, 3.0 eq.) at 0° C. under a nitrogen atmosphere. The reaction mixture was stirred at room temperature for 3 h. Completion of the reaction was confirmed by LCMS.

B. After completion, the reaction mixture was quenched with saturated aqueous sodium sulphate solution (10 mL) at 0° C. and stirred for 30 min. Inorganic solids were collected by filtration. The filtrate was washed with brine solution (25 mL×2). Organic layers were dried (Na$_2$SO$_4$) and evaporated to dryness to afford (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexan-1-ol (Compound 16, 2.7 g, Yield 96.7%) as a white solid. LCMS (Method A): MS m/z: 322.5 [M+1], Retention time: 2.02 min, Purity 94.8 area %.

C. AQX-1125 may be prepared from Compound 16 in the same manner as described above in Synthetic Example 16.

D. Synthetic Methods 14-15

In addition to the methods disclosed above, the following methods may be utilized in preparing AQX-1125.

AQX-1125 may be prepared according to the method disclosed below in Reaction Scheme 14 wherein Pg$^2$ is a carbonyl protecting group:

REACTION SCHEME 14

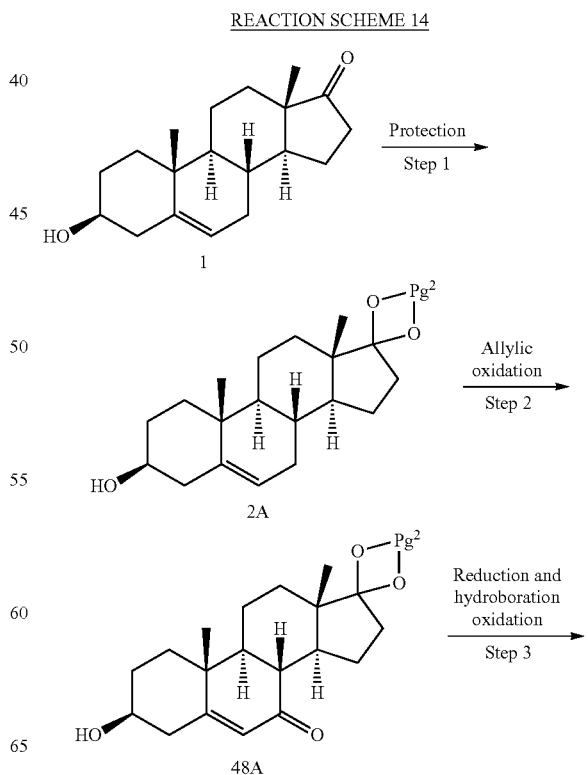

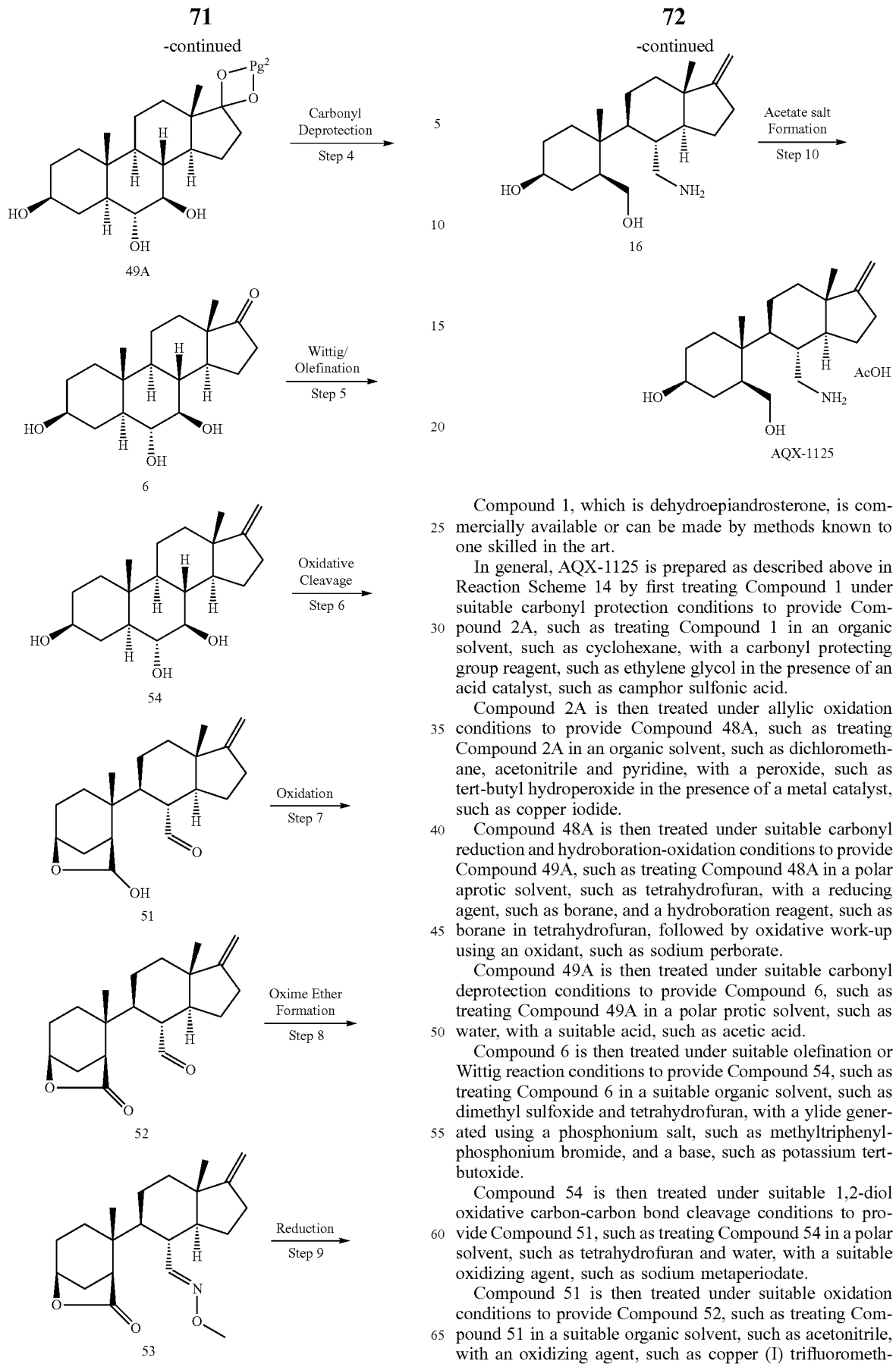

Compound 1, which is dehydroepiandrosterone, is commercially available or can be made by methods known to one skilled in the art.

In general, AQX-1125 is prepared as described above in Reaction Scheme 14 by first treating Compound 1 under suitable carbonyl protection conditions to provide Compound 2A, such as treating Compound 1 in an organic solvent, such as cyclohexane, with a carbonyl protecting group reagent, such as ethylene glycol in the presence of an acid catalyst, such as camphor sulfonic acid.

Compound 2A is then treated under allylic oxidation conditions to provide Compound 48A, such as treating Compound 2A in an organic solvent, such as dichloromethane, acetonitrile and pyridine, with a peroxide, such as tert-butyl hydroperoxide in the presence of a metal catalyst, such as copper iodide.

Compound 48A is then treated under suitable carbonyl reduction and hydroboration-oxidation conditions to provide Compound 49A, such as treating Compound 48A in a polar aprotic solvent, such as tetrahydrofuran, with a reducing agent, such as borane, and a hydroboration reagent, such as borane in tetrahydrofuran, followed by oxidative work-up using an oxidant, such as sodium perborate.

Compound 49A is then treated under suitable carbonyl deprotection conditions to provide Compound 6, such as treating Compound 49A in a polar protic solvent, such as water, with a suitable acid, such as acetic acid.

Compound 6 is then treated under suitable olefination or Wittig reaction conditions to provide Compound 54, such as treating Compound 6 in a suitable organic solvent, such as dimethyl sulfoxide and tetrahydrofuran, with a ylide generated using a phosphonium salt, such as methyltriphenylphosphonium bromide, and a base, such as potassium tert-butoxide.

Compound 54 is then treated under suitable 1,2-diol oxidative carbon-carbon bond cleavage conditions to provide Compound 51, such as treating Compound 54 in a polar solvent, such as tetrahydrofuran and water, with a suitable oxidizing agent, such as sodium metaperiodate.

Compound 51 is then treated under suitable oxidation conditions to provide Compound 52, such as treating Compound 51 in a suitable organic solvent, such as acetonitrile, with an oxidizing agent, such as copper (I) trifluoromethanesulfonate, and suitable catalyst such as (2,2,6,6-tetramethylpiperidin-1-yl)oxyl and 2,2-bipyridyl and N-methyl-imidazole, and base such as potassium carbonate.

Compound 52 is then treated under suitable oxime or oxime O-ether formation conditions to provide Compound 53, such as treating Compound 52 in a suitable basic organic solvent, such as pyridine, with a suitable reagent, such as O-methyl hydroxylamine hydrochloride.

Compound 53 is then treated under suitable lactone and oxime O-ether reduction conditions to provide Compound 16, such as treating Compound 53 in a polar aprotic solvent, such as tetrahydrofuran, with a reducing agent, such as lithium aluminum hydride.

Compound 16 is then treated under suitable acetic salt formation conditions to provide AQX-1125, such as treating Compound 16 in a polar protic solvent, such as methanol, with glacial acetic, followed by a less polar organic solvent, such as methyl tert-butyl ether.

Compound 16 is then treated under suitable acetic salt formation conditions to provide AQX-1125, such as treating Compound 16 in a polar protic solvent, such as methanol, with glacial acetic, followed by a less polar organic solvent, such as methyl tert-butyl ether.

A specific method of preparing AQX-1125, as set forth above in Reaction Scheme 14, is illustrated below in Reaction Scheme 14A:

REACTION SCHEME 14A

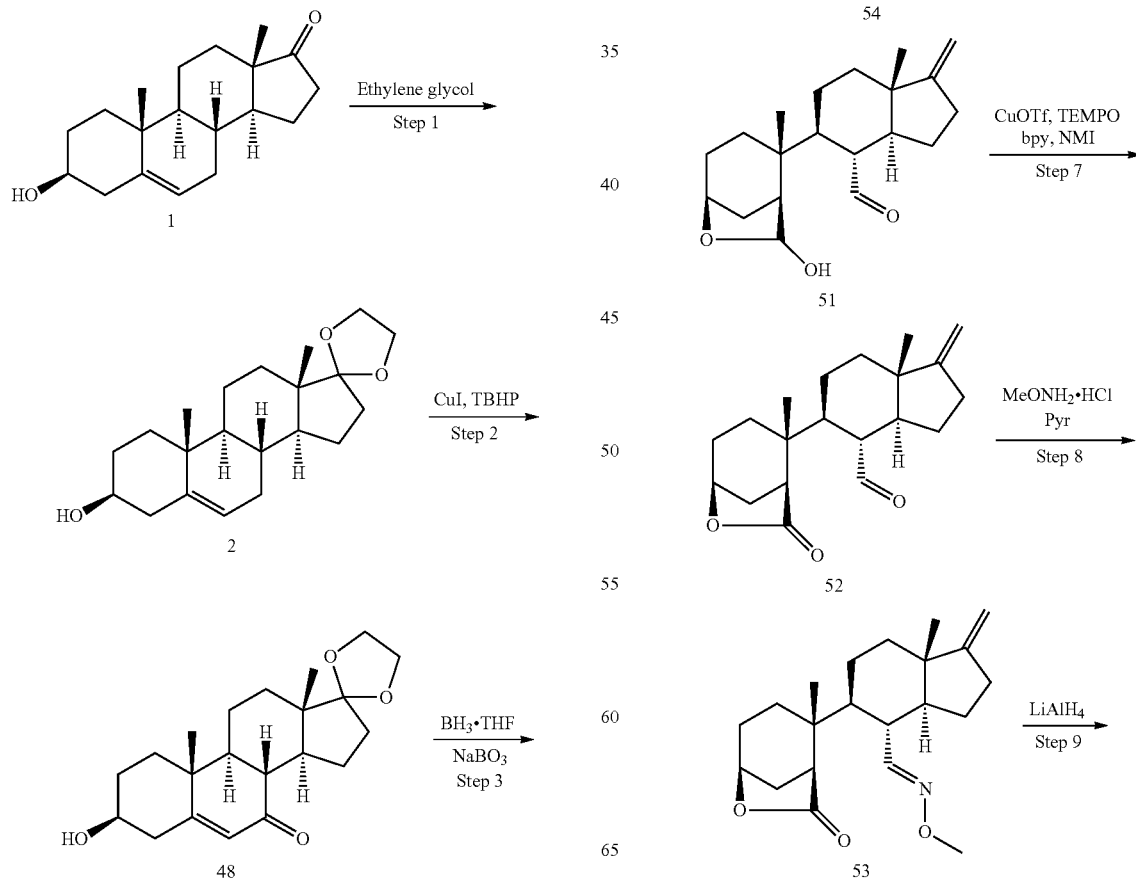
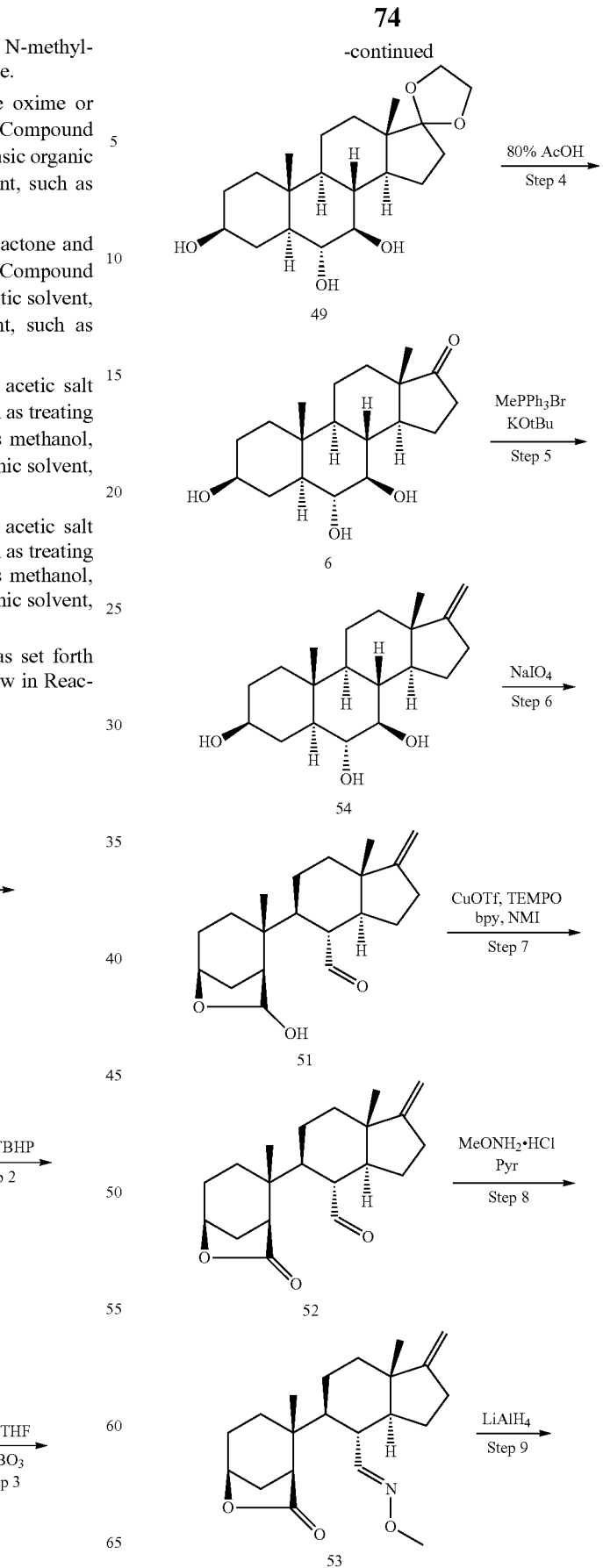

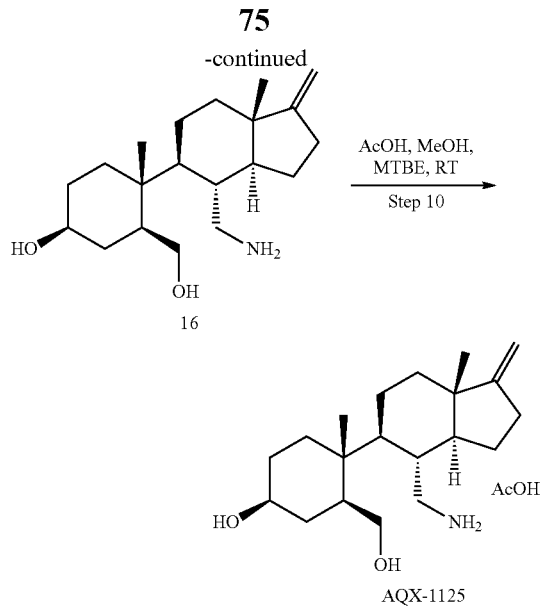

The following Synthetic Examples, which are directed to the steps and products as set forth above in Reaction Scheme 14 are provided as a guide to assist in the practice of the invention, and are not intended as a limitation on the scope of the invention.

Synthetic Example 33

Step 1: Conversion of Compound 1 to Compound 2

A. To a solution of (3S,8R,9S,10R,13S,14S)-3-hydroxy-10,13-dimethyl-1,2,3,4,7,8,9,10,11,12,13,14,15,16-tetradecahydro-17H-cyclopenta[a]phenanthren-17-one (DHEA, Compound 1, 500.0 g, 1.733 mol, 1.0 eq.) in cyclohexane (5 L) in a dry 10 L RB flask fitted with a Dean-Stark apparatus was added (+/−) camphor sulphonic acid (8.0 g, 0.0346 mol) followed by ethylene glycol (538.0 g, 8.667 mol) at room temperature. The reaction mass was heated to 85° C. under reflux for 16 hours for azeotropic removal of water. The reaction mass was monitored by HPLC analysis.

B. After completion of reaction, the reaction mixture was cooled to room temperature (RT). Cyclohexane was removed under vacuum below 50° C. and a solution of 10% sodium bicarbonate (2.5 L) was added followed by dichloromethane (5 L) (Note: The sequence of addition was critical as the ketal can reverse back to starting material in acidic conditions). The slurry was stirred to get a clear biphasic solution. The layers were separated and combined dichloromethane layers were again washed with 10% aqueous sodium bicarbonate solution (2.5 L). The organic layer was washed with brine solution (2.5 L) and dried ($Na_2SO_4$). The organic layer was evaporated to dryness to afford (3S,8R,9S,10R,13S,14S)-10,13-dimethyl-1,2,3,4,7,8,9,10,11,12,13,14,15,16-tetradecahydrospiro[cyclopenta[a]phenanthrene-17,2'-[1,3]dioxolan]-3-ol as white solid (Compound 2, 561 g, yield 97%). $^1$H NMR (400 MHz, DMSO-d6): δ 5.27 (d, J=3.2 Hz, 1H), 4.61-4.60 (m, 1H), 3.84-3.77 (m, 4H), 3.28-3.22 (m, 1H), 2.18-2.05 (m, 2H), 1.97-1.82 (m, 2H), 1.78-1.59 (m, 3H), 1.56-1.46 (m, 4H), 1.42-1.28 (m, 5H), 1.22-1.13 (m, 1H), 1.04-0.82 (m, 2H), 0.93 (s, 3H), 0.79 (s, 3H). LCMS: (Method A) 333.3 (M+1), Retention time: 3.234 min, HPLC (Method A): 98.3%, Retention time, 3.24 min.

Synthetic Example 34

Step 2: Conversion of Compound 2 to Compound 48

A. To a solution of (3S,9S,10R,13S,14S)-10,13-dimethyl-1,2,3,4,7,8,9,10,11,12,13,14,15,16-tetradecahydrospiro[cyclopenta(a)phenanthrene-17,2'-[1,3]dioxolan]-3-ol (Compound 2, 500 g, 1.505 mol, 1.0 eq., from Synthetic Example 33) in dichloromethane/acetonitrile (4.0 L, 1:1) and was added pyridine (500 mL) at 25° C. A CuI solution (5.73 g, 0.0301 mol, 0.02 eq.) was dissolved in pyridine/acetonitrile (1:2, 75 mL, 0.05 V/0.1 V) and a TBHP solution (70% aqueous, 2.06 L, 15.053 mol, 10.0 eq.) were added to the reaction mixture simultaneously at 20-25° C. for 3 h. After completion of the addition, the reaction mixture was heated at 45° C. for 3 h. The reaction was monitored by LCMS which showed absence of starting material.

B. The reaction mixture was cooled to 20° C. and then a 33% aqueous solution of $Na_2S_2O_3$ (4.0 L) was added. The organic layer was separated and the aqueous layer was washed with dichloromethane (2.0 L). The combined organic layers were washed with 10% aqueous solution of $Na_2S_2O_3$ (2.0 L) and followed by a brine solution (2.0 L). The organic layer was dried ($Na_2SO_4$) and evaporated to dryness. The crude product was purified by silica gel column chromatography (60-120 mesh; eluted with 35-40% of ethyl acetate/petroleum ether) to afford (3S,8R,9S,10R,13S,14S)-3-hydroxy-10,13-dimethyl-1,3,4,8,9,10,11,12,13,14,15,16-dodecahydrospiro[cyclopenta[a]phenanthrene-17,2'-[1,3]dioxolan]-7(2H)-one as an off-white solid (Compound 48, 261 g, yield 50%). $^1$H NMR (400 MHz, DMSO-d6): δ 5.60 (s, 1H), 4.92 (d, J=6.4 Hz, 1H), 3.84-3.77 (m, 4H), 3.41-3.31 (m, 1H), 2.38-2.24 (m, 3H), 1.88-1.83 (m, 2H), 1.72-1.56 (m, 5H), 1.53-1.25 (m, 5H), 1.24-1.10 (m, 2H), 1.15 (s, 3H), 0.76 (s, 3H). LCMS: (Method A) 347.2 (M+1), Retention time: 2.64 min, HPLC (Method B): 90.17%, Retention time: 3.87 min.

Synthetic Example 35

Step 3: Conversion of Compound 48 to Compound 49

A. To a stirred solution of (3S,8R,9S,10R,13S,14S)-3-hydroxy-10,13-dimethyl-1,3,4,8,9,10,11,12,13,14,15,16-dodecahydrospiro[cyclopenta[a]phenanthrene-17,2'-[1,3]dioxolan]-7(2H)-one (Compound 48, 210 g, 0.612 mol, 1.0 eq., from Synthetic Example 34) in THF (2.12 L, 10 V) at −5° C. under a nitrogen atmosphere was added a 1.0 M solution of $BH_3$ in THF (1.22 L, 1.226 mol, 2.0 eq.) for 3 h. The reaction was stirred for another 3 h at 20-25° C. The progress of the reaction was monitored by HPLC.

B. After completion, the reaction mixture was quenched with cold water (400 mL) at 0° C. and stirred for another 1 h. Sodium perborate tetrahydrate (188.4 g, 1.224 mol, 2.0 eq.) was added to the reaction mixture followed by water (400 mL) and the mixture stirred for 12 h at 20-25° C. After completion of the reaction, as monitored by TLC (19:1 dichloromethane/methanol, $R_f$=0.3, $KMnO_4$ stain), the reaction mixture was filtered to remove inorganic solids. The organic layer was separated and the aqueous layer washed with THF/ethyl acetate (600 mL, 2:1 ratio). The combined organic layers were washed with brine solution (600 mL) and dried ($Na_2SO_4$), evaporated to dryness to afford (3S,5S,6R,7R,8R,9S,10R,13S,14S)-10,13-dimethylhexadecahydrospiro[cyclopenta[a]phenanthrene]-2',2'-[1,3]dioxolane]-

3,6,7-triol as a white solid (Compound 49, 246 g, crude was taken for next step without further purification). LCMS: (Method A) 367.3 (M+1), Retention time: 2.24 min, HPLC (Method A): 77.16%, Retention time: 2.24 min.

Synthetic Example 36

Step 4: Conversion of Compound 49 to Compound 6

A. To an aqueous solution of 80% acetic acid (1020 mL, 4.15 V) was added (3S,5S,6R,7R,8R,9S,10R,13S,14S)-10,13-dimethylhexadecahydrospiro[cyclopenta[a]phenanthrene-17,2'-[1,3]dioxolane]-3,6,7-triol (Compound 49, 246 g, 1.0 eq., from Synthetic Example 35) and the mixture stirred for 12 h at RT. The reaction was monitored by TLC (18:2 dichloromethane/methanol, $R_f$=0.2, KMnO$_4$ stain).

B. After completion, the reaction mixture was washed with petroleum ether (2×500 mL). The separated bottom layer was diluted with cold water (1020 mL). The crude suspension was further stirred at 10-15° C. for 1 h and filtered through a Büchner funnel. The filtered solid was washed with cold water (250 mL). The solid was dried under vacuum at 45° C. for 12 h to afford (3S,5S,6R,7R,8R,9S,10R,13S,14S)-3,6,7-trihydroxy-10,13-dimethylhexadecahydro-17H-cyclopenta[a]phenanthren-17-one as a white solid (Compound 6, 132 g, yield 67%). $^1$H NMR (400 MHz, DMSO-d6): δ 4.46 (d, J=4.40 Hz, 1H), 4.41 (s, 1H), 4.27 (s, 1H), 3.32-3.22 (m, 1H), 2.94 (br s, 2H), 2.37-2.27 (m, 1H), 2.24-2.14 (m, 1H), 2.07-1.88 (m, 2H), 1.82-1.71 (m, 1H), 1.63-1.48 (m, 5H), 1.45-1.35 (m, 1H), 1.30-1.20 (m, 2H), 1.16-1.06 (m, 1H), 1.00-0.82 (m, 3H), 0.80-0.71 (m, 4H), 0.79 (s, 3H). HPLC (Method A): 98.17%, Retention time: 1.98 min.

Synthetic Example 37

Step 5: Conversion of Compound 6 to Compound 54

A. To a suspension of methyltriphenylphosphonium bromide (461 g, 1.291 mol, 3.2 eq.) in THF (910 mL, 7 V) under a nitrogen atmosphere was added potassium tertiary-butoxide (181 g, 1.614 mol, 4.0 eq.) at 20-25° C. for 30 min. The reaction mixture was stirred at RT for 2 h. A solution of (3S,5S,6R,7R,8R,9S,10R,13S,14S)-3,6,7-trihydroxy-10,13-dimethylhexadecahydro-17H-cyclopenta[a]phenanthren-17-one (Compound 6, 130 g, 0.403 mol, 1.0 eq., from Synthetic Example 36) in DMSO/THF (1:3, 520 mL, 4 V) was added to the reaction mixture. The reaction was stirred at RT for an additional 4 h. Progress of the reaction was monitored by TLC (9:1 dichloromethane/methanol, $R_f$=0.4, KMnO$_4$ stain).

B. After completion, the reaction mixture was diluted with ethyl acetate (650 mL) and water (650 mL). The organic layer was separated and aqueous layer was washed with ethyl acetate (650 mL). The combined organic layers were washed with brine solution (2×650 mL). The separated organic layer was dried (Na$_2$SO$_4$), evaporated to dryness and purified by silica gel flash column chromatography, using 3% methanol in dichloromethane (1 L/35 L), to afford (3S,5S,6R,7R,8R,9S,10R,13S,14S)-10,13-dimethyl-17-methylenehexadecahydro-1H-cyclopenta[a]phenanthrene-3,6,7-triol as an off-white solid (Compound 54, 103 g, yield 79.8%). $^1$H NMR (400 MHz, DMSO-d6): δ 4.60 (s, 2H), 4.45 (d, J=6.00 Hz, 1H), 4.35 (d, J=6.40 Hz, 1H), 4.14 (d, J=7.20 Hz, 1H), 3.32-3.22 (m, 1H), 2.98-2.88 (m, 1H), 2.87-2.77 (m, 1H), 2.45-2.32 (m, 2H), 2.20-2.10 (m, 1H), 2.08-1.95 (m, 2H), 1.80-1.72 (m, 1H), 1.65-1.50 (m, 4H), 1.45-1.22 (m, 4H), 1.18-1.02 (m, 1H), 0.98-0.83 (m, 3H), 0.77 (s, 3H), 0.73 (s, 3H). HPLC (Method B): 98.64%, Retention time: 4.18 min.

Synthetic Example 38

Step 6: Conversion of Compound 54 to Compound 51

A. To a stirred solution of (3S,5S,6R,7R,8R,9S,10R,13S,14S)-10,13-dimethyl-17-methylenehexadecahydro-1H-cyclopenta[a]phenanthrene-3,6,7-triol (Compound 54, 103 g, 0.321 mol, 1.0 eq., from Synthetic Example 37) in THF/Water (721 mL/309 mL, 10 V) at 10° C. was added sodium metaperiodate (137.6 g, 0.643 mol, 2.0 eq.) in several portions over 30 min. The reaction mixture was stirred 2 h at 25° C. The progress of the reaction was monitored by LCMS.

B. After completion, the reaction mixture was diluted with water (500 mL) and extracted with ethyl acetate (2×500 mL). The combined organic layers were washed with brine solution (500 mL), dried (Na$_2$SO$_4$) and evaporated to dryness to afford (3aS,4R,5S,7aS)-5-((1S,2R,5S,7R)-7-hydroxy-2-methyl-6-oxabicyclo[3.2.1]octan-2-yl)-7a-methyl-1-methyleneoctahydro-1H-indene-4-carbaldehyde as a white solid (Compound 51, 102 g, yield 99.5%, crude was taken for next step without further purification). $^1$H NMR (400 MHz, DMSO-d6): δ 9.51 (d, J=6.80 Hz, 1H), 5.94 (d, J=7.20 Hz, 1H), 5.21 (d, J=7.20 Hz, 1H), 4.68 (m, 2H), 4.25 (s, 1H), 2.47-2.26 (m, 3H), 2.00-1.82 (m, 2H), 1.77-1.67 (m, 2H), 1.67-1.47 (m, 4H), 1.46-1.05 (m, 7H), 0.90 (s, 3H), 0.77 (s, 3H). HPLC (Method B): 98.62%, Retention time: 4.60 min.

Synthetic Example 39

Step 7: Conversion of Compound 51 to Compound 52

A. To a stirred solution of (3aS,4R,5S,7aS)-5-((1S,2R,5S,7R)-7-hydroxy-2-methyl-6-oxabicyclo[3.2.1]octan-2-yl)-7a-methyl-1-methyleneoctahydro-1H-indene-4-carbaldehyde (Compound 51, 71 g, 0.223 mol, 1.0 eq., from Synthetic Example 38) in acetonitrile (710 mL, 10 V) was added solutions of Copper (I) trifluoromethanesulfonate toluene complex (11.54 g, 0.0223 mol, 0.1 eq.) in acetonitrile (71 mL), TEMPO (3.48 g, 0.0223 mol, 0.1 eq.) in acetonitrile (71 mL), bpy (3.48 g, 0.0223 mol, 0.1 eq.) in acetonitrile (71 mL) and N-methylimidazole (3.66 g, 0.0446 mol, 0.2 eq.) in acetonitrile (71 mL) under an oxygen atmosphere. The reaction mixture was heated at 60° C. for 12 h. The reaction was monitored by LCMS.

B. After completion, the acetonitrile was evaporated under vacuum. The crude mixture was suspended in ethyl acetate (350 mL) for 10 min and filtered through CELITE™. The CELITE™ bed was washed with ethyl acetate (200 mL). The combined filtrates were washed with water (2×200 mL) and brine solution (200 mL). The organic layer was dried (Na$_2$SO$_4$) and evaporated to dryness. The crude product was suspended in heptane (500 mL) and collected by filtration to afford (3aS,4R,5S,7aS)-7a-methyl-5-((1S,2R,5S)-2-methyl-7-oxo-6-oxabicyclo[3.2.1]octan-2-yl)-1-methyleneoctahydro-1H-indene-4-carbaldehyde as an off-white solid (Compound 52, 65.7 g, yield 93%). $^1$H NMR (400 MHz, DMSO-d6): δ 9.51 (d, J=5.56 Hz, 1H), 4.73 (br s, 1H), 4.69 (br s, 2H), 2.54-2.44 (m, 2H), 2.37-2.15 (m, 3H), 2.05-1.98 (m, 2H), 1.97-1.83 (m, 2H), 1.79-1.76 (m, 1H), 1.68-1.61 (m, 2H), 1.61-1.51 (m, 1H), 1.50-1.32 (m, 3H), 1.31-1.21 (m, 1H), 1.20-1.10 (m, 1H), 0.97 (s, 3H), 0.76 (s, 3H). HPLC (Method A): 99.35%, Retention time: 3.10 min.

Synthetic Example 40

Step 8: Conversion of Compound 52 to Compound 53

A. To a stirred solution of (3aS,4R,5S,7aS)-7a-methyl-5-((1S,2R,5S)-2-methyl-7-oxo-6-oxabicyclo[3.2.1]octan-2-yl)-1-methyleneoctahydro-1H-indene-4-carbaldehyde (Compound 52, 64 g, 0.2024 mol, 1.0 eq., from Synthetic Example 39) in pyridine (320 mL, 5 V) was added O-methyl hydroxylamine hydrochloride (84.45 g, 1.011 mol, 5.0 eq.). The reaction mixture was heated at 70° C. for 12 h. The progress of the reaction was monitored by TLC (7:3 petroleum ether/ethyl acetate, $R_f$=0.3, KMnO$_4$ stain).

B. After completion, excess pyridine was removed by vacuum at 50° C. The crude mixture was suspended in water (500 mL) and stirred for 30 min. The solids were collected by filtration and washed with water (100 mL). The crude product was suspended in IPA (100 mL) at 10° C. for 30 min and filtered. The solids were washed with cold IPA (30 mL) to afford 7a-methyl-5-((1S,2R,5S)-2-methyl-7-oxo-6-oxabicyclo[3.2.1]octan-2-yl)-1-methyleneoctahydro-1H-indene-4-carbaldehyde O-methyl oxime as a white solid (Compound 53, 63 g, yield 90%). $^1$H NMR (400 MHz, DMSO-d6): δ 7.23 (d, J=9.20 Hz, 1H), 4.75 (br s, 1H), 4.66 (br s, 2H), 3.69 (s, 3H), 2.54-2.35 (m, 2H), 2.34-2.26 (m, 2H), 2.23-2.08 (m, 2H), 2.09-1.83 (m, 3H), 1.75-1.53 (m, 3H), 1.50-1.36 (m, 3H), 1.34-1.22 (m, 2H), 1.16-1.06 (m, 1H), 0.98 (s, 3H), 0.78 (s, 3H). LCMS: (Method A) 346.3 (M+1), Retention time: 3.23 min, HPLC (Method B): 99.63%, Retention time: 5.65 min.

Synthetic Example 41

Step 9: Conversion of Compound 53 to Compound 16

A. To a stirred solution of 7a-methyl-5-((1S,2R,5S)-2-methyl-7-oxo-6-oxabicyclo[3.2.1]octan-2-yl)-1-methyleneoctahydro-1H-indene-4-carbaldehyde O-methyl oxime (Compound 53, 48 g, 0.139 mol, 1.0 eq., from Synthetic Example 40) in dioxane (480 mL, 10 V) was added LiAlH$_4$, 1.0 M in THF (695 mL, 0.695 mol, 5.0 eq.) dropwise at 15° C. under a nitrogen atmosphere for 1 h 30 min. The reaction mixture was heated at 80° C. for 24 h. The progress of reaction was monitored by LCMS.

B. After completion, the reaction was cooled to 0° C. and quenched with saturated aqueous Na$_2$SO$_4$ solution (150 mL). After quenching, the reaction mixture was stirred at RT for 1 h and filtered through CELITE™. The CELITE™ bed was washed with dichloromethane/THF (900 mL, 1:2). The combined filtrates were washed with brine solution (2×300 mL) followed by water (300 mL). The separated organic layers were dried (Na$_2$SO$_4$) and evaporated to dryness. The crude mixture was suspended in MTBE (200 mL) and stirred for 30 min. Filtered the suspension to afford (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexan-1-ol as a white solid (Compound 16, 40.5 g, yield 90%). $^1$H NMR (400 MHz, CD$_3$OD): δ 4.64 (br s, 2H), 3.77-3.73 (m, 1H), 3.51-3.41 (m, 1H), 3.18-3.07 (m, 2H), 2.75-2.70 (m, 1H), 2.57-2.47 (m, 1H), 2.35-2.25 (m, 1H), 2.20-2.14 (m, 1H), 1.90-1.75 (m, 5H), 1.64-1.25 (m, 10H), 1.11 (s, 3H), 0.84 (s, 3H). LCMS: (Method A) 322.5 (M+1), Retention time: 2.02 min, HPLC (Method B): 96.7%, Retention time: 2.93 min.

Synthetic Example 42

Step 10: Preparation of AQX-1125 from Compound 16

A. To a stirred solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexan-1-ol (Compound 16, 40 g, 0.139 mol, 1.0 eq., from Synthetic Example 41) in methanol (120 mL, 3 V) was added acetic acid (12.4 mL, 0.31 V) dropwise at 10° C. under a nitrogen atmosphere for 20 min. The reaction mixture was stirred at RT for 1 h. MTBE (240 mL, 6 V) was added to reaction mixture and stirred for 2 h. During the MTBE addition, slow precipitation of product was observed. The solids were filtered to afford (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexan-1-ol, acetic acid salt, as a white solid (AQX-1125, 36.5 g, yield 76%). LCMS: (Method A) 322.5 (M+1), Retention time: 2.02 min.

AQX-1125 may also be prepared according to the method disclosed below in Reaction Scheme 15, wherein Pg$^2$ is a carbonyl protecting group:

REACTION SCHEME 15

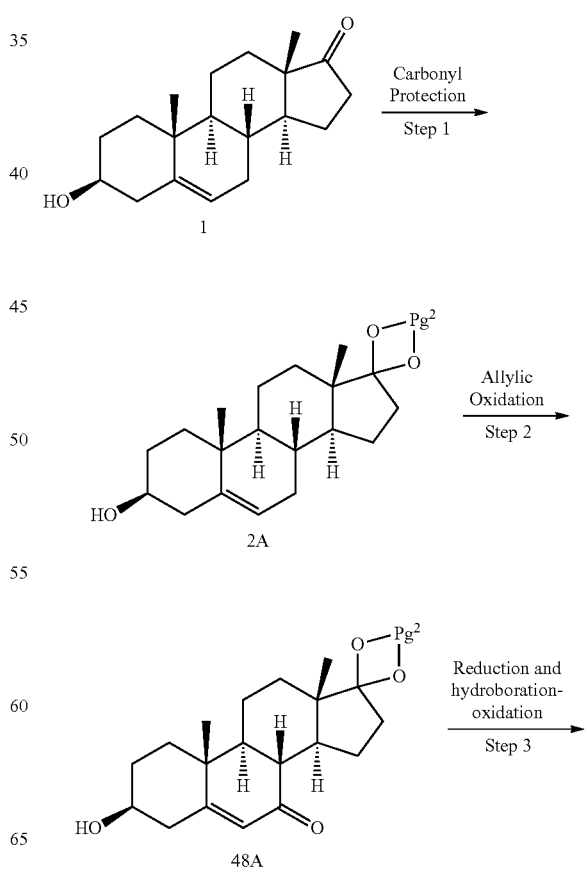

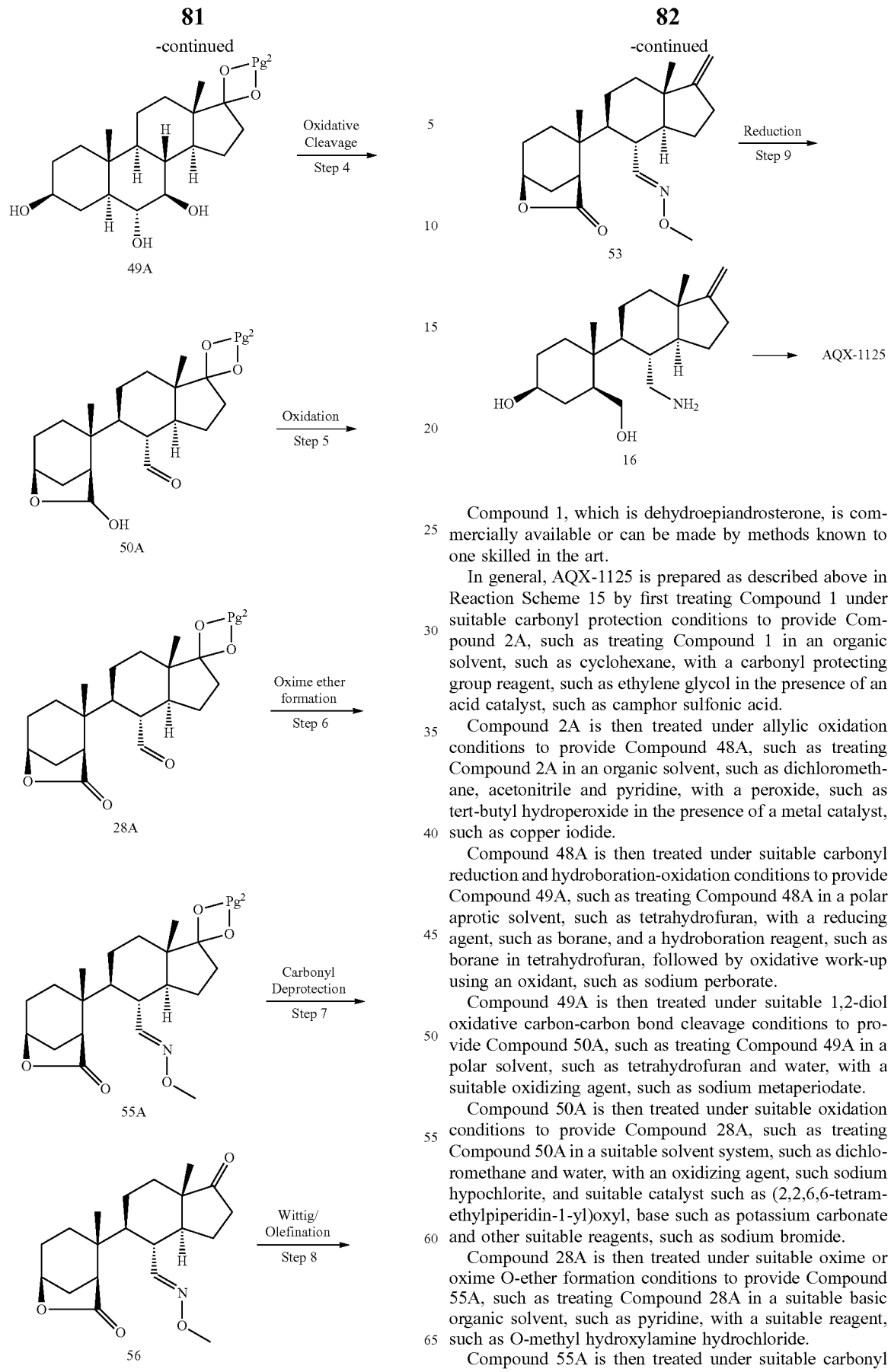

Compound 1, which is dehydroepiandrosterone, is commercially available or can be made by methods known to one skilled in the art.

In general, AQX-1125 is prepared as described above in Reaction Scheme 15 by first treating Compound 1 under suitable carbonyl protection conditions to provide Compound 2A, such as treating Compound 1 in an organic solvent, such as cyclohexane, with a carbonyl protecting group reagent, such as ethylene glycol in the presence of an acid catalyst, such as camphor sulfonic acid.

Compound 2A is then treated under allylic oxidation conditions to provide Compound 48A, such as treating Compound 2A in an organic solvent, such as dichloromethane, acetonitrile and pyridine, with a peroxide, such as tert-butyl hydroperoxide in the presence of a metal catalyst, such as copper iodide.

Compound 48A is then treated under suitable carbonyl reduction and hydroboration-oxidation conditions to provide Compound 49A, such as treating Compound 48A in a polar aprotic solvent, such as tetrahydrofuran, with a reducing agent, such as borane, and a hydroboration reagent, such as borane in tetrahydrofuran, followed by oxidative work-up using an oxidant, such as sodium perborate.

Compound 49A is then treated under suitable 1,2-diol oxidative carbon-carbon bond cleavage conditions to provide Compound 50A, such as treating Compound 49A in a polar solvent, such as tetrahydrofuran and water, with a suitable oxidizing agent, such as sodium metaperiodate.

Compound 50A is then treated under suitable oxidation conditions to provide Compound 28A, such as treating Compound 50A in a suitable solvent system, such as dichloromethane and water, with an oxidizing agent, such sodium hypochlorite, and suitable catalyst such as (2,2,6,6-tetramethylpiperidin-1-yl)oxyl, base such as potassium carbonate and other suitable reagents, such as sodium bromide.

Compound 28A is then treated under suitable oxime or oxime O-ether formation conditions to provide Compound 55A, such as treating Compound 28A in a suitable basic organic solvent, such as pyridine, with a suitable reagent, such as O-methyl hydroxylamine hydrochloride.

Compound 55A is then treated under suitable carbonyl deprotection conditions to provide Compound 56, such as treating Compound 55A in a polar protic solvent, such as water, with a suitable acid, such as acetic acid.

Compound 56 is then treated under suitable olefination or Wittig reaction conditions to provide Compound 53, such as treating Compound 56 in a suitable organic solvent, such as tetrahydrofuran, with a ylide generated using a phosphonium salt, such as methyltriphenylphosphonium bromide, and a base, such as potassium tert-butoxide.

Compound 53 is then treated under suitable lactone and oxime O-ether reduction conditions to provide Compound 16, such as treating Compound 53 in a polar aprotic solvent, such as tetrahydrofuran, with a reducing agent, such as lithium aluminum hydride.

Compound 16 may then be treated under suitable acetic salt formation conditions to provide AQX-1125, such as treating Compound 16 in a polar protic solvent, such as methanol, with glacial acetic, followed by a less polar organic solvent, such as methyl tert-butyl ether.

A specific method of preparing AQX-1125, as set forth above in Reaction Scheme 15, is illustrated below in Reaction Scheme 15A:

REACTION SCHEME 15A

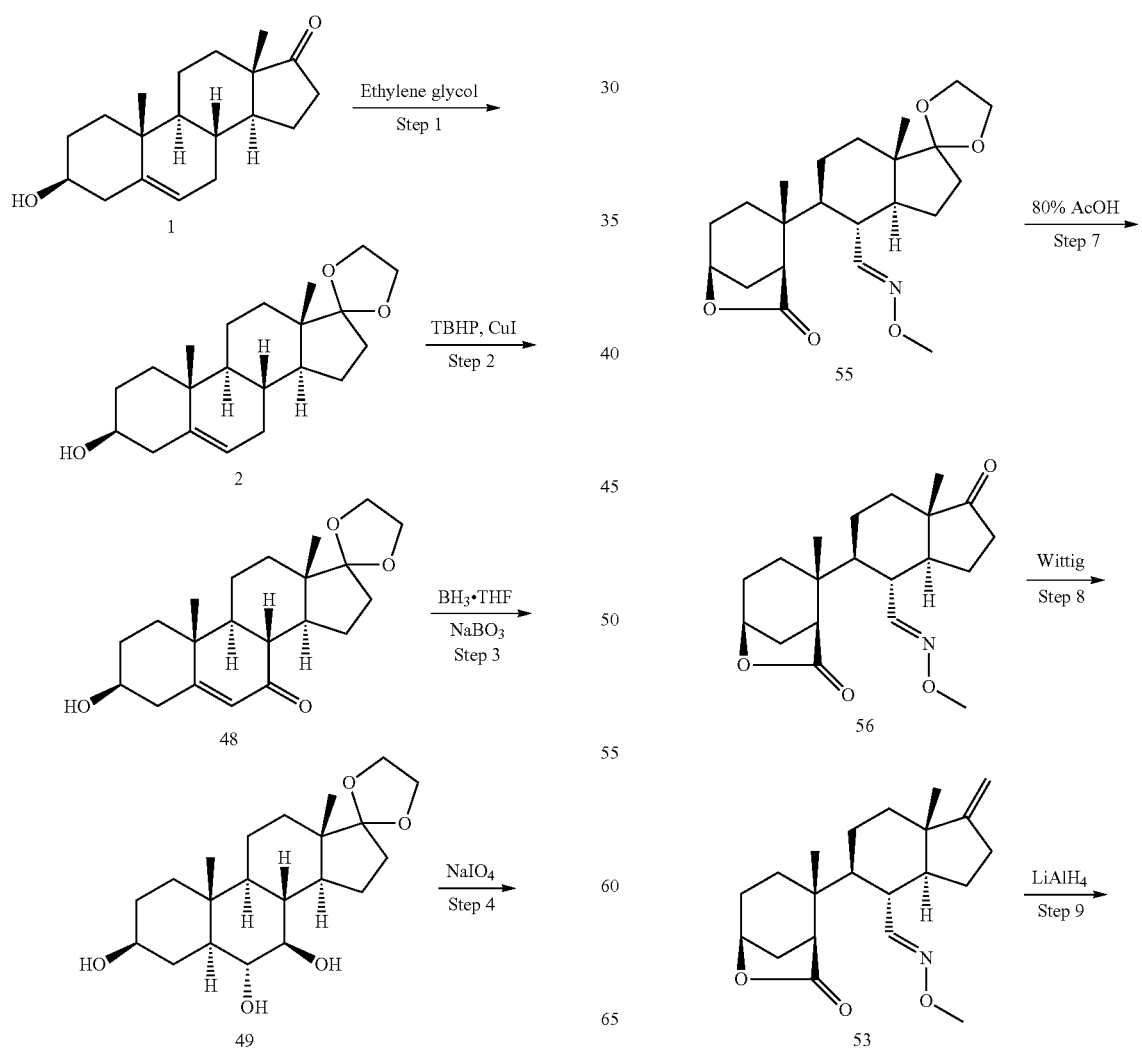

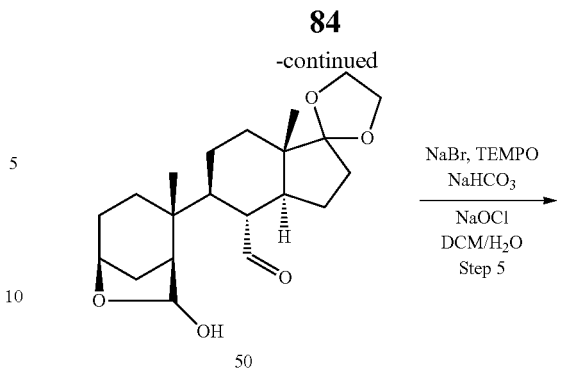

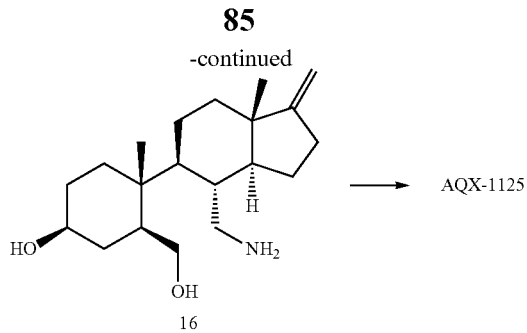

The following Examples, which are directed to the steps and products as set forth above in Reaction Scheme 15 are provided as a guide to assist in the practice of the invention, and are not intended as a limitation on the scope of the invention.

Synthetic Example 43

Step 1: Conversion of Compound 1 to Compound 2

A. To a solution of (3S,8R,9S,10R,13S,14S)-3-hydroxy-10,13-dimethyl-1,2,3,4,7,8,9,10,11,12,13,14,15,16-tetradecahydro-17H-cyclopenta[a]phenanthren-17-one (DHEA, Compound 1, 500.0 g, 1.733 mol, 1.0 eq.) in cyclohexane (5 L) in a dry 10 L RB flask fitted with a Dean-Stark apparatus was added (+/−) Camphor sulphonic acid (8.0 g, 0.0346 mol) followed by ethylene glycol (538.0 g, 8.667 mol) at room temperature. The reaction mass was heated to 85° C. under reflux for 16 hours for azeotropic removal of water. The reaction mass was monitored by HPLC analysis.

B. After completion of reaction, the reaction mixture cooled to room temperature (RT). Cyclohexane was removed under vacuum below 50° C. and a solution of 10% sodium bicarbonate (2.5 L) was added followed by dichloromethane (5 L) (Note: The sequence of addition was critical as the ketal can reverse back to starting material in acidic conditions). The slurry was stirred to get a clear biphasic solution. The layers were separated and combined dichloromethane layers were again washed with 10% aqueous sodium bicarbonate solution (2.5 L). The organic layer was washed with brine solution (2.5 L) and dried ($Na_2SO_4$). The organic layer was evaporated to dryness to afford (3S,8R,9S,10R,13S,14S)-10,13-dimethyl-1,2,3,4,7,8,9,10,11,12,13,14,15,16-tetradecahydrospiro[cyclopenta[a]phenanthrene-17,2'-[1,3]dioxolan]-3-ol as white solid (Compound 2, 561 g, yield 97%). $^1$H NMR (400 MHz, DMSO-d6): δ 5.27 (br s, 1H), 4.59 (d, J=4.4 Hz, 1H), 3.90-3.77 (m, 4H), 3.32-3.22 (m, 1H), 2.20-2.05 (m, 2H), 1.97-1.82 (m, 2H), 1.78-1.60 (m, 3H), 1.59-1.46 (m, 4H), 1.43-1.28 (m, 5H), 1.22-1.13 (m, 1H), 0.95 (s, 3H), 1.02-0.82 (m, 2H), 0.79 (s, 3H). HPLC (Method A): 96.3%, Retention time, 3.22 min.

Synthetic Example 44

Step 2: Conversion of Compound 2 to Compound 48

A. To a solution of (3S,9S,10R,13S,14S)-10,13-dimethyl-1,2,3,4,7,8,9,10,11,12,13,14,15,16-tetradecahydrospiro[cyclopenta(a)phenanthrene-17,2'-[1,3]dioxolan]-3-ol (Compound 2, 560 g, 1.68 mol, 1.0 eq., from Synthetic Example 43) in dichloromethane/acetonitrile (4.6 L, 1:1, 8 V) and was added pyridine (560 mL, 1 V) at 20° C. A CuI solution (6.5 g, 0.03 mol, 0.02 eq.) dissolved in pyridine/acetonitrile (1:2, 90 mL, 0.05 V/0.1 V) and a TBHP solution (70% aqueous, 2.17 L, 16.8 mol, 10.0 eq.) were added to the reaction mixture simultaneously at 20-25° C. for 2 h. After completion of the addition, the reaction mixture was heated at 45° C. for 4 h. The reaction was monitored by LCMS which showed absence of starting material.

B. The reaction mixture was cooled to 0° C. and then a 33% aqueous solution of $Na_2S_2O_3$ (2.0 L) was added. The organic layer was separated and the aqueous layer was washed with dichloromethane (2×3.0 L). The combined organic layers were washed with 33% aqueous solution of $Na_2S_2O_3$ (2.5 L) and followed by a brine solution (2.5 L). The organic layer was dried ($Na_2SO_4$) and evaporated to dryness. The crude product was purified by silica gel column chromatography (60-120 mesh; eluted at 45% of ethyl acetate/petroleum ether) to afford (3S,8R,9S,10R,13S,14S)-3-hydroxy-10,13-dimethyl-1,3,4,8,9,10,11,12,13,14,15,16-dodecahydrospiro[cyclopenta[a]phenanthrene-17,2'-[1,3]dioxolan]-7(2H)-one as an off-white solid (Compound 48, 240 g, yield 41.2%). $^1$H NMR (400 MHz, DMSO-d6): δ 5.59 (s, 1H), 4.89 (d, J=4.8 Hz, 1H), 3.87-3.75 (m, 4H), 3.47-3.37 (m, 1H), 2.45-2.35 (m, 1H), 2.32-2.21 (m, 2H), 1.91-1.81 (m, 2H), 1.77-1.56 (m, 4H), 1.53-1.32 (m, 5H), 1.34-1.32 (m, 2H), 1.16 (s, 3H), 1.25-1.10 (m, 1H), 0.78 (s, 3H). LCMS (Method A): 347.2 (M+1), Retention time: 2.63 min, HPLC (Method A): 97.9%.

Synthetic Example 45

Step 3: Conversion of Compound 48 to Compound 49

A. To a stirred solution of (3S,8R,9S,10R,13S,14S)-3-hydroxy-10,13-dimethyl-1,3,4,8,9,10,11,12,13,14,15,16-dodecahydrospiro[cyclopenta[a]phenanthrene-17,2'-[1,3]dioxolan]-7(2H)-one (Compound 48, 230 g, 0.664 mol, 1.0 eq., from Synthetic Example 44) in THF (1.6 L, 7 V) at −10° C. under a nitrogen atmosphere was added a 1.0 M solution of $BH_3$ in THF (1.33 L, 1.328 mol, 2.0 eq.) and the reaction stirred for 2 h. The reaction was stirred for another 3 h at 20-25° C. The completion of the reaction was confirmed by TLC (9:1 dichloromethane/methanol, $R_f$=0.3, $KMnO_4$ stain).

B. After completion, the reaction mixture was quenched with cold water (460 mL, 2 V) at −10° C. and stirred for another 1 h. Sodium perborate tetrahydrate (204.5 g, 1.329 mol, 2.0 eq.) was added to the reaction mixture followed by water (400 mL) and the mixture stirred for 12 h at 20-25° C. After completion of the reaction, as monitored by TLC (19:1 dichloromethane/methanol, $R_f$=0.3, $KMnO_4$ stain), the reaction mixture was filtered to remove inorganic solids. The organic layer was separated and the aqueous layer washed with THF/ethyl acetate (600 mL, 2:1 ratio). The combined organic layers were washed with brine solution (600 mL) and dried ($Na_2SO_4$), evaporated to dryness to afford (3S,5S,6R,7R,8R,9S,10R,13S,14S)-10,13-dimethylhexadecahydrospiro[cyclopenta[a]phenanthrene-17,2'-[1,3]dioxolane]-3,6,7-triol as a white solid (Compound 49, 248 g, crude was taken for next step without further purification). LCMS (Method A): 367.5 (M+1), Retention time: 2.28 min, HPLC (Method A): 89.6%.

Synthetic Example 46

Step 4: Conversion of Compound 49 to Compound 50

A. To a solution of (3S,5S,6R,7R,8R,9S,10R,13S,14S)-10,13-dimethylhexadecahydrospiro[cyclopenta[a]phenanthrene-17,2'-[1,3]dioxolane]-3,6,7-triol (Compound 49, 248 g, 0.677 mol, 1 eq., from Synthetic Example 45) in THF (1 L) and water (500 mL) was added sodium metaperiodate (290 g, 1.354 mol, 2 eq.) portion-wise and the reaction mixture was stirred at room temperature for 1 h. Completion of the reaction was confirmed by TLC (1:1 hexanes/ethyl acetate, $R_f$=0.4, $KMnO_4$ stain).

B. After completion, the reaction mixture was diluted with water (4 L) and extracted with ethyl acetate (2×2.5 L). The combined organic layers were washed with brine (2 L), dried ($Na_2SO_4$) and concentrated by rotary evaporation. The obtained residue was washed with DCM/petroleum ether (1:1, 2 L) to afford (3aS,4R,5S,7aS)-5-((1S,2R,5S,7R)-7-hydroxy-2-methyl-6-oxabicyclo[3.2.1]octan-2-yl)-7a-methyloctahydrospiro[indene-1,2'-[1,3]dioxolane]-4-carbaldehyde (Compound 50, 207 g, 85% yield over two steps) as an off-white solid. LCMS (Method A): 347.5 (M+1), Retention time: 2.49 min, HPLC (Method A): 77.6 area %, Retention time 2.49 min.

Synthetic Example 47

Step 5: Conversion of Compound 50 to Compound 28

A. To a solution of (3aS,4R,5S,7aS)-5-((1S,2R,5S,7R)-7-hydroxy-2-methyl-6-oxabicyclo[3.2.1]octan-2-yl)-7a-methyloctahydrospiro[indene-1,2'-[1,3]dioxolane]-4-carbaldehyde (Compound 50, 95 g 0.260 mol, 1 eq., from Synthetic Example 46) in dichloromethane/water (9:1, 2.6 L, 10 V) at 0° C. was added TEMPO (4 g, 0.026 mol, 0.1 eq.), NaBr (32.6 g, 0.317 mol, 1.2 eq.) and $NaHCO_3$ (110 g, 1.32 mol, 5 eq.). The resulting yellow colored reaction mixture was stirred for 15 min. A NaOCl solution (12% in water, 1315 mL, 7 V) was added to the yellow solution at 0° C. and stirred for 30 min. The reaction mixture was cooled to 0° C. and stirred for a further 15 min. The completion of the reaction was confirmed by TLC (1:1 hexanes/ethyl acetate, $R_f$=0.5, $KMnO_4$ stain).

B. After completion, the reaction mixture was diluted with water (1 L) and extracted with DCM (2×1 L). The combined organic layers were washed with a brine solution (500 mL), dried ($Na_2SO_4$) and concentrated by rotary evaporation. The crude product was suspended in hexane/diethyl ether (10:1, 1 L) and the resulting suspension was stirred for 2 h at room temperature. The precipitated solid was filtered. The solid obtained was washed with hexane (2×500 mL) and dried under vacuum to afford (3aS,4R,5S,7aS)-7a-methyl-5-((1S,2R,5S)-2-methyl-7-oxo-6-oxabicyclo[3.2.1]octan-2-yl)octahydrospiro[indene-1,2'-[1,3]dioxolane]-4-carbaldehyde (Compound 28, 62.2 g, yield 66%) as an off-white solid. This reaction was performed at several additional batch sizes, 2 g, 10 g, and 2×50 g, yielding 740 mg (37% yield), 7 g (70% yield) and 65 g (65% yield) of final compound 28, respectively. $^1$H NMR (400 MHz, DMSO-d6): δ 9.49 (d, J=5.6 Hz, 1H), 4.78 (br s, 1H), 3.91-3.75 (m, 4H), 2.48-2.38 (m, 1H), 2.35-2.22 (m, 2H), 2.07-1.85 (m, 5H), 1.78-1.62 (m, 5H), 1.45-1.10 (m, 5H), 0.98 (s, 3H), 0.78 (s, 3H). LCMS (Method A): 363.3 (M+1) and 380.2 [M+18], Retention time: 2.78 min, HPLC (Method A): 92.4 area %.

Synthetic Example 48

Step 6: Conversion of Compound 28 to Compound 55

A. To a solution of (3aS,4R,5S,7aS)-7a-methyl-5-((1S,2R,5S)-2-methyl-7-oxo-6-oxabicyclo[3.2.1]octan-2-yl)octahydrospiro[indene-1,2'-[1,3]dioxolane]-4-carbaldehyde (Compound 28, 78 g 0.215 mol, 1 eq., from Synthetic Example 47) in pyridine (780 mL, 10 V) was added O-methyl hydroxyl amine hydrochloride (90 g, 1.075 mol, 5 eq.) portion-wise at room temperature and the reaction mixture was heated at 70° C. for 3 h. The progress of the reaction was monitored by TLC (1:1 hexanes/ethyl acetate, $R_f$=0.6, $KMnO_4$ stain).

B. After completion, the reaction mixture was concentrated to dryness. The crude product was dissolved in DCM (2.5 L). The organic layer was washed with water (2×1 L), brine solution (500 mL), dried ($Na_2SO_4$) and concentrated under vacuum. The resulting solid was stirred with hexane/diethyl ether (9:1, 780 mL, 10 V) for 30 min. The suspension was filtered and dried under vacuum to afford 7a-methyl-5-((1S,2R,5S)-2-methyl-7-oxo-6-oxabicyclo[3.2.1]octan-2-yl)octahydrospiro[indene-1,2'-[1,3]dioxolane]-4-carbaldehyde O-methyl oxime (Compound 55, 70 g, yield 83%) as an off-white solid. This reaction was performed at several additional batch sizes, 2 g, 6 g, 10 g, and 40 g, yielding 1.4 g (65% yield), 4.5 g (70% yield), 9 g (83% yield) and 37 g (85.6% yield) of final compound 55, respectively. $^1$H NMR (400 MHz, DMSO-d6): δ 7.21 (d, J=9.20 Hz, 1H), 4.78-4.71 (m, 1H), 3.88-3.71 (m, 4H), 3.70 (s, 3H), 2.40-2.31 (m, 1H), 2.30-2.20 (m, 1H), 2.11-1.95 (m, 2H), 1.94-1.76 (m, 3H), 1.72-1.57 (m, 5H), 1.45-1.10 (m, 6H), 0.96 (s, 3H), 0.80 (s, 3H). LCMS (Method A): 392.3 (M+1), Retention time: 2.87 min, HPLC (Method A): 99.0 area %.

Synthetic Example 49

Step 7: Conversion of Compound 55 to Compound 56

A. A solution of 7a-methyl-5-((1S,2R,5S)-2-methyl-7-oxo-6-oxabicyclo[3.2.1]octan-2-yl)octahydrospiro[indene-1,2'-[1,3]dioxolane]-4-carbaldehyde O-methyl oxime (Compound 55, 107 g, 0.273 mol, from Synthetic Example 48) in acetic acid (856 mL) and water (214 mL) in a 2 L RB flask fitted with a reflux condenser was stirred at 60° C. using a magnetic stirrer for 2 h. Completion of the reaction was confirmed by TLC (1:1 hexanes/ethyl acetate, $R_f$=0.4, $KMnO_4$ stain).

B. After completion, the reaction mixture was concentrated by rotary evaporation. The crude residue was diluted with water (1 L). The aqueous layer was extracted with ethyl acetate (2×1 L). The combined organic layers were washed with a 10% aqueous sodium bicarbonate solution (1 L) and brine (500 mL), dried ($Na_2SO_4$) and concentrated by rotary evaporation. The resulting solid was stirred with hexane/diethyl ether (9:1, 1070 mL, 10 V) for 30 min. The suspension was filtered and dried under vacuum to afford 7a-methyl-5-((1S,2R,5S)-2-methyl-7-oxo-6-oxabicyclo [3.2.1]octan-2-yl)-1-oxooctahydro-1H-indene-4-carbaldehyde O-methyl oxime (Compound 56, 78 g, Yield 82%) as an off-white solid. This reaction was performed at several additional batch sizes, 2 g, 1.4 g, and 9 g, yielding 2 g (57% yield), 1 g (80% yield), and 6.8 g (82% yield) of final compound 56, respectively. $^1$H NMR (400 MHz, DMSO-d6): δ 7.27 (d, J=9.20 Hz, 1H), 4.78-4.74 (m, 1H), 3.72 (s, 3H), 2.50-2.21 (m, 4H), 2.20-2.10 (m, 1H), 2.07-1.85 (m, 2H), 1.97-1.87 (m, 1H), 1.78-1.56 (m, 6H), 1.55-1.23 (m, 3H), 1.20-1.10 (m, 1H), 0.99 (s, 3H), 0.82 (s, 3H). LCMS (Method A): 348.3 (M+1), Retention time: 2.5 min, HPLC (method A): 94.5 area %.

Synthetic Example 50

Step 8: Conversion of Compound 56 to Compound 53

A. A mixture of methyltriphenylphosphonium bromide (97 g, 0.270 mol, 2 eq.) and potassium tert-butoxide (30.3 g, 0.270 mol, 2 eq.) in anhydrous THF (235 mL, 5 V) in a dry 2 L RB flask was stirred at 0° C. using a magnetic stirrer for 2 h under a nitrogen atmosphere. A solution of 7a-methyl-5-((1S,2R,5S)-2-methyl-7-oxo-6-oxabicyclo[3.2.1]octan-2-yl)-1-oxooctahydro-1H-indene-4-carbaldehyde O-methyl oxime (Compound 56, 47 g, 0.135 mol, 1 eq., from Synthetic Example 49) in THF (235 mL, 5 V) was added drop-wise at 0° C. via dropping funnel into the reaction mixture. The reaction mixture was stirred at room temperature for 3 h. Completion of the reaction was confirmed by TLC (1:1 hexane/ethyl acetate, $R_f$=0.65, KMnO$_4$ stain).

B. After completion, the reaction mixture was diluted with water (1 L). The organic layer was extracted with dichloromethane (2×1 L). The combined organic layers were washed with brine (1 L), dried (Na$_2$SO$_4$) and concentrated by rotary evaporation. The residue was purified by column chromatography using silica gel (60-120 mesh). The product was eluted at 35-40% ethyl acetate in hexane to afford 7a-methyl-5-((1S,2R,5S)-2-methyl-7-oxo-6-oxabicyclo[3.2.1]octan-2-yl)-1-methyleneoctahydro-1H-indene-4-carbaldehyde O-methyl oxime (Compound 53, 23 g, Yield 49%) as a white solid. This reaction was performed at several additional batch sizes, 2×500 mg, 2×2 g, 2×5 g, 6.5 g, and 20 g, yielding 450 mg (45% yield), 1 g (50% yield), 4.6 g (46% yield), 3 g (46% yield), and 9.3 g (47% yield) of final compound 53, respectively. $^1$H NMR (400 MHz, DMSO-d6): δ 7.23 (d, J=9.0 Hz, 1H), 4.80-4.75 (m, 1H), 4.73-4.65 (br s, 2H), 3.69 (s, 3H), 2.48-2.36 (m, 2H), 2.35-2.23 (m, 2H), 2.21-2.08 (m, 2H), 2.05-1.95 (m, 1H), 1.94-1.80 (m, 2H), 1.78-1.50 (m, 3H), 1.50-1.38 (m, 3H), 1.36-1.10 (m, 3H), 0.99 (s, 3H), 0.78 (s, 3H). LCMS (Method A): 346.3 (M+1), Retention time: 3.21 min, HPLC (Method A): 99.6 area %.

Synthetic Example 51

Step 9: Conversion of Compound 53 to Compound 16

A. To a solution of 7a-methyl-5-((1S,2R,5S)-2-methyl-7-oxo-6-oxabicyclo[3.2.1]octan-2-yl)-1-methyleneoctahydro-1H-indene-4-carbaldehyde O-methyl oxime (Compound 53, 11 g, 0.032 mol 1 eq., from Synthetic Example 50) in anhydrous 1,4-dioxane (110 mL, 10 V) in a dry 500 mL RB flask was added a solution of lithium aluminum hydride (2 M THF, 80 mL, 0.159 mol, 5 eq.) at 0° C. under a nitrogen atmosphere and the mixture stirred for 1 h. The reaction mixture was then heated to 80° C. and stirred for 32 h. The internal temperature was monitored using a thermos-socket. Completion of the reaction was monitored by LCMS.

B. After completion, the reaction mixture was cooled to 0° C. and quenched by the drop-wise addition of a saturated aqueous solution of Na$_2$SO$_4$ (100 mL) at 0° C. The resulting suspension was filtered through CELITE™ using a glass-fritted funnel and washed with dichloromethane/THF (1:2, 200 mL). The filtrate was washed with a brine solution (100 mL), dried (Na$_2$SO$_4$) and evaporated to dryness. The resulting residue was stirred with MTBE (50 mL) for 10 min and filtered to afford (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexan-1-ol (Compound 16, 9.2 g, Yield 90%) as an off-white solid. LCMS (Method A): 322.5 (M+1), Retention time: 2.01 min, HPLC (Method A): 86.5 area %.

C. AQX-1125 may be prepared from Compound 16 in the same manner as described above in Synthetic Example 16.

E. Additional Methods 16-20

The following Reaction Schemes provide additional methods of preparing intermediates utilized in the methods of preparing AQX-1125, as disclosed herein, or additional methods of preparing AQX-1125.

The following Reaction Scheme 16 demonstrates introduction of an amine group through reductive amination:

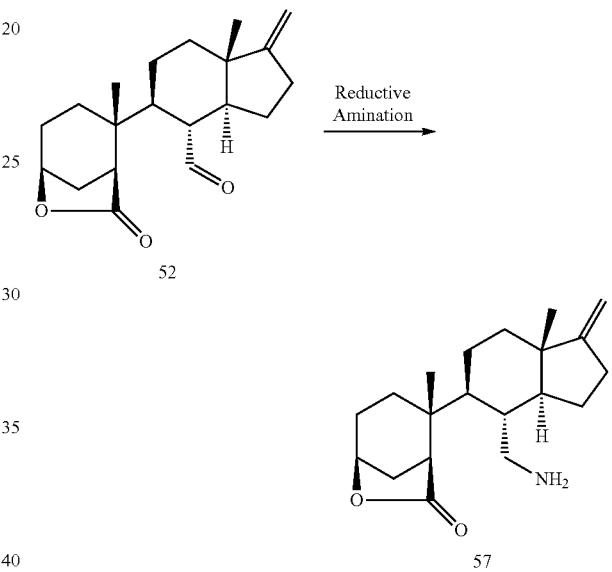

REACTION SCHEME 16

In general, Compound 57 is prepared as described above by first treating Compound 52 under suitable reductive amination conditions to provide Compound 57, such as treating Compound 52 in an organic solvent, such as methanol, with a nitrogen source, such as ammonium acetate, and a reducing agent, such as sodium cyanoborohydride.

A specific method of preparing Compound 57, as set forth above in Reaction Scheme 16, is illustrated below in Reaction Scheme 16A:

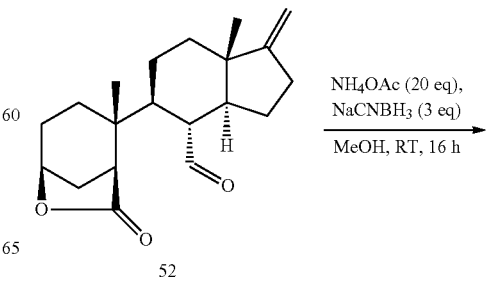

REACTION SCHEME 16A

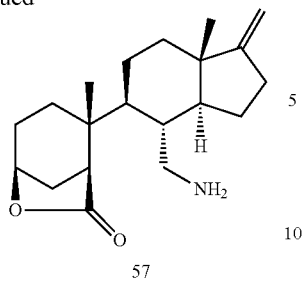

57

The following Synthetic Example, which are directed to the steps and products as set forth above in Reaction Scheme 16A, are provided as a guide to assist in the practice of the invention, and are not intended as a limitation on the scope of the invention.

Synthetic Example 52

Conversion of Compound 52 to Compound 57

A. To a solution of (3aS,4R,5S,7aS)-7a-methyl-5-((1S,2R,5S)-2-methyl-7-oxo-6-oxabicyclo[3.2.1]octan-2-yl)-1-methyleneoctahydro-1H-indene-4-carbaldehyde (Compound 52, 0.5 g, 1.58 mmol, 1 eq., see Synthetic Example 39) in methanol (10 mL) were added NH$_4$OAc (2.43 g, 31.64 mmol, 20 eq.) and NaCNBH$_3$ (0.29 g, 4.74 mmol, 3 eq.) under a nitrogen atmosphere. The reaction was stirred at room temperature for 16 h. Completion of the reaction was confirmed by TLC analysis (5:5 petroleum ether/ethyl acetate $R_f$=0.5, KMnO$_4$ stain).

B. After completion, the reaction mixture was quenched with a 33% aqueous ammonia solution (20 mL) and stirred for 1 h. The reaction mixture was extracted with MTBE (3×20 mL). Combined organic layers were washed with 10% aq. solution of NaHCO$_3$ (25 mL) followed by brine solution (25 mL). The organic layer was dried (Na$_2$SO$_4$) and evaporated to dryness. The crude product was purified by silica gel column chromatography (230-400 mesh; eluted at 65-70% of ethyl acetate/petroleum ether) to afford (1S,2R,5S)-2-((3aS,4R,5S,7aS)-4-(aminomethyl)-7a-methyl-1-methyleneoctahydro-1H-inden-5-yl)-2-methyl-6-oxabicyclo[3.2.1]octan-7-one (Compound 57, 0.21 g, yield 42%) as a brown solid. $^1$H NMR (400 MHz, DMSO-d6): δ 4.74 (br s, 1H), 4.62 (s, 2H), 2.85-2.77 (m, 1H), 2.71-2.62 (m, 2H), 2.49-2.41 (m, 2H), 2.28-2.13 (m, 2H), 2.03-1.96 (m, 1H), 1.99-1.88 (m, 1H), 1.85-1.73 (m, 2H), 1.72-1.53 (m, 4H), 1.50-1.21 (m, 6H), 1.18-1.06 (m, 1H), 0.98 (s, 3H), 0.75 (s, 3H). LCMS: (Method A) 318.5 (M+1), Retention time: 2.41 min, 96.2 area %.

The following Reaction Scheme 17 demonstrates an alternative method of introducing an amine group through reductive amination:

REACTION SCHEME 17

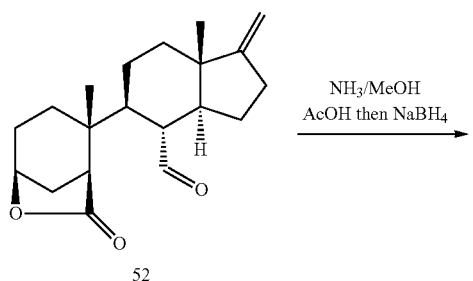

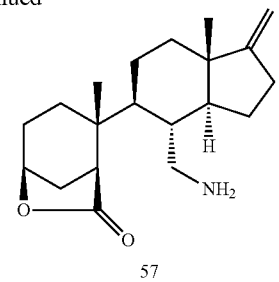

57

58

59

60

In general, Compound 57 is prepared as described above by first treating Compound 52 under suitable reductive amination conditions to provide Compound 57, such as treating Compound 52 in an organic solvent, such as methanol and acetic acid, with a nitrogen source, such as ammonia, and a reducing agent, such as sodium cyanoborohydride.

The following Synthetic Example, which are directed to the steps and products as set forth above in Reaction Scheme 17 are provided as a guide to assist in the practice of the invention, and are not intended as a limitation on the scope of the invention.

Synthetic Example 53

Preparation of Compound 57 from Compound 52 as Well as Intermediate Compounds 58, 59 and 60

A. To a solution of (3aS,4R,5S,7aS)-7a-methyl-5-((1S,2R,5S)-2-methyl-7-oxo-6-oxabicyclo[3.2.1]octan-2-yl)-1-methyleneoctahydro-1H-indene-4-carbaldehyde (Compound 52, 0.1 g, 0.316 mmol, 1 eq., see Synthetic Example 39) in NH₃ (7 M in MeOH, 2 mL, 20 V) was added acetic acid (0.1 mL, 1 V) at 0° C. The reaction mixture was warmed to room temperature and stirred under a nitrogen atmosphere for 30 min. Completion of the reaction was confirmed by LCMS (93.0% of Compound 58 and 5.1% of Compound 59). LCMS: (Method A) 316.5 (M+1), Retention time: 2.35 min, 93.0 area %.

B. NaBH₄ (0.06 g, 4.74 mmol, 3 eq.) was then added to the reaction mixture at room temperature and stirred for another 2 h. Completion of the reaction was confirmed by LCMS (85.6% of Compound 57 and 13.6% of Compound 60). LCMS: (Method A) 318.5 (M+1), Retention time: 2.43 min, 85.6 area %.

C. After completion, the reaction mixture was quenched with a 33% aqueous ammonia solution (10 mL) and stirred for 1 h. The reaction mixture was extracted with MTBE (3×10 mL). The combined organic layers were washed with a 10% aqueous solution of NaHCO₃ (10 mL) followed by a brine solution (10 mL). The organic layer was dried (Na₂SO₄) and evaporated to dryness. The crude product was purified by silica gel column chromatography (230-400 mesh; eluted with 65-70% ethyl acetate/petroleum ether) to afford (1S,2R,5S)-2-((3aS,4R,5S,7aS)-4-(aminomethyl)-7a-methyl-1-methyleneoctahydro-1H-inden-5-yl)-2-methyl-6-oxabicyclo[3.2.1]octan-7-one (Compound 57, 55 mg, yield 55%) as a brown solid. ¹H NMR (400 MHz, pyridine-d5): δ 4.74 (br s, 1H), 4.62 (s, 2H), 2.85-2.75 (m, 1H), 2.71-2.64 (m, 2H), 2.49-2.42 (m, 2H), 2.26-2.16 (m, 2H), 2.01-1.88 (m, 2H), 1.84-1.53 (m, 6H), 1.50-1.00 (m, 7H), 0.98 (s, 3H), 0.75 (s, 3H).

The following Reaction Scheme 18 demonstrates a method of amine introduction through oxime formation followed by Raney Nickel reduction:

REACTION SCHEME 18:

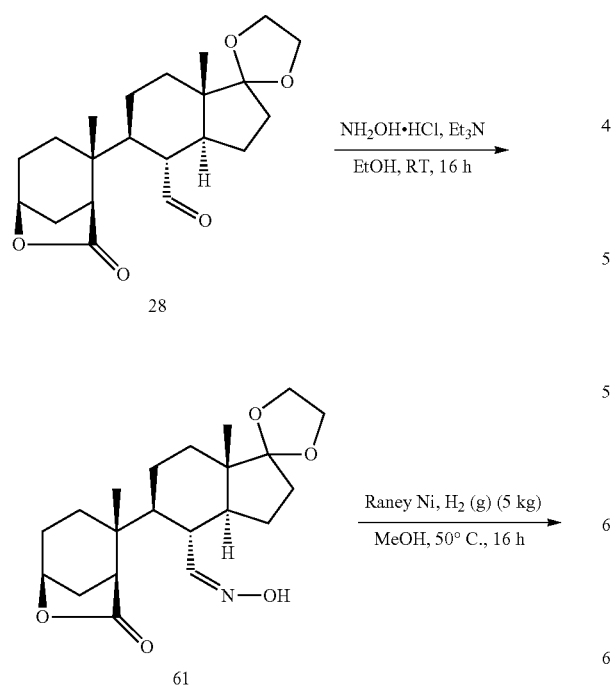

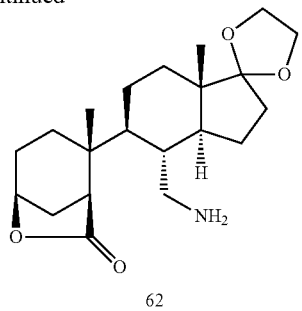

62

In general, Compound 62 is prepared as described in Reaction Scheme 18 by first treating Compound 28 under suitable oxime or oxime O-ether formation conditions to provide Compound 61, such as treating Compound 28 in a suitable polar protic solvent, such as ethanol, with a suitable reagent, such as hydroxylamine hydrochloride, in the presence of a base, such as trimethylamine.

Compound 61 is then treated under suitable oxime reduction conditions to provide Compound 62, such as treating Compound 61 in a polar protic solvent, such as methanol, with an appropriate reducing agent, such as hydrogen gas, in the presence of a metal catalyst, such as Raney nickel.

The following Synthetic Example, which are directed to the steps and products as set forth above in Reaction Scheme 18 are provided as a guide to assist in the practice of the invention, and are not intended as a limitation on the scope of the invention.

Synthetic Example 54

Conversion of Compound 28 to Compound 61

A. To a suspension of (3aS,4R,5S,7aS)-7a-methyl-5-((1S,2R,5S)-2-methyl-7-oxo-6-oxabicyclo[3.2.1]octan-2-yl)octahydrospiro[indene-1,2'-[1,3]dioxolane]-4-carbaldehyde (Compound 28, from Synthetic Example 21, 5 g 0.0138 mol, 1 eq.) in ethanol (50 mL, 10 V) were added hydroxylamine hydrochloride (1.93 g, 0.0276 mol, 2 eq.) portion-wise and triethylamine (4.19 g, 0.0414 mol, 3.0 eq.) at RT. The reaction mixture was stirred at RT for 10 h. The progress of the reaction was monitored by TLC (1:1 hexanes/ethyl acetate, R_f=0.6, KMnO₄ stain).

B. After completion, the reaction mixture was concentrated to dryness. The crude product was suspended in water (50 mL, 10 V) and stirred at RT for 30 min. The suspension was filtered and dried under vacuum to afford 7a-methyl-5-((1S,2R,5S)-2-methyl-7-oxo-6-oxabicyclo[3.2.1]octan-2-yl)octahydrospiro[indene-1,2'-[1,3]dioxolane]-4-carbaldehyde oxime (Compound 61, 5.0 g, yield 96%) as an off-white solid. ¹H NMR (400 MHz, DMSO-d6): δ 10.36 (s, 1H), 7.06 (d, J=9.2 Hz, 1H), 4.76 (br s, 1H), 3.86-3.79 (m, 4H), 2.40-2.21 (m, 2H), 2.11-1.95 (m, 2H), 1.94-1.76 (m, 3H), 1.72-1.57 (m, 5H), 1.45-1.10 (m, 6H), 0.96 (s, 3H), 0.80 (s, 3H). LCMS: (Method A): 378.3 (M+1), Retention time: 2.55 min.

Synthetic Example 55

Conversion of Compound 61 to Compound 62

A. In a mini clave pressure reactor (Buchi, 250 mL glass reactor, maximum capacity of 71 psi), a suspension of 7a-methyl-5-((1S,2R,5S)-2-methyl-7-oxo-6-oxabicyclo

[3.2.1]octan-2-yl)octahydrospiro[indene-1,2'-[1,3]dioxo-lane]-4-carbaldehyde oxime (Compound 61, 2.0 g, 5.3 mmol, 1.0 eq., from Synthetic Example 54) in methanol (20 mL, 10 V) was added Raney Nickel (400 mg, 20% w/w). The reaction mixture was stirred under a hydrogen atmosphere (71 psi, mini clave) at 50° C. for 12 h. The reaction progress was monitored by TLC (9:1, dichloromethane:methanol, $R_f$=0.1, KMnO$_4$ stain).

B. After completion, the reaction mixture was filtered through CELITE™ and washed with methanol (2×10 mL). The filtrates were evaporated to dryness under vacuum at 45° C. to afford (1S,2R,5S)-2-((3aS,4R,5S,7aS)-4-(aminomethyl)-7a-methyloctahydrospiro[indene-1,2'-[1,3]dioxolan]-5-yl)-2-methyl-6-oxabicyclo[3.2.1]octan-7-one as white solid (Compound 62, 1.4 g, Yield 72.7%. LCMS (Method A): 364.5 (M+1), Retention time: 2.17 min, 77.8 area %, 89.8 area % (ELSD). This reaction was performed at two additional batch sizes, affording Compound 62, a) 0.1 g, and b) 1.5 g, with slight changes in the conditions as follows: a) Reaction was carried out under hydrogen gas (71 psi, mini clave) at room temperature for 12 h (purity 89.8%, yield 78.2%) and b) reaction was carried out under hydrogen gas (71 psi, mini clave) at 50° C. for 12 h (1.2% of unreacted starting material was observed)—(purity 79.9%, yield 68.2%).

The following Reaction Scheme 19 demonstrates a method of amine introduction through ether oxime formation followed by Birch reduction:

REACTION SCHEME 19:

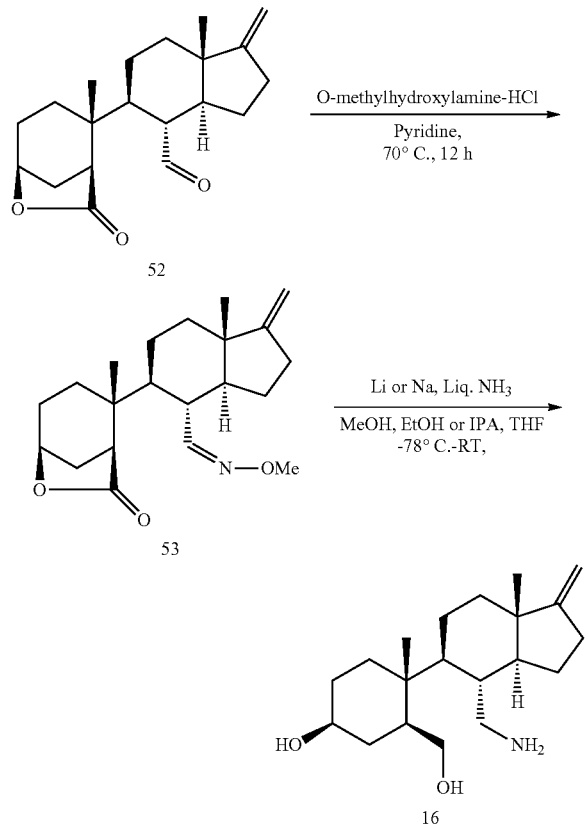

In general, Compound 16 is prepared by the method disclosed above in Reaction 19 by first treating Compound 52 under suitable oxime or oxime O-ether formation conditions to provide Compound 53, such as treating Compound 52 in a suitable basic organic solvent, such as pyridine, with a suitable reagent, such as O-methyl hydroxylamine hydrochloride.

Compound 53 is then treated under suitable oxime O-ether and lactone reduction conditions, such as the Birch reduction, to provide Compound 16, such as treating Compound 53 in a polar protic solvent, such as methanol, ethanol and isopropanol in liquid ammonia, with a suitable reducing agent, such as lithium and sodium metal.

The following Examples, which are directed to the steps and products as set forth above in Reaction Scheme 19 are provided as a guide to assist in the practice of the invention, and are not intended as a limitation on the scope of the invention.

Synthetic Example 56

Conversion of Compound 52 to Compound 53

A. To a solution of (3aS,4R,5S,7aS)-7a-methyl-5-((1S,2R,5S)-2-methyl-7-oxo-6-oxabicyclo[3.2.1]octan-2-yl)-1-methyleneoctahydro-1H-indene-4-carbaldehyde (Compound 52, 1.0 g, 3.1 mmol, 1 eq., see Synthetic Example 39) in pyridine (30 mL) was added O-methylhydroxylamine hydrochloride (1.3 g, 15.6 mmol, 5 eq.) in one portion and the reaction was stirred at RT in a 100 mL three-necked RB flask under a nitrogen atmosphere. The reaction mass was then heated to 70° C. and stirring was continued for 12 h for reaction completion.

B. Completion of the reaction was confirmed by TLC analysis (7:3 petroleum ether:ethyl acetate, $R_f$=0.5, KMnO$_4$ stain). The contents of the flask were concentrated on a rotary evaporator at 45° C. to get a crude residue, which was diluted with a cold 1.5 N aq. HCl solution (20 mL). Extraction of the product was carried out with ethyl acetate (3×50 mL) and the combined organic layers were washed with a 10% aq. solution of sodium bicarbonate (25 mL) followed by brine (25 mL). The organic phase was dried over anhydrous sodium sulphate and concentrated under vacuum. Further purification was done by flash column chromatography using silica 230-400 mesh silica gel and 30% ethyl acetate in petroleum ether as eluent. This purification afforded Compound 53, 7a-methyl-5-((1S,2R,5S)-2-methyl-7-oxo-6-oxabicyclo[3.2.1]octan-2-yl)-1-methyleneoctahydro-1H-indene-4-carbaldehyde O-methyl oxime, 850 mg, 84% yield as an off-white solid. $^1$H NMR (400 MHz, CD$_3$OD): δ 7.21 (d, J=9.20 Hz, 1H), 4.78 (t, J=5.20 Hz, 1H), 4.70-4.69 (m, 2H), 3.79 (s, 3H), 2.60-1.30 (m, 18H), 1.11 (s, 3H), 0.87 (s, 3H). LCMS: (Method B) 346.4 (M+1), Retention time: 3.27 min, 99.6 area %.

Synthetic Example 57

Conversion of Compound 53 to Compound 16

A. 7a-methyl-5-((1S,2R,5S)-2-methyl-7-oxo-6-oxabicyclo[3.2.1]octan-2-yl)-1-methyleneoctahydro-1H-indene-4-carbaldehyde O-methyl oxime (Compound 53, 0.5 g, 1.43 mmol, 1 eq., from Synthetic Example 56) was added to a mixture of anhydrous tetrahydrofuran (20 mL) and isopropyl alcohol (5 mL) taken in a 100 mL three-necked flask equipped with a mechanical stirrer. One neck of the flask was fitted with an ammonia condensing unit which had dry ice in acetone as a coolant to condense the ammonia gas. A calcium chloride guard tube was used at the top of the unit. Ammonia gas was passed through the condenser for 2 minutes and approx. 20 mL of liquid ammonia were collected in the flask. The reaction flask was cooled to −78° C. and finely ground lithium metal (0.20 g, 28.6 mmol, 20 eq.) was added to the reaction flask in three equal lots. The color of the reaction mass turned reddish brown. Stirring of the reaction mass at −78° C. was continued for 1 h. The reaction mass was then gradually warmed to 0° C. over 1 h (during this period, the red color of the reaction mass changed to off-white). The reaction mass was carefully quenched by adding solid ammonium chloride (5 g) in to the reaction flask at 0° C. The mixture was stirred for an additional 1 h and then allowed to stand uncovered at RT until the ammonia evaporated.

B. The residue was dissolved in water (100 mL). The solution was extracted with ethyl acetate (2×100 mL) and the combined organic layers washed with brine (25 mL). The organic phase was dried over anhydrous sodium sulphate, concentrated over a rotary evaporator at 45° C. Further purification was done by flash column chromatography using 230-400 meshed silica gel and 8% methanol (100 mL of methanol was diluted with 1 mL of aq. ammonia solution) in dichloromethane as eluent to afford Compound 16, (1S, 3S,4R)-4-((3aS,4R,5S,7aS)-4-(aminomethyl)-7a-methyl-1-methyleneoctahydro-1H-inden-5-yl)-3-(hydroxymethyl)-4-methylcyclohexan-1-ol, 380 mg, 83% yield) as an off-white solid. $^1$H NMR (400 MHz, CD$_3$OD): δ 4.47 (s, 2H), 3.74 (d, J=10.5 Hz, 1H), 3.48-3.45 (m, 1H), 3.19-3.14 (m, 2H), 2.82 (d, J=14.3 Hz, 1H), 2.53-2.16 (m, 3H), 1.91-1.34 (m, 15H), 1.11 (s, 3H), 0.84 (s, 3H). LCMS: (Method B) 322.5 (M+1), Retention time: 2.78 min, 99.2%. HPLC: (Method B) Retention time: 2.78 min, 98.3 area %.

This reaction was performed with various conditions, each affording Compound 16, as shown below in Table 1. Conditions explored include choice of metal (Li, Na), alcohol (MeOH, EtOH, IPA), temperature range, reaction time, and batch size.

AQX-1125 may also be prepared according to the method described below in Reaction Scheme 20:

REACTION SCHEME 20

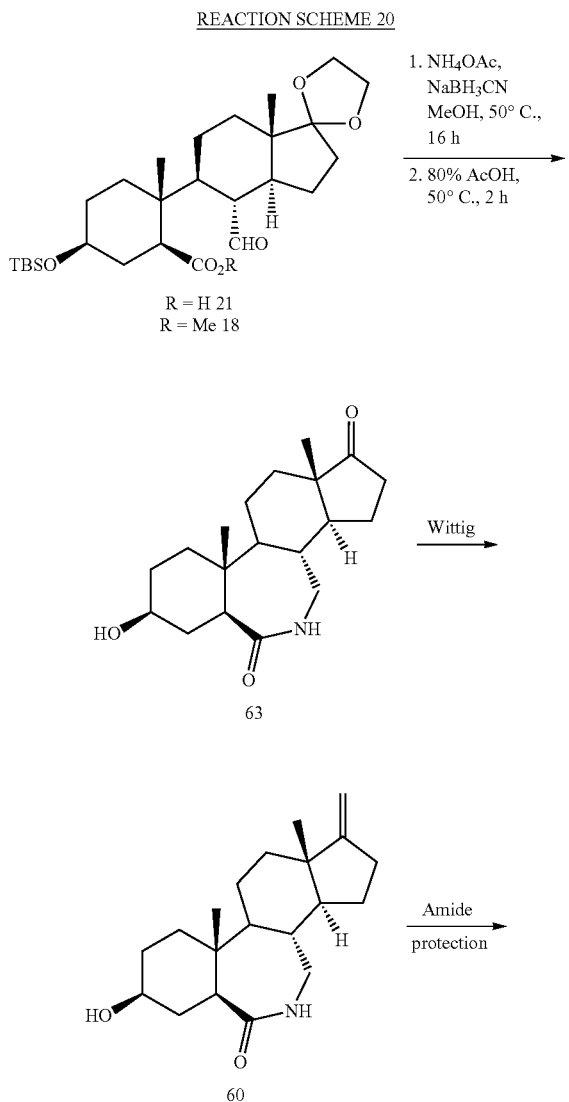

TABLE 1

Conditions for reaction in Example 57

| Metal (eq.) | Batch size | THF (V) | Alcohol (V) | ° C. | Reaction Time (h) | % Product by LCMS | % Double bond reduced products by LCMS | % Other byproducts by LCMS |
|---|---|---|---|---|---|---|---|---|
| Li (20) | 0.8 g | 20 | IPA (5 V) | −78 | 1 | 43.48 | | 56.52 |
| Li (20) | 0.5 g | 20 | IPA (5 V) | −40 to −33 | 2 | 55.66 | 22.39 | 18.28 |
| Li (20) | 1.0 g | 20 | IPA (5 V) | −60 to −50 | 2 | 55.16 | 6.8 | 36.5 |
| Na (20) | 0.5 g | 20 | IPA (5 V) | −78 | 2 | 47.87 | 4.23 | 47.90 |
| Na (40) | 0.5 g | 20 | MeOH (2.5 V) | −78 | 2 | 96.42 | 0.71 | 2.53 |
| Na (40) | 0.5 g | 20 | EtOH (5 V) | −78 | 2 | 92.05 | | 9.86 |
| Na (40) | 5.0 g | 20 | MeOH (2.5 V) | −78 | 3 | 66.17 | | 33.04 |

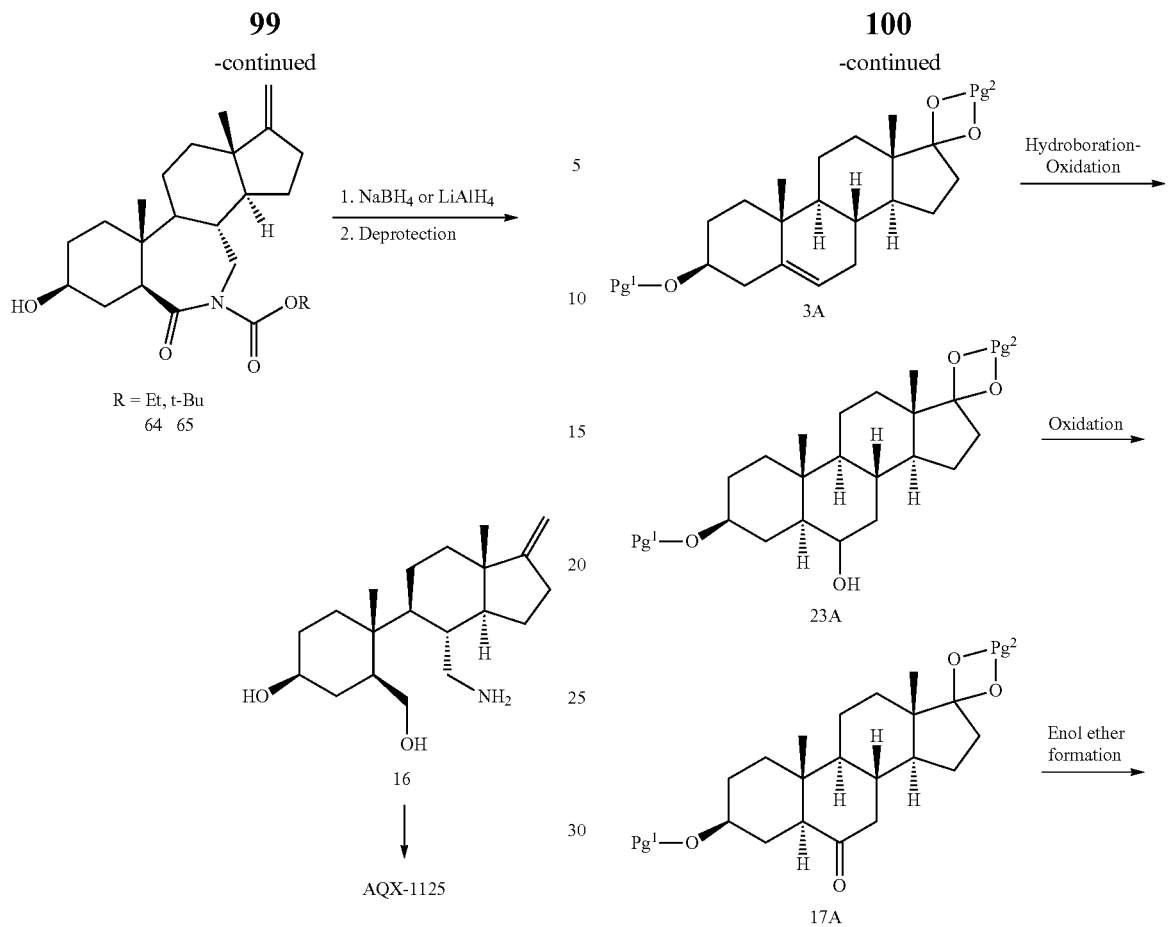
F. Synthetic Methods 21-22
AQX-1125 was prepared according to the method disclosed below in Reaction Scheme 21, wherein $R^1$ is hydrogen, methyl or ethyl, $Pg^1$ is an oxygen-protecting group and $Pg^2$ is a carbonyl protecting group:
REACTION SCHEME 21
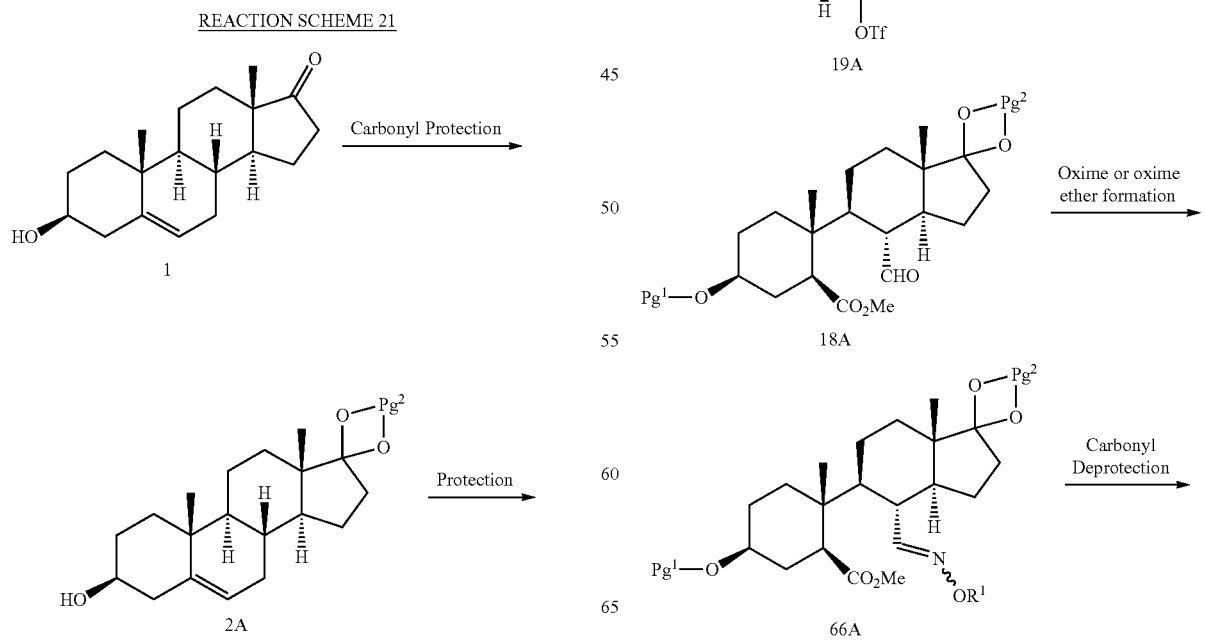

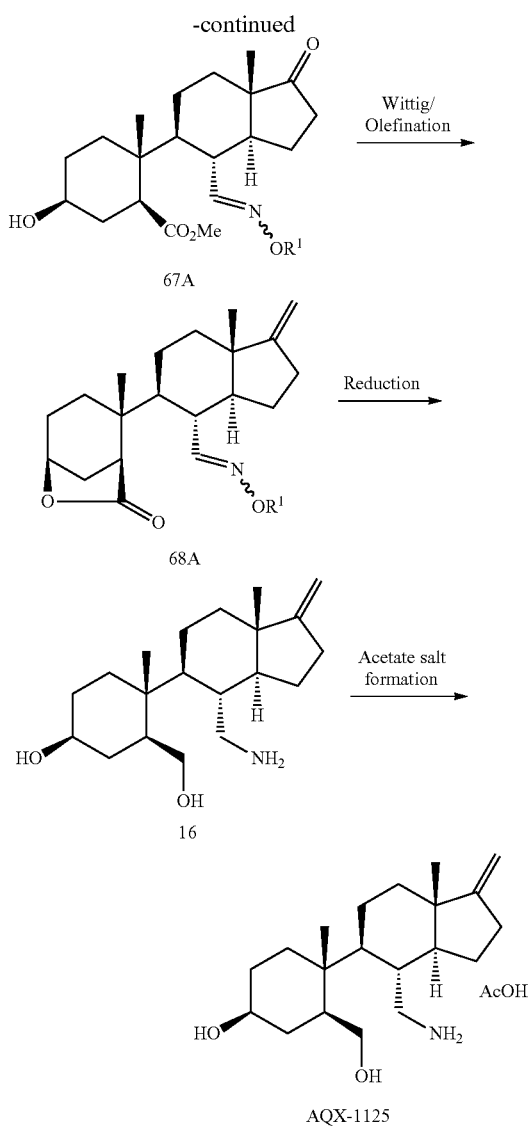

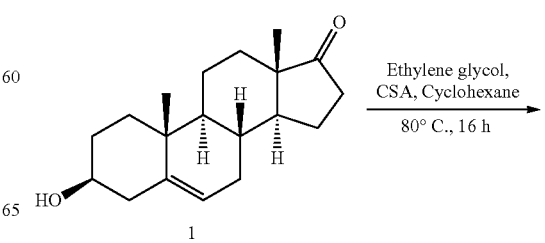

Compound 23A is then treated under suitable oxidation conditions, such as the Parikh-Doering oxidation, to provide Compound 17A, such as treating Compound 23A in a suitable organic solvent, such as dichloromethane, with an oxidizing agent, such as dimethyl sulfoxide, and a suitable activating reagent, such as pyridine-sulfur trioxide complex, in the presence of a base, such as triethylamine.

Compound 17A is then treated under suitable enol ether formation conditions to provide Compound 19A, such as treating Compound 17A in a suitable polar aprotic solvent, such as tetrahydrofuran, with a strong base, such as lithium diisopropylamide, and suitable electrophilic reagent, such as N-phenyl triflimide.

Compound 19A is then treated under suitable oxidative carbon-carbon bond cleavage conditions, such as ozonolysis, to provide Compound 18A, such as treating Compound 19A in a polar protic solvent, such as methanol, with a suitable oxidizing agent, such as ozone, followed by reductive work-up with a suitable reducing agent, such as sodium borohydride.

Compound 18A is then treated under suitable oxime or oxime O-ether formation conditions to provide Compound 66A, such as treating Compound 18A in a suitable polar protic solvent, such as methanol, with a suitable reagent, such as hydroxylamine hydrochloride, in the presence of a base, such as trimethylamine.

Compound 66A is then treated under suitable carbonyl deprotection conditions to provide Compound 67A, such as treating Compound 66A in a polar protic solvent, such as water, with a suitable acid, such as acetic acid.

Compound 67A is then treated under suitable olefination or Wittig reaction conditions to provide Compound 68A, such as treating Compound 67A in a suitable organic solvent, such as toluene or tetrahydrofuran, with a ylide generated using a phosphonium salt, such as methyltriphenylphosphonium bromide, and a base, such as potassium tert-butoxide.

Compound 68A is then treated under suitable lactone and oxime reduction conditions to provide Compound 16, such as treating Compound 68A in a polar aprotic solvent, such as tetrahydrofuran or dioxane, with a reducing agent, such as lithium aluminum hydride.

Compound 16 is then treated under suitable acetic salt formation conditions to provide AQX-1125, such as treating Compound 16 in a polar protic solvent, such as methanol, with glacial acetic, followed by a less polar organic solvent, such as methyl tert-butyl ether.

A specific method of preparing AQX-1125, as set forth above in Reaction Scheme 21, is illustrated below in Reaction Scheme 21A:

REACTION SCHEME 21A

Compound 1, which is dehydroepiandrosterone, is commercially available or can be made by methods known to one skilled in the art.

In general, AQX-1125 is prepared as described above in Reaction Scheme 1 by first treating Compound 1 in an organic solvent, such as cyclohexane, with a carbonyl protecting group reagent, such as ethylene glycol in the presence of an acid catalyst, such as camphor sulfonic acid or p-toluene sulfonic acid.

Compound 2A is then treated under suitable hydroxyl protection conditions to provide Compound 3A, such as treating Compound 2A in an organic solvent, such as dichloromethane, with a hydroxyl protecting group reagent, such as tert-butyldimethylsilyl chloride, in the presence of a base, such as imidazole.

Compound 3A is then treated under suitable hydroboration-oxidation conditions to provide Compound 23A, such as treating Compound 3A in a polar aprotic solvent, such as tetrahydrofuran, with a hydroboration reagent, such as borane in tetrahydrofuran, followed by oxidative work-up using an oxidant, such as hydrogen peroxide.

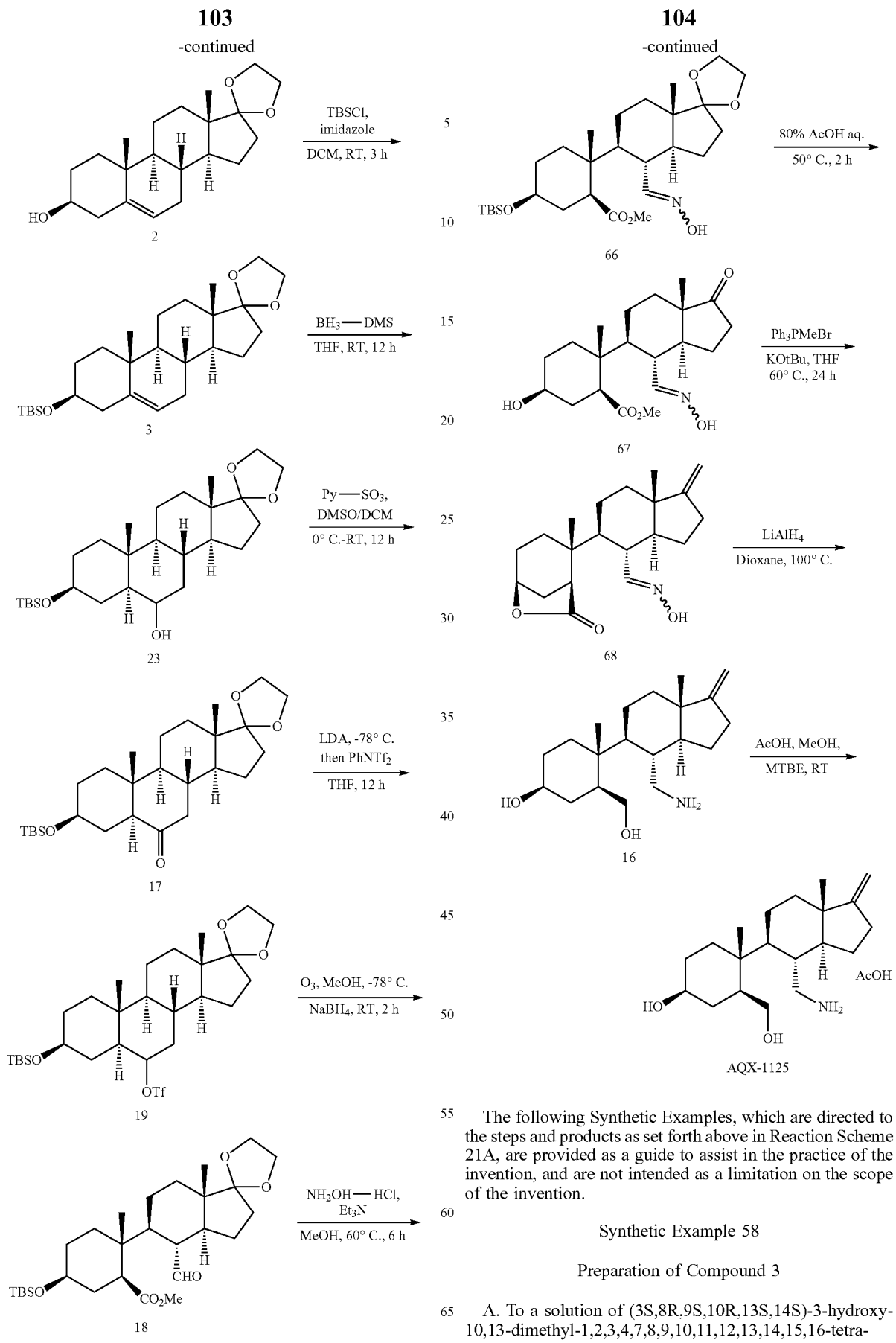

The following Synthetic Examples, which are directed to the steps and products as set forth above in Reaction Scheme 21A, are provided as a guide to assist in the practice of the invention, and are not intended as a limitation on the scope of the invention.

Synthetic Example 58

Preparation of Compound 3

A. To a solution of (3S,8R,9S,10R,13S,14S)-3-hydroxy-10,13-dimethyl-1,2,3,4,7,8,9,10,11,12,13,14,15,16-tetradecahydro-17H-cyclopenta[a]phenanthren-17-one (Compound 1, 50.0 g, 173.3 mmol) in cyclohexane (500 mL) in a dry 1000 mL RB flask fitted with a Dean-Stark apparatus was added (+/−)-10-camphor sulphonic acid (800 mg, 3.43 mmol) followed by ethylene glycol (54.0 g, 866.7 mmol) at RT (room temperature). The reaction mass was heated to 80° C. under reflux for 16 hours for azeotropic removal of water. The reaction mass was monitored by HPLC analysis.

B. After completion of the reaction, the reaction mixture was concentrated under vacuum by rotary evaporation at a temperature below 40° C. The residue obtained was diluted with an aqueous sodium bicarbonate solution (8% w/v, 20 g in 250 mL $H_2O$) and extracted with dichloromethane (2×500 mL). The combined organic layers containing Compound 2, were washed with brine (500 mL) and dried over anhydrous sodium sulfate, filtered and concentrated under vacuum by rotary evaporation until a volume of ~450-500 mL remained.

C. Imidazole (29.95 g, 440.3 mmol) was charged into the concentrated mass, containing Compound 2, at 25° C. followed by the addition of tert-butyldimethylsilylchloride (35.5 g, 235.7 mmol) in 3 equal lots by maintaining the temperature at 25° C. The reaction mass was stirred at 25° C. for 3 h and the reaction progress was monitored by HPLC analysis.

D. The organic layer was washed with purified water (2×250 mL) and concentrated under vacuum (NLT 550 mm/Hg). Methanol was charged (150 mL) into the concentrated mass below 35° C. and stirred for 10-15 minutes. The mass was cooled to −2° C. and stirred for 1 h. The slurry was filtered and the cake was washed with water (50 mL). The solids were dried under vacuum at 35° C. to obtain tert-butyl(((3S,8R,9S,10R,13S,14S)-10,13-dimethyl-1,2,3,4,7,8,9,10,11,12,13,14,15,16-tetradecahydrospiro[cyclopenta[a]phenanthrene-17,2'-[1,3]dioxolan]-3-yl)oxy)dimethylsilane (Compound 3, 70 g, 90.3% yield) as an off-white solid. $^1$H-NMR (400 MHz, $CDCl_3$): δ 5.35-5.28 (m, 1H), 3.96-3.86 (m, 4H), 3.55-3.45 (m, 1H), 2.32-1.95 (m, 4H), 1.84-0.87 (m, 30H), 0.07 (s, 3H), 0.06 (s, 3H). LCMS (Method C): MS m/z: 447.4 [M+1]$^+$, Retention time: 8.27 min, HPLC (Method D); Retention time: 29.27 min, Purity: 98.4 area %.

Synthetic Example 59

Preparation of Compound 23

A. To a solution of tert-butyl(((3S,8R,9S,10R,13S,14S)-10,13-dimethyl-1,2,3,4,7,8,9,10,11,12,13,14,15,16-tetradecahydrospiro[cyclopenta[a]phenanthrene-17,2'-[1,3]dioxolan]-3-yl)oxy)dimethylsilane (Compound 3, 50.0 g, 11.9 mmol, from Synthetic Example 58) in tetrahydrofuran (450 mL) in a 1 L RB flask was added $BH_3$-DMS (13.4 g, ~10.0 M concentration) in tetrahydrofuran (26 mL) drop-wise via syringe over a period of 10 min at 2° C. The reaction mixture was allowed to stir at RT and reaction progress was monitored by HPLC analysis. After the consumption of the starting material, the reaction mixture was cooled to −3 to 0° C. in an ice bath and quenched by very slow addition of 30% hydrogen peroxide in water (68 mL) and NaOH solution (3 M, 195 mL) via a dropping funnel. The reaction mixture was stirred for 2 h at 0° C. and then stirred overnight at 25-30° C.

B. The reaction mass was diluted with ethyl acetate (450 mL) and the layers separated. The aqueous layer was further extracted with ethyl acetate (200 mL) and the combined organic layers were dried over sodium sulfate, filtered and concentrated in vacuo by rotary evaporation. The crude residue was dissolved in acetone (750 mL) and water (750 mL) was slowly added. The resultant precipitate was filtered off on a glass frit and dried under vacuum to obtain (3S,5S,8R,9S,10R,13S,14S)-3-((tert-butyldimethylsilyl)oxy)-10,13-dimethylhexadecahydrospiro[cyclopenta[a]phenanthrene-17,2'-[1,3]dioxolan]-6-ol (Compound 23, 38 g, 73% yield) as an off-white solid. $^1$H-NMR (400 MHz, $CDCl_3$): δ 3.96-3.86 (m, 4H), 3.65-3.31 (m, 2H), 2.10-1.95 (m, 3H), 1.84-1.20 (m, 15H), 1.07-0.95 (m, 2H), 0.90 (s, 9H), 0.85 (s, 3H), 0.83 (s, 3H), 0.78-0.68 (m, 1H), 0.07 (s, 3H), 0.06 (s, 3H). LCMS (Method E): MS m/z: 465.4 [M+1]$^+$, Retention time: 5.43 min, HPLC (Method F): Retention time: 12.97 min, Purity: 98.5 area %.

Synthetic Example 60

Preparation of Compound 17

A. To a solution of (3S,5S,8R,9S,10R,13S,14S)-3-((tert-butyldimethylsilyl)oxy)-10,13-dimethylhexadecahydrospiro[cyclopenta[a]phenanthrene-17,2'-[1,3]dioxolan]-6-ol (Compound 23, 3.2 g, 6.88 mmol, from Synthetic Example 59) in dichloromethane (32 mL) in a dry 100 mL RB flask was added triethylamine (5.8 mL, 41.3 mmol) and DMSO (19.6 mL) at RT. The reaction mass was cooled to −5° C. in an ice bath. Pyridine sulphur trioxide (5.5 g, 34.4 mmol) was added in 3 portions into the RB flask by maintaining the temperature at below 10° C. The solution was stirred using a magnetic stirrer at 0° C. for 30 min and then at 25-30° C. for 12 h. The reaction progress was monitored by TLC analysis (9:1 hexanes:ethyl acetate, $R_f$=0.35, $KMnO_4$ stain).

B. After completion of the reaction, dichloromethane was evaporated under vacuum by rotary evaporation at 35° C. The residue was cooled to ~5° C. in an ice bath and then treated with $Na_2CO_3$ solution (saturated (aq.), 170 mL) and the mixture was stirred at ~0-3° C. for 90 min to form a solid suspension. The slurry was filtered through a glass frit and the filter cake was washed with cold water (~5° C., 2×30 mL) and dried under vacuum for 12 h to afford crude product as a pale brown solid. The crude product was dissolved in acetone (50 mL) to obtain a solution. Water (7.5 mL) was slowly added to the solution. Precipitation was observed and the slurry was filtered through a glass frit. The solid cake was dried under vacuum at 35° C. to obtain (3S,5S,8R,9S,10R,13S,14S)-3-((tert-butyldimethylsilyl)oxy)-10,13-dimethyltetradecahydrospiro[cyclopenta[a]phenanthrene-17,2'-[1,3]dioxolan]-6(1H)-one (Compound 17, 2.1 g, 66% yield) as a pale brown colour solid. $^1$H-NMR (400 MHz, $CDCl_3$): δ 3.96-3.84 (m, 4H), 3.60-3.50 (m, 1H), 2.38-2.32 (m, 1H), 2.33-2.17 (m, 1H), 2.05-1.95 (m, 2H), 1.83-1.45 (m, 16H), 0.89-0.86 (m, 12H), 0.77 (s, 3H), 0.06 (s, 6H). LCMS (Method E): MS m/z: 463.4 [M+1]$^+$, Retention time: 5.41 min, HPLC (Method G): Retention time: 16.19 min, Purity: 98.3 area %.

Synthetic Example 61

Preparation of Compound 19

A. To a solution of diisopropylamine (0.91 mL, 6.49 mmol) in anhydrous tetrahydrofuran (5 mL) in a dry 100 mL RB flask was added n-butyl lithium (1.6 M solution in hexane, 4 mL, 6.49 mmol) drop-wise via syringe at −78° C. under a nitrogen atmosphere. The reaction mass was stirred using a magnetic stirrer and slowly warmed up to 0° C. over 1 hour. A solution of (3S,5S,8R,9S,10R,13S,14S)-3-((tert-butyldimethylsilyl)oxy)-10,13-dimethyltetradecahydrospiro

[cyclopenta[a]phenanthrene-17,2'-[1,3]dioxolan]-6(1H)-one (Compound 17, 2 g, 4.33 mmol, from Synthetic Example 60) in tetrahydrofuran (20 mL) was added to the reaction mass drop-wise via syringe at −78° C. and stirring was continued for 2 hours. A solution of N-phenyl triflimide (1.85 g, 5.19 mmol) in tetrahydrofuran (10 mL) was added drop-wise via syringe into the reaction mass. Stirring was continued for 2 h at −78° C. and then 12 hours at RT until the reaction completion was confirmed by TLC analysis.

B. Completion of the reaction was confirmed by TLC analysis (7:3 hexanes:ethyl acetate, $R_f$=0.7, KMnO$_4$ stain). The reaction mass was quenched with solution of ammonium chloride (saturated, 20 mL) and extracted with ethyl acetate (2×25 mL). The combined organic extracts were washed with brine (25 mL), dried over anhydrous sodium sulfate and concentrated by rotary evaporation. The residue was purified by chromatography on silica gel (8:2 hexanes:ethyl acetate) to afford (3S,5S,8R,9S,10R,13S,14S)-3-((tert-butyldimethylsilyl)oxy)-10,13-dimethyl-1,2,3,4,5,8,9,10,11,12,13,14,15,16-tetradecahydrospiro[cyclopenta[a]phenanthrene-17,2'-[1,3]dioxolan]-6-yl trifluoromethanesulfonate (Compound 19, 2.3 g, 89% yield) as an off-white solid. LCMS (Method A) m/z: 596.0 (M+2), Retention time: 4.60 min, Purity: 99.1 area % (ELSD).

Synthetic Example 62

Preparation of Compound 18

A. A solution of (3S,5S,8R,9S,10R,13S,14S)-3-((tert-butyldimethylsilyl)oxy)-10,13-dimethyl-1,2,3,4,5,8,9,10,11,12,13,14,15,16-tetradecahydrospiro[cyclopenta[a]phenanthrene-17,2'-[1,3]dioxolan]-6-yl trifluoromethanesulfonate (Compound 19, 2.3 g, 3.87 mmol, from Synthetic Example 61) in a mixture of dichloromethane (20 mL) and methanol (20 mL) in a dry 100 mL RB flask fitted with bubbler tubing and outlet was cooled at −78° C. and stirred using a magnetic stirrer. The inlet of the bubbler was connected to the ozonolysis apparatus (Ozoniser) while the outlet of the flask was dipped into a beaker containing an aqueous solution of potassium iodide (20 g dissolved in 250 mL). The reaction mass was flushed with oxygen gas for 10 minutes. Ozone gas was then bubbled through the reaction for the next 1 hour. The completion of the ozonolysis was monitored by the change of reaction mass color from pale yellow to dark blue. Again, oxygen gas was bubbled through the reaction mass for 10 minutes. The inlet and outlet connectors were removed from the RB flask and the reaction paced under a nitrogen atmosphere using a nitrogen U-tube. Sodium borohydride (0.28 g, 7.74 mmol) was added to the reaction mass at −78° C. and stirring continued for another 1 hour. Completion of the reaction was monitored by TLC analysis (7:3 hexanes:ethyl acetate, $R_f$=0.6, KMnO$_4$ stain).

B. The reaction mass was concentrated by rotary evaporation and the crude residue obtained was partitioned between ethyl acetate (25 mL) and water (25 mL). The aqueous layer was extracted with ethyl acetate (2×50 mL). The combined organic layers were washed with brine (25 mL), dried over anhydrous sodium sulfate and concentrated by rotary evaporation. The residue was purified using chromatography on silica gel (7:3 hexanes:ethyl acetate) to afford methyl (1S,2R,5S)-5-((tert-butyldimethylsilyl)oxy)-2-((3aS,4R,5S,7aS)-4-formyl-7a-methyloctahydrospiro[indene-1,2'-[1,3]dioxolan]-5-yl)-2-methylcyclohexane-1-carboxylate (Compound 18, 1.7 g, 86% yield) as an off-white solid. $^1$H-NMR (400 MHz, DMSO-d$_6$): δ 9.39 (d, J=5.9 Hz, 1H), 3.96-3.85 (m, 4H), 3.69 (s, 3H), 3.67-3.60 (m, 1H), 2.76-2.68 (m, 1H), 2.40-2.30 (m, 1H), 2.08-1.28 (m, 16H), 1.03-0.83 (m, 15H), 0.06 (s, 6H). LCMS (Method B) m/z: 509.2 (M+1), Retention time: 6.68 min, Purity: 94.5 area % (ELSD).

Synthetic Example 63

Preparation of Compound 66

A. To a solution of methyl (1S,2R,5S)-5-((tert-butyldimethylsilyl)oxy)-2-((3aS,4R,5S,7aS)-4-formyl-7a-methyloctahydrospiro[indene-1,2'-[1,3]dioxolan]-5-yl)-2-methylcyclohexane-1-carboxylate (Compound 18, 1.7 g, 3.34 mmol, from Synthetic Example 62) in methanol (20 mL) in a 50 mL RB flask fitted with a reflux condenser was added hydroxylamine hydrochloride (0.46 g, 6.68 mmol) and triethylamine (0.92 ml, 3.34 mmol) at RT and the reaction stirred using a magnetic stirrer for 6 h at 60° C. The completion of the reaction was monitored by TLC (1:1 hexanes:ethyl acetate, $R_f$=0.4, KMnO$_4$ stain).

B. The reaction mass was concentrated by rotary evaporation and the crude residue obtained was partitioned between ethyl acetate (25 mL) and water (25 mL). The aqueous layer was extracted with ethyl acetate (2×25 mL). The combined organic layers were washed with brine (25 mL), dried over anhydrous sodium sulfate and concentrated by rotary evaporation. The residue was purified using chromatography on silica gel (6:4 hexanes:ethyl acetate) to afford methyl (1S,2R,5S)-5-((tert-butyldimethylsilyl)oxy)-2-((3aS,4R,5S,7aS)-4-((hydroxyimino)methyl)-7a-methyloctahydrospiro[indene-1,2'-[1,3]dioxolan]-5-yl)-2-methylcyclohexane-1-carboxylate (Compound 66, 1.2 g, 69% yield) as an off-white solid. $^1$H-NMR (400 MHz, DMSO-d$_6$): δ 10.21 (s, 1H), 7.05 (d, J=9.2 Hz, 1H), 3.85-3.77 (m, 4H), 3.58 (s, 3H), 3.58-3.50 (m, 1H), 2.78-2.69 (m, 1H), 2.35-2.30 (m, 1H), 1.88-1.31 (m, 16H), 0.96 (s, 3H), 0.82 (s, 9H), 0.76 (s, 3H), 0.04 (s, 3H), 0.03 (s, 3H). LCMS (Method A) m/z: 524.3 (M+1), Retention time: 3.55 min, Purity: 97.4 area %.

Synthetic Example 64

Preparation of Compound 67

A. A solution of methyl (1S,2R,5S)-5-((tert-butyldimethylsilyl)oxy)-2-((3aS,4R,5S,7aS)-4-((hydroxyimino)methyl)-7a-methyloctahydrospiro[indene-1,2'-[1,3]dioxolan]-5-yl)-2-methylcyclohexane-1-carboxylate (Compound 66, 1.2 g, 2.29 mmol, from Synthetic Example 63) in acetic acid (80% (aq.), 20 mL) in a 50 mL RB flask was stirred at 50 C for 2 hours. Completion of the reaction was monitored by TLC analysis (9:1 dichloromethane:methanol, $R_f$=0.3, KMnO$_4$ stain).

B. The reaction mass was concentrated and the crude mass obtained was partitioned between ethyl acetate (20 mL) and a solution of sodium bicarbonate (10% (aq), 20 mL). The aqueous layer was extracted with ethyl acetate (2×25 mL). The combined organic layers were washed with brine (25 mL), dried over anhydrous sodium sulfate and concentrated by rotary evaporation to afford methyl (1S,2R,5S)-5-hydroxy-2-((3aS,4R,5S,7aS)-4-((hydroxyimino)methyl)-7a-methyl-1-oxooctahydro-1H-inden-5-yl)-2-methylcyclohexane-1-carboxylate (Compound 67, 700 mg, 84% yield) as an off-white solid. $^1$H-NMR (400 MHz, DMSO-d$_6$): δ 10.36 (s, 1H), 7.13 (d, J=9.2 Hz, 1H), 4.63 (d, J=5.2 Hz, 1H), 3.57 (s, 3H), 3.33-3.26 (m, 1H), 2.77-2.70 (m, 1H), 2.41-2.32 (m, 1H), 2.04-1.88 (m, 3H), 1.74-1.14

(m, 13H), 0.99 (s, 3H), 0.80 (s, 3H). LCMS (Method A) m/z: 366.3 (M+1), Retention time: 2.19 min, Purity: 95.5 area %

Synthetic Example 65

Preparation of Compound 68

A. A mixture of methyltriphenylphosphonium bromide (2.73 g, 7.66 mmol) and potassium tert-butoxide (0.86 g, 7.66 mmol) in anhydrous tetrahydrofuran (10 mL) in a dry 100 mL RB flask fitted with a reflux condenser was stirred using a magnetic stirrer for 2 hours at RT. A solution of methyl (1S,2R,5S)-5-hydroxy-2-((3aS,4R,5S,7aS)-4-((hydroxyimino)methyl)-7a-methyl-1-oxooctahydro-1H-inden-5-yl)-2-methylcyclohexane-1-carboxylate (Compound 67, 0.7 g, 1.91 mmol, from Synthetic Example 64) in tetrahydrofuran (10 mL) was added drop-wise via dropping funnel into the reaction mass at RT. The reaction was stirred at 60° C. for 24 hours. Completion of the reaction was monitored by TLC analysis (8:2 dichloromethane:acetone, R$_f$=0.6, KMnO$_4$ stain).

B. The reaction mass was concentrated by rotary evaporation and the crude residue obtained was partitioned between ethyl acetate (10 mL) and water (10 mL). The aqueous layer was extracted with ethyl acetate (2×25 mL). The combined organic layers were washed with brine (25 mL), dried over anhydrous sodium sulfate and concentrated by rotary evaporation. The residue was purified using chromatography on silica gel (8:2 hexanes:ethyl acetate) to afford 7a-methyl-5-((1S,2R,5S)-2-methyl-7-oxo-6-oxabicyclo[3.2.1]octan-2-yl)-1-methyleneoctahydro-1H-indene-4-carbaldehyde oxime (Compound 68, 210 mg, 33% yield) as an off-white solid. $^1$H-NMR (400 MHz, DMSO-d$_6$): δ 10.36 (s, 1H), 7.08 (d, J=9.2 Hz, 1H), 4.74 (t, J=5.2 Hz, 1H), 4.64 (d, J=3.2 Hz, 2H), 2.39-2.25 (m, 3H), 2.20-1.82 (m, 6H), 1.72-1.55 (m, 3H), 1.45-1.37 (m, 3H), 1.34-1.07 (m, 3H), 0.98 (m, 3H), 0.77 (s, 3H). LCMS (Method A) m/z: 332.3 (M+1), Retention time: 2.94 min, Purity: 95.3 area %.

Synthetic Example 66

Preparation of Compound 16 and AQX-1125

A. To a solution of 7a-methyl-5-((1S,2R,5S)-2-methyl-7-oxo-6-oxabicyclo[3.2.1]octan-2-yl)-1-methyleneoctahydro-1H-indene-4-carbaldehyde oxime (Compound 68, 100 mg, 0.30 mmol, from Synthetic Example 65) in 1,4-dioxane (5 mL) in a 25 mL RB flask fitted with reflux condenser was added a solution of lithium aluminum hydride (1 M in THF, 1.51 ml, 1.50 mmol) at RT under nitrogen and the reaction mass was stirred using a magnetic stirrer at 100° C. for 24 hours. Another lot of a solution of lithium aluminum hydride (1 M in THF, 1.51 ml, 1.50 mmol) was added and the reaction was further refluxed for 24 hours. Completion of the reaction was monitored by LCMS analysis.

B. The reaction mass was quenched by the drop-wise addition of saturated aq. sodium sulfate solution, filtered through a CELITE™ bed on glass frit funnel and concentrated by rotary evaporation to get a crude mass which was further purified by preparative HPLC to afford (1S,3S,4R)-4-((4R,5S,7aS)-4-(aminomethyl)-7a-methyl-1-methyleneoctahydro-1H-inden-5-yl)-3-(hydroxymethyl)-4-methylcyclohexan-1-ol (Compound 16, 35 mg, 36% yield) as an off-white solid. $^1$H-NMR (400 MHz, CD$_3$OD): δ 4.69 (s, 2H), 3.73 (br d, J=10.0 Hz, 1H), 3.52-3.45 (m, 1H), 3.22-3.15 (m, 1H), 3.05-2.98 (m, 1H), 2.62-2.55 (m, 1H), 2.38-2.25 (m, 1H), 2.20-2.15 (m, 1H), 1.95-1.81 (m, 6H), 1.62-1.25 (m, 10H), 1.10 (s, 3H), 0.86 (s, 3H). LCMS (Method A) m/z: 322.5 (M+1), Retention time: 2.06 min, Purity: 98.9 area % (ELSD). HPLC (Method A): Retention time: 2.70 min, Purity: 99.3 area %.

C. AQX-1125 was prepared from Compound 16 in the same manner as described above in Synthetic Example 16.

AQX-1125 was also prepared according to the method disclosed below in Reaction Scheme 22, wherein R$^1$ is hydrogen, methyl or ethyl, Pg$^1$ is an oxygen-protecting group and Pg$^2$ is a carbonyl protecting group:

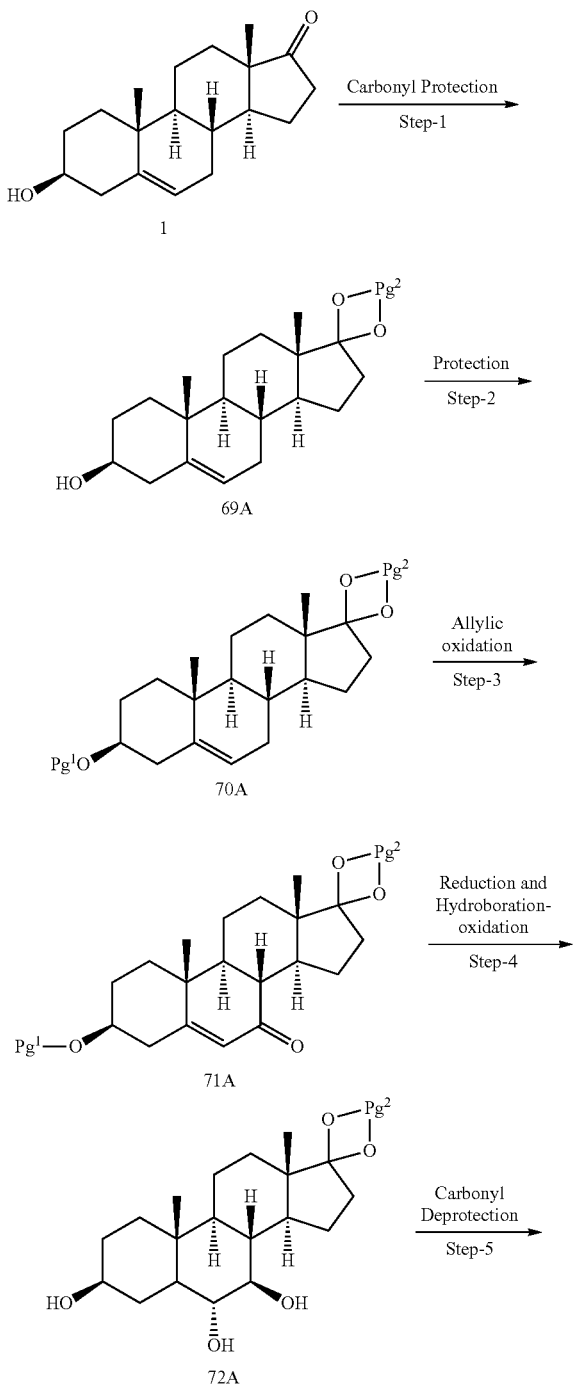

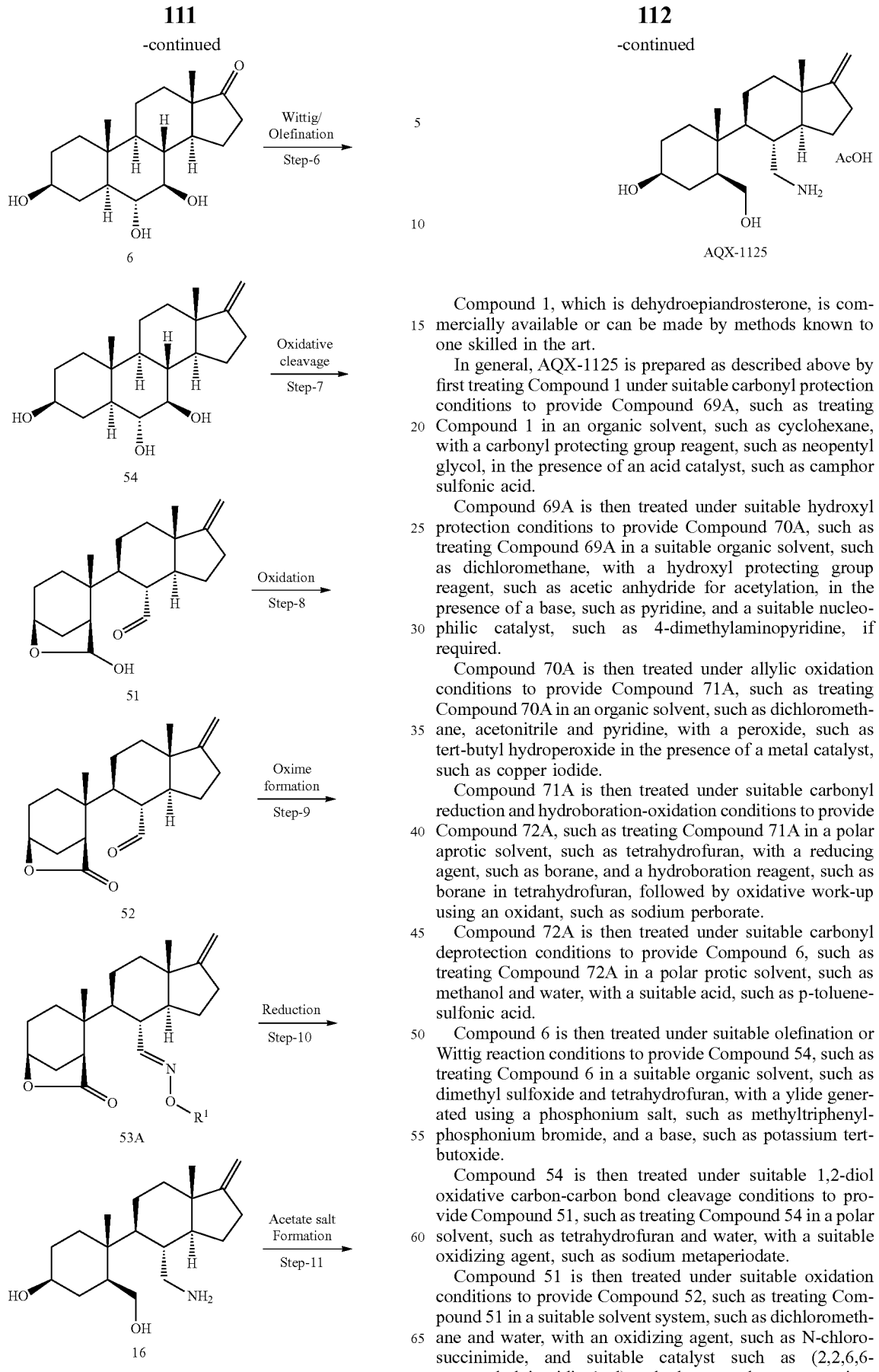

Compound 1, which is dehydroepiandrosterone, is commercially available or can be made by methods known to one skilled in the art.

In general, AQX-1125 is prepared as described above by first treating Compound 1 under suitable carbonyl protection conditions to provide Compound 69A, such as treating Compound 1 in an organic solvent, such as cyclohexane, with a carbonyl protecting group reagent, such as neopentyl glycol, in the presence of an acid catalyst, such as camphor sulfonic acid.

Compound 69A is then treated under suitable hydroxyl protection conditions to provide Compound 70A, such as treating Compound 69A in a suitable organic solvent, such as dichloromethane, with a hydroxyl protecting group reagent, such as acetic anhydride for acetylation, in the presence of a base, such as pyridine, and a suitable nucleophilic catalyst, such as 4-dimethylaminopyridine, if required.

Compound 70A is then treated under allylic oxidation conditions to provide Compound 71A, such as treating Compound 70A in an organic solvent, such as dichloromethane, acetonitrile and pyridine, with a peroxide, such as tert-butyl hydroperoxide in the presence of a metal catalyst, such as copper iodide.

Compound 71A is then treated under suitable carbonyl reduction and hydroboration-oxidation conditions to provide Compound 72A, such as treating Compound 71A in a polar aprotic solvent, such as tetrahydrofuran, with a reducing agent, such as borane, and a hydroboration reagent, such as borane in tetrahydrofuran, followed by oxidative work-up using an oxidant, such as sodium perborate.

Compound 72A is then treated under suitable carbonyl deprotection conditions to provide Compound 6, such as treating Compound 72A in a polar protic solvent, such as methanol and water, with a suitable acid, such as p-toluenesulfonic acid.

Compound 6 is then treated under suitable olefination or Wittig reaction conditions to provide Compound 54, such as treating Compound 6 in a suitable organic solvent, such as dimethyl sulfoxide and tetrahydrofuran, with a ylide generated using a phosphonium salt, such as methyltriphenylphosphonium bromide, and a base, such as potassium tert-butoxide.

Compound 54 is then treated under suitable 1,2-diol oxidative carbon-carbon bond cleavage conditions to provide Compound 51, such as treating Compound 54 in a polar solvent, such as tetrahydrofuran and water, with a suitable oxidizing agent, such as sodium metaperiodate.

Compound 51 is then treated under suitable oxidation conditions to provide Compound 52, such as treating Compound 51 in a suitable solvent system, such as dichloromethane and water, with an oxidizing agent, such as N-chlorosuccinimide, and suitable catalyst such as (2,2,6,6-tetramethylpiperidin-1-yl)oxyl, base such as potassium carbonate and sodium bicarbonate, and a phase transfer reagent, such as tetrabutylammonium chloride.

Compound 52 is then treated under suitable oxime or oxime O-ether formation conditions to provide Compound 53A, such as treating Compound 52 in a suitable basic organic solvent, such as pyridine, with a suitable reagent, such as O-methyl hydroxylamine hydrochloride.

Compound 53A is then treated under suitable lactone and oxime O-ether reduction conditions to provide Compound 16, such as treating Compound 53A in a polar aprotic solvent, such as tetrahydrofuran, 2-methyl tetrahydrofuran or dioxane, with a reducing agent, such as lithium aluminum hydride.

Compound 16 is then treated under suitable acetic salt formation conditions to provide AQX-1125, such as treating Compound 16 in a polar protic solvent, such as methanol, with glacial acetic, followed by a less polar organic solvent, such as methyl tert-butyl ether.

A specific method of preparing AQX-1125, as set forth above in Reaction Scheme 22, is illustrated below in Reaction Scheme 22A:

REACTION SCHEME 22A

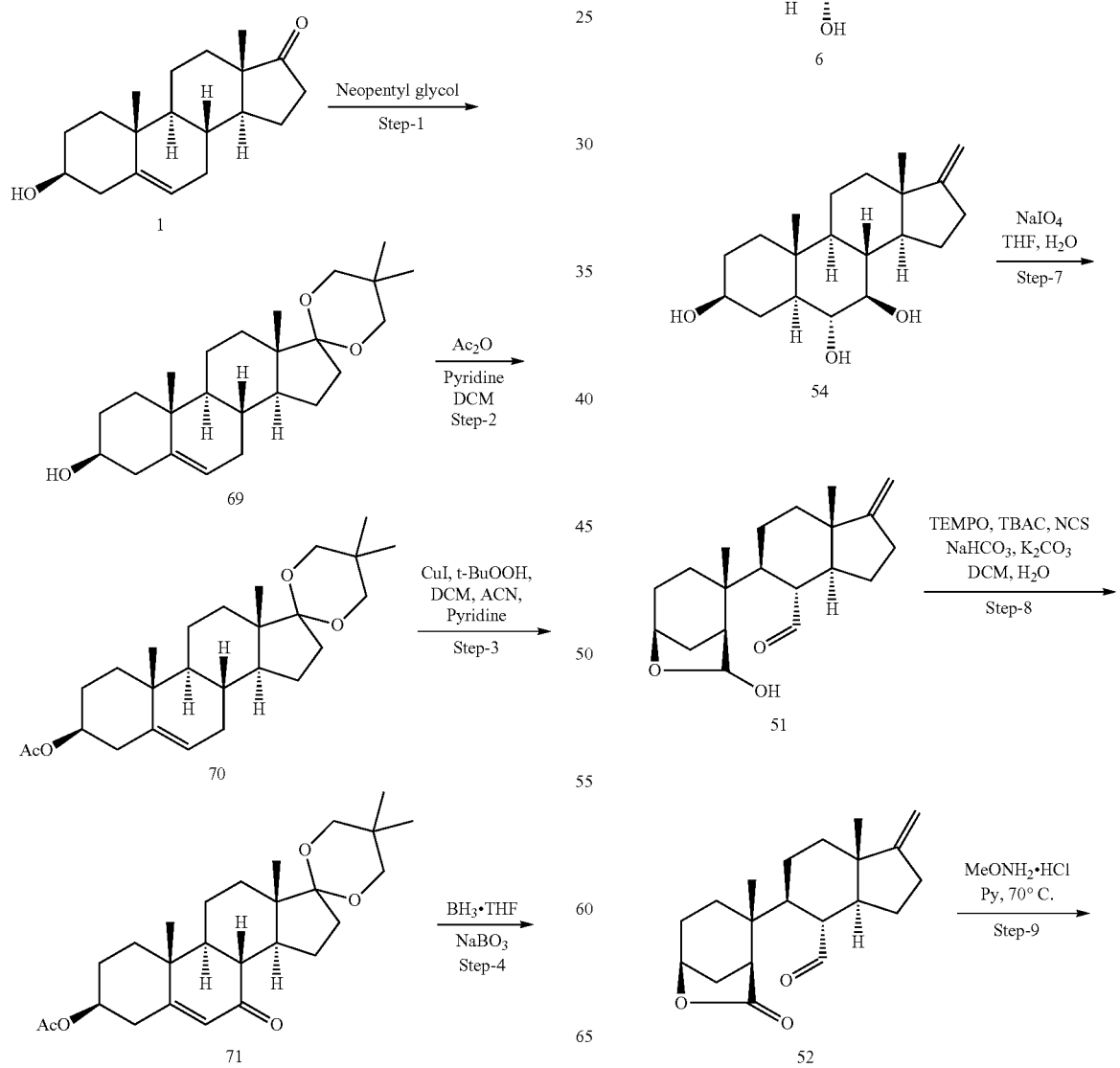

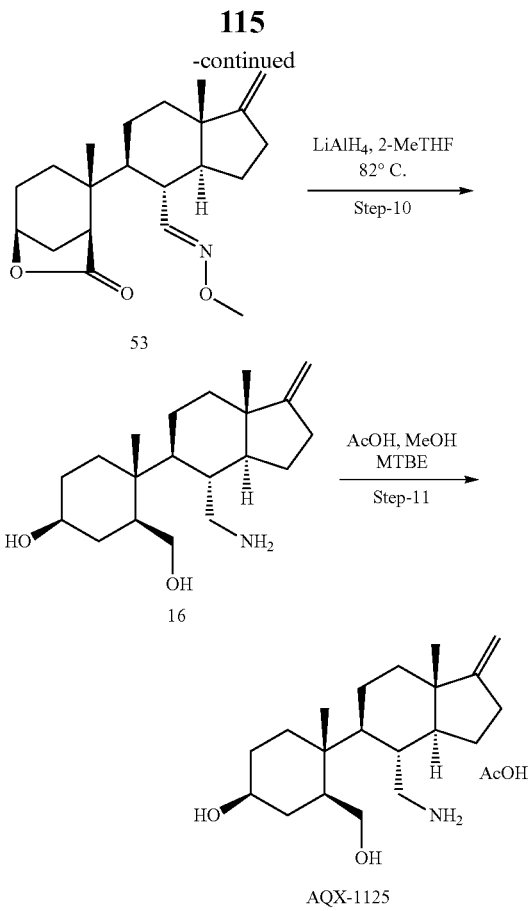

The following Synthetic Examples, which are directed to the steps and products as set forth above in Reaction Scheme 22A, are provided as a guide to assist in the practice of the invention, and are not intended as a limitation on the scope of the invention.

Synthetic Example 67

Step 1: Conversion of Compound 1 to Compound 69

A. To a solution of (3S,8R,9S,10R,13S,14S)-3-hydroxy-10,13-dimethyl-1,2,3,4,7,8,9,10,11,12,13,14,15,16-tetradecahydro-17H-cyclopenta[a]phenanthren-17-one (Compound 1, 240.0 g, 0.832 mol, 1.0 eq.) in cyclohexane (2.0 L) in a dry 5 L RB flask fitted with a Dean-Stark apparatus was added (+/−)-camphor sulphonic acid (3.9 g, 0.0167 mol) followed by neopentyl glycol (433.3 g, 4.160 mol, 5 eq.) at room temperature. The reaction mixture was heated to 85° C. under reflux for 16 hours for azeotropic removal of water. The reaction mixture was monitored by LCMS.

B. After completion, the reaction mixture was cooled to room temperature. Cyclohexane was removed under vacuum below 50° C. A 10% aqueous solution of sodium bicarbonate solution (2 L) was added followed by dichloromethane (2.5 L). Note: The sequence of addition was critical as the protected neopentyl glycol group can revert back to starting material under acidic conditions. The slurry was stirred to get a clear biphasic solution. The layers were separated and the combined dichloromethane layers were again washed with water (2×2.0 L). The organic layer was dried (Na$_2$SO$_4$) and evaporated to afford (3S,8R,9S,10R,13S,14S)-5',5',10,13-tetramethyl-1,2,3,4,7,8,9,10,11,12,13,14,15,16-tetradecahydrospiro[cyclopenta[a]phenanthrene-17,2'-[1,3]dioxan]-3-ol, Compound 69 as white solid (311 g, yield 99.8%). $^1$H NMR (400 MHz, DMSO-d6): δ 5.27-5.23 (m, 1H), 4.59 (d, J=4.80 Hz, 1H), 3.61 (d, J=11.2 Hz, 1H), 3.40 (d, J=11.2 Hz, 1H), 3.30-3.20 (m, 2H), 2.30-2.05 (m, 3H), 1.98-1.88 (m, 1H), 1.78-1.62 (m, 3H), 1.60-1.50 (m, 4H), 1.45-1.20 (m, 7H), 1.05 (s, 3H), 0.98-0.93 (m, 1H), 0.95 (s, 3H), 0.88-0.78 (m, 1H), 0.75 (s, 3H), 0.68 (s, 3H). LCMS: (Method A) 375.5 (M+1), Retention time: 3.76 min, HPLC (Method A): 99.6 area % (ELSD), Retention time: 6.17 min.

Synthetic Example 68

Step 2: Conversion of Compound 69 to Compound 70

A. To a solution of (3S,8R,9S,10R,13S,14S)-5',5',10,13-tetramethyl-1,2,3,4,7,8,9,10,11,12,13,14,15,16-tetradecahydrospiro[cyclopenta[a]phenanthrene-17,2'-[1,3]dioxan]-3-ol (Compound 69, 311 g, 0.830 mol, 1.0 eq., from Synthetic Example 67) in dichloromethane (3.1 L) in a dry 5 L RB flask under nitrogen atmosphere were added pyridine (131.3 g, 1.661 mol, 2.0 eq.) and DMAP (10.1 g, 0.083 mol, 0.1 eq.) followed by the dropwise addition of acetic anhydride (127.15 g, 1.245 mol, 1.5 eq.) at 0° C. The reaction mixture was stirred at 0-10° C. for 2 h. The reaction mixture was monitored by TLC (2:8 ethyl acetate: petroleum ether, R$_f$=0.4, KMnO$_4$ stain).

B. After completion of the reaction, the mixture was diluted with water (3.0 L). The organic layer was separated and aqueous layer back washed with dichloromethane (2.0 L). The combined organic layers were washed with brine solution (3.0 L) and dried (Na$_2$SO$_4$). The organic layers were evaporated completely and suspended in n-hexane (466 mL, 1.5 V) with stirring at 5° C. for 1 h. The solids were collected by filtration and washed with cold n-hexane (155 mL, 0.5 V). The product was dried under vacuum at 45° C. for 12 h to afford (3S,8R,9S,10R,13S,14S)-5',5',10,13-tetramethyl-1,2,3,4,7,8,9,10,11,12,13,14,15,16-tetradecahydrospiro[cyclopenta[a]phenanthrene-17,2'-[1,3]dioxan]-3-yl acetate, Compound 70, as an off-white solid (325.5 g, yield 94%). $^1$H NMR (400 MHz, DMSO-d6): δ 5.40-5.30 (m, 1H), 4.50-4.40 (m, 1H), 3.62 (d, J=11.2 Hz, 1H), 3.42 (d, J=11.2 Hz, 1H), 3.40-3.30 (m, 2H), 2.35-2.22 (m, 3H), 1.98 (s, 3H), 1.95-1.71 (m, 4H), 1.70-1.25 (m, 10H), 1.08 (s, 3H), 0.98 (s, 3H), 0.95-0.85 (m, 2H), 0.78 (s, 3H), 0.68 (s, 3H). LCMS: (Method A) 417.5 (M+1), Retention time: 4.23 min, HPLC (Method B): 99.5 area % (ELSD), Retention time: 4.22 min.

Synthetic Example 69

Step 3: Conversion of Compound 70 to Compound 71

A. To a solution of (3S,8R,9S,10R,13S,14S)-5',5',10,13-tetramethyl-1,2,3,4,7,8,9,10,11,12,13,14,15,16-tetradecahydrospiro[cyclopenta[a]phenanthrene-17,2'-[1,3]dioxan]-3-yl acetate (Compound 70, 325 g, 0.780 mol, 1.0 eq., from Synthetic Example 68) in dichloromethane/acetonitrile (2.3 L, 5:2) was added pyridine (325 mL) at 25° C. A solution of CuI (2.97 g, 0.0156 mol, 0.02 eq.) in pyridine (30 mL) and acetonitrile (30 mL) was prepared in a separate flask under a nitrogen atmosphere. One third of the CuI solution prepared in the second flask was added to the reaction mass followed by one third of the 70% TBHP aqueous solution (1.523 mL, 10.922 mol, 14.0 eq.) and the reaction stirred at 25° C. for 40 min. The remaining portions of the CuI and TBHP solutions were added to the reaction mass at 45° C. at 20-30 min intervals. After completion of the additions, the reaction mixture was further stirred at 45° C. for 2 h. The progress of the reaction was monitored by LCMS, until absence of starting material.

B. The reaction mixture was cooled to 0-5° C. and a 33% aqueous solution of sodium thiosulfate added (2.0 L). The organic layer was separated and the aqueous layer was washed with dichloromethane (2.0 L). The combined organic layers were washed with a 10% aqueous sodium thiosulfate solution (2.0 L) and followed by brine (2.0 L). The organic layers were dried ($Na_2SO_4$) and concentrated. The crude product was suspended in methanol (488 mL, 1.5 V) with stirring at 0-5° C. for 1 h. The solids were collected by filtration and washed with cold methanol (163 mL) to yield ~200 g of wet solid. The filtrate was evaporated under vacuum at 45° C. The gummy viscous mass was again suspended in methanol (325 mL, 1 V) with stirring at 0-5° C. for 1 h. The solids obtained were collected by filtration and washed with cold methanol (75 mL) to yield ~65 g wet solid.

C. The combined solids were dried under vacuum at 45° C. for 16 h to afford (3S,8R,9S,10R,13S,14S)-5',5',10,13-tetramethyl-7-oxo-1,2,3,4,7,8,9,10,11,12,13,14,15,16-tetradecahydrospiro[cyclopenta[a]phenanthrene-17,2'-[1,3]dioxan]-3-yl acetate, Compound 71, as an off-white solid (197 g, yield 58.8%). $^1$H NMR (400 MHz, DMSO-d6): δ 5.64 (m, 1H), 4.65-4.55 (m, 1H), 3.65 (d, J=11.2 Hz, 1H), 3.42 (d, J=11.2 Hz, 1H), 3.30-3.25 (m, 2H), 2.35-2.22 (m, 3H), 2.02 (s, 3H), 1.94-1.84 (m, 2H), 1.70-1.55 (m, 6H), 1.50-1.35 (m, 4H), 1.30-1.18 (m, 2H), 1.19 (s, 3H), 1.06 (s, 3H), 0.76 (s, 3H), 0.69 (s, 3H). LCMS: (Method A) 431.3 (M+1), Retention time: 3.55 min, HPLC (Method B): 98.8 area % (ELSD), Retention time: 3.54 min.

Synthetic Example 70

Step 4: Conversion of Compound 71 to Compound 72

A. To a solution of (3S,8R,9S,10R,13S,14S)-5',5',10,13-tetramethyl-7-oxo-1,2,3,4,7,8,9,10,11,12,13,14,15,16-tetradecahydrospiro[cyclopenta[a]phenanthrene-17,2'-[1,3]dioxan]-3-yl acetate (Compound 71, 120 g, 0.279 mol, 1.0 eq., from Synthetic Example 69) in THF (840 mL, 7 V) in a dry 5 L RB flask under a nitrogen atmosphere was slowly added $BH_3$-THF (947 ml, 0.949 mol, 3.4 eq.) at −5 to 0° C. for 1 h. The reaction mixture was stirred at 0-5° C. for 3 h. The reaction progress was monitored by LCMS, until absence of starting material. The reaction mixture was cooled to −10° C. and quenched by dropwise addition of cold water (600 mL, 5 V). The reaction mixture was stirred for 30 min at room temperature. THF (360 mL, 3 V) was added to the reaction mixture followed by solid sodium perborate tetrahydrate (85.8 g, 0.558 mol, 2.0 eq.). The reaction mixture was stirred at 25° C. for 12 h. The progress of the reaction was monitored by LCMS.

B. After completion, the inorganic solids were removed by filtration and washed with THF/Water (500 mL, 1:1). To this filtrate was added NaCl (300 g) and the layers were separated. The aqueous layer was again washed with THF (250 mL). The combined THF layers were dried ($Na_2SO_4$) and the organic layers were evaporated to dryness to afford (3S,5S,6R,7R,8R,9S,10R,13S,14S)-5',5',10,13-tetramethylhexadecahydrospiro[cyclopenta[a]phenanthrene-17,2'-[1,3]dioxane]-3,6,7-triol, Compound 72, (145 g, wet solid) as an off-white solid. Note: The crude product was taken to the next step without further purification. LCMS: (Method A) 409.5 [M+1] Retention time: 2.75 min and 323.2 [M+1-neopentyl glycol], Retention time: 1.98 min, HPLC (Method B): 79.0 area % (ELSD), Retention time: 2.75 min.

Synthetic Example 71

Step 5: Conversion of Compound 72 to Compound 6

A. To a stirred solution of (3S,5S,6R,7R,8R,9S,10R,13S,14S)-5',5',10,13-tetramethylhexadecahydrospiro[cyclopenta[a]phenanthrene-17,2'-[1,3]dioxane]-3,6,7-triol (Compound 72, 145 g, wet solid, from Synthetic Example 70) in methanol/water (1140 mL, 9:1) was added p-toluenesulfonic acid (2.65 g, 0.014 mol, 0.05 eq.) at room temperature and the reaction stirred for 3 h. The progress of the reaction was monitored by LCMS.

B. After completion, excess methanol was removed under vacuum at 45° C. Water (340 mL, 3 V) was added to the reaction mixture and stirred for 1 h at 10-15° C. The solids were collected by filtration and washed with cold water (114 mL, 1 V) followed by washing with n-hexane (285 mL, 2.5 V). The wet cake was dried under vacuum at 50° C. for 12 h to afford (3S,5S,6R,7R,8R,9S,10R,13S,14S)-3,6,7-trihydroxy-10,13-dimethylhexadecahydro-17H-cyclopenta[a]phenanthren-17-one, Compound 6, as a white solid (71 g, yield over 2 steps 79%). $^1$H NMR (400 MHz, DMSO-d6): δ 4.46 (d, J=4.0 Hz, 1H), 4.42 (br s, 1H), 4.29 (br s, 1H), 3.35-3.22 (m, 1H), 2.99-2.89 (m, 2H), 2.37-2.27 (m, 1H), 2.24-2.14 (m, 1H), 2.07-1.88 (m, 2H), 1.82-1.71 (m, 1H), 1.67-1.48 (m, 5H), 1.45-1.35 (m, 1H), 1.30-1.18 (m, 2H), 1.16-1.06 (m, 1H), 1.00-0.82 (m, 3H), 0.80-0.70 (m, 1H), 0.78 (s, 6H). LCMS: (Method A) 323.2 (M+1), Retention time: 1.99 min, HPLC (Method B): 97.8 area % (ELSD), Retention time: 1.99 min.

Synthetic Example 72

Step 6: Conversion of Compound 6 to Compound 54

A. To a suspension of methyltriphenylphosphonium bromide (349 g, 0.978 mol, 3.0 eq.) in THF (630 mL, 6 V) under a nitrogen atmosphere was added potassium tertiary-butoxide (110 g, 0.978 mol, 3.0 eq.) at room temperature in several portions over 30 min and the reaction mixture was stirred at room temperature for an additional 2 h. A solution of (3S,5S,6R,7R,8R,9S,10R,13S,14S)-3,6,7-trihydroxy-10,13-dimethylhexadecahydro-17H-cyclopenta[a]phenanthren-17-one (Compound 6, 105 g, 0.326 mol, 1.0 eq., from Synthetic Example 71) in DMSO/THF (1:3, 420 mL, 4 V) was added to the reaction and the mixture stirred at room temperature for an additional 4 h. Progress of the reaction was monitored by TLC (9:1 dichloromethane/methanol, $R_f$=0.4, $KMnO_4$ stain).

B. After completion, the reaction mixture was diluted with ethyl acetate (525 mL) and water (525 mL). The organic layer was separated and the aqueous layer was washed with ethyl acetate (525 mL). The combined organic layers were washed with brine solution (2×525 mL). The separated organic layer was dried ($Na_2SO_4$), evaporated to dryness and purified by silica gel flash column chromatography using 3% methanol in dichloromethane (1 L:35 L) to afford (3S,5S,6R,7R,8R,9S,10R,13S,14S)-10,13-dimethyl-17-methylene-hexadecahydro-1H-cyclopenta[a]phenanthrene-3,6,7-triol (Compound 54) as an off-white solid (83 g, yield 79.5%). $^1$H NMR (400 MHz, DMSO-d6): δ 4.60 (s, 2H), 4.45 (d, J=6.0 Hz, 1H), 4.35 (d, J=6.4 Hz, 1H), 4.14 (d, J=7.2 Hz, 1H), 3.32-3.22 (m, 1H), 2.98-2.77 (m, 2H), 2.45-2.32 (m, 2H), 2.20-1.95 (m, 3H), 1.82-1.72 (m, 1H), 1.65-1.50 (m, 4H), 1.45-1.02 (m, 5H), 0.98-0.83 (m, 3H), 0.77 (s, 3H), 0.73 (s, 3H). LCMS: (Method A) 303.2 (M+1), Retention time: 2.70 min, HPLC (Method A): 99.4 area %, Retention time: 2.69 min.

Synthetic Example 73

Step 7: Conversion of Compound 54 to Compound 51

A. To a stirred solution of (3S,5S,6R,7R,8R,9S,10R,13S,14S)-10,13-dimethyl-17-methylenehexadecahydro-1H-cyclopenta[a]phenanthrene-3,6,7-triol (Compound 54, 90 g, 0.281 mol, 1.0 eq., from Synthetic Example 72) in THF/Water (630 mL:270 mL, 10 V) at 10° C. was added sodium metaperiodate (120 g, 0.562 mol, 2.0 eq.) in several portions over 30 min. The reaction mixture was stirred 2 h at 25° C. The progress of the reaction was monitored by LCMS.

B. After completion, the reaction mixture was diluted with water (1.0 L) and extracted with ethyl acetate (2×500 mL). The combined organic layers were dried ($Na_2SO_4$) and evaporated to dryness to afford (3aS,4R,5S,7aS)-5-((1S,2R,5S,7R)-7-hydroxy-2-methyl-6-oxabicyclo[3.2.1]octan-2-yl)-7a-methyl-1-methyleneoctahydro-1H-indene-4-carbaldehyde (Compound 51) as a white solid (89 g, yield 99.5%, crude was taken to next step without further purification). LCMS: (Method A) 301.2 (M+1), Retention time: 2.82 min, HPLC (Method A): 99.6 area %, Retention time: 2.82 min.

Synthetic Example 74

Step 8: Conversion of Compound 51 to Compound 52

A. To a stirred solution of (3aS,4R,5S,7aS)-5-((1S,2R,5S,7R)-7-hydroxy-2-methyl-6-oxabicyclo[3.2.1]octan-2-yl)-7a-methyl-1-methyleneoctahydro-1H-indene-4-carbaldehyde (Compound 51, 65 g, 0.204 mol, 1.0 eq., from Synthetic Example 73) in dichloromethane (975 mL, 15 V) was added potassium carbonate (29 g, 0.204 mol, 1.0 eq.), a solution of sodium bicarbonate (171 g, 2.04 mol, 10 eq.) in water (975 mL, 15 V), tetrabutylammonium chloride (5.8 g, 0.021 mol, 0.1 eq.) and TEMPO (3.3 g, 0.021 mol, 0.1 eq.) at room temperature. N-Chlorosuccinimide (68 g, 0.51 mol, 2.5 eq.) was added portion-wise to the reaction over 30 min and the mixture stirred at room temperature for 4 h. The reaction was monitored by LCMS.

B. After completion, the organic layer was separated and the aqueous phase washed with dichloromethane (200 mL). The combined organic layers were washed with water (2×200 mL), dried ($Na_2SO_4$) and evaporated to dryness. The crude product was suspended in IPA (130 mL) and stirred for 1 h at 10° C. The solids were collected by filtration to afford (3aS,4R,5S,7aS)-7a-methyl-5-((1S,2R,5S)-2-methyl-7-oxo-6-oxabicyclo[3.2.1]octan-2-yl)-1-methyleneoctahydro-1H-indene-4-carbaldehyde (Compound 52) as an off-white solid (55 g, yield 85%). $^1$H NMR (400 MHz, DMSO-d6): δ 9.51 (d, J=5.6 Hz, 1H), 4.77 (br s, 1H), 4.69 (br s, 2H), 2.54-2.44 (m, 2H), 2.37-2.15 (m, 3H), 2.08-1.98 (m, 2H), 1.97-1.83 (m, 2H), 1.81-1.71 (m, 1H), 1.68-1.58 (m, 2H), 1.58-1.48 (m, 1H), 1.48-1.32 (m, 3H), 1.31-1.21 (m, 1H), 1.20-1.10 (m, 1H), 0.97 (s, 3H), 0.76 (s, 3H). LCMS: (Method A) 317.2 (M+1), Retention time: 3.14 min, HPLC (Method A): 99.0 area %, Retention time: 3.12 min.

Synthetic Example 75

Step 9: Conversion of Compound 52 to Compound 53

A. To a stirred solution of (3aS,4R,5S,7aS)-7a-methyl-5-((1S,2R,5S)-2-methyl-7-oxo-6-oxabicyclo[3.2.1]octan-2-yl)-1-methyleneoctahydro-1H-indene-4-carbaldehyde (Compound 52, 72 g, 0.228 mol, 1.0 eq., from Synthetic Example 74) in pyridine (320 mL, 5 V) was added O-methyl hydroxylamine hydrochloride (95.06 g, 1.138 mol, 5.0 eq.). The reaction mixture was stirred at room temperature for 3 h. The progress of the reaction was monitored by TLC (7:3 pet ether/ethyl acetate, $R_f$=0.3, $KMnO_4$ stain).

B. After completion, excess pyridine was removed in vacuo at 45° C. The crude mixture was suspended in water (500 mL) and stirred for 30 min. The solids were collected by filtration and washed with water (300 mL). The wet product was suspended in IPA (140 mL) at 10° C. for 30 min and filtered. The solids were washed with cold IPA (40 mL) to afford 7a-methyl-5-((1S,2R,5S)-2-methyl-7-oxo-6-oxabicyclo[3.2.1]octan-2-yl)-1-methyleneoctahydro-1H-indene-4-carbaldehyde O-methyl oxime (Compound 53) as a white solid (71 g, yield 90.3%). $^1$H NMR (400 MHz, DMSO-d6): δ 7.23 (d, J=9.2 Hz, 1H), 4.75 (br s, 1H), 4.66 (br s, 2H), 3.68 (s, 3H), 2.54-2.35 (m, 2H), 2.34-2.24 (m, 2H), 2.23-2.08 (m, 2H), 2.05-1.83 (m, 3H), 1.75-1.53 (m, 3H), 1.50-1.36 (m, 3H), 1.34-1.22 (m, 2H), 1.16-1.06 (m, 1H), 0.98 (s, 3H), 0.78 (s, 3H).H), 1.48-1.32 (m, 3H), 1.31-1.21 (m, 1H), 1.20-1.10 (m, 1H), 0.97 (s, 3H), 0.76 (s, 3H). LCMS: (Method A 346.4 (M+1), Retention time: 3.27 min, HPLC (Method A): 99.9 area %, Retention time: 3.27 min.

Synthetic Example 76

Step 10: Conversion of Compound 53 to Compound 16

A. To a stirred solution of 7a-methyl-5-((1S,2R,5S)-2-methyl-7-oxo-6-oxabicyclo[3.2.1]octan-2-yl)-1-methyleneoctahydro-1H-indene-4-carbaldehyde O-methyl oxime (Compound 53, 65 g, 0.188 mol, 1.0 eq., from Synthetic Example 75) in 2-methyltetrahydrofuran (975 mL, 15 V) was added $LiAlH_4$ (2.0 M in THF, 470 mL, 0.94 mol, 5.0 eq.) dropwise at 10° C. under a nitrogen atmosphere for 1 h. The reaction mixture was heated at 82° C. for 24 h. The progress of reaction was monitored by LCMS.

B. After completion, the reaction was cooled to 0° C. and quenched with saturated aqueous $Na_2SO_4$ solution (350 mL). After quenching, the reaction mixture was stirred at room temperature for 1 h and filtered through CELITE™. The CELITE™ bed was washed with dichloromethane/THF (900 mL, 1:2). The combined filtrates were washed with brine solution (2×500 mL). The separated organic layers were dried ($Na_2SO_4$) and evaporated to dryness. The crude mixture was suspended in MTBE (300 mL) and stirred for 30 min. The suspension was filtered to afford (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexan-1-ol (Compound 16) as a white solid (58.0 g, yield 96.0%). $^1$H NMR (400 MHz, DMSO-d6): δ 4.58 (br s, 2H), 4.52-4.42 (m, 1H), 4.30-4.20 (m, 1H), 3.58-3.48 (m, 1H), 3.43-3.23 (m, 2H), 2.98-2.88 (m, 2H), 2.61-2.51 (m, 1H), 2.50-2.35 (m, 1H), 2.21-2.11 (m, 1H), 2.05-1.95 (m, 1H), 1.79-1.69 (m, 3H), 1.62-1.52 (m, 2H) 1.50-1.20 (m, 8H), 1.20-1.02 (m, 3H), 0.98 (s, 3H), 0.72 (s, 3H). LCMS: (Method A) 322.4 (M+1), Retention time: 1.96 min, HPLC (Method A): 97.8 area %, Retention time: 2.02 min.

Synthetic Example 77

Step 11: Preparation of AQX-1125 from Compound 16

A. To a stirred solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexan-1-ol (Compound 16, 58.0 g, 0.180 mol, 1.0 eq, from Synthetic Example 76) in methanol (174 mL, 3 V) was added acetic acid (23.5 mL, 0.4 V) dropwise at 10° C. under a nitrogen atmosphere over 20 min. The reaction mixture was stirred at room temperature for 1 h. The solution was filtered to remove undissolved particles and washed with methanol (58 mL, 1 V). The filtrate was collected and evaporated at 35° C. to half the volume (~125 mL). MTBE (348 mL, 6 V) was slowly added to the above concentrated mixture and the reaction stirred at 10° C. for 2 h. During the MTBE addition, slow precipitation of the product was observed. The solids were filtered and washed with MTBE (116 mL, 2V) to afford (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexan-1-ol, acetic acid salt, (AQX-1125) as a white solid (50 g, yield 72.6%). $^1$H NMR (400 MHz, pyridine-d5): δ 5.85 (br s, 5H), 4.70 (s, 2H), 4.08 (dd, J=10.4, 2 Hz, 1H), 3.95-3.85 (m, 1H), 3.60-3.50 (m, 1H), 3.18 (d, J=14 Hz, 1H), 2.92-2.86 (m, 1H), 2.80 (d, J=13.6 Hz, 1H), 2.50-2.40 (m, 1H), 2.25-1.97 (m, 3H), 2.15 (s, 3H), 1.90-1.65 (m, 4H), 1.56-1.40 (m, 4H), 1.39-1.20 (m, 2H), 1.25 (s, 3H), 0.78 (s, 3H). LCMS: (Method A) 322.4 (M+1), Retention time: 1.95 min, HPLC (Method H): 95.5 area %, Retention time: 16.66 min.

All of the U.S. patents, U.S. patent application publications, U.S. patent applications, PCT published patent applications, foreign patents, foreign patent applications and non-patent publications referred to in this specification are incorporated herein by reference in their entirety.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of preparing AQX-1125 having the following formula:

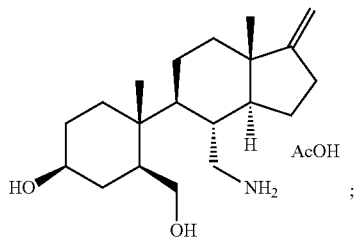 [SMILES: "AcOH" ; C=C1CC[C@H]2[C@H](CN)[C@@H]([C@@]3(C)CC[C@H](O)C[C@@H]3CO)CC[C@]12C]

wherein the method comprises:
(a) treating compound 53A having the formula:

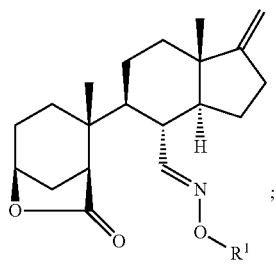

where $R^1$ is hydrogen, methyl or ethyl, under suitable lactone and oxime O-ether reduction conditions to provide compound 16 having the formula:

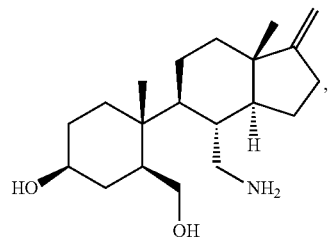

wherein the suitable lactone and oxime O-ether reduction conditions comprise treating Compound 53A in a polar aprotic solvent with a reducing agent;

(b) treating compound 16 under suitable acetate salt formation conditions to provide AQX-1125, wherein the suitable acetate salt formation conditions comprise treating compound 16 in a polar protic solvent with glacial acetic acid followed by treating with a less polar organic solvent.

2. The method of claim 1 wherein $R^1$ is hydrogen.

3. The method of claim 1 where $R^1$ is methyl.

4. The method of claim 1 wherein the polar aprotic solvent comprises lithium aluminum hydride.

5. The method of claim 1 further comprising an oxime or oxime O-ether formation step prior to treating Compound 53A under suitable lactone and oxime O-ether reduction conditions, wherein the oxime or oxime O-ether formation step comprises treating Compound 52 having the formula:

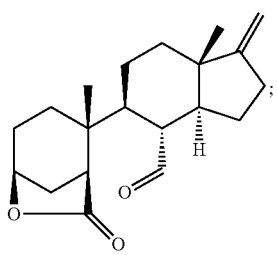

under suitable oxime or oxime O-ether formation conditions to provide Compound 53A, wherein the suitable oxime or oxime O-ether formation conditions comprise treating Compound 52 in a suitable basic organic solvent with a suitable reagent.

6. The method of claim 5 wherein the suitable basic organic solvent comprises pyridine and the suitable reagent comprises O-methyl hydroxylamine hydrochloride.

7. The method of claim 5 further comprising an oxidation step prior to treating Compound 52 under suitable oxime or oxime O-ether formation conditions, wherein the oxidation step comprises treating Compound 51 having the formula:

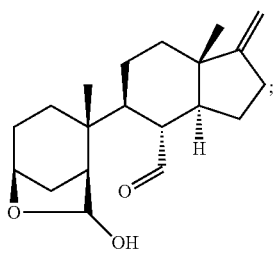

under suitable oxidation conditions to provide Compound 52 wherein the suitable oxidation conditions comprise treating Compound 51 in a suitable solvent system with an oxidizing agent and a suitable catalyst, a base and a phase transfer reagent.

8. The method of claim 7 wherein the suitable solvent system comprises dichloromethane or water, the oxidizing agent comprises N-chlorosuccinimide, the suitable catalyst comprises (2,2,6,6-tetramethylpiperidin-1-yl)oxyl, the base comprises potassium carbonate or sodium bicarbonate, and the phase transfer reagent comprises tetrabutylammonium chloride.

9. The method of claim 7 further comprising an 1,2-diol oxidative carbon-carbon bond cleaving step prior to treating Compound 51 under suitable oxidation conditions, wherein the 1,2-diol oxidative carbon-carbon bond cleaving step comprises treating Compound 54 having the formula:

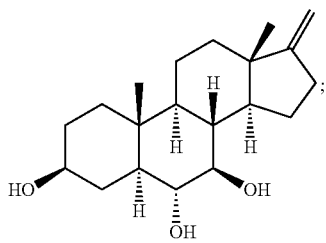

54 under suitable 1,2-diol oxidative carbon-carbon bond cleavage conditions to provide Compound 51, wherein the suitable 1,2-diol oxidative carbon-carbon bond cleavage conditions comprise treating Compound 54 in a polar solvent with a suitable oxidizing agent.

10. The method of claim 9 wherein the polar solvent comprises tetrahydrofuran or water and the suitable oxidizing agent comprises sodium metaperiodate.

11. The method of claim 9 further comprising a Wittig or olefination step prior to treating Compound 54 under suitable 1,2-diol oxidative carbon-carbon bond cleavage conditions, wherein the Wittig or olefination step comprises treating Compound 6 having the formula:

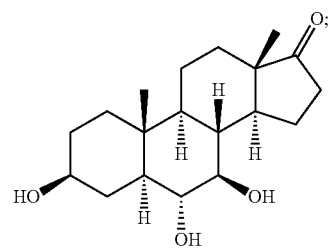

6 under suitable olefination or Wittig reaction conditions to provide Compound 54, wherein the suitable olefination or Wittig reaction conditions comprise treating Compound 6 in a suitable organic solvent with a ylide generated using a phosphonium salt and base.

12. The method of claim 11 wherein the suitable organic solvent comprises dimethyl sulfoxide or tetrahydrofuran, the phosphonium salt comprises methyltriphenylphosphonium bromide and the base comprises potassium tert-butoxide.

13. The method of claim 11 further comprising a carbonyl deprotection step prior to treating Compound 6 under suitable olefination or Wittig reaction conditions, wherein the carbonyl deprotection step comprises treating Compound 72A having the formula:

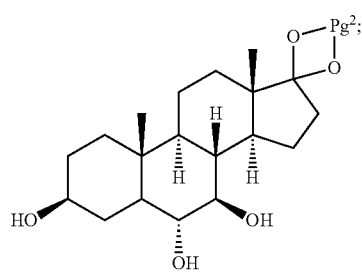

72A where $Pg^2$ is a carbonyl protecting group, under suitable carbonyl protection conditions to provide Compound 6, wherein the suitable carbonyl deprotection conditions comprise treating Compound 71A in a polar protic solvent with a suitable acid.

14. The method of claim 13 wherein the polar erotic solvent comprises methanol or water and the suitable add comprises p-toluenesulfonic acid.

15. The method of claim 13 further comprising a carbonyl reduction and hydroboration-oxidation step prior to treating Compound 72A under suitable carbonyl protection conditions, wherein the carbonyl reduction and hydroboration-oxidation step comprises treating Compound 71A having the formula:

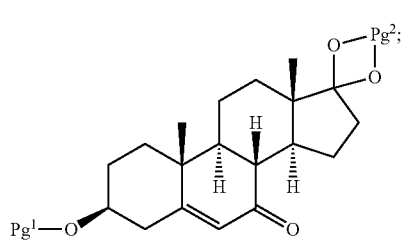

71A where $Pg^1$ is an oxygen-protecting group and $Pg^2$ is a carbonyl protecting group, under suitable carbonyl reduction and hydroboration-oxidation conditions to provide Compound 72A, wherein the suitable carbonyl reduction and hydroboration-oxidation conditions comprise treating Compound 71A in a polar aprotic solvent with a reducing agent and a hydroboration reagent, followed by oxidation using an oxidant.

16. The method of claim 15 wherein the polar aprotic solvent comprises tetrahydrofuran, the reducing agent comprises borane, the hydroboration reagent comprises borane in tetrahydrofuran, and the oxidant comprises sodium perborate.

17. The method of claim 15 further comprising an allylic oxidation step prior to treating Compound 71A under suitable carbonyl reduction and hydroboration-oxidation conditions, wherein the allylic oxidation step comprises treating Compound 70A having the following formula:

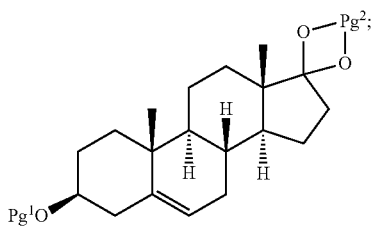

wherein Pg¹ is an oxygen-protecting group and Pg² is a carbonyl protecting group, under suitable allylic oxidation conditions to provide Compound 71A, wherein the suitable allylic oxidation conditions comprises treating Compound 70A in an organic solvent with a peroxide in the presence of a metal catalyst.

18. The method of claim 17 wherein the organic solvent comprises one or more of dichloromethane, acetonitrile and pyridine, the peroxide comprises ter-butyl hydroperoxide and the metal catalyst comprises copper iodide.

19. The method of claim 17 further comprising a hydroxyl protection step prior to treating Compound 70A under suitable allylic oxidation conditions, wherein the hydroxyl protection step comprises treating Compound 69A having the formula:

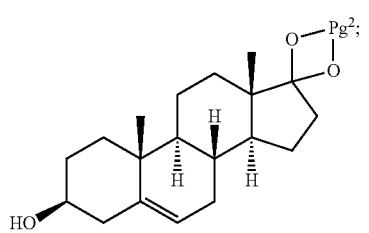

where Pg² is a carbonyl protecting group, under suitable hydroxyl protection conditions to provide Compound 70A, wherein the suitable hydroxyl protection conditions comprise treating Compound 69A in a suitable organic solvent with a hydroxyl-protecting group reagent in the presence of a base, and, optionally, a suitable nucleophilic catalyst.

20. The method of claim 19 wherein the suitable organic solvent comprises dichloromethane, the hydroxyl-protecting group reagent comprises acetic anhydride, the base comprises pyridine or imidazole and the suitable nucleophilic catalyst comprises 4-dimethylaminopyridine.

21. The method of claim 19 further comprising a carbonyl protection step prior to treating Compound 69A under suitable hydroxyl protection conditions, wherein the carbonyl protection step comprises treating Compound 1 having the formula:

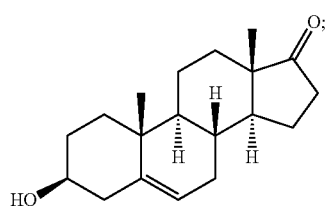

under suitable carbonyl protection conditions to provide Compound 69A, wherein the suitable carbonyl protection conditions comprise treating Compound 1 in an organic solvent with a carbonyl protecting group reagent in the presence of an acid catalyst.

22. The method of claim 21 wherein the organic solvent comprises cyclohexane, the carbonyl protecting group reagent comprises neopentyl glycol or ethylene glycol an the acid catalyst comprises camphor sulfonic acid.

23. A method of preparing AQX-1125 having the following formula:

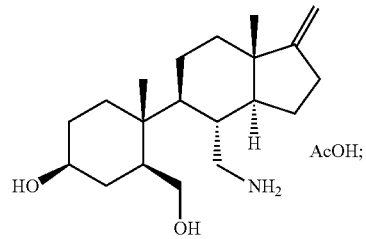

wherein the method comprises:
(a) treating Compound 1 having the formula:

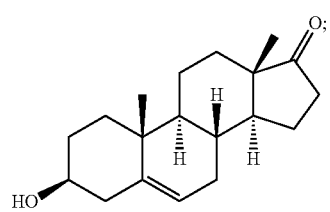

under suitable carbonyl protection conditions to provide Compound 69A having the formula:

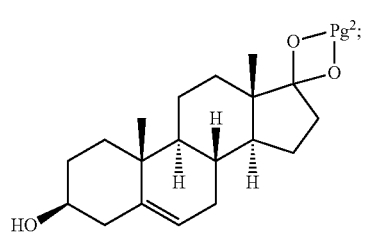

wherein Pg² is a carbonyl protecting group and wherein the suitable carbonyl protection conditions comprise treating Compound 1 in an organic solvent with a carbonyl protecting group reagent in the presence of an add catalyst;
(b) treating Compound 69A under suitable hydroxyl protection conditions to provide Compound 70A having the formula:

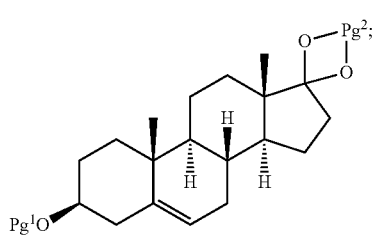

wherein Pg¹ is an oxygen-protecting group and Pg² is a carbonyl protecting group and wherein the suitable hydroxyl protection conditions comprise treating Compound 69A in a suitable organic solvent with a hydroxyl-protecting group reagent in the presence of a base, and, optionally, a suitable nucleophilic catalyst;

(c) treating Compound 70A under suitable allylic oxidation conditions to provide Compound 71A having the formula:

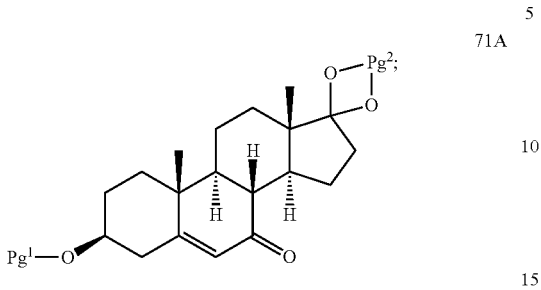

71A wherein Pg¹ is an oxygen-protecting group and Pg² is a carbonyl protecting group and wherein the suitable allylic oxidation conditions comprise treating Compound 70A in an organic solvent with a peroxide in the presence of a metal catalyst;
(d) treating Compound 71A under suitable carbonyl reduction and hydroboration-oxidation conditions to provide Compound 72A having the formula:

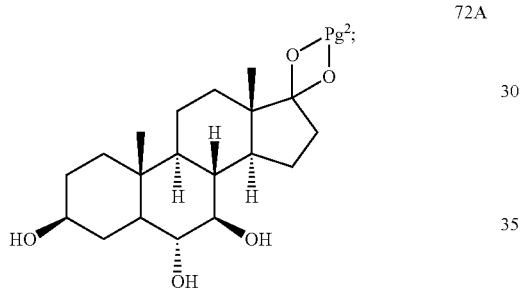

72A wherein Pg² is a carbonyl protecting group and wherein the suitable carbonyl reduction and hydroboration-oxidation conditions comprise treating Compound 71A in a polar aprotic solvent with a reducing agent and a hydroboration reagent, followed by oxidation using an oxidant;
(e) treating Compound 72A under suitable carbonyl deprotection conditions to provide Compound 6 having the formula:

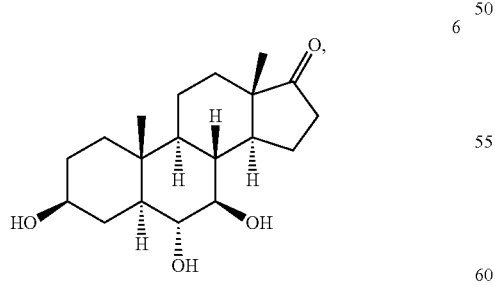

6 wherein the suitable carbonyl deprotection conditions comprise treating Compound 72A in a polar protic solvent with a suitable acid;
(f) treating Compound 6 under suitable olefination or Wittig reaction conditions to provide Compound 54 having the formula:

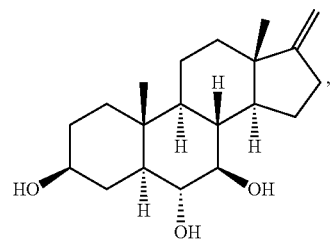

54 wherein the suitable olefination or Wittig reaction conditions comprise treating Compound 6 in a suitable organic solvent with a ylide generated using a phosphonium salt and a base;
(g) treating Compound 54 under suitable 1,2-diol oxidative carbon-carbon bond cleavage conditions to provide Compound 51 having the formula:

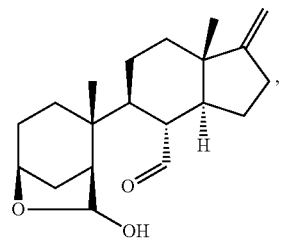

51 wherein the suitable 1,2-diol oxidative carbon-carbon bond cleavage conditions comprise treating Compound 54 in a polar solvent with a suitable oxidizing agent;
(h) treating Compound 51 under suitable oxidation conditions to provide Compound 52 having the formula:

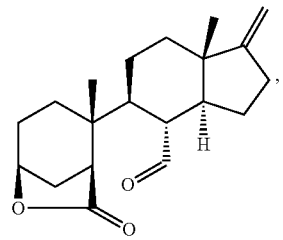

52 wherein the suitable oxidation conditions comprise treating Compound 51 in a suitable solvent system with an oxidizing agent and a suitable catalyst, a base and a phase transfer reagent;
(i) treating Compound 52 under suitable oxime or oxime O-ether formation conditions to provide Compound 53A having the formula:

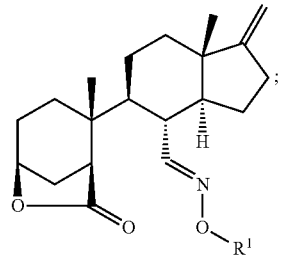

53A where R¹ is hydrogen, methyl or ethyl and wherein the suitable oxime or oxime O-ether formation conditions comprise treating Compound 52 in a suitable basic organic solvent with a suitable reagent;

(j) treating Compound 53A under suitable lactone and oxime O-ether reduction conditions to provide compound 16 having the formula:

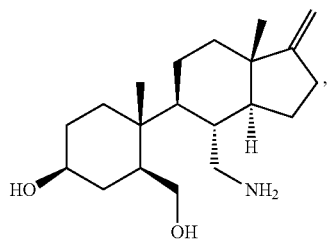

16 wherein the suitable lactone and oxime O-ether reduction conditions comprise treating Compound 53A in a polar aprotic solvent with a reducing agent; and (k) treating Compound 16 under suitable acetate salt formation conditions to provide AQX-1125, wherein the suitable acetate salt formation conditions comprise treating compound 16 in a polar protic solvent with glacial acetic add followed by treating with a less polar organic solvent.

24. The method of claim 1 further comprising a Wittig reaction or olefination step prior to treating Compound 53A under suitable lactone and oxime O-ether reduction conditions, wherein the Wittig or olefination step comprises treating Compound 67A having the formula:

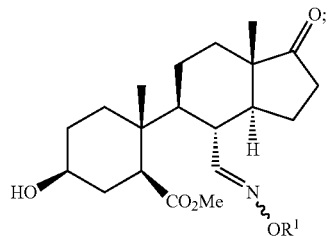

where $R^1$ is hydrogen, methyl or ethyl, under suitable Wittig reaction or olefination conditions to provide Compound 53A, wherein the suitable Wittig reaction or olefination conditions comprise treating Compound 67A in a suitable organic solvent with a ylide generated using a phosphonium salt and a base.

25. The method of claim 24 wherein the suitable organic solvent comprises toluene or tetrahydrofuran, the phosphonium salt comprises methyltriphenylphosphonium bromide and the base comprises potassium tert-butoxide.

26. The method of claim 24 further comprising a carbonyl deprotection step prior to treating Compound 67A under suitable Wittig reaction or olefination conditions, wherein the carbonyl deprotection step comprises treating Compound 66A having the formula:

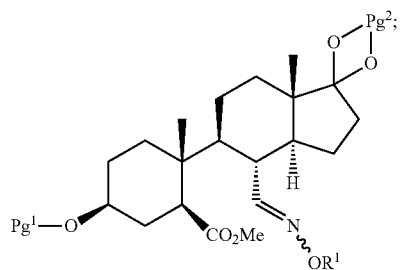

66A where $R^1$ is hydrogen, methyl or ethyl, $Pg^1$ is an oxygen-protecting group and $Pg^2$ is a carbonyl protecting group, under suitable carbonyl deprotection conditions to provide Compound 67A, wherein the suitable carbonyl deprotection conditions comprise treating Compound 66A in a polar protic solvent with a suitable acid.

27. The method of claim 26 wherein the polar orotic solvent comprises water and the suitable acid comprises as acetic acid.

28. The method of claim 26 further comprising an oxime or oxime O-ether formation step prior to treating Compound 66A under suitable carbonyl deprotection conditions, wherein the oxime or oxime O-ether formation step comprises treating Compound 18A having the formula:

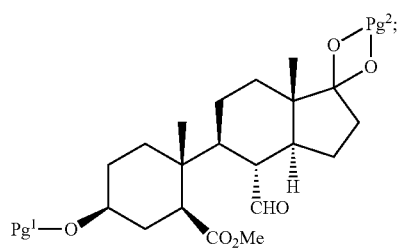

18A where $Pg^1$ is an oxygen-protecting group and $Pg^2$ is a carbonyl protecting group, under suitable oxime or oxime O-ether formation conditions to provide Compound 66A, wherein the suitable oxime or oxime O-ether formation conditions comprise treating Compound 18A in a suitable polar erotic solvent with a suitable reagent in the presence of a base.

29. The method of claim 28 wherein the suitable polar protic solvent comprises methanol, the suitable reagent comprises hydroxylamine hydrochloride and the base comprises trimethylamine.

30. The method of claim 28 further comprising an oxidative carbon-carbon bond cleavage step prior to treating Compound 18A under suitable oxime or oxime O-ether formation conditions, wherein the oxidative carbon-carbon bond cleavage step comprises treating Compound 19A having the formula:

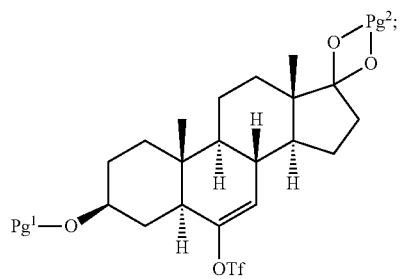

19A where Pg¹ is an oxygen-protecting group and Pg² is a carbonyl protecting group, under suitable oxidative carbon-carbon bond cleavage conditions to provide Compound 18A, wherein the suitable oxidative carbon-carbon bond cleavage conditions comprise treating Compound 19A in a polar erotic solvent with a suitable oxidizing agent, followed by reduction with a suitable reducing agent.

31. The method of claim 30 wherein the polar protic solvent comprises methanol, the suitable oxidizing agent comprises ozone and the suitable reducing agent comprises sodium borohydride.

32. The method of claim 30 further comprising an enol ether formation step prior to treating Compound 19A under suitable oxidative carbon-carbon bond cleavage conditions, wherein the enol ether formation step comprises treating Compound 17A having the formula:

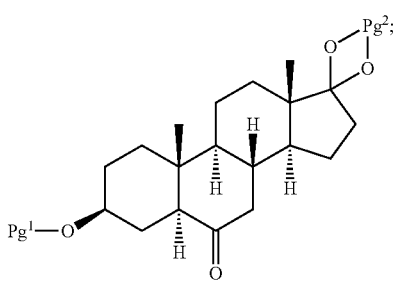

17A where Pg¹ is an oxygen-protecting group and Pg² is a carbonyl protecting group, under suitable enol ether formation conditions to provide Compound 19A, wherein the suitable enol ether formation conditions comprise treating Compound 17A in a suitable polar aprotic solvent with a strong base and a suitable electrophilic reagent.

33. The method of claim 32 wherein the suitable polar aprotic solvent comprises tetrahydrofuran, the strong base comprises lithium diisopropylamide and the suitable electrophilic reagent comprises N-phenyl triflimide.

34. The method of claim 32 further comprising an oxidation step prior to treating Compound 17A under suitable enol ether formation conditions, wherein the oxidation step comprises treating Compound 23A having the formula:

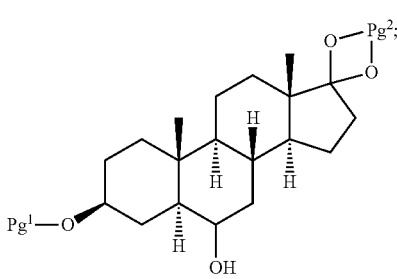

23A where Pg¹ is an oxygen-protecting group and Pg² is a carbonyl protecting group, under suitable oxidation conditions to provide Compound 17A, wherein the suitable oxidation conditions comprise treating Compound 23A in a suitable organic solvent with an oxidizing agent and a suitable activating reagent in the presence of a base.

35. The method of claim 34 wherein the suitable organic solvent comprises dichloromethane, the oxidizing agent comprises dimethyl sulfoxide, the suitable activating reagent comprises pyridine-sulfur trioxide complex and the base comprises triethylamine.

36. The method of claim 34 further comprising a hydroboration-oxidation step prior to treating Compound 23A under suitable oxidation conditions, wherein the hydroboration-oxidation step comprises treating Compound 3A having the following formula:

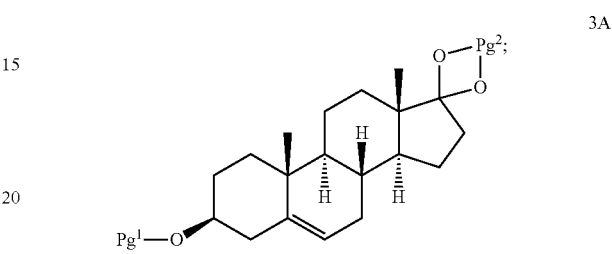

3A wherein Pg¹ is an oxygen-protecting group and Pg² is a carbonyl protecting group, under suitable hydroboration-oxidation conditions to provide Compound 23A, wherein the suitable hydroboration-oxidation conditions comprise treating Compound 3A in a polar aprotic solvent with a hydroboration reagent, followed by oxidation using an oxidant.

37. The method of claim 36 wherein the polar aprotic solvent comprises tetrahydrofuran, the hydroboration reagent comprises borane in tetrahydrofuran and the oxidant comprises hydrogen peroxide.

38. The method of claim 36 further comprising a hydroxyl protection step prior to treating Compound 3A under suitable hydroboration-oxidation conditions, wherein the hydroxyl protection step comprises treating Compound 2A having the formula:

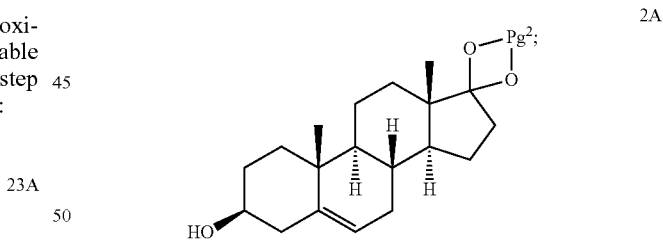

2A where Pg² is a carbonyl protecting group, under suitable hydroxyl protection conditions to provide Compound 3A, wherein the suitable hydroxyl protection conditions comprise treating Compound 2A in an organic solvent with a hydroxyl protecting group reagent in the presence of a base.

39. The method of claim 38 wherein the organic solvent comprises dichloromethane, the hydroxy protecting group reagent comprises tert-butyldimethylsilyl chloride and the base comprises imidazole.

40. The method of claim 38 further comprising a carbonyl protection step prior to treating Compound 2A under suitable hydroxyl protection conditions, wherein the carbonyl protection step comprises treating Compound 1 having the formula:

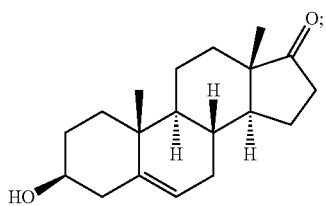

1 under suitable carbonyl protection conditions to provide Compound 2A, wherein the suitable carbonyl protection conditions comprise treating Compound 1 in an organic solvent with a carbonyl protecting group reagent in the presence of an acid catalyst.

41. The method of claim 40 wherein the organic solvent comprises cyclohexane, the carbonyl protecting group reagent comprises ethylene glycol and the acid catalyst comprises camphor sulfonic acid or p-toluene sulfonic acid.

42. A method of preparing AQX-1125 having the following formula:

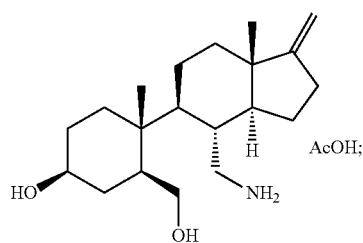 [SMILES: C=C1CC[C@H]2[C@H](CN)[C@@H]([C@@]3(C)CC[C@H](O)C[C@@H]3CO)CC[C@]12C]

AcOH;

wherein the method comprises:
(a) treating Compound 1 having the formula:

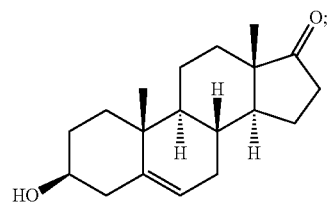

1 under suitable carbonyl protection conditions to provide Compound 2A having the formula:

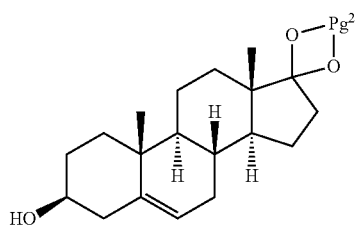

2A wherein Pg² is a carbonyl protecting group and wherein the suitable carbonyl protection conditions comprise treating Compound 1 in an organic solvent with a carbonyl protecting group reagent in the presence of an acid catalyst;

(b) treating Compound 2A under suitable hydroxyl protection conditions to provide Compound 3A having the formula:

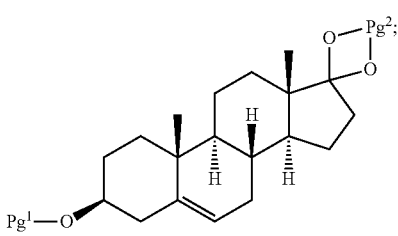

3A wherein Pg¹ is an oxygen-protecting group and Pg² is a carbonyl protecting group and wherein the suitable hydroxyl protection conditions comprise treating Compound 2A in an organic solvent with a hydroxyl protecting group reagent in the presence of a base;

(c) treating Compound 3A under suitable hydroboration-oxidation conditions to provide Compound 23A having the formula:

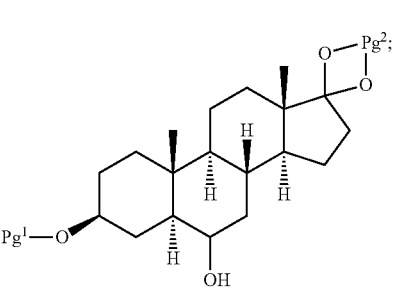

23A wherein Pg¹ is an oxygen-protecting group and Pg² is a carbonyl protecting group and wherein the suitable hydroboration-oxidation conditions comprise treating Compound 3A in a polar aprotic solvent with a hydroboration reagent, followed by oxidation using an oxidant;

(d) treating Compound 23A under suitable oxidation conditions to provide Compound 17A having the formula:

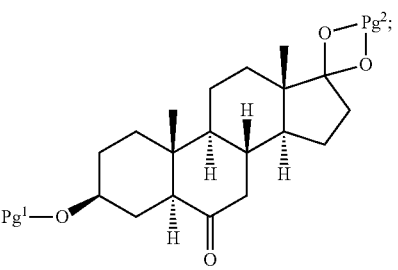

17A wherein Pg¹ is an oxygen-protecting group and Pg² is a carbonyl protecting group and wherein the suitable oxidation conditions comprise treating Compound 23A in a suitable organic solvent with an oxidizing agent and a suitable activating reagent in the presence of a base;

(e) treating Compound 17A under suitable enol ether formation conditions to provide Compound 19A having the formula:

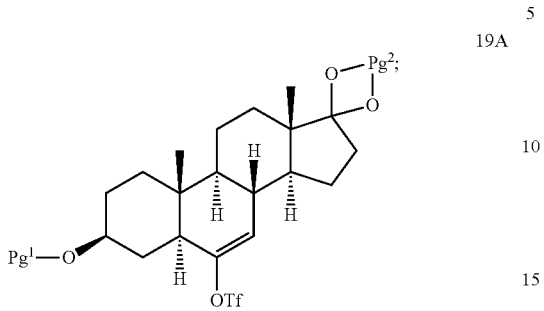

19A wherein Pg$^1$ is an oxygen-protecting group and Pg$^2$ is a carbonyl protecting group and wherein the suitable enol ether formation conditions comprise treating Compound 17A in a suitable polar aprotic solvent with a strong base and a suitable electrophilic reagent;

(f) treating Compound 19A under suitable oxidative carbon-carbon bond cleavage conditions to provide Compound 18A having the formula:

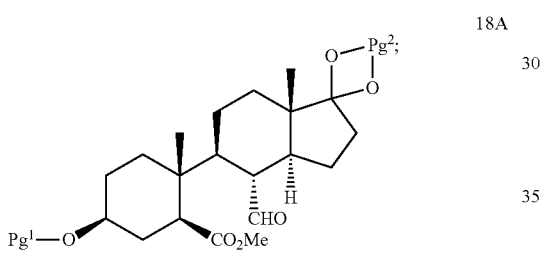

18A wherein Pg$^1$ is an oxygen-protecting group and Pg$^2$ is a carbonyl protecting group and wherein the suitable oxidative carbon-carbon bond cleavage conditions comprise treating Compound 19A in a polar protic solvent with a suitable oxidizing agent, followed by reduction with a suitable reducing agent;

(g) treating Compound 18A under suitable oxime or oxime O-ether formation conditions to provide Compound 66A having the formula:

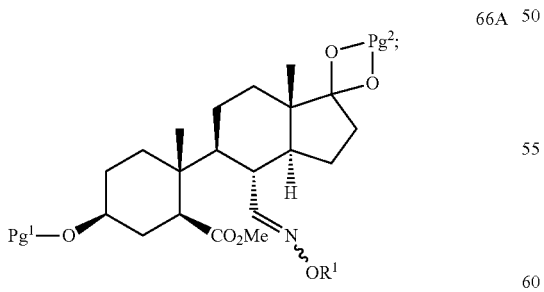

66A wherein R$^1$ is hydrogen, methyl or ethyl, Pg$^1$ is an oxygen-protecting group and Pg$^2$ is a carbonyl protecting group and wherein the suitable oxime or oxime O-ether formation conditions comprise treating Compound 18A in a suitable polar erotic solvent with a suitable reagent in the presence of a base;

(h) treating Compound 66A under suitable carbonyl deprotection conditions to provide Compound 67A having the formula:

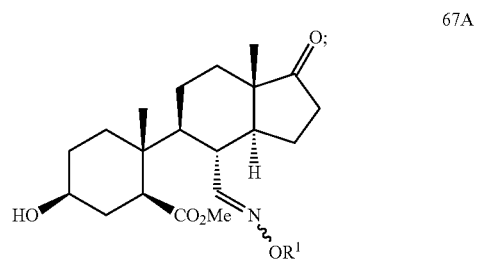

67A wherein R$^1$ is hydrogen, methyl or ethyl and wherein the suitable carbonyl deprotection conditions comprise treating Compound 66A in a polar protic solvent with a suitable acid;

(i) treating Compound 67A under suitable Wittig reaction or olefination conditions to provide Compound 53A having the formula:

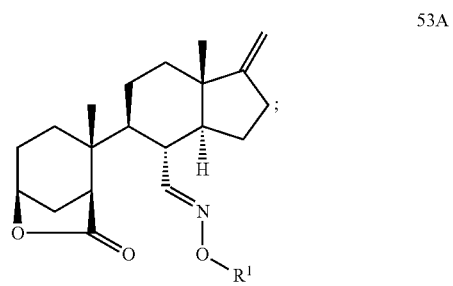

53A wherein R$^1$ is hydrogen, methyl or ethyl and wherein the suitable Wittig reaction or olefination conditions comprise treating Compound 67A in a suitable organic solvent with a ylide generated using a phosphonium salt and a base;

(j) treating Compound 53A under suitable lactone and oxime O-ether reduction conditions to provide compound 16 having the formula:

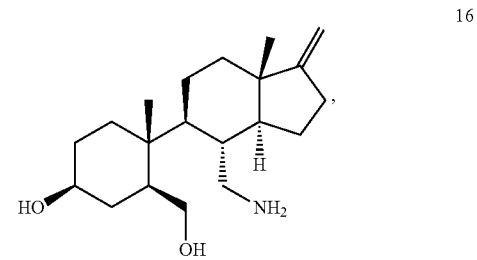

16 wherein the suitable lactone and oxime O-ether reduction conditions comprise treating Compound 53A in a polar aprotic solvent with a reducing agent; and (k) treating Compound 16 under suitable acetate salt formation conditions to provide AQX-1125, wherein the suitable acetate salt formation conditions comprise treating compound 16 in a polar protic solvent with glacial acetic acid followed by treating with a less polar organic solvent.

\* \* \* \* \*

UNITED STATES PATENT AND TRADEMARK OFFICE
CERTIFICATE OF CORRECTION

Page 1 of 2

PATENT NO. : 10,053,415 B2
APPLICATION NO. : 15/411863
DATED : August 21, 2018
INVENTOR(S) : Curtis Harwig et al.

It is certified that error appears in the above-identified patent and that said Letters Patent is hereby corrected as shown below:

In the Claims

Column 122, Line 24-25:
"The method of claim 1 wherein the polar aprotic solvent comprises lithium aluminum hydride."
should read, --The method of Claim 1 wherein the polar aprotic solvent comprises tetrahydrofuran, 2-methyl tetrahydrofuran or dioxane and the reducing agent comprises lithium aluminum hydride.--.

Column 124, Line 24:
"Compound 71A" should read, --Compound 72A--.

Column 124, Line 26:
"the polar erotic" should read, --the polar protic--.

Column 124, Line 27:
"suitable add" should read, --suitable acid--.

Column 125, Line 20:
"ter-butyl" should read, --tert-butyl--.

Column 126, Line 47:
"add catalyst;" should read, --acid catalyst;--.

Column 130, Line 20:
"polar orotic" should read, --polar protic--.

Column 130, Line 44:
"polar erotic" should read, --polar protic--.

Column 131, Line 6:
"polar erotic" should read, --polar protic--.

Signed and Sealed this
Twenty-seventh Day of August, 2019

Andrei Iancu
*Director of the United States Patent and Trademark Office*

Column 135, Line 66:
"polar erotic" should read, --polar protic--.